(12) United States Patent
Kim et al.

(10) Patent No.: US 9,102,616 B2
(45) Date of Patent: Aug. 11, 2015

(54) ORGANIC COMPOUND, ORGANIC ELECTRONIC DEVICE USING SAME, AND TERMINAL FOR SAME

(75) Inventors: Dongha Kim, Seongnam-si (KR); Soungyun Mun, Yongin-si (KR); Jungcheol Park, Jinhae-si (KR); Jinuk Ju, Gyeongsangnam-do (KR); Jangyeol Baek, Sacheon-si (KR); Wonsam Kim, Seongnam-si (KR); Eunkyung Kim, Jinju-si (KR); Daehyuk Choi, Suwon-si (KR); Junghwan Park, Seoul (KR)

(73) Assignee: DUK SAN NEOLUX CO., LTD., Cheonan-si, Chungcheongnam-do (KR)

( * ) Notice: Subject to any disclaimer, the term of this patent is extended or adjusted under 35 U.S.C. 154(b) by 564 days.

(21) Appl. No.: 13/508,229

(22) PCT Filed: Oct. 29, 2010

(86) PCT No.: PCT/KR2010/007526
§ 371 (c)(1),
(2), (4) Date: May 7, 2012

(87) PCT Pub. No.: WO2011/055932
PCT Pub. Date: May 12, 2011

(65) Prior Publication Data
US 2012/0217492 A1    Aug. 30, 2012

(30) Foreign Application Priority Data

Nov. 5, 2009 (KR) .................. 10-2009-0106439
Feb. 8, 2010 (KR) .................. 10-2010-0011499
Apr. 6, 2010 (KR) .................. 10-2010-0031311
Sep. 30, 2010 (KR) .................. 10-2010-0095400

(51) Int. Cl.
H01L 51/54       (2006.01)
C07D 209/80      (2006.01)
(Continued)

(52) U.S. Cl.
CPC ............ C07D 209/80 (2013.01); C07D 209/86 (2013.01); C07D 403/04 (2013.01);
(Continued)

(58) Field of Classification Search
CPC .. C07D 209/80; C07D 209/86; C07D 403/04; C07D 405/04; C07D 405/14; C07D 409/04; C07D 409/10; C07D 409/14; C07D 471/06; C09K 11/06; C09K 2211/1007; C09K 2211/1011; C09K 2211/1014; C09K 2211/1029; C09K 2211/1088; C09K 2211/1092; H01L 51/0052; H01L 51/0055; H01L 51/006; H01L 51/0061; H01L 51/5012; H01L 51/5056; H05B 33/10; Y02E 10/549
See application file for complete search history.

(56) References Cited

U.S. PATENT DOCUMENTS

2002/0074936 A1*  6/2002  Yamazaki et al. ............ 313/504
2010/0244008 A1    9/2010  Lee et al.
(Continued)

FOREIGN PATENT DOCUMENTS

JP    2009029725 A    2/2009
JP    2009123976 A    6/2009
(Continued)

OTHER PUBLICATIONS

Computer-generated English translation for JP 2009-123976 A (Publication date: Jun. 2009).*
(Continued)

*Primary Examiner* — Dawn Garrett
(74) *Attorney, Agent, or Firm* — Vorys, Sater, Seymour and Pease LLP; Mihsun Koh

(57) ABSTRACT

Disclosed are an organic compound, an organic electronic device using the same, and a terminal thereof.

15 Claims, 6 Drawing Sheets

(51) Int. Cl.

| | | |
|---|---|---|
| *C07D 209/86* | (2006.01) | |
| *C07D 471/06* | (2006.01) | |
| *H01L 51/30* | (2006.01) | |
| *H01L 51/46* | (2006.01) | |
| *C07D 403/04* | (2006.01) | |
| *C07D 405/04* | (2006.01) | |
| *C07D 405/14* | (2006.01) | |
| *C07D 409/04* | (2006.01) | |
| *C07D 409/10* | (2006.01) | |
| *C07D 409/14* | (2006.01) | |
| *H01L 51/00* | (2006.01) | |
| *C09K 11/06* | (2006.01) | |
| *H05B 33/10* | (2006.01) | |
| *H01L 51/50* | (2006.01) | |

(52) U.S. Cl.
CPC ............ *C07D 405/04* (2013.01); *C07D 405/14* (2013.01); *C07D 409/04* (2013.01); *C07D 409/10* (2013.01); *C07D 409/14* (2013.01); *C07D 471/06* (2013.01); *C09K 11/06* (2013.01); *H01L 51/006* (2013.01); *H01L 51/0052* (2013.01); *H01L 51/0055* (2013.01); *H01L 51/0061* (2013.01); *H05B 33/10* (2013.01); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *H01L 51/5012* (2013.01); *H01L 51/5056* (2013.01); *Y02E 10/549* (2013.01)

(56) References Cited

U.S. PATENT DOCUMENTS

| | | |
|---|---|---|
| 2011/0127495 A1 | 6/2011 | Hong et al. |
| 2012/0018717 A1 | 1/2012 | Kim et al. |
| 2012/0080670 A1 | 4/2012 | Park et al. |

FOREIGN PATENT DOCUMENTS

| | | |
|---|---|---|
| JP | 2009194042 A | 8/2009 |
| KR | 1020090041999 A | 4/2009 |
| KR | 1020090051140 A | 5/2009 |
| KR | 1020110034103 A | 4/2011 |
| KR | 1020110044587 A | 4/2011 |

OTHER PUBLICATIONS

Kundu, Parimal et al., "High-Tg Carbazole Derivatives as Blue-Emitting Hole-Transporting Materials for Electroluminescent Devices," Advanced Functional Materials 2003, vol. 13, No. 6, pp. 445-452.

International Search Report in Korean (with English Translation) and Written Opinion of the International Searching Authority (in Korean) for PCT/KR2010/007526, mailed Jul. 28, 2011; ISA/KR.

\* cited by examiner

ORGANIC COMPOUND, ORGANIC ELECTRONIC DEVICE USING SAME, AND TERMINAL FOR SAME

TECHNICAL FIELD

The present invention relates to an organic compound, an organic electronic device using the same, and a terminal for the same.

BACKGROUND ART

In general, an organic light emitting phenomenon indicates conversion of electric energy into light energy by means of an organic material. An organic electronic device using the organic light emitting phenomenon generally has a structure including an anode, a cathode, and an organic material layer interposed therebetween. Herein, in many cases, the organic material layer may have a multi-layered structure having respective different materials in order to improve efficiency and stability of an organic electronic device. For example, it may include a hole injection layer, a hole transport layer, an emitting layer, an electron transport layer, an electron injection layer, and the like.

Materials used as an organic material layer in an organic electronic device may be classified into a light emitting material and a charge transport material, for example, a hole injection material, a hole transport material, an electron transport material, an electron injection material, etc. according to their functions. Then, the light emitting material may be divided into a high molecular weight type and a low molecular weight type according to their molecular weight, and may be divided into a fluorescent material from electronic singlet excited states and a phosphorescent material from electronic triplet excited states according to their light emitting mechanism. Further, the light emitting material can be classified into a blue, green or red light emitting material and a yellow or orange light emitting material required for giving a more natural color, according to a light emitting color.

Meanwhile, when only one material is used as a light emitting material, an efficiency of a device is lowered owing to a maximum luminescence wavelength being shifted to a longer wavelength due to the interaction between the molecules, the deterioration of color purity and the reduction in luminous efficiency. Therefore, a host/dopant system can be used as the light emitting material for the purpose of enhancing the color purity and the luminous efficiency through energy transfer. It is based on the principle that if a small amount of a dopant having a smaller energy band gap than a host forming an emitting layer is mixed with the emitting layer, excitons which are generated in the emitting layer are transported to the dopant, thus emitting a light having a high efficiency. Here, since the wavelength of the host is shifted according to the wavelength of the dopant, a light having a desired wavelength can be obtained according to the kind of the dopant.

In order to allow the organic electronic device to fully exhibit the above-mentioned excellent characteristics, a material constituting the organic material layer in the device, for example, a hole injection material, a hole transport material, a light emitting material, an electron transport material and an electron injection material should be essentially composed of a stable and efficient material. However, the development of a stable and efficient organic material layer material for the organic electronic device has not yet been fully realized. Accordingly, the development of new materials is continuously desired.

DETAILED DESCRIPTION OF THE INVENTION

Technical Problem

In order to solve the above-mentioned problems occurring in the prior art, the inventors of the present invention have developed a compound including a substituted or unsubstituted carbazole derivative in which two tertiary amines are substituted. Also, they have found that the compound can be used as a material for hole injection, hole transport, electron injection, electron transport, light emission, and passivation (capping) in an organic electronic device, and especially, can be used alone as a light emitting material, a host or a dopant in host/dopant, and can be used as a hole injection layer or a hole transport layer. Then, they found that when the compound is employed in an organic electronic device, it is possible to achieve efficiency improvement, driving voltage reduction, life span prolongation, and stability improvement.

Accordingly, an object of the present invention is to provide a compound including a substituted or unsubstituted carbazole derivative in which two tertiary amines are substituted, an organic electronic device using the same, and an electronic device including the organic electronic device.

Technical Solution

In accordance with an aspect of the present invention, there is provided a compound represented by Formula below.

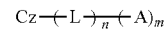

$$Cz-(-L-)_n-(-A)_m$$

The inventive compound including a substituted or unsubstituted carbazole derivative in which two tertiary amines are substituted may be used as a material for hole injection, hole transport, electron injection, electron transport, light emission, and passivation (capping) in an organic electronic device, and especially, may be used alone as a light emitting material, a host or a dopant in host/dopant, and may be used as a hole injection layer or a hole transport layer.

Accordingly, the present invention provides a compound including a substituted or unsubstituted carbazole derivative in which two tertiary amines are substituted, an organic electronic device using the same, and an electronic device or terminal including the organic electronic device.

Advantageous Effects

The inventive compound including a substituted or unsubstituted carbazole derivative in which two tertiary amines are substituted can perform various roles in an organic electronic device and a terminal. Also, when it is employed in an organic electronic device and a terminal, it is possible to achieve device efficiency increase, driving voltage reduction, life span prolongation, and stability increase.

MODE FOR CARRYING OUT THE INVENTION

Figure 1:
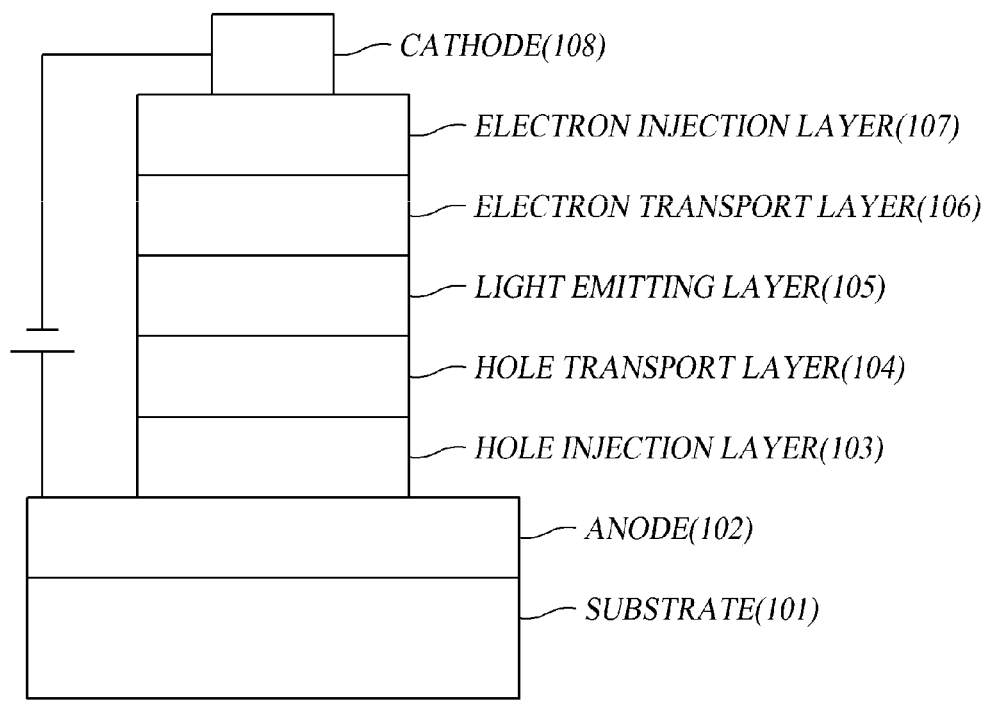
FIGS. 1 to 6 show examples of an organic electroluminescence element which can employ a compound according to the present invention.

Hereinafter, exemplary embodiments of the present invention will be described with reference to the accompanying drawings. In the following description, the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

The present invention provides a compound represented by Formula 1 below.

[Formula 1]

In Formula 1, Cz may represent a substituted or unsubstituted carbazole derivative represented by Formula 2 below.

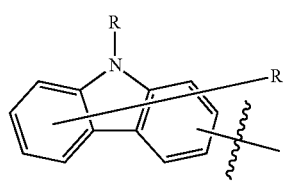

[Formula 2]

Herein, each R, which can substitute a carbon atom of carbazole, may be the same or different, and may be independently selected from the group consisting of a hydrogen atom, deuterium, tritium; a substituted or unsubstituted aryl group having 5~60 nuclear carbon atoms, a substituted or unsubstituted hetero aryl group having 5~60 nuclear carbon atoms, a substituted or unsubstituted $C_1$~$C_{60}$ alkyl group, a substituted or unsubstituted $C_1$~$C_{60}$ alkoxy group, a substituted or unsubstituted aryloxy group having 5~60 nuclear carbon atoms, a substituted or unsubstituted arylthio group having 5~60 nuclear carbon atoms, a substituted or unsubstituted alkoxycarbonyl group having 5~60 nuclear carbon atoms, an amino group substituted by a substituted or unsubstituted alkyl or aryl group having 5~60 nuclear carbon atoms, a halogen atom, a cyano group, a nitro group, a hydroxyl group, and a carboxyl group. Herein, R may form an aliphatic or hetero ring together with an adjacent group. Also, N of carbazole may form a ring together with an adjacent group.

Meanwhile, in Formula 1, L may represent a group selected from the group including a substituted or unsubstituted arylene group having 5~40 nuclear carbon atoms, a substituted or unsubstituted hetero arylene group having 5~60 nuclear atoms, and a divalent or trivalent, substituted or unsubstituted aliphatic hydrocarbon. Also, n may represent an integer of 0 to 3, but the present invention is not limited thereto. L may be specifically selected from the group including a phenyl group, a biphenyl group, a 1-naphthal group, a 2-naphtyl group, a pyridyl group, stilbene, an anthracenyl group, a phenanthrene group, a pyrenyl group, etc., but the present invention is not limited thereto.

Meanwhile, in Formula 1, A may represent a diamine derivative represented by Formula 3 below.

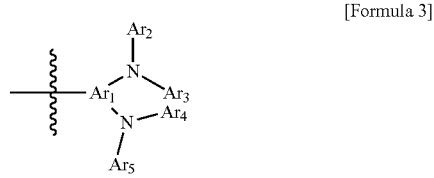

[Formula 3]

In Formula 3, $Ar_1$ through $Ar_5$ may be the same or different, and each may be independently selected from the group consisting of a substituted or unsubstituted aryl group having 1~60 nuclear atoms, and a substituted or unsubstituted heteroaryl group having 5~60 nuclear atoms. Meanwhile, $Ar_2$ through $Ar_5$ may be a substituted or unsubstituted alkyl group, but the present invention is not limited thereto. Meanwhile, m represents an integer of 1 to 4.

Also, $Ar_1$ through $Ar_5$ may satisfy that $Ar_2=Ar_3=Ar_4=Ar_5$, $Ar_2=Ar_4$, $Ar_3=Ar_5$, $Ar_2 \neq Ar_3$, and $Ar_4 \neq Ar_5$, but the present invention is not limited thereto.

Meanwhile, $Ar_1$ may be specifically selected from the group including a substituted or unsubstituted phenyl group, a biphenyl group, a 1-naphtyl group, a 2-naphtyl group, a thiophene group, a pyrrole group, a furan group, and a pyridyl group, but the present invention is not limited thereto.

In Formula 3, $Ar_2$ through $Ar_5$ may be the same or different, and each may be independently selected from the group consisting of functional groups noted in Table below, but the present invention is not limited thereto.

TABLE 1

| | $Ar_2$, $Ar_4$ | $Ar_3$, $Ar_5$ |
|---|---|---|
| 1 | phenyl | phenyl |
| 2 | phenyl | 4-substituted phenyl |

TABLE 1-continued
| | Ar$_2$, Ar$_4$ | Ar$_3$, Ar$_5$ |
|---|---|---|
| 3 | 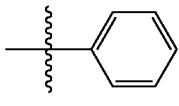 | 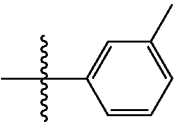 |
| 4 | 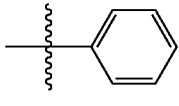 [SMILES: *c1ccccc1] | 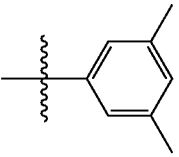 [SMILES: *c1cc(C)cc(C)c1] |
| 5 | 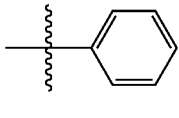 | 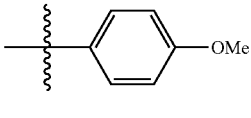 |
| 6 | 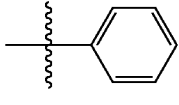 | 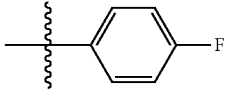 [SMILES: *c1ccc(F)cc1] |
| 7 | 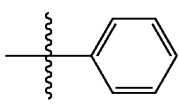 | 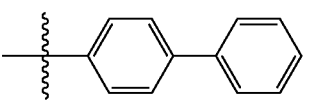 |
| 8 | 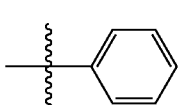 | 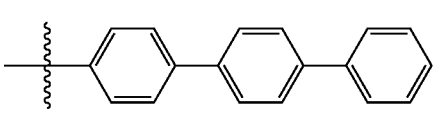 [SMILES: *c1ccc(-c2ccc(-c3ccccc3)cc2)cc1] |
| 9 | 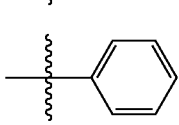 | 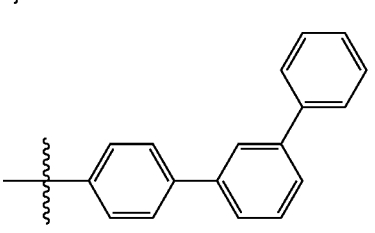 |
| 9 | 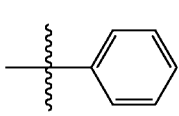 [SMILES: *c1ccccc1] | 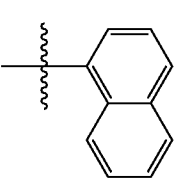 |
| 10 | 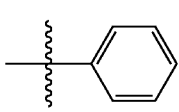 | 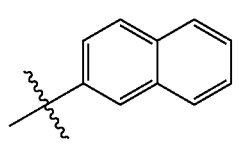 [SMILES: *c1ccc2ccccc2c1] |
| 11 | 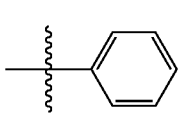 | 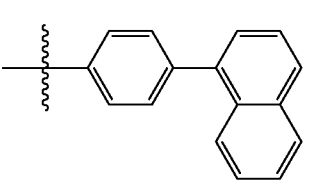 [SMILES: *c1ccc(-c2cccc3ccccc23)cc1] |
| 12 | 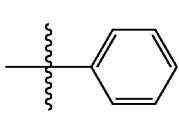 | 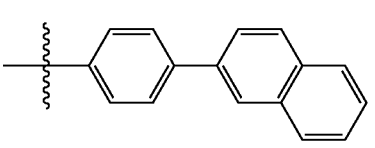 [SMILES: *c1ccc(-c2ccc3ccccc3c2)cc1] |

TABLE 1-continued
| | Ar₂, Ar₄ | Ar₃, Ar₅ |
|---|---|---|
| 13 | 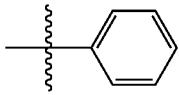 | 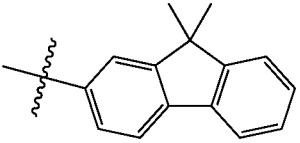 [SMILES: *c1ccc2c(c1)C(C)(C)c1ccccc1-2] |
| 14 | 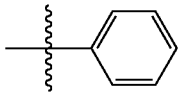 | 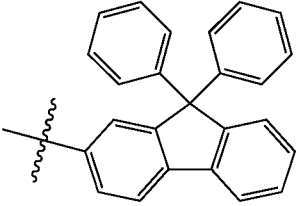 [SMILES: *c1ccc2c(c1)C(c1ccccc1)(c1ccccc1)c1ccccc1-2] |
| 15 | 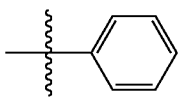 | 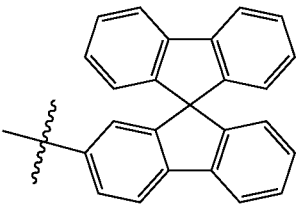 [SMILES: *c1ccc2c(c1)C1(c3ccccc3-c3ccccc31)c1ccccc1-2] |
| 16 | 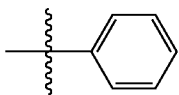 | 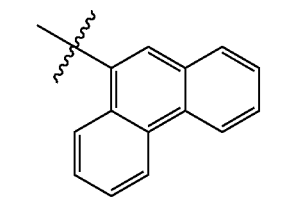 [SMILES: *c1cc2ccccc2c2ccccc12] |
| 17 | 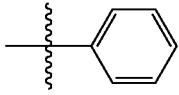 [SMILES: *c1ccccc1] | 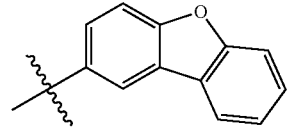 |
| 18 | 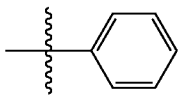 | 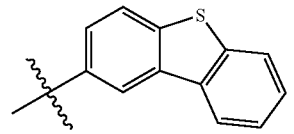 [SMILES: *c1ccc2sc3ccccc3c2c1] |
| 19 | 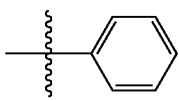 [SMILES: *c1ccccc1] | 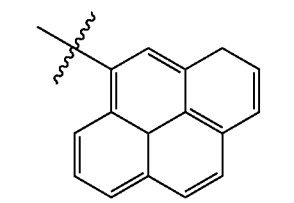 [SMILES: *C1=C2C=CC=C3C=CC4=C(C(=C1)CC=C4)C32] |
| 20 | 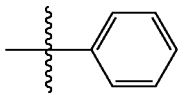 | 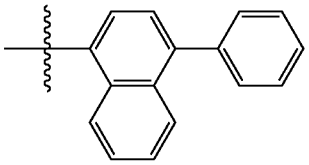 [SMILES: *c1ccc(-c2ccccc2)c2ccccc12] |

TABLE 1-continued
| | Ar₂, Ar₄ | Ar₃, Ar₅ |
|---|---|---|
| 21 | 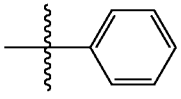 [SMILES: *c1ccccc1] | 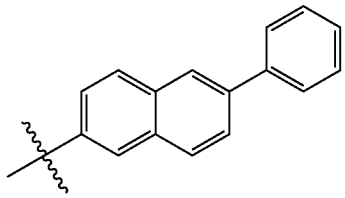 [SMILES: *c1ccc2cc(-c3ccccc3)ccc2c1] |
| 22 | 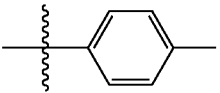 | 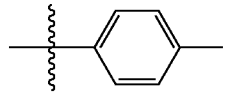 |
| 23 | 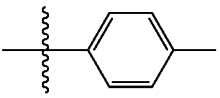 [SMILES: *c1ccc(C)cc1] | 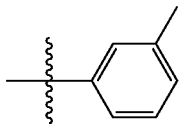 |
| 24 | 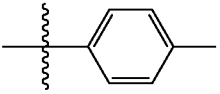 | 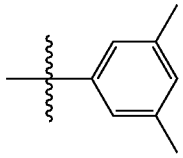 |
| 25 | 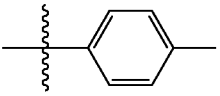 [SMILES: *c1ccc(C)cc1] | 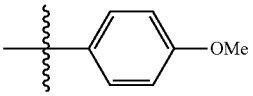 [SMILES: *c1ccc(OC)cc1] |
| 26 | 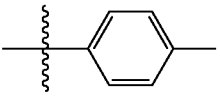 | 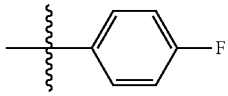 |
| 27 | 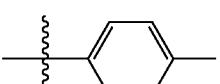 | 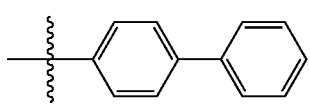 |
| 28 | 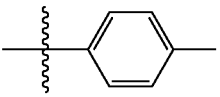 | 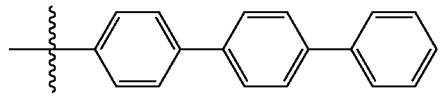 |
| 29 | 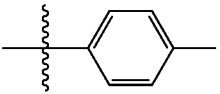 [SMILES: *c1ccc(C)cc1] | 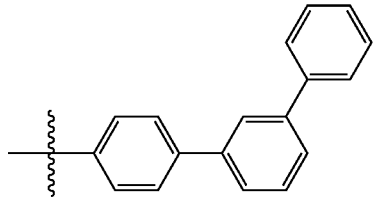 [SMILES: *c1ccc(-c2cccc(-c3ccccc3)c2)cc1] |
| 30 | 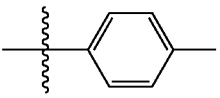 [SMILES: *c1ccc(C)cc1] | 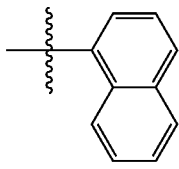 |
| 31 | 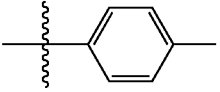 | 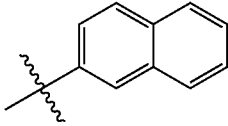 [SMILES: *c1ccc2ccccc2c1] |

TABLE 1-continued

| | Ar₂, Ar₄ | Ar₃, Ar₅ |
|---|---|---|
| 32 | phenylene | 4-(1-naphthyl)phenyl |
| 33 | phenylene | 4-(2-naphthyl)phenyl |
| 34 | phenylene | 9,9-dimethylfluoren-2-yl |
| 35 | phenylene | 9,9-diphenylfluoren-2-yl |
| 36 | phenylene | 9,9'-spirobifluoren-2-yl |
| 37 | phenylene | phenanthrenyl |
| 38 | phenylene | dibenzofuran-2-yl |
| 39 | phenylene | dibenzothiophen-2-yl |

TABLE 1-continued

| | Ar₂, Ar₄ | Ar₃, Ar₅ |
|---|---|---|
| 40 | 1,4-phenylene | pyrenyl |
| 41 | 1,4-phenylene | 4-phenylnaphthalen-1-yl |
| 42 | 1,4-phenylene | 6-phenylnaphthalen-2-yl |
| 43 | 1,3-phenylene | 1,3-phenylene |
| 44 | 1,3-phenylene | 3,5-dimethylphenyl |
| 45 | 1,3-phenylene | 4-methoxyphenyl |
| 46 | 1,3-phenylene | 4-fluorophenyl |
| 47 | 1,3-phenylene | biphenyl-4-yl |
| 48 | 1,3-phenylene | [1,1':4',1''-terphenyl]-4-yl |

TABLE 1-continued
| | Ar₂, Ar₄ | Ar₃, Ar₅ |
|---|---|---|
| 49 | 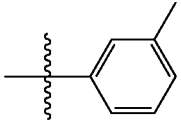 | 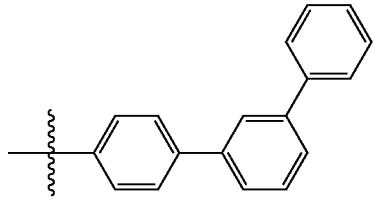 |
| 50 | 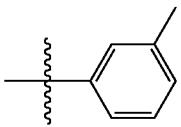 [SMILES: *c1cccc(C)c1] | 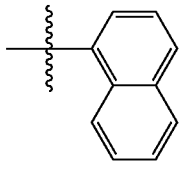 |
| 51 | 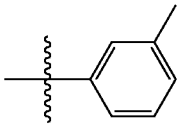 [SMILES: *c1cccc(C)c1] | 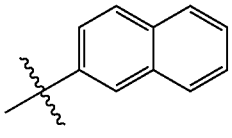 [SMILES: *c1ccc2ccccc2c1] |
| 52 | 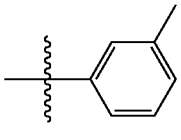 [SMILES: *c1cccc(C)c1] | 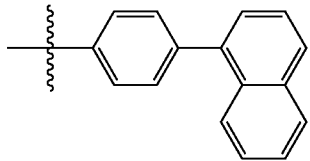 [SMILES: *c1ccc(-c2cccc3ccccc23)cc1] |
| 53 | 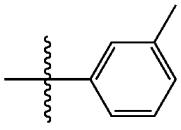 | 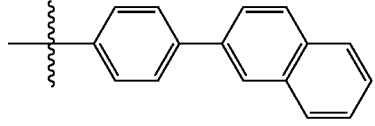 [SMILES: *c1ccc(-c2ccc3ccccc3c2)cc1] |
| 54 | 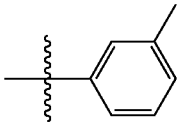 | 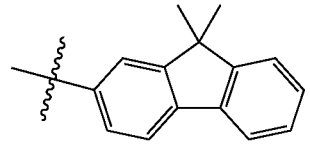 [SMILES: *c1ccc2c(c1)C(C)(C)c1ccccc1-2] |
| 55 | 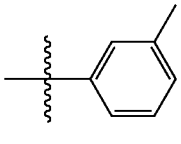 | 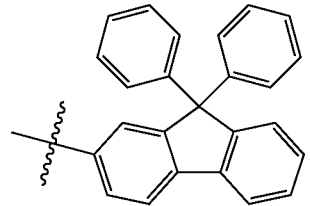 [SMILES: *c1ccc2c(c1)C(c1ccccc1)(c1ccccc1)c1ccccc1-2] |
| 56 | 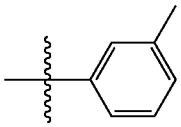 | 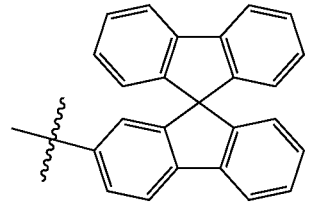 [SMILES: *c1ccc2c(c1)C1(c3ccccc3-c3ccccc31)c1ccccc1-2] |

TABLE 1-continued
| | Ar$_2$, Ar$_4$ | Ar$_3$, Ar$_5$ |
|---|---|---|
| 57 | 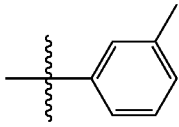 | 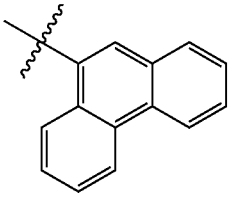 [SMILES: *c1cc2ccccc2c2ccccc12] |
| 58 | 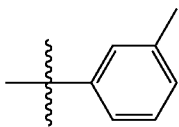 [SMILES: *c1cccc(C)c1] | 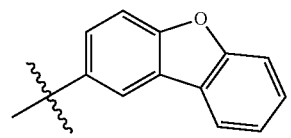 |
| 59 | 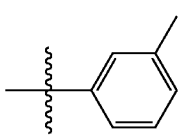 [SMILES: *c1cccc(C)c1] | 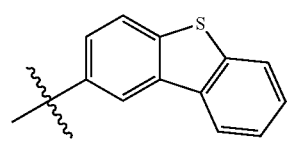 |
| 60 | 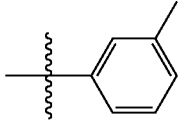 [SMILES: *c1cccc(C)c1] | 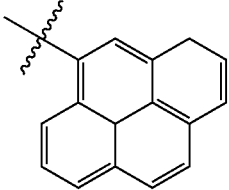 [SMILES: *C1=C2C=CC=C3C=CC4=C(C(=C1)CC=C4)C32] |
| 61 | 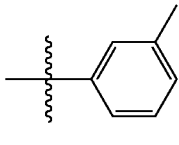 | 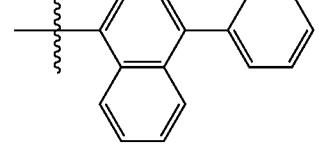 |
| 62 | 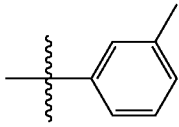 [SMILES: *c1cccc(C)c1] | 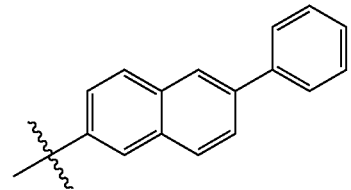 [SMILES: *c1ccc2cc(-c3ccccc3)ccc2c1] |
| 63 | 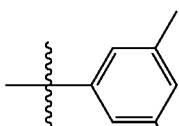 | 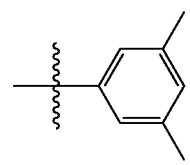 [SMILES: *c1cc(C)cc(C)c1] |
| 64 | 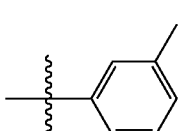 | 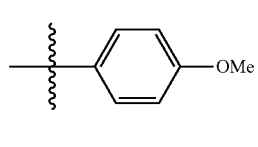 [SMILES: *c1ccc(OC)cc1] |
| 65 | 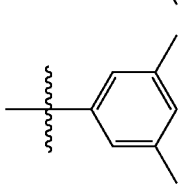 | 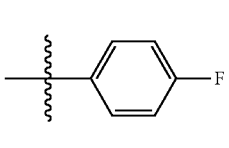 |

TABLE 1-continued

| | Ar₂, Ar₄ | Ar₃, Ar₅ |
|---|---|---|
| 66 | 3,5-dimethylphenyl | 4-biphenyl |
| 67 | 3,5-dimethylphenyl | 4-(4-biphenylyl)phenyl (p-terphenyl) |
| 68 | 3,5-dimethylphenyl | 4-(3-biphenylyl)phenyl |
| 69 | 3,5-dimethylphenyl | 1-naphthyl |
| 70 | 3,5-dimethylphenyl | 2-naphthyl |
| 71 | 3,5-dimethylphenyl | 4-(1-naphthyl)phenyl |
| 72 | 3,5-dimethylphenyl | 4-(2-naphthyl)phenyl |
| 73 | 3,5-dimethylphenyl | 9,9-dimethyl-2-fluorenyl |

TABLE 1-continued

| | Ar₂, Ar₄ | Ar₃, Ar₅ |
|---|---|---|
| 74 | 3,5-dimethylphenyl | 9,9-diphenylfluoren-2-yl |
| 75 | 3,5-dimethylphenyl | 9,9'-spirobifluoren-2-yl |
| 76 | 3,5-dimethylphenyl | phenanthren-9-yl |
| 77 | 3,5-dimethylphenyl | dibenzofuran-2-yl |
| 78 | 3,5-dimethylphenyl | dibenzothiophen-2-yl |
| 79 | 3,5-dimethylphenyl | pyren-1-yl |
| 80 | 3,5-dimethylphenyl | 4-phenylnaphthalen-1-yl |
| 81 | 3,5-dimethylphenyl | 6-phenylnaphthalen-2-yl |

TABLE 1-continued
| | Ar₂, Ar₄ | Ar₃, Ar₅ |
|---|---|---|
| 82 | 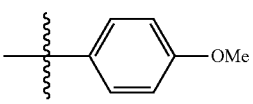 | 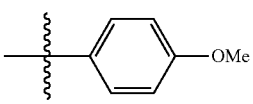 |
| 83 | 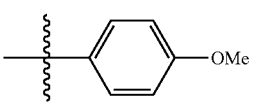 | 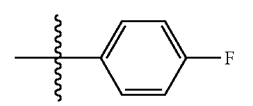 |
| 84 | 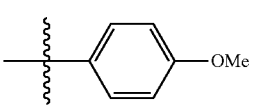 | 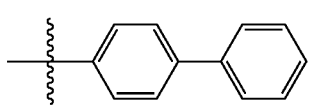 [SMILES: *c1ccc(-c2ccccc2)cc1] |
| 85 | 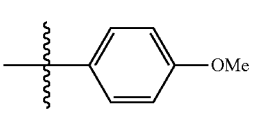 | 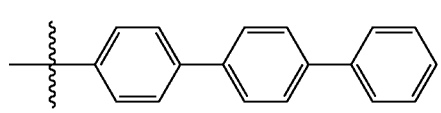 [SMILES: *c1ccc(-c2ccc(-c3ccccc3)cc2)cc1] |
| 86 | 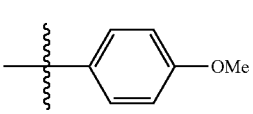 | 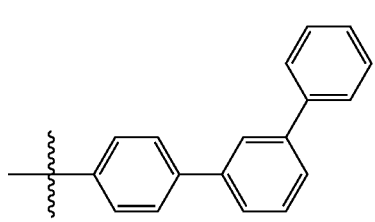 [SMILES: *c1ccc(-c2cccc(-c3ccccc3)c2)cc1] |
| 87 | 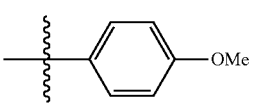 | 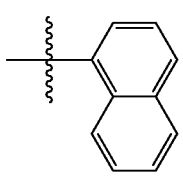 |
| 88 | 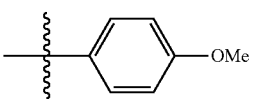 | 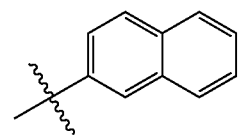 [SMILES: *c1ccc2ccccc2c1] |
| 89 | 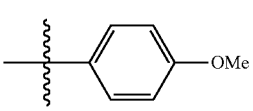 [SMILES: *c1ccc(OC)cc1] | 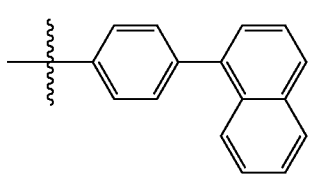 [SMILES: *c1ccc(-c2cccc3ccccc23)cc1] |
| 90 | 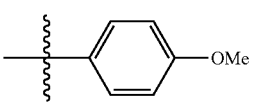 [SMILES: *c1ccc(OC)cc1] | 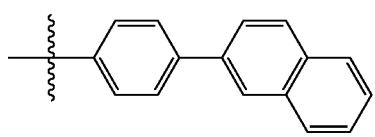 |
| 91 | 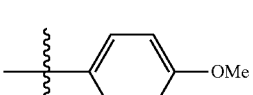 | 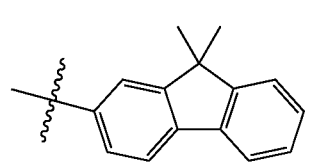 [SMILES: *c1ccc2c(c1)C(C)(C)c1ccccc1-2] |

TABLE 1-continued
| | Ar₂, Ar₄ | Ar₃, Ar₅ |
|---|---|---|
| 92 | 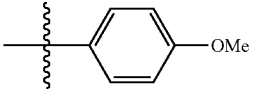 | 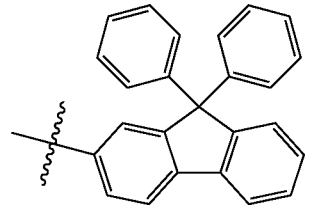 [SMILES: *c1ccc2c(c1)C(c1ccccc1)(c1ccccc1)c1ccccc1-2] |
| 93 | 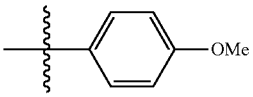 | 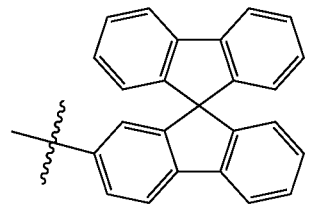 |
| 94 | 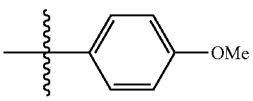 [SMILES: *c1ccc(OC)cc1] | 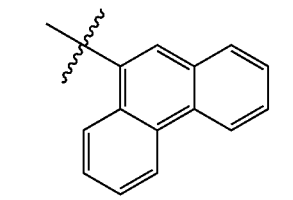 [SMILES: *c1cc2ccccc2c2ccccc12] |
| 95 | 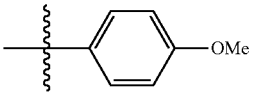 | 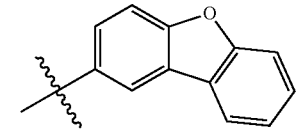 |
| 96 | 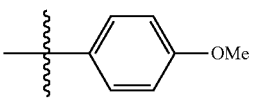 [SMILES: *c1ccc(OC)cc1] | 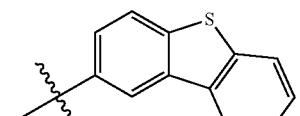 |
| 97 | 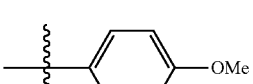 | 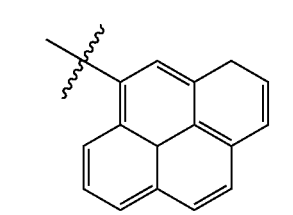 [SMILES: *C1=C2C=CC=C3C=CC4=C(C(=C1)CC=C4)C32] |
| 98 | 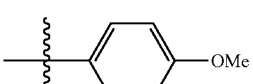 | 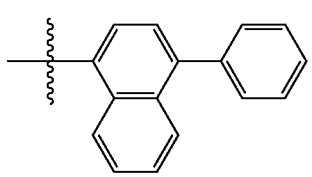 |
| 99 | 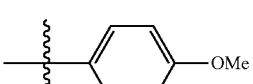 | 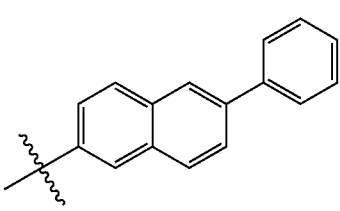 [SMILES: *c1ccc2cc(-c3ccccc3)ccc2c1] |

TABLE 1-continued

| | Ar₂, Ar₄ | Ar₃, Ar₅ |
|---|---|---|
| 100 | 4-fluorophenyl | 4-fluorophenyl |
| 101 | 4-fluorophenyl | 4-biphenylyl |
| 102 | 4-fluorophenyl | 4-(4'-phenylbiphenyl-4-yl) (p-terphenyl) |
| 103 | 4-fluorophenyl | 4-(3'-phenylphenyl)phenyl |
| 104 | 4-fluorophenyl | 1-naphthyl |
| 105 | 4-fluorophenyl | 2-naphthyl |
| 106 | 4-fluorophenyl | 4-(1-naphthyl)phenyl |
| 107 | 4-fluorophenyl | 4-(2-naphthyl)phenyl |
| 108 | 4-fluorophenyl | 9,9-dimethylfluoren-2-yl |
| 109 | 4-fluorophenyl | 9,9-diphenylfluoren-2-yl |

TABLE 1-continued
| | Ar₂, Ar₄ | Ar₃, Ar₅ |
|---|---|---|
| 110 | 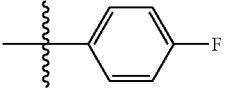 [SMILES: *c1ccc(F)cc1] | 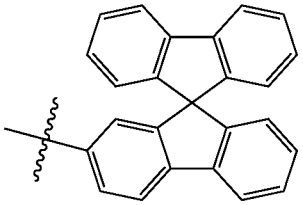 |
| 111 | 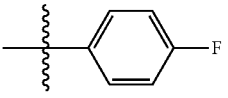 [SMILES: *c1ccc(F)cc1] | 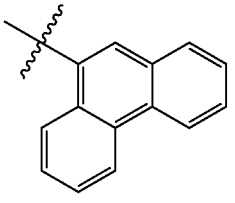 |
| 112 | 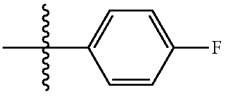 [SMILES: *c1ccc(F)cc1] | 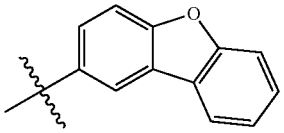 |
| 113 | 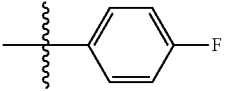 [SMILES: *c1ccc(F)cc1] | 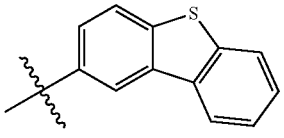 |
| 114 | 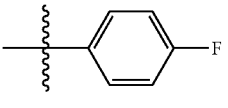 [SMILES: *c1ccc(F)cc1] | 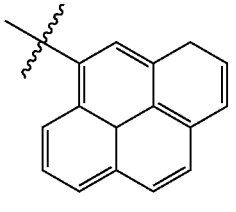 [SMILES: *C1=C2C=CC=C3C=CC4=C(C(=C1)CC=C4)C32] |
| 115 | 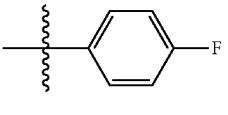 | 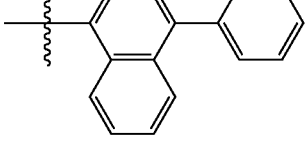 |
| 116 | 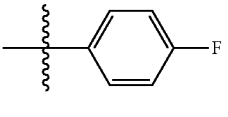 [SMILES: *c1ccc(F)cc1] | 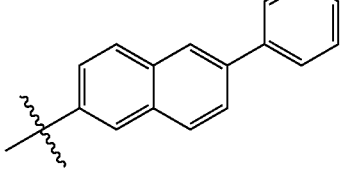 |
| 117 | 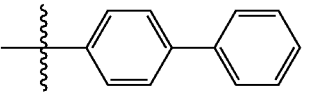 | 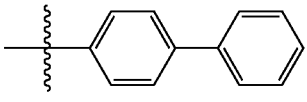 |
| 118 | 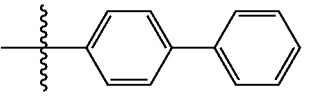 | 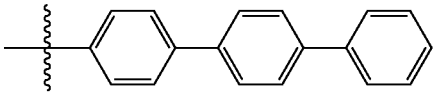 |

TABLE 1-continued

| | Ar₂, Ar₄ | Ar₃, Ar₅ |
|---|---|---|
| 119 | 4-biphenyl | 4-(3-phenylphenyl)phenyl |
| 120 | 4-biphenyl | 1-naphthyl |
| 121 | 4-biphenyl | 2-naphthyl |
| 122 | 4-biphenyl | 4-(1-naphthyl)phenyl |
| 123 | 4-biphenyl | 4-(2-naphthyl)phenyl |
| 124 | 4-biphenyl | 9,9-dimethylfluoren-2-yl |
| 125 | 4-biphenyl | 9,9-diphenylfluoren-2-yl |
| 126 | 4-biphenyl | 9,9'-spirobifluoren-2-yl |

TABLE 1-continued

| | Ar₂, Ar₄ | Ar₃, Ar₅ |
|---|---|---|
| 127 | [biphenyl] | [phenanthrenyl] |
| 128 | [biphenyl] | [dibenzofuranyl] |
| 129 | [biphenyl] | [dibenzothiophenyl] |
| 130 | [biphenyl] | [pyrenyl] |
| 131 | [biphenyl] | [4-phenylnaphthalen-1-yl] |
| 132 | [biphenyl] | [6-phenylnaphthalen-2-yl] |
| 133 | [terphenyl] | [terphenyl] |
| 134 | [terphenyl] | [3'-phenyl-biphenyl] |
| 135 | [terphenyl] | [naphthalen-1-yl] |

TABLE 1-continued

| | Ar₂, Ar₄ | Ar₃, Ar₅ |
|---|---|---|
| 136 | [terphenyl] | [2-naphthyl] |
| 137 | [terphenyl] | [phenyl-1-naphthyl] |
| 138 | [terphenyl] | [phenyl-2-naphthyl] |
| 139 | [terphenyl] | [9,9-dimethylfluorenyl] |
| 140 | [terphenyl] | [9,9-diphenylfluorenyl] |
| 141 | [terphenyl] | [9,9'-spirobifluorenyl] |
| 142 | [terphenyl] | [phenanthrenyl] |
| 143 | [terphenyl] | [dibenzofuranyl] |
| 144 | [terphenyl] | [dibenzothiophenyl] |

TABLE 1-continued

| | Ar₂, Ar₄ | Ar₃, Ar₅ |
|---|---|---|
| 145 | terphenyl | pyrenyl |
| 146 | terphenyl | 4-phenylnaphthalen-1-yl |
| 147 | terphenyl | 6-phenylnaphthalen-2-yl |
| 148 | 3'-phenyl-biphenyl-4-yl | 3'-phenyl-biphenyl-4-yl |
| 149 | 3'-phenyl-biphenyl-4-yl | naphthalen-1-yl |
| 150 | 3'-phenyl-biphenyl-4-yl | naphthalen-2-yl |
| 151 | 3'-phenyl-biphenyl-4-yl | 4-(naphthalen-1-yl)phenyl |

TABLE 1-continued

| | Ar₂, Ar₄ | Ar₃, Ar₅ |
|---|---|---|
| 152 | | |
| 153 | | |
| 154 | | |
| 155 | | |
| 156 | | |
| 157 | | |
| 158 | | |

TABLE 1-continued
| | Ar₂, Ar₄ | Ar₃, Ar₅ |
|---|---|---|
| 159 | 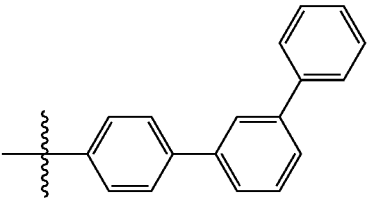 [SMILES: *c1ccc(-c2cccc(-c3ccccc3)c2)cc1] | 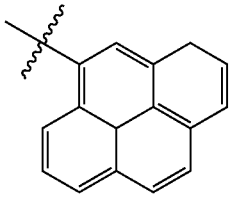 [SMILES: *C1=C2C=CC=C3C=CC4=C(C(=C1)CC=C4)C32] |
| 160 | 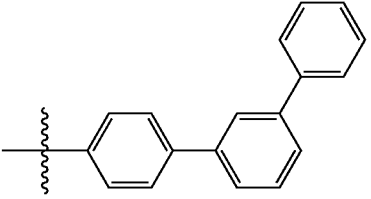 | 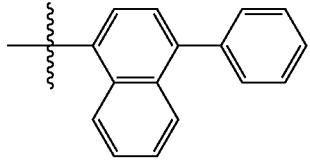 [SMILES: *c1ccc(-c2ccccc2)c2ccccc12] |
| 161 | 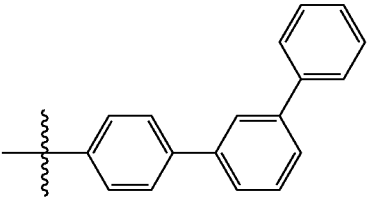 [SMILES: *c1ccc(-c2cccc(-c3ccccc3)c2)cc1] | 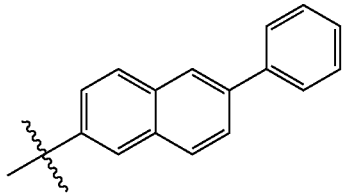 [SMILES: *c1ccc2cc(-c3ccccc3)ccc2c1] |
| 162 | 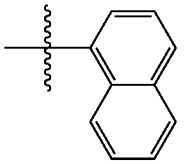 | 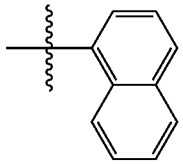 |
| 163 | 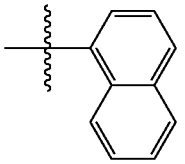 [SMILES: *c1cccc2ccccc12] | 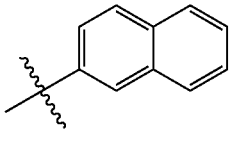 [SMILES: *c1ccc2ccccc2c1] |
| 164 | 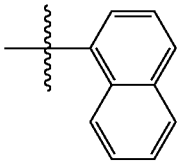 [SMILES: *c1cccc2ccccc12] | 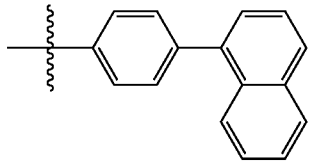 |
| 165 | 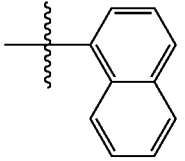 [SMILES: *c1cccc2ccccc12] | 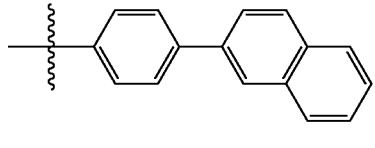 |
| 166 | 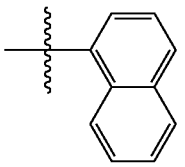 [SMILES: *c1cccc2ccccc12] | 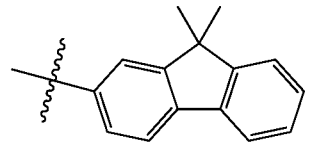 [SMILES: *c1ccc2c(c1)C(C)(C)c1ccccc1-2] |

TABLE 1-continued
| | Ar₂, Ar₄ | Ar₃, Ar₅ |
|---|---|---|
| 167 | 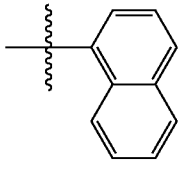 [SMILES: *c1cccc2ccccc12] | 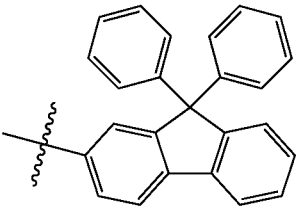 [SMILES: *c1ccc2c(c1)C(c1ccccc1)(c1ccccc1)c1ccccc1-2] |
| 168 | 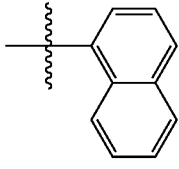 | 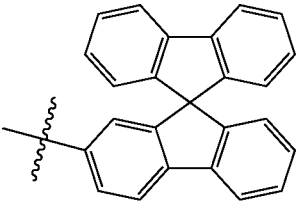 [SMILES: *c1ccc2c(c1)C1(c3ccccc3-c3ccccc31)c1ccccc1-2] |
| 170 | 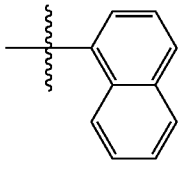 [SMILES: *c1cccc2ccccc12] | 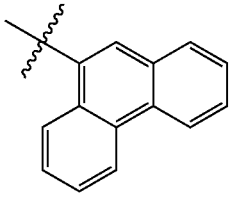 [SMILES: *c1cc2ccccc2c2ccccc12] |
| 171 | 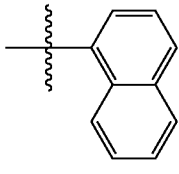 | 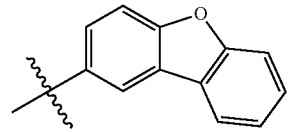 [SMILES: *c1ccc2oc3ccccc3c2c1] |
| 172 | 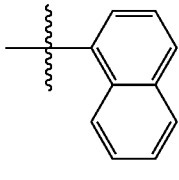 [SMILES: *c1cccc2ccccc12] | 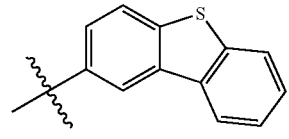 |
| 173 | 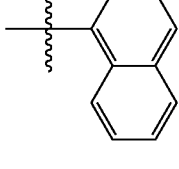 | 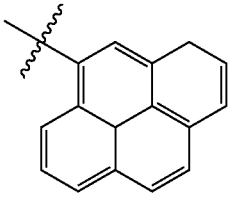 [SMILES: *C1=C2C=CC=C3C=CC4=C(C(=C1)CC=C4)C32] |
| 174 | 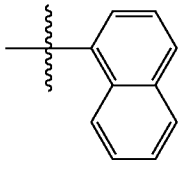 [SMILES: *c1cccc2ccccc12] | 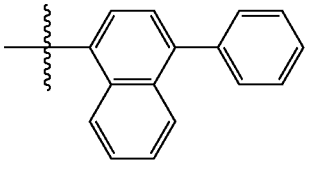 [SMILES: *c1ccc(-c2ccccc2)c2ccccc12] |
| 175 | 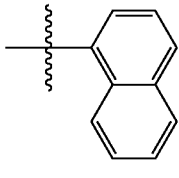 [SMILES: *c1cccc2ccccc12] | 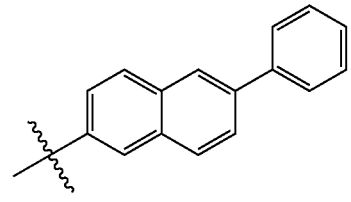 [SMILES: *c1ccc2cc(-c3ccccc3)ccc2c1] |

TABLE 1-continued

| | Ar₂, Ar₄ | Ar₃, Ar₅ |
|---|---|---|
| 176 | 2-naphthyl | 2-naphthyl |
| 177 | 2-naphthyl | 4-(1-naphthyl)phenyl |
| 178 | 2-naphthyl | 4-(2-naphthyl)phenyl |
| 179 | 2-naphthyl | 9,9-dimethyl-2-fluorenyl |
| 180 | 2-naphthyl | 9,9-diphenyl-2-fluorenyl |
| 181 | 2-naphthyl | 9,9-diphenyl-2-fluorenyl |
| 182 | 2-naphthyl | 9,9'-spirobifluoren-2-yl |
| 183 | 2-naphthyl | 9-phenanthryl |

TABLE 1-continued
| | Ar$_2$, Ar$_4$ | Ar$_3$, Ar$_5$ |
|---|---|---|
| 184 | 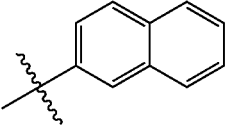 [SMILES: *c1ccc2ccccc2c1] | 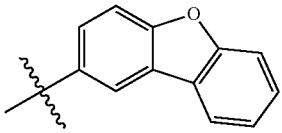 |
| 185 | 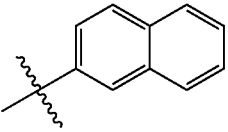 [SMILES: *c1ccc2ccccc2c1] | 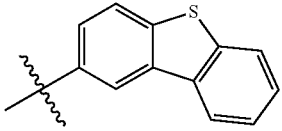 |
| 186 | 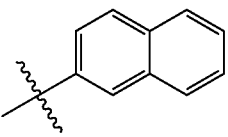 [SMILES: *c1ccc2ccccc2c1] | 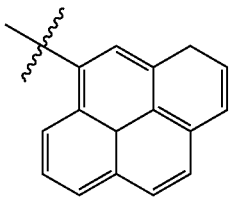 [SMILES: *C1=C2C=CC=C3C=CC4=C(C(=C1)CC=C4)C32] |
| 187 | 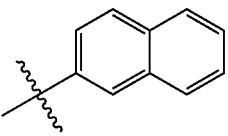 [SMILES: *c1ccc2ccccc2c1] | 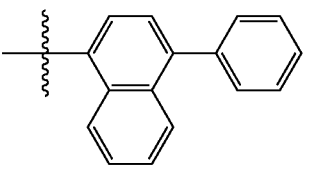 [SMILES: *c1ccc(-c2ccccc2)c2ccccc12] |
| 188 | 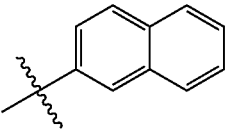 [SMILES: *c1ccc2ccccc2c1] | 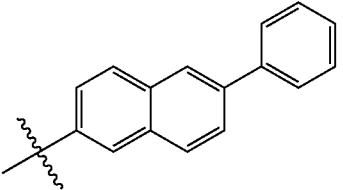 [SMILES: *c1ccc2cc(-c3ccccc3)ccc2c1] |
| 189 | 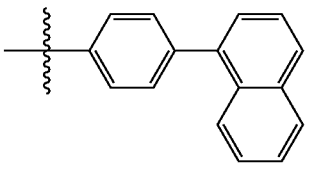 | 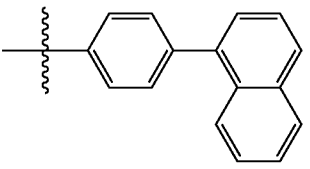 [SMILES: *c1ccc(-c2cccc3ccccc23)cc1] |
| 190 | 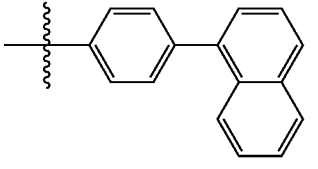 | 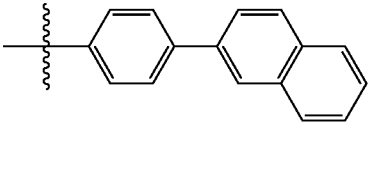 |
| 191 | 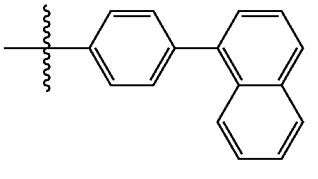 [SMILES: *c1ccc(-c2cccc3ccccc23)cc1] | 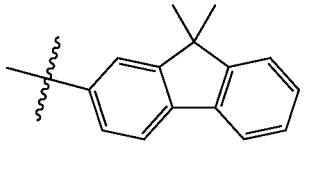 [SMILES: *c1ccc2c(c1)C(C)(C)c1ccccc1-2] |

US 9,102,616 B2
TABLE 1-continued
| | Ar$_2$, Ar$_4$ | Ar$_3$, Ar$_5$ |
|---|---|---|
| 192 | 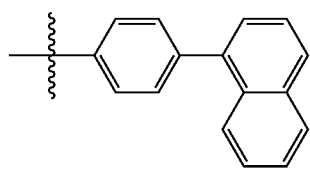 | 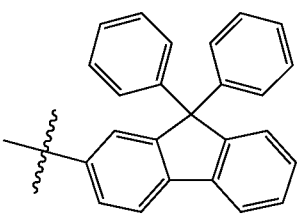 [SMILES: *c1ccc2c(c1)C(c1ccccc1)(c1ccccc1)c1ccccc1-2] |
| 193 | 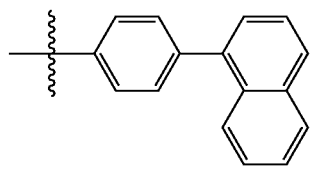 | 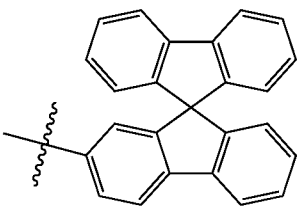 [SMILES: *c1ccc2c(c1)C1(c3ccccc3-c3ccccc31)c1ccccc1-2] |
| 194 | 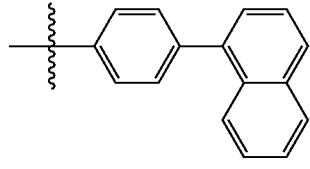 [SMILES: *c1ccc(-c2cccc3ccccc23)cc1] | 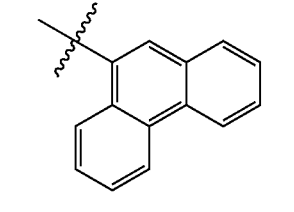 |
| 195 | 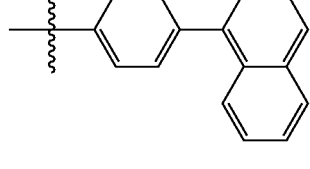 | 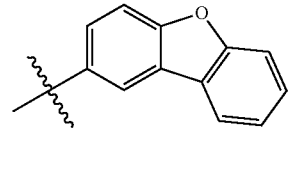 [SMILES: *c1ccc2oc3ccccc3c2c1] |
| 196 | 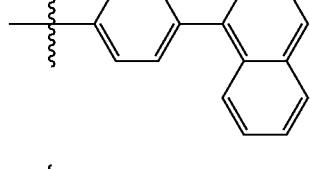 | 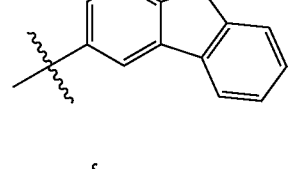 |
| 197 | 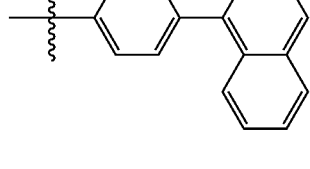 | 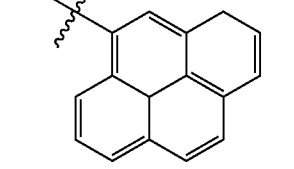 |
| 198 | 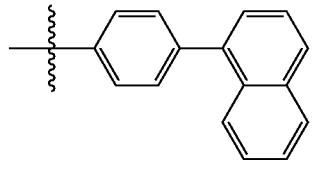 [SMILES: *c1ccc(-c2cccc3ccccc23)cc1] | 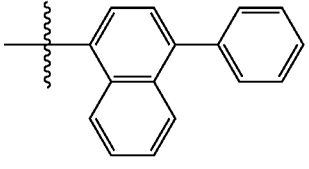 [SMILES: *c1ccc(-c2ccccc2)c2ccccc12] |
| 199 | 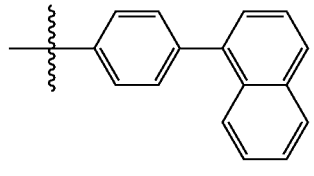 [SMILES: *c1ccc(-c2cccc3ccccc23)cc1] | 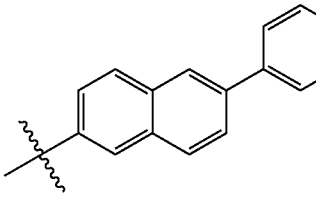 |

TABLE 1-continued
| | Ar₂, Ar₄ | Ar₃, Ar₅ |
|---|---|---|
| 200 | 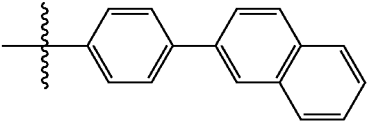 | 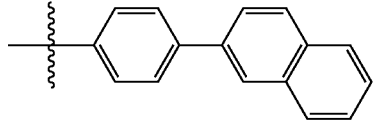 [SMILES: *c1ccc(-c2ccc3ccccc3c2)cc1] |
| 201 | 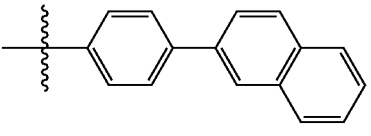 [SMILES: *c1ccc(-c2ccc3ccccc3c2)cc1] | 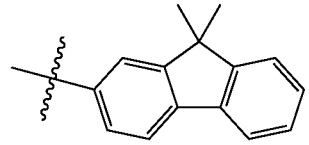 [SMILES: *c1ccc2c(c1)C(C)(C)c1ccccc1-2] |
| 202 | 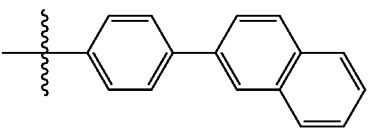 | 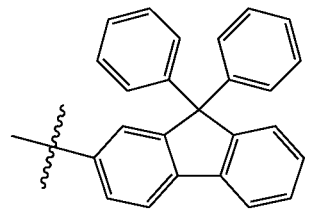 [SMILES: *c1ccc2c(c1)C(c1ccccc1)(c1ccccc1)c1ccccc1-2] |
| 203 | 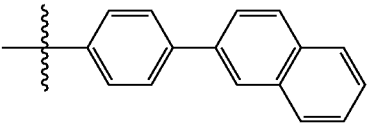 | 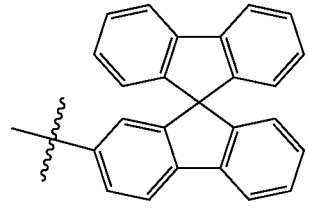 [SMILES: *c1ccc2c(c1)C1(c3ccccc3-c3ccccc31)c1ccccc1-2] |
| 204 | 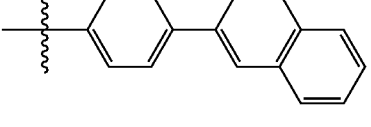 | 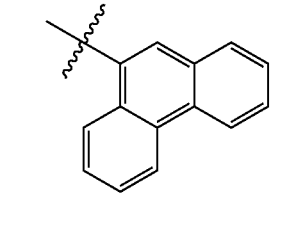 [SMILES: *c1cc2ccccc2c2ccccc12] |
| 205 | 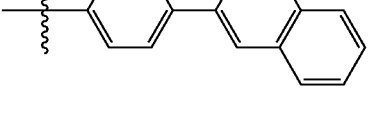 | 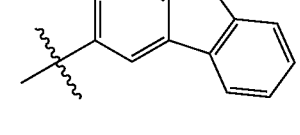 |
| 206 | 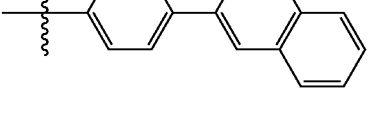 | 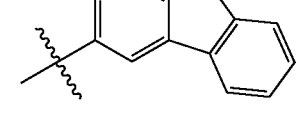 |
| 207 | 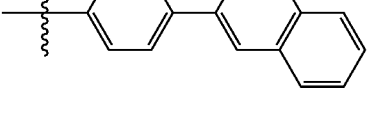 | 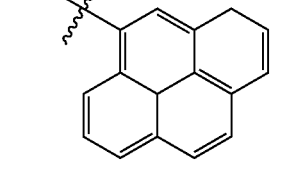 |

TABLE 1-continued
| | Ar₂, Ar₄ | Ar₃, Ar₅ |
|---|---|---|
| 208 | 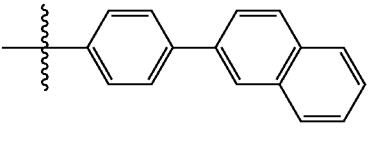 [SMILES: *c1ccc(-c2ccc3ccccc3c2)cc1] | 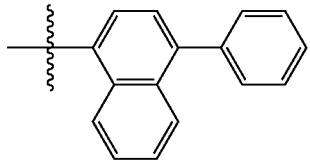 [SMILES: *c1ccc(-c2ccccc2)c2ccccc12] |
| 209 | 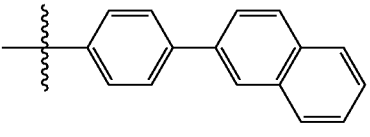 | 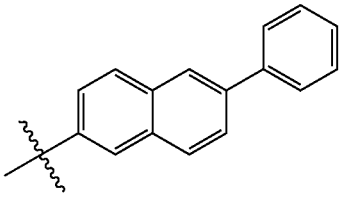 [SMILES: *c1ccc2cc(-c3ccccc3)ccc2c1] |
| 210 | 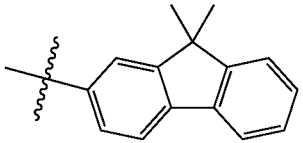 [SMILES: *c1ccc2c(c1)C(C)(C)c1ccccc1-2] | 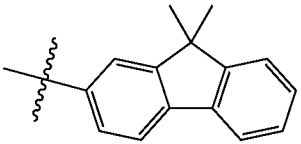 [SMILES: *c1ccc2c(c1)C(C)(C)c1ccccc1-2] |
| 211 | 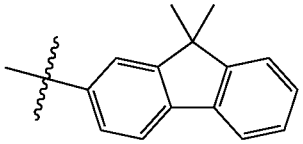 [SMILES: *c1ccc2c(c1)C(C)(C)c1ccccc1-2] | 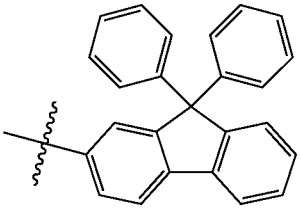 [SMILES: *c1ccc2c(c1)C(c1ccccc1)(c1ccccc1)c1ccccc1-2] |
| 212 | 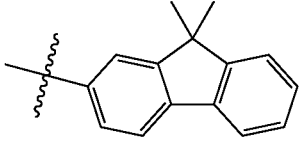 [SMILES: *c1ccc2c(c1)C(C)(C)c1ccccc1-2] | 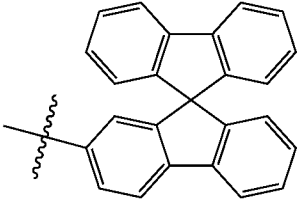 [SMILES: *c1ccc2c(c1)C1(c3ccccc3-c3ccccc31)c1ccccc1-2] |
| 213 | 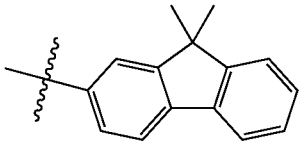 [SMILES: *c1ccc2c(c1)C(C)(C)c1ccccc1-2] | 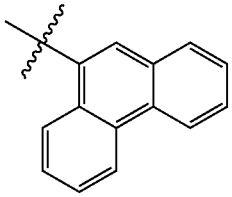 [SMILES: *c1cc2ccccc2c2ccccc12] |
| 214 | 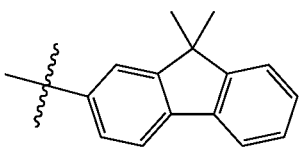 [SMILES: *c1ccc2c(c1)C(C)(C)c1ccccc1-2] | 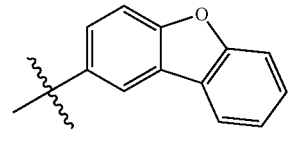 [SMILES: *c1ccc2oc3ccccc3c2c1] |
| 215 | 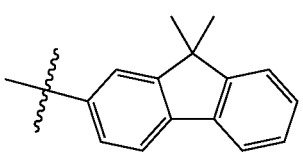 [SMILES: *c1ccc2c(c1)C(C)(C)c1ccccc1-2] | 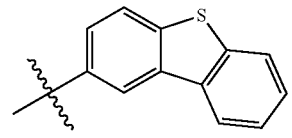 |

TABLE 1-continued

| | Ar₂, Ar₄ | Ar₃, Ar₅ |
|---|---|---|
| 216 | 9,9-dimethylfluoren-2-yl | pyren-1-yl |
| 217 | 9,9-dimethylfluoren-2-yl | 4-phenylnaphthalen-1-yl |
| 218 | 9,9-dimethylfluoren-2-yl | 6-phenylnaphthalen-2-yl |
| 219 | 9,9-diphenylfluoren-2-yl | 9,9-diphenylfluoren-2-yl |
| 220 | 9,9-diphenylfluoren-2-yl | 9,9'-spirobifluoren-2-yl |
| 221 | 9,9-diphenylfluoren-2-yl | phenanthren-9-yl |
| 223 | 9,9-diphenylfluoren-2-yl | dibenzofuran-2-yl |

TABLE 1-continued

| | Ar₂, Ar₄ | Ar₃, Ar₅ |
|---|---|---|
| 224 | | |
| 225 | | |
| 226 | | |
| 227 | | |
| 228 | | |
| 229 | | |
| 230 | | |

TABLE 1-continued
| | Ar₂, Ar₄ | Ar₃, Ar₅ |
|---|---|---|
| 231 | 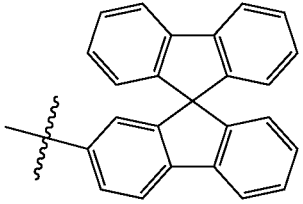 [SMILES: *c1ccc2c(c1)C1(c3ccccc3-c3ccccc31)c1ccccc1-2] | 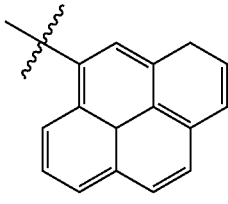 [SMILES: *C1=C2C=CC=C3C=CC4=C(C(=C1)CC=C4)C32] |
| 232 | 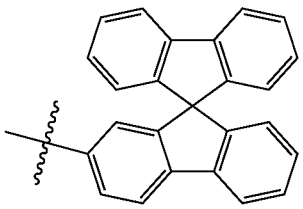 [SMILES: *c1ccc2c(c1)C1(c3ccccc3-c3ccccc31)c1ccccc1-2] | 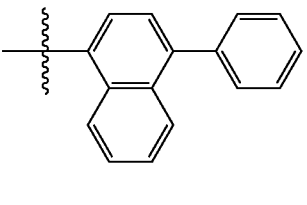 [SMILES: *c1ccc(-c2ccccc2)c2ccccc12] |
| 233 | 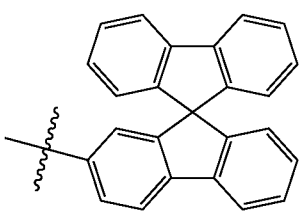 [SMILES: *c1ccc2c(c1)C1(c3ccccc3-c3ccccc31)c1ccccc1-2] | 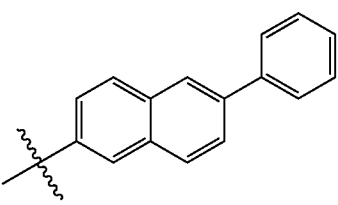 [SMILES: *c1ccc2cc(-c3ccccc3)ccc2c1] |
| 234 | 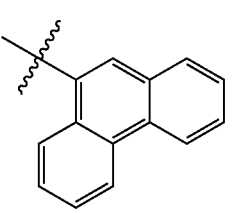 [SMILES: *c1cc2ccccc2c2ccccc12] | 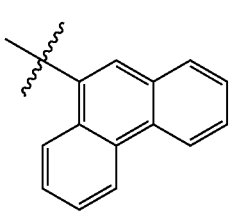 [SMILES: *c1cc2ccccc2c2ccccc12] |
| 235 | 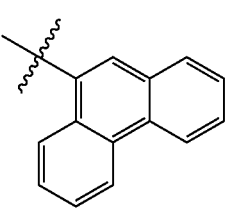 [SMILES: *c1cc2ccccc2c2ccccc12] | 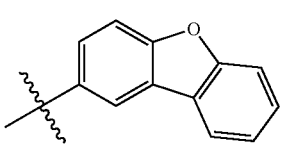 |
| 236 | 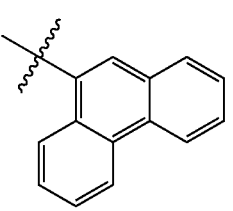 | 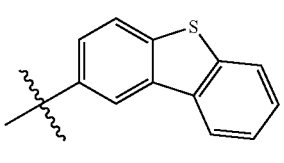 |
| 237 | 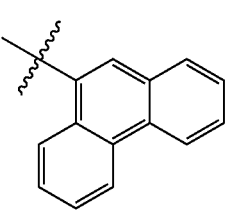 [SMILES: *c1cc2ccccc2c2ccccc12] | 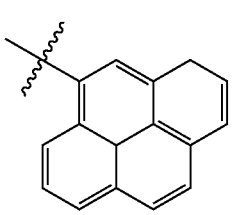 [SMILES: *C1=C2C=CC=C3C=CC4=C(C(=C1)CC=C4)C32] |

TABLE 1-continued

| | Ar₂, Ar₄ | Ar₃, Ar₅ |
|---|---|---|
| 238 | phenanthrenyl | 4-phenylnaphthalen-1-yl |
| 239 | phenanthrenyl | 6-phenylnaphthalen-2-yl |
| 240 | dibenzofuran-2-yl | dibenzofuran-2-yl |
| 241 | dibenzofuran-2-yl | dibenzothiophen-2-yl |
| 242 | dibenzofuran-2-yl | pyrenyl |
| 243 | dibenzofuran-2-yl | 4-phenylnaphthalen-1-yl |
| 244 | dibenzofuran-2-yl | 6-phenylnaphthalen-2-yl |
| 245 | dibenzothiophen-2-yl | dibenzothiophen-2-yl |

TABLE 1-continued

| | Ar$_2$, Ar$_4$ | Ar$_3$, Ar$_5$ |
|---|---|---|
| 246 | dibenzothiophene | pyrenyl |
| 247 | dibenzothiophene | 4-phenylnaphthyl |
| 248 | dibenzothiophene | 6-phenyl-2-naphthyl |
| 249 | pyrenyl | pyrenyl |
| 250 | pyrenyl | 4-phenylnaphthyl |
| 251 | pyrenyl | 6-phenyl-2-naphthyl |
| 252 | 4-phenylnaphthyl | 4-phenylnaphthyl |
| 253 | 4-phenylnaphthyl | 6-phenyl-2-naphthyl |

TABLE 1-continued

| Ar₂, Ar₄ | Ar₃, Ar₅ |
|---|---|
| 254 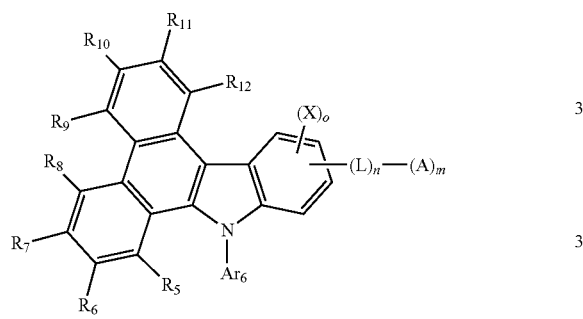 | |

The compound may be used in a soluble process so as to form an organic material layer of an organic electronic device (to be described later).

Further, substituents in Formulas 1 to 3 may be further substituted or unsubstituted although not mentioned above. In other words, the substituents may be substituted again by others.

The compound of Formula 1 above may be a compound including an aromatic diamine group, represented by Formula 4 below.

[Formula 4]

In Formula 4, $R_5$ through $R_{12}$ may be the same or different, and each may be independently selected from the group consisting of a hydrogen atom; and a substituted or unsubstituted aryl group having 5~60 nuclear carbon atoms, a substituted or unsubstituted hetero aryl group having 5~60 nuclear carbon atoms, a substituted or unsubstituted aryl group having 5~60 nuclear carbon atoms, a substituted or unsubstituted $C_1$~$C_{60}$ alkyl group, a substituted or unsubstituted $C_1$~$C_{60}$ alkoxy group, a substituted or unsubstituted aryloxy group having 5~60 nuclear carbon atoms, a substituted or unsubstituted arylthio group having 5~60 nuclear carbon atoms, a substituted or unsubstituted alkoxycarbonyl group having 5~60 nuclear carbon atoms, an amino group substituted by a substituted or unsubstituted aryl group having 5~60 nuclear carbon atoms, a halogen atom, a cyano group, a nitro group, a hydroxyl group and a carboxyl group.

For example, each $Ar_6$ may be the same or different, and may be independently selected from the group consisting of a substituted or unsubstituted aryl group having 1~60 nuclear atoms, a substituted or unsubstituted heteroaryl group having 5~60 nuclear atoms, and a substituted or unsubstituted alkyl group, but the present invention is not limited thereto.

Meanwhile, X may be the same as $R_5$ through $R_{12}$, but the present invention is not limited thereto. Meanwhile, o of X may be 4-n, but the present invention is not limited thereto.

Herein, L and A, and n and m may be the same as described in Formulas 1 to 3.

The compound represented by Formula 4 above may include compounds represented by Formula 5 below. However, the present invention is not limited thereto.

[Formula 5]

3-A1

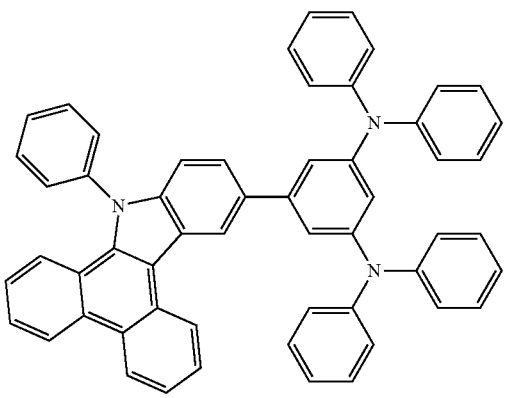

3-A2

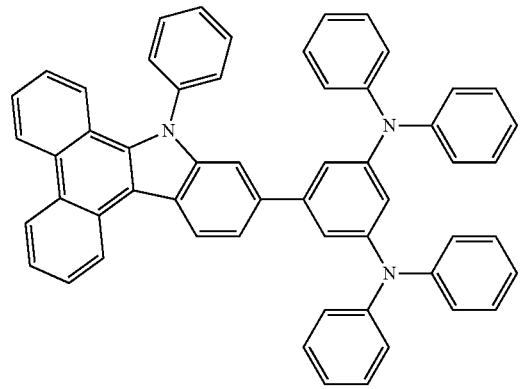

3-A3

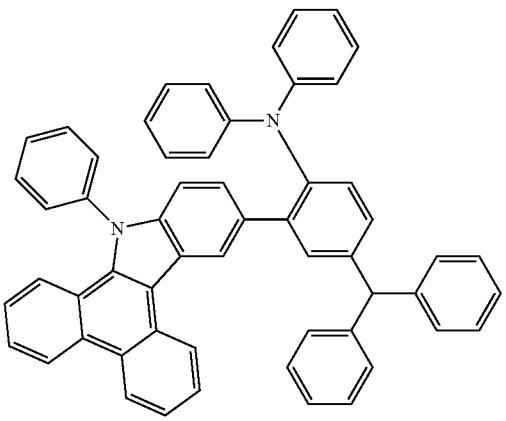

3-A4
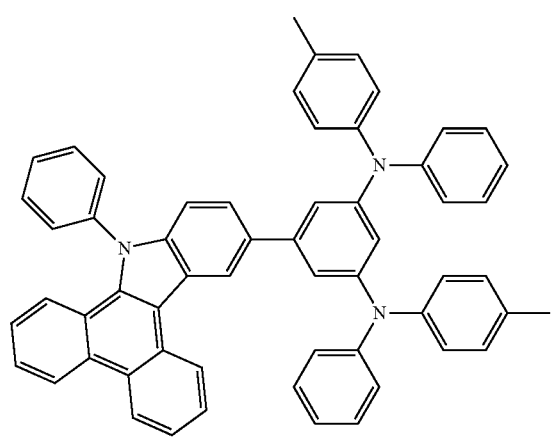
3-A7
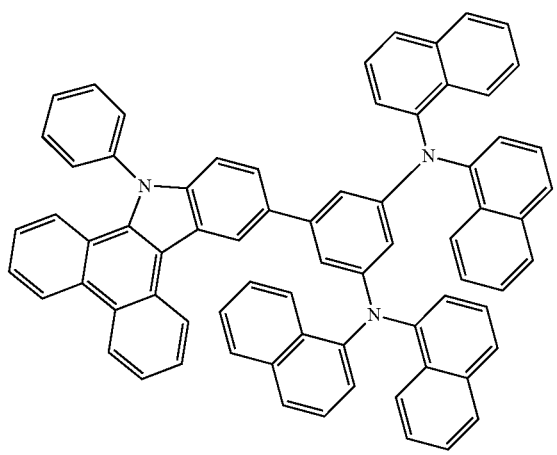
3-A5
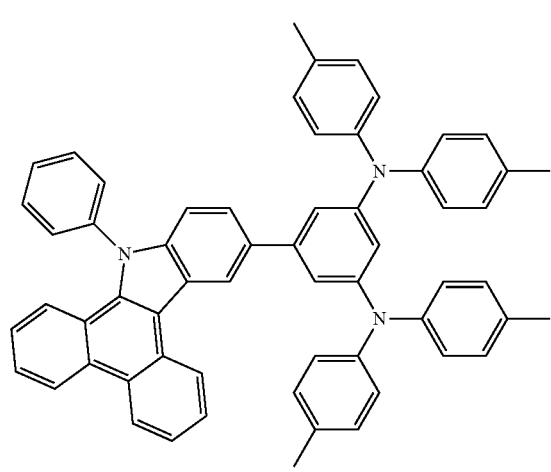
3-A8
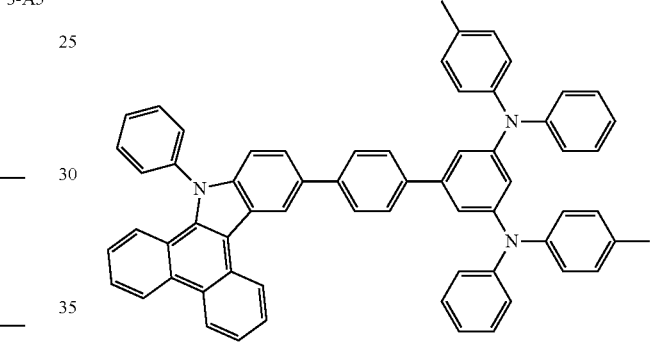
3-A6
3-A9
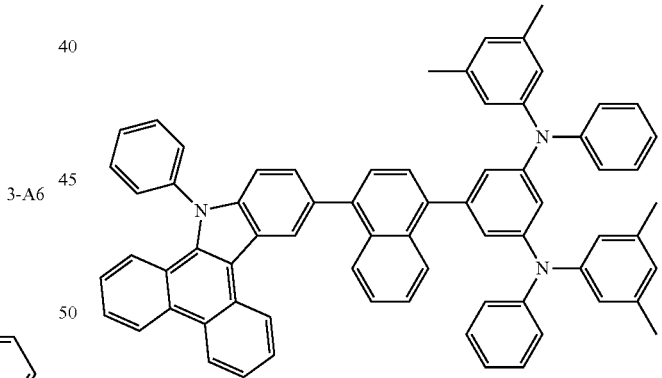
3-A10
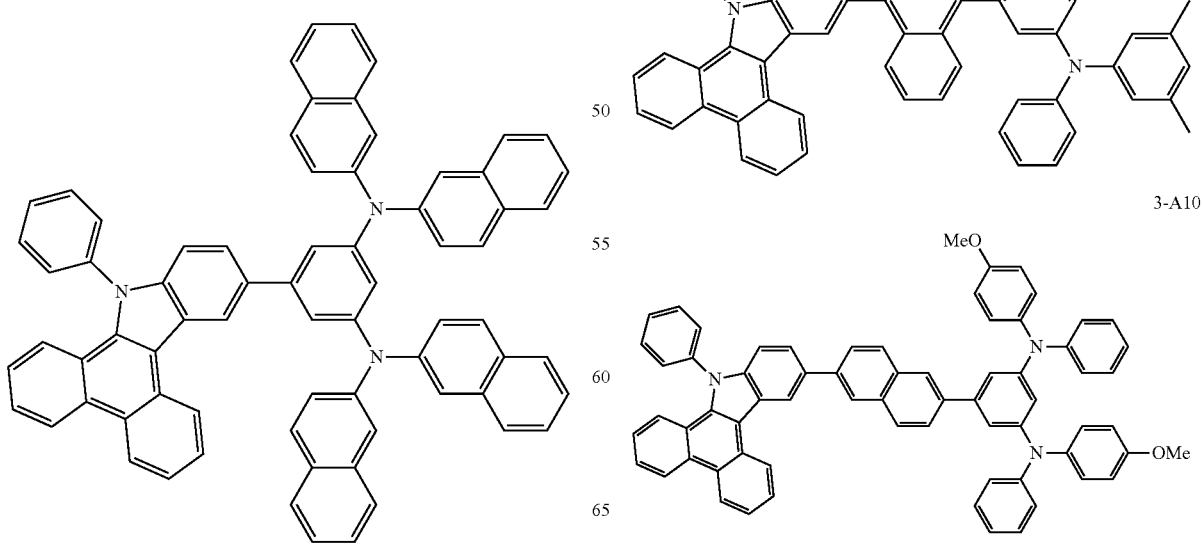

3-A11
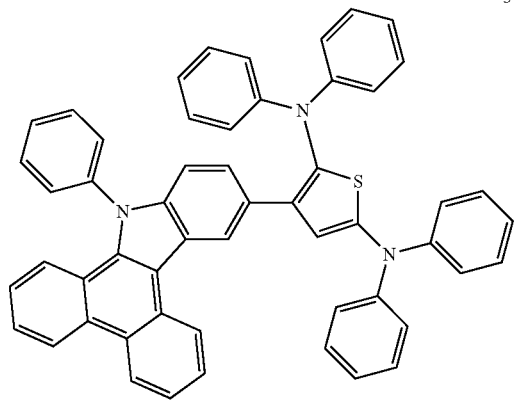
3-A12
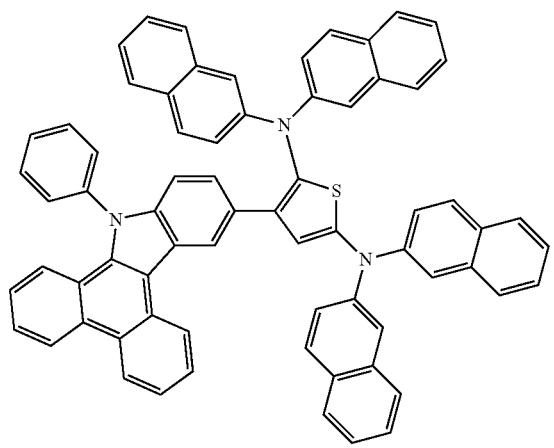
3-A13
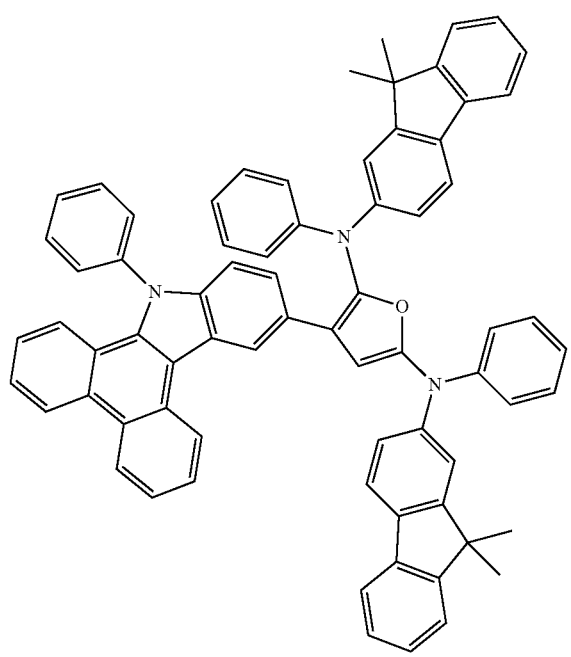
3-A14
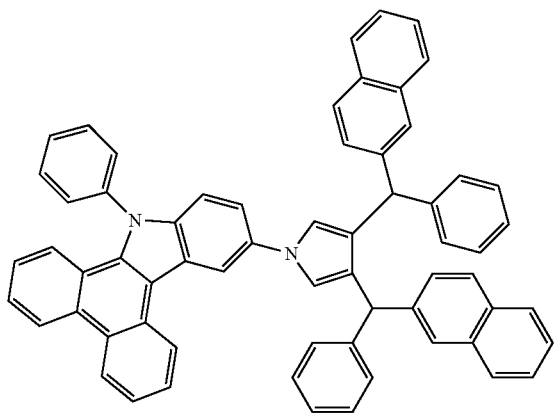
3-A15
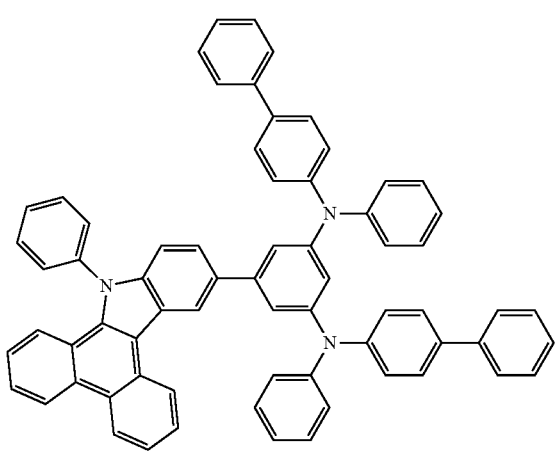
3-A16
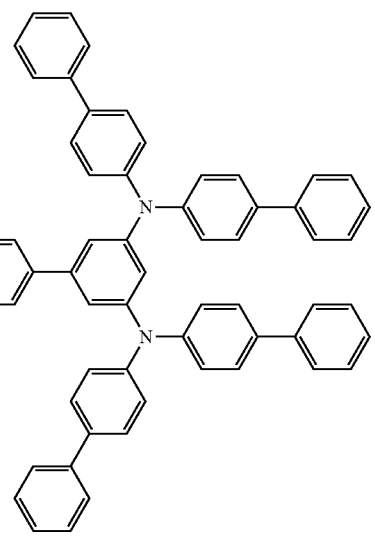

3-A17
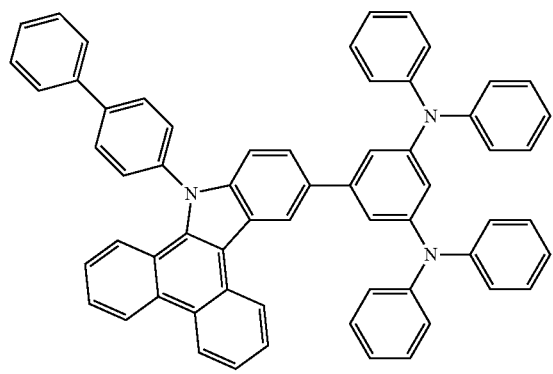
3-A18
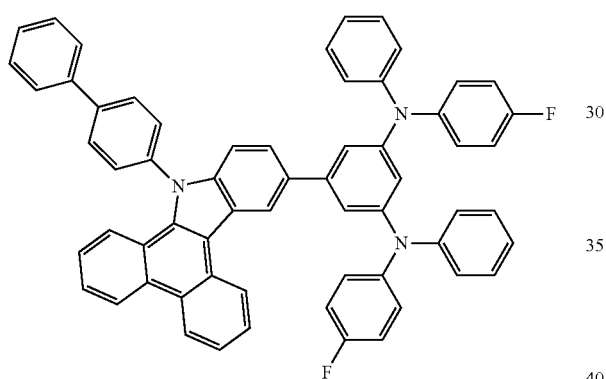
3-A19
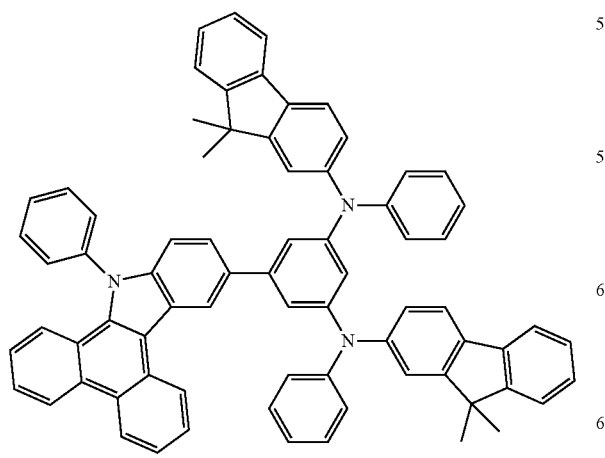
3-A20
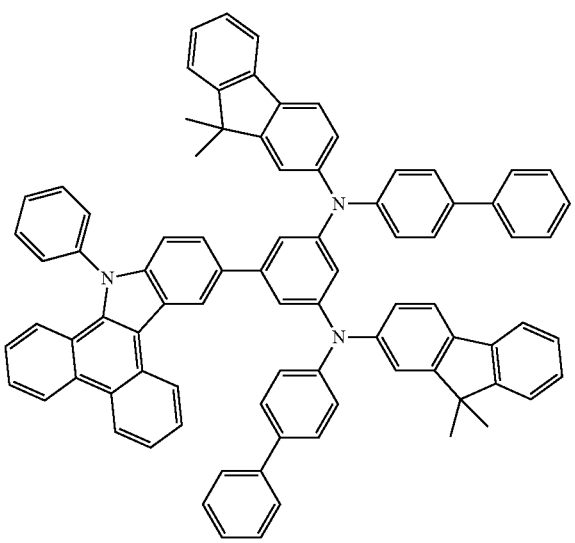
3-A21
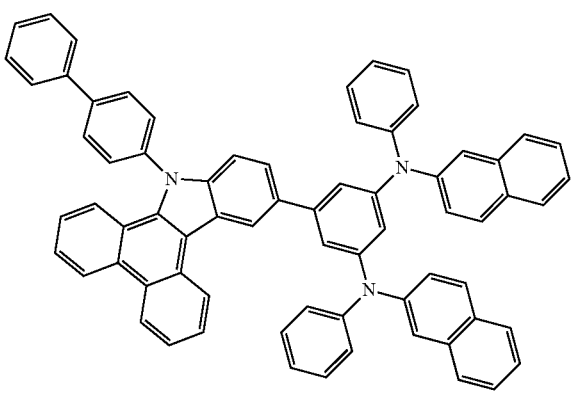
3-A22

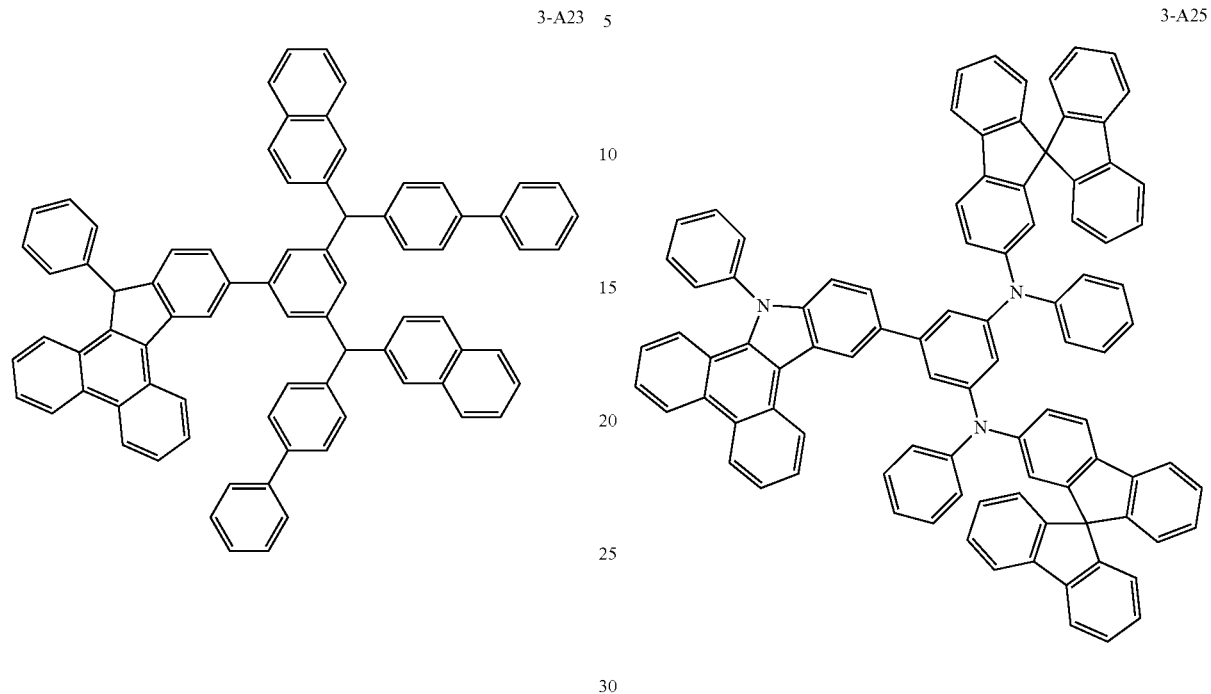

3-A27
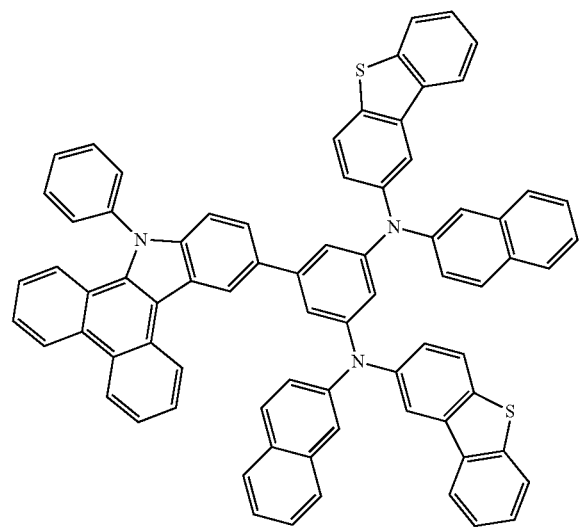
3-A28
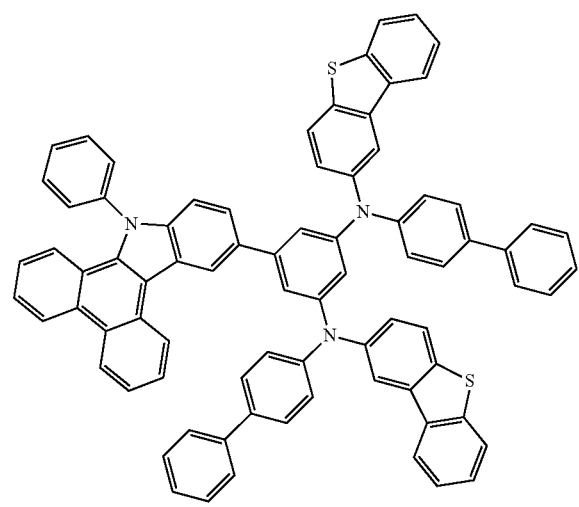
3-A29
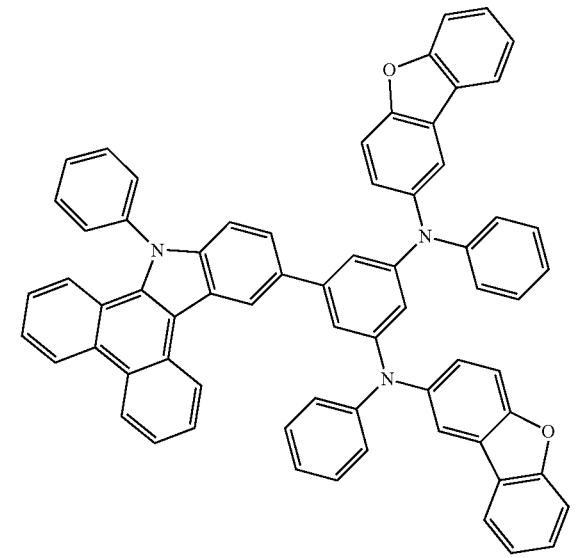
3-A30
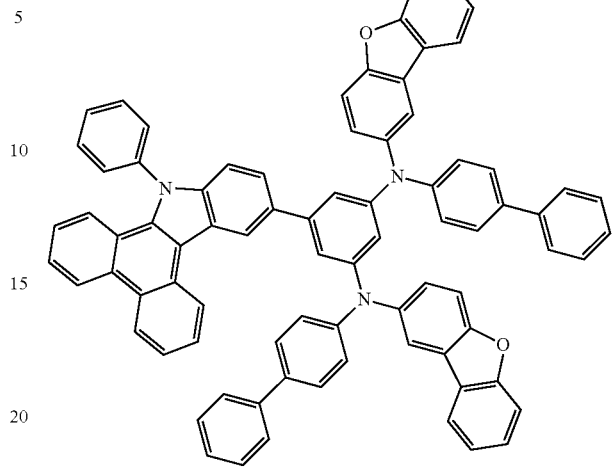
3-A31
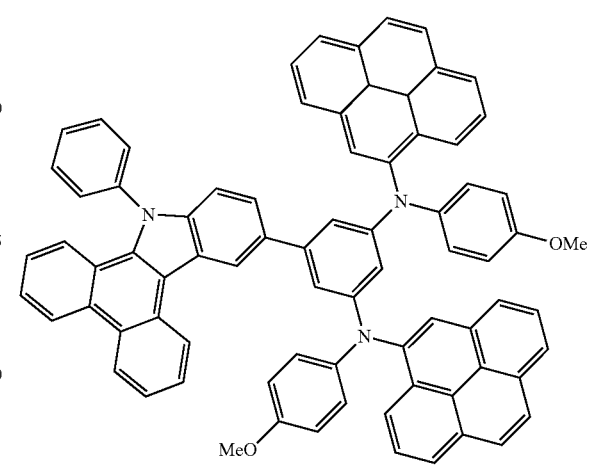
3-A32
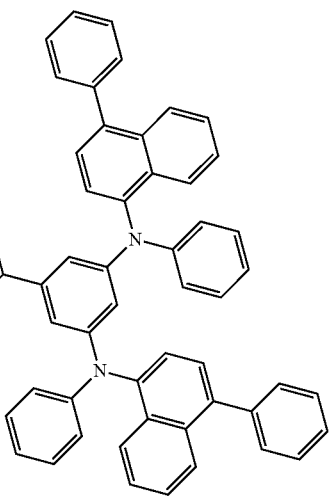

-continued

3-A33

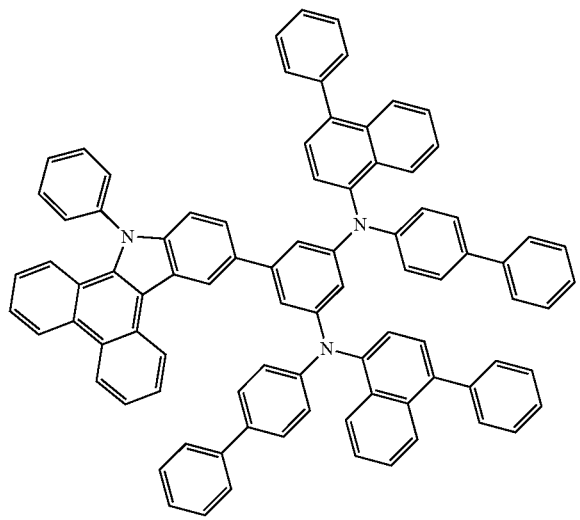

3-A34

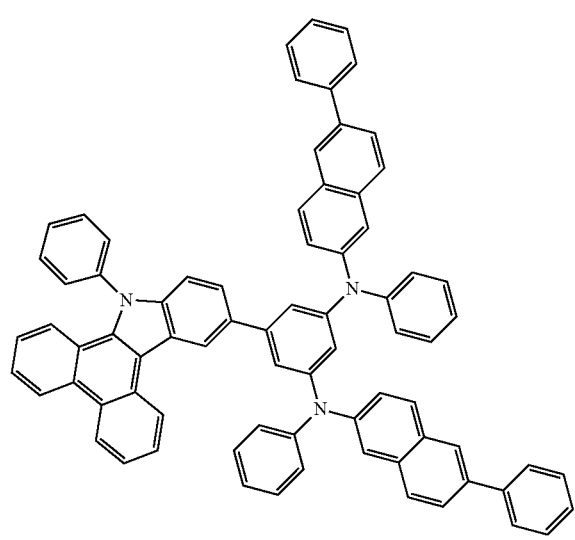

3-A35

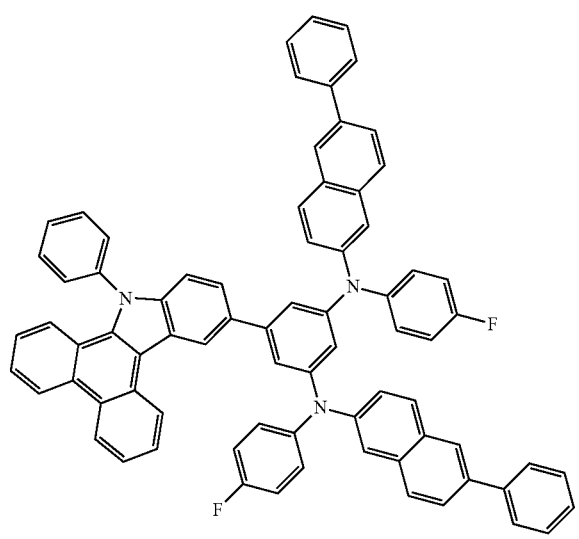

The compound represented by Formula 1 may be a compound including two or more diamine groups in an indoloacridine derivative, represented by Formula 6.

[Formula 6]

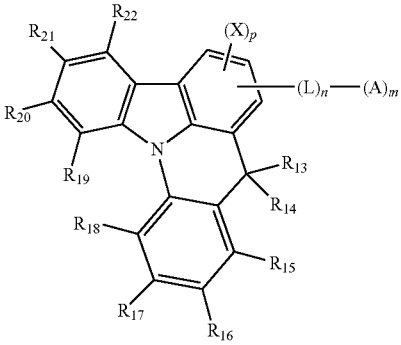

In Formula 6, $R_{13}$ through $R_{22}$ are the same or different, and each is independently selected from the group consisting of a hydrogen atom; and a substituted or unsubstituted aryl group having 5~60 nuclear carbon atoms, a substituted or unsubstituted heteroaryl group having 5~60 nuclear carbon atoms, a substituted or unsubstituted aryl group having 5~60 nuclear carbon atoms, a substituted or unsubstituted $C_1$~$C_{60}$ alkyl group, a substituted or unsubstituted $C_1$~$C_{60}$ alkoxy group, a substituted or unsubstituted aryloxy group having 5~60 nuclear carbon atoms, a substituted or unsubstituted arylthio group having 5~60 nuclear carbon atoms, a substituted or unsubstituted alkoxycarbonyl group having 5~60 nuclear carbon atoms, an amino group substituted by a substituted or unsubstituted aryl group having 5~60 nuclear carbon atoms, a halogen atom, a cyano group, a nitro group, a hydroxyl group and a carboxyl group.

Meanwhile, X may be the same as $R_{13}$ through $R_{22}$, but the present invention is not limited thereto. p of X may be 3-n, but the present invention is not limited thereto.

Meanwhile, L and A, and n and m may be the same as described in Formulas 1 to 3.

The compound represented by Formula 6 above may include compounds represented by Formula 7 below. However, the present invention is not limited thereto.

[Formula 7]

4-B1

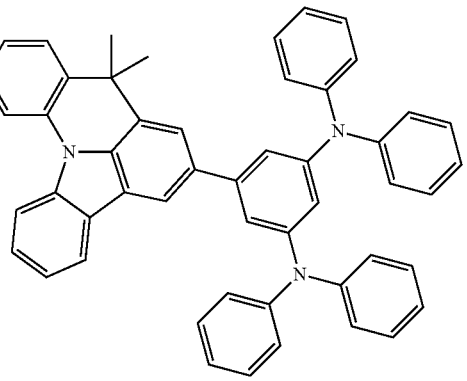

4-B2
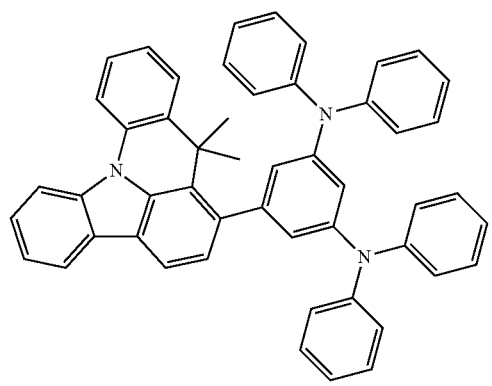
4-B5
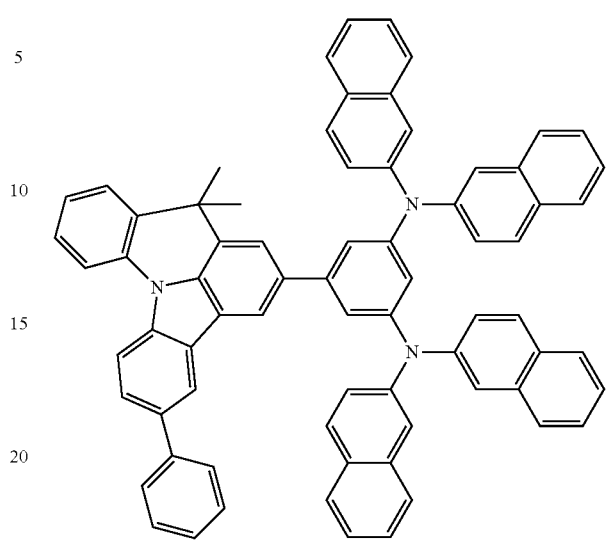
4-B3
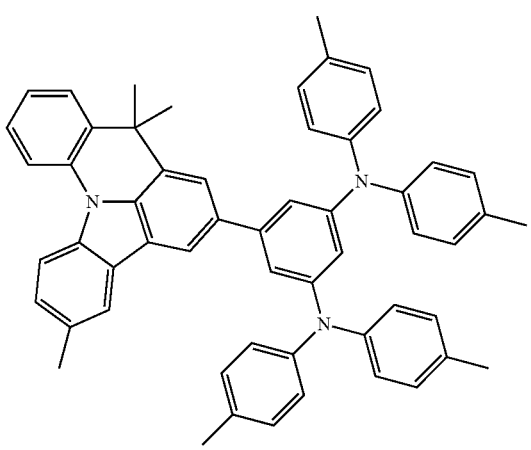
4-B6
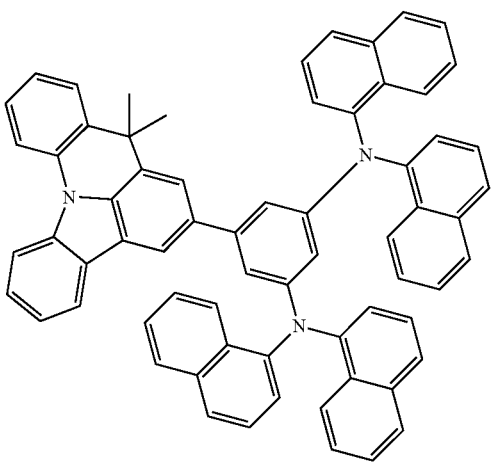
4-B4
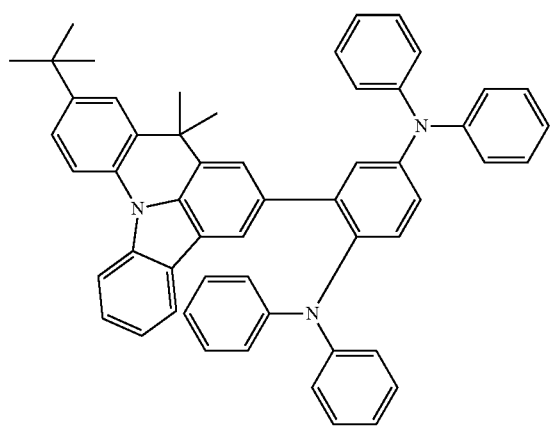
4-B7
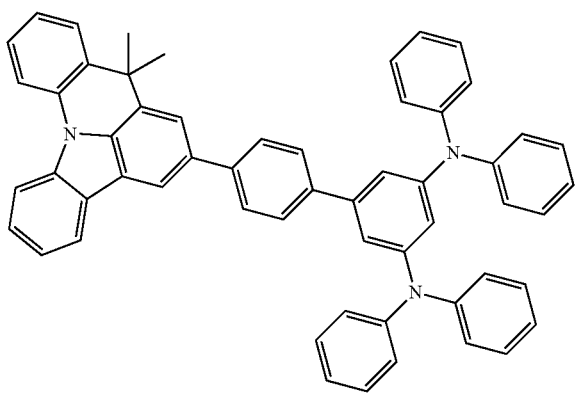

4-B8
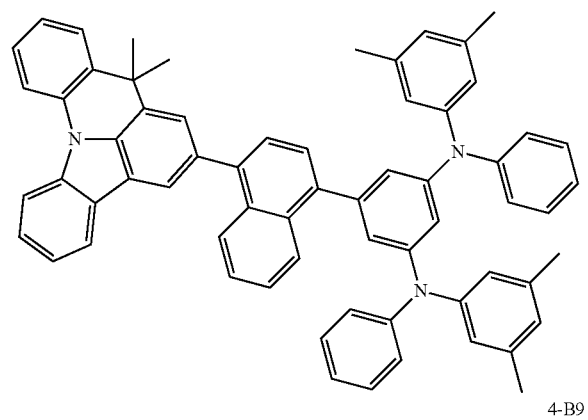
4-B9
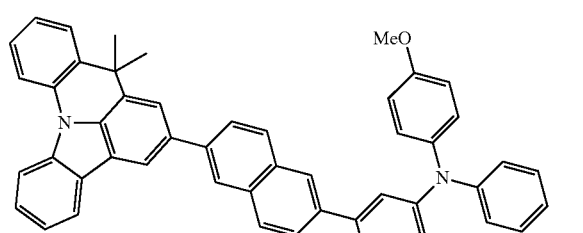
4-B10
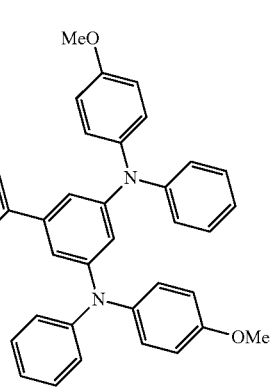
4-B11
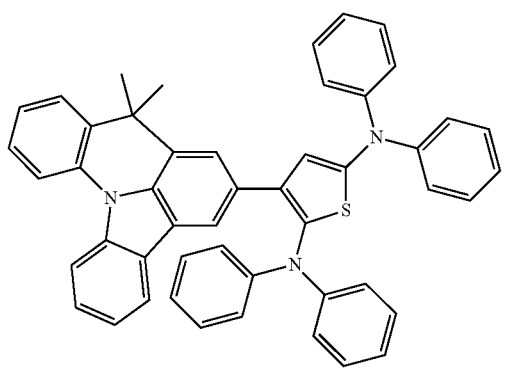
4-B12
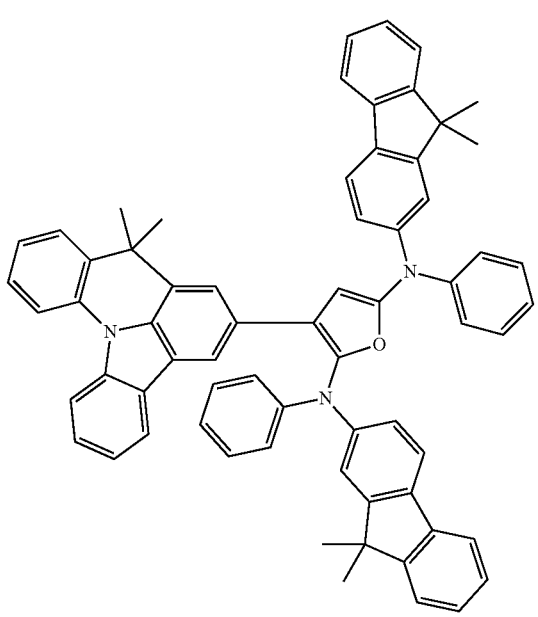
4-B13
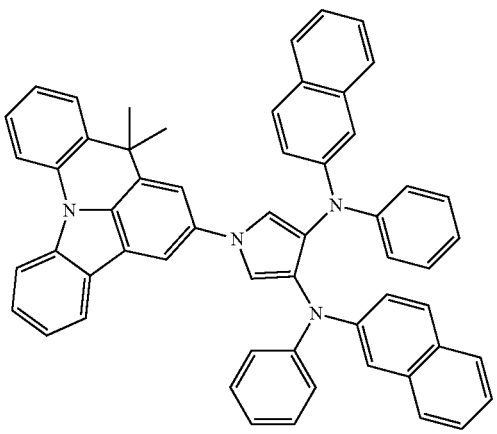
4-B14
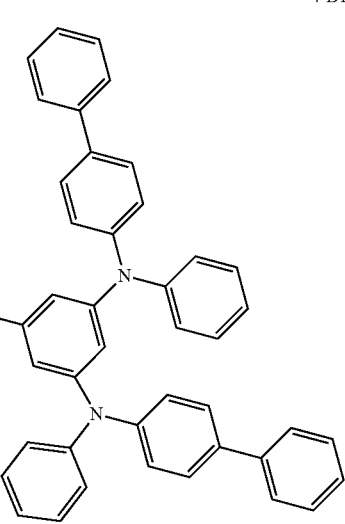

4-B15
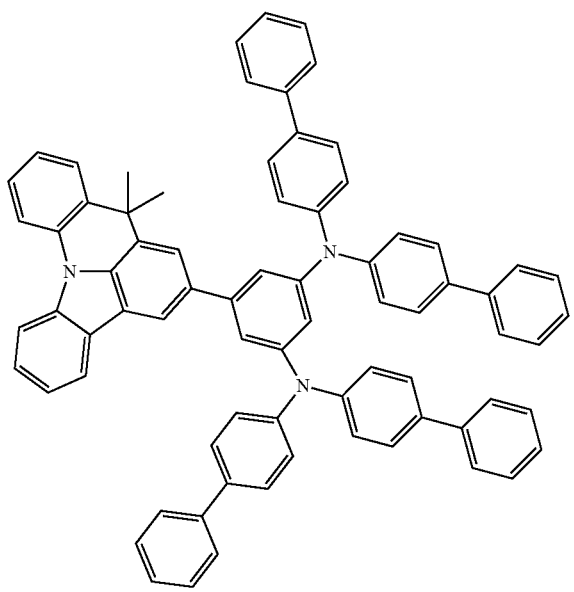
4-B16
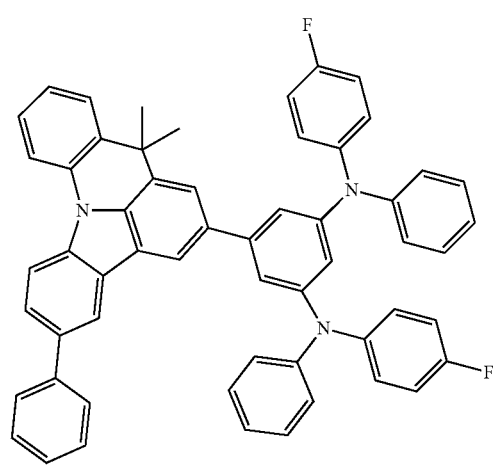
4-B17
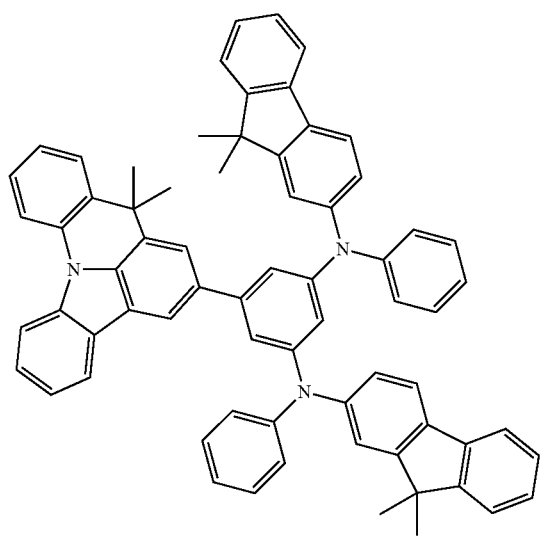
4-B18
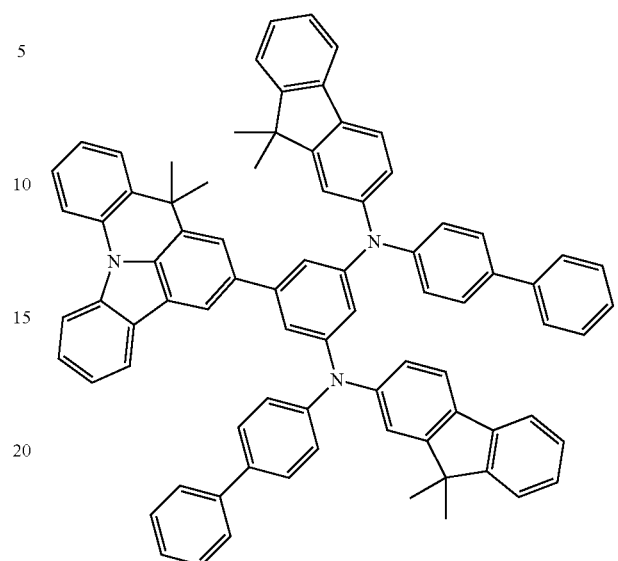
4-B19
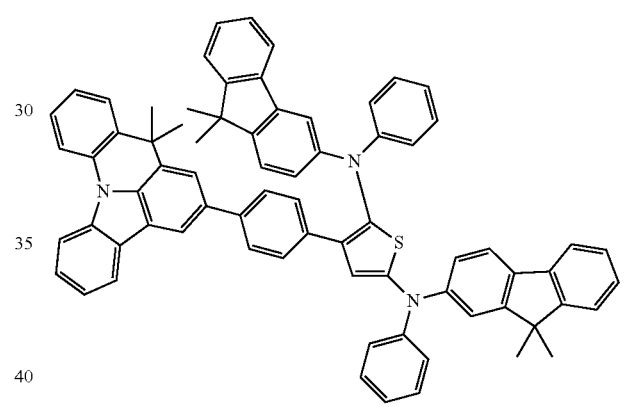
4-B20
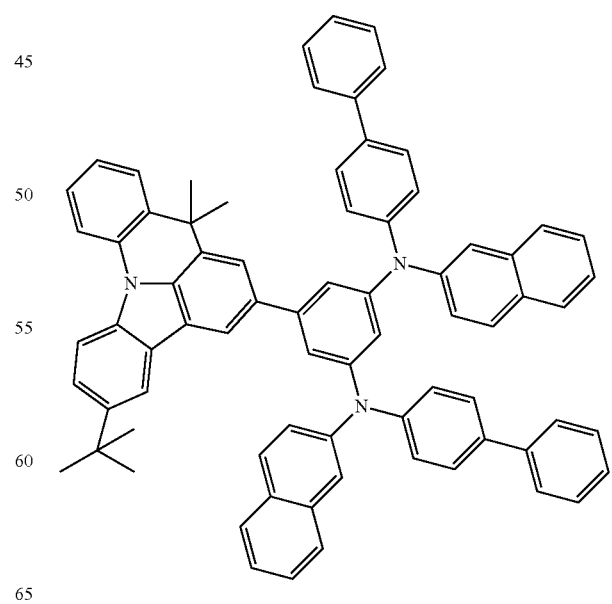

4-B21
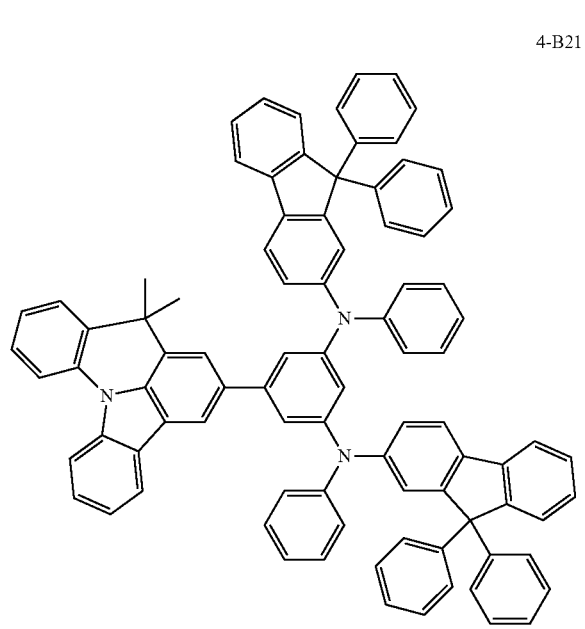
4-B23
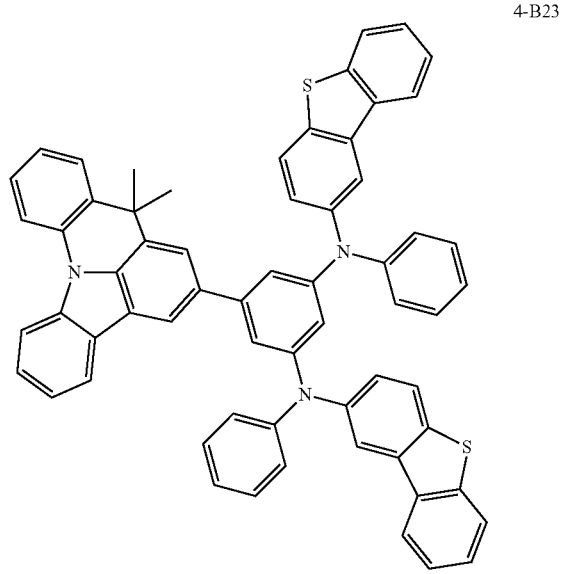
4-B22
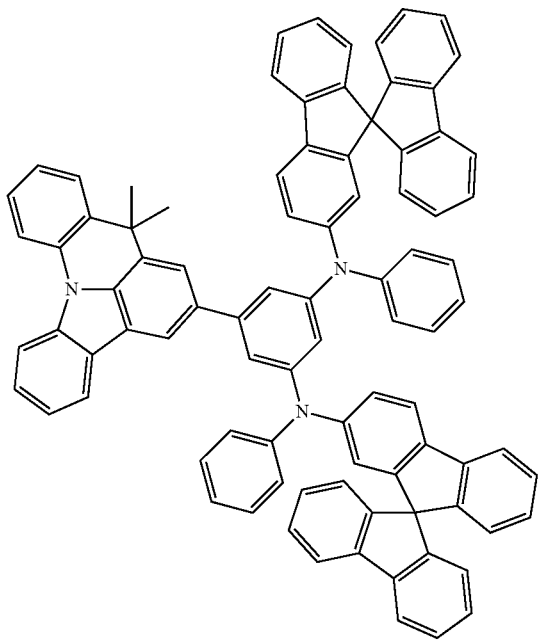
4-B24
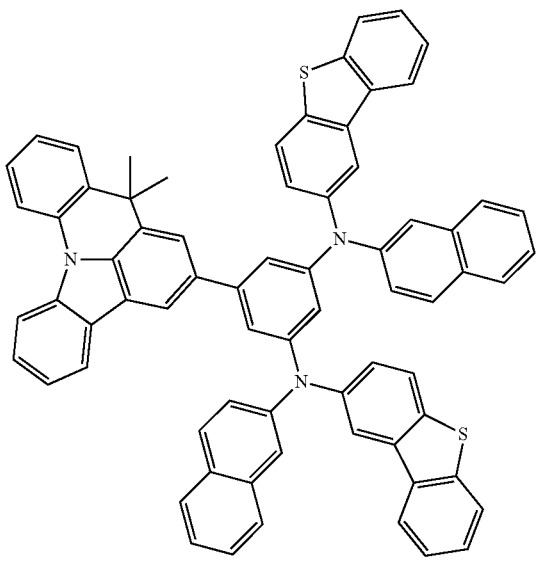

4-B25
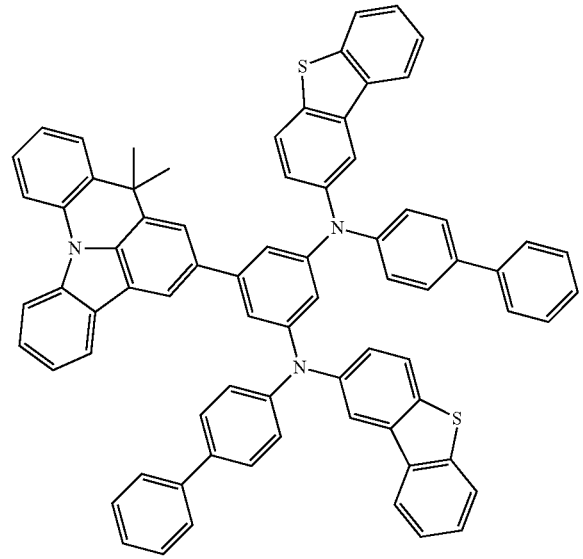
4-B27
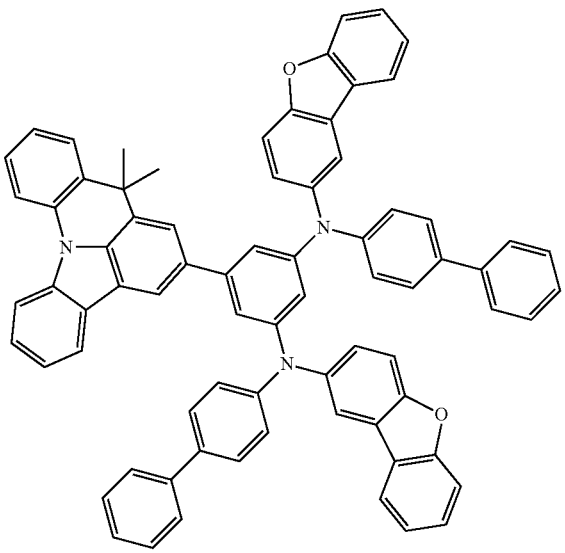
4-B28
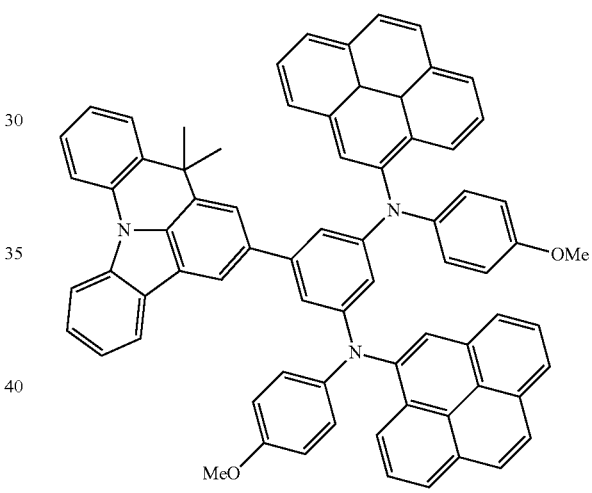
4-B26
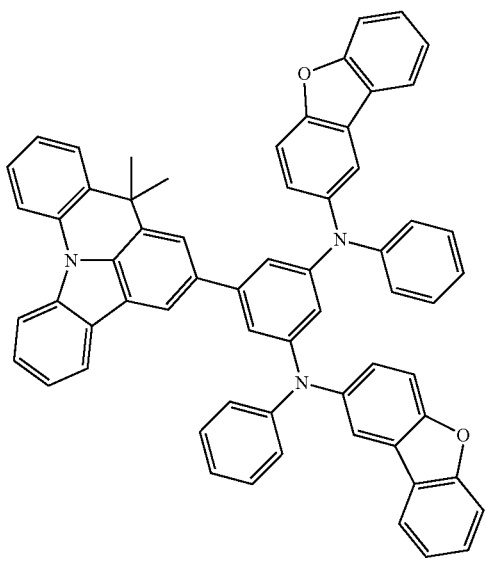
4-B29
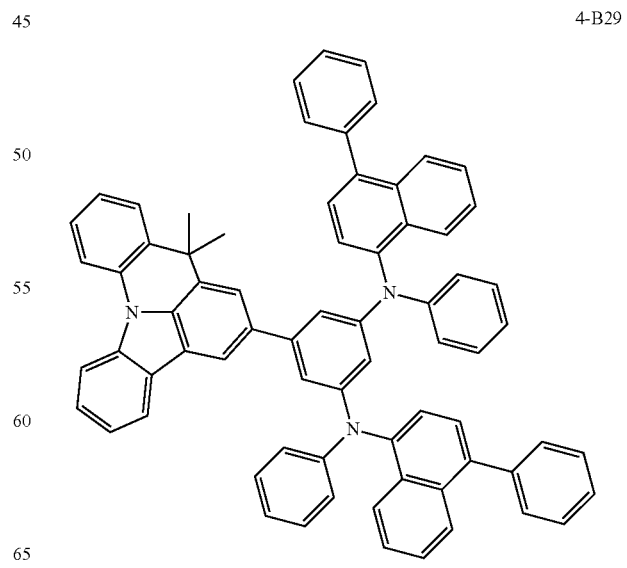

4-B30

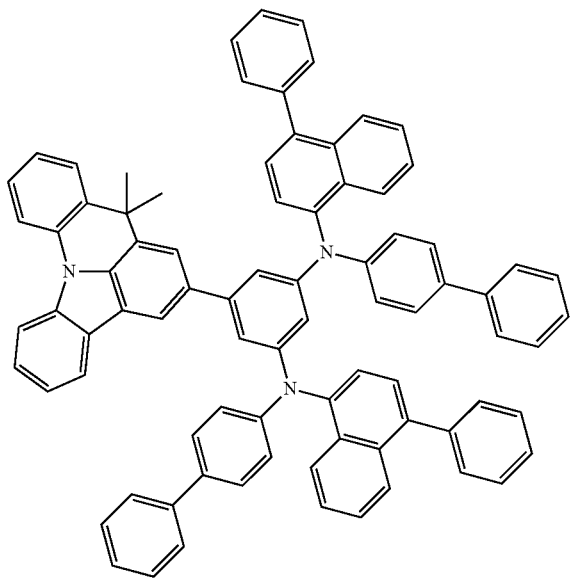

4-B31

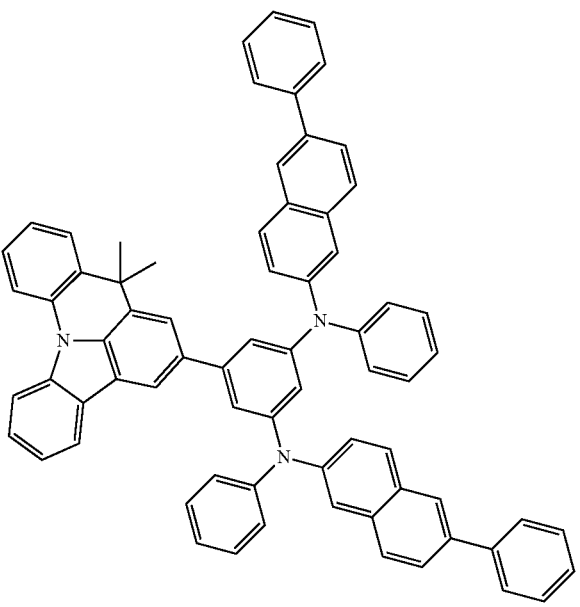

4-B32

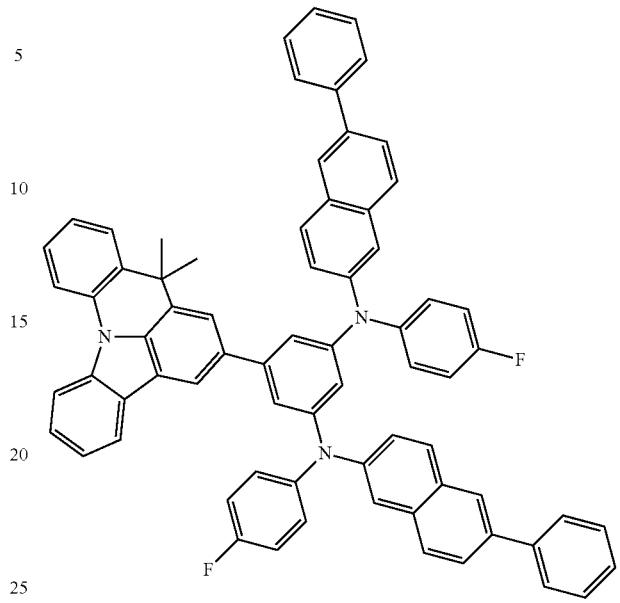

Also, the compound represented by Formula 1 may be a compound including a diamine group, represented by Formula 8 below.

[Formula 8]

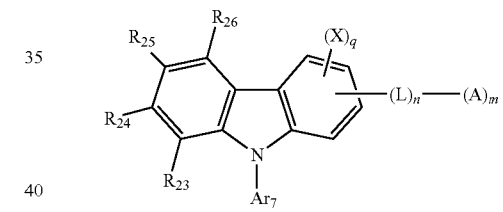

In Formula 8, $R_{23}$ through $R_{26}$ are the same or different, and each is independently selected from the group consisting of a hydrogen atom; and a substituted or unsubstituted aryl group having 5~60 nuclear carbon atoms, a substituted or unsubstituted heteroaryl group having 5~60 nuclear carbon atoms, a substituted or unsubstituted aryl group having 5~60 nuclear carbon atoms, a substituted or unsubstituted $C_1$~$C_{60}$ alkyl group, a substituted or unsubstituted $C_1$~$C_{60}$ alkoxy group, a substituted or unsubstituted aryloxy group having 5~60 nuclear carbon atoms, a substituted or unsubstituted arylthio group having 5~60 nuclear carbon atoms, a substituted or unsubstituted alkoxycarbonyl group having 5~60 nuclear carbon atoms, an amino group substituted by a substituted or unsubstituted aryl group having 5~60 nuclear carbon atoms, a halogen atom, a cyano group, a nitro group, a hydroxyl group and a carboxyl group.

Meanwhile, X may be the same as $R_{13}$ through $R_{22}$, but the present invention is not limited thereto. Also, p of X may be 4-n, but the present invention is not limited thereto.

Meanwhile, L and A, n and m may be the same as described in Formulas 1 to 3.

The compound represented by Formula 8 above may include compounds represented by Formula 9 below. However, the present invention is not limited thereto.

[Formula 9]
5-C1
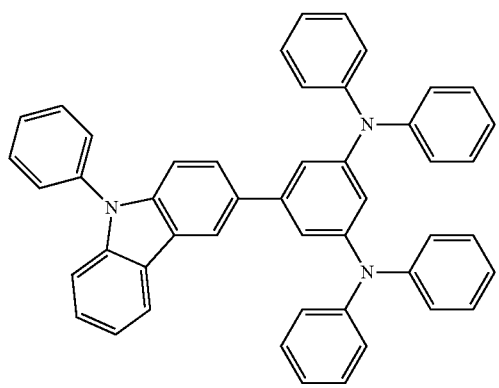
5-C2
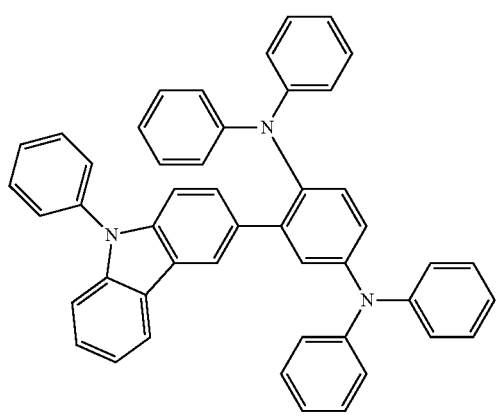
5-C3
5-C4
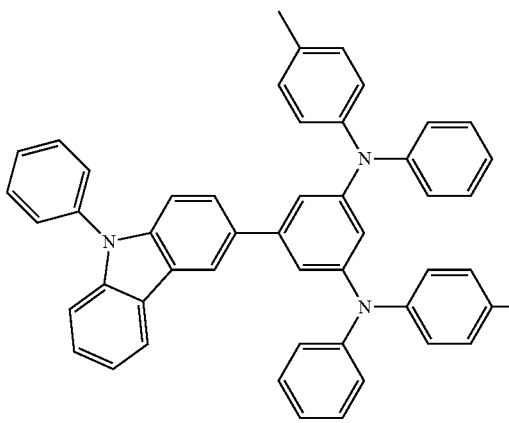
5-C5
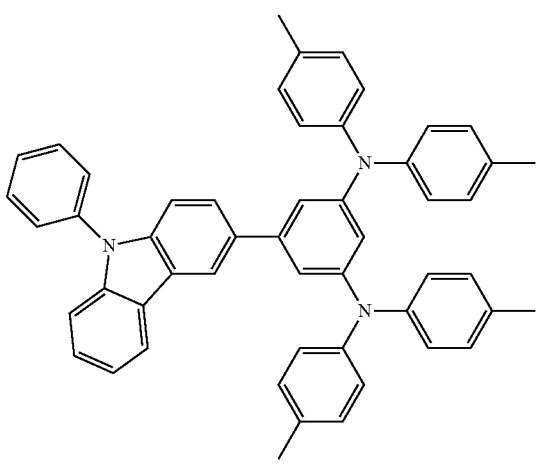
5-C6
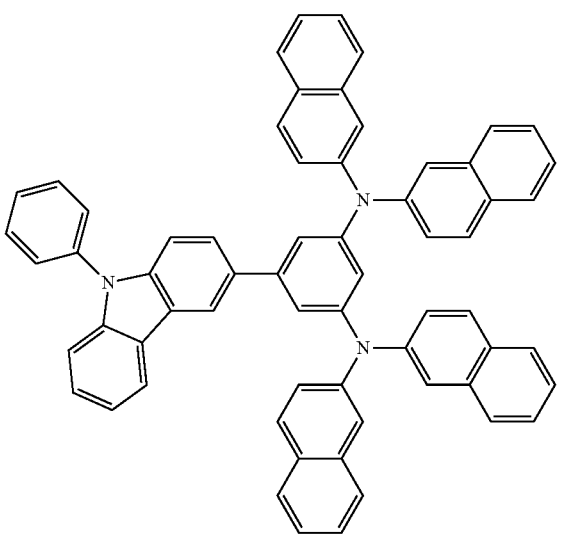

5-C7
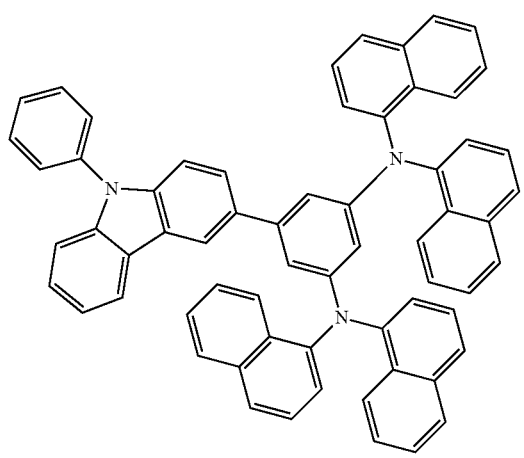
5-C8
5-C9
5-C10
5-C11
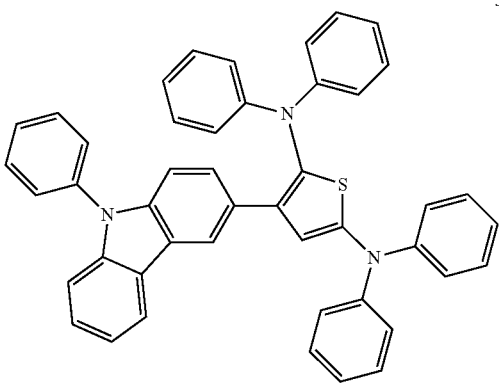
5-C12
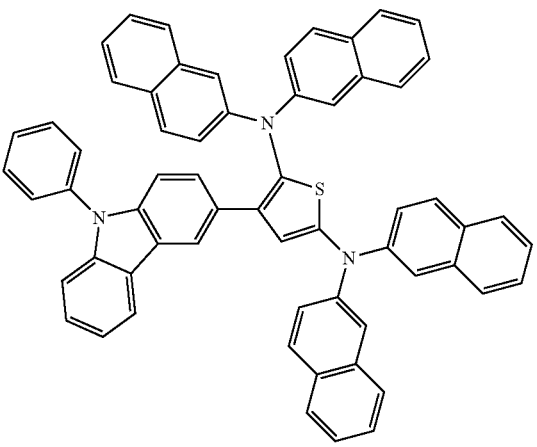
5-C13
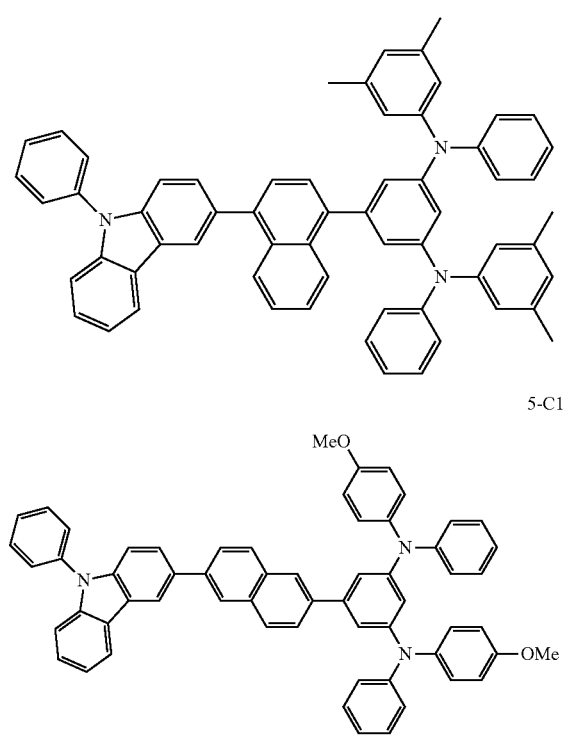

5-C14
5-C17
5-C15
5-C18
5-C16
5-C19
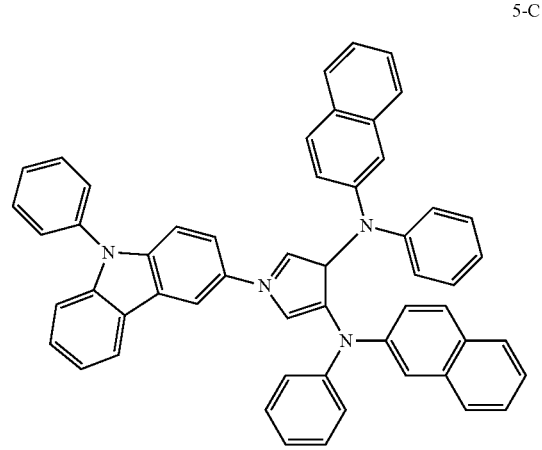
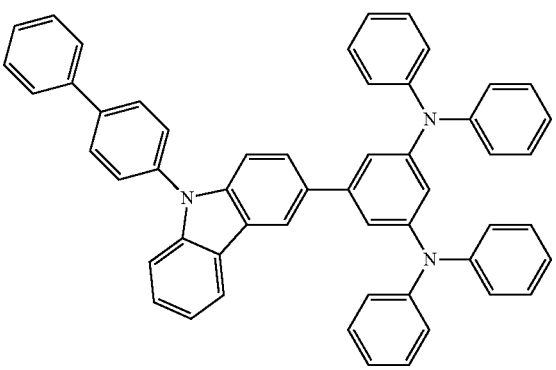
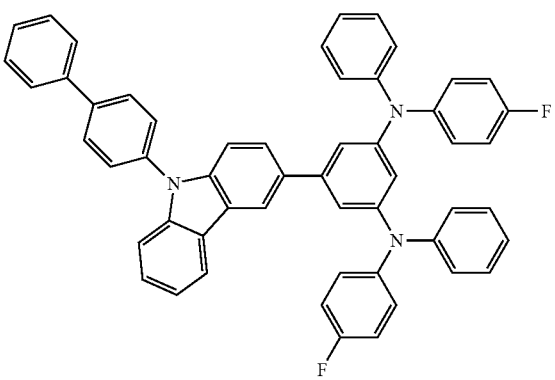
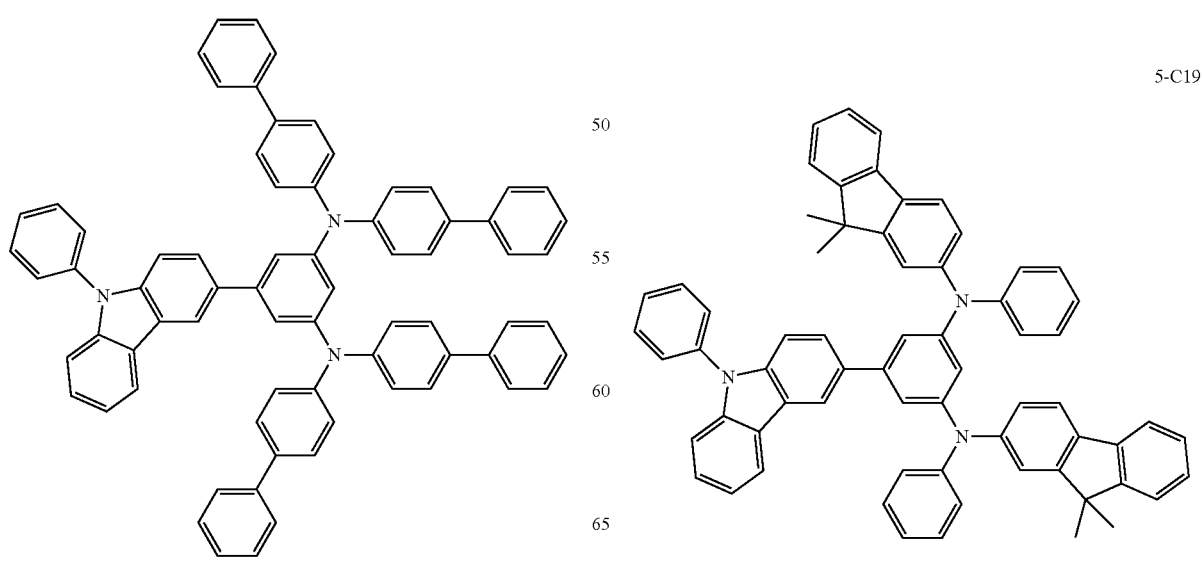

-continued
5-C20
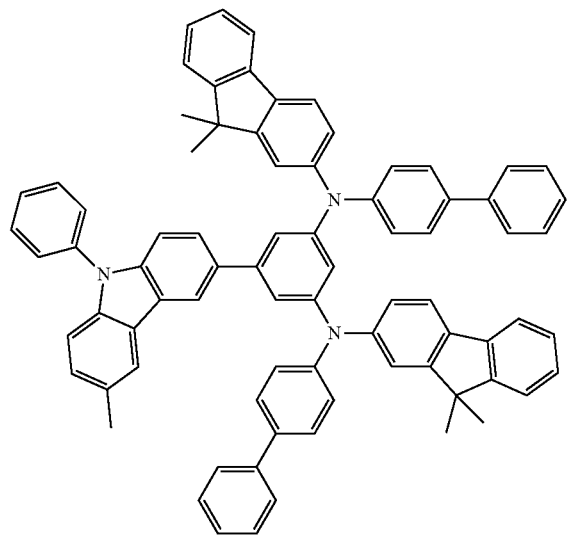
5-C21
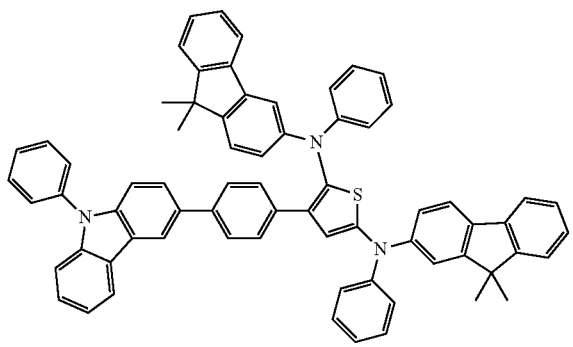
5-C22
5-C23
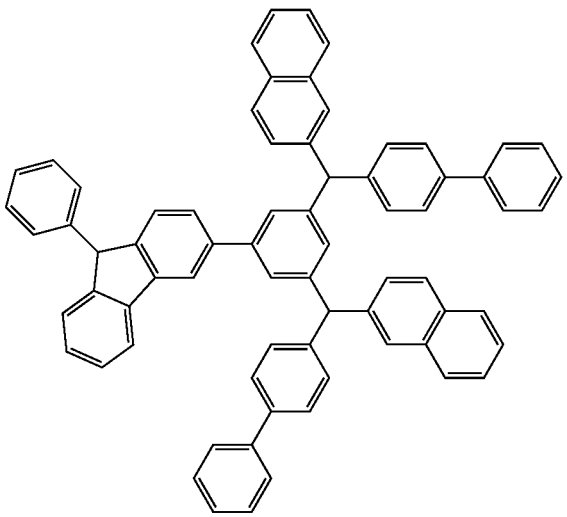
5-C24
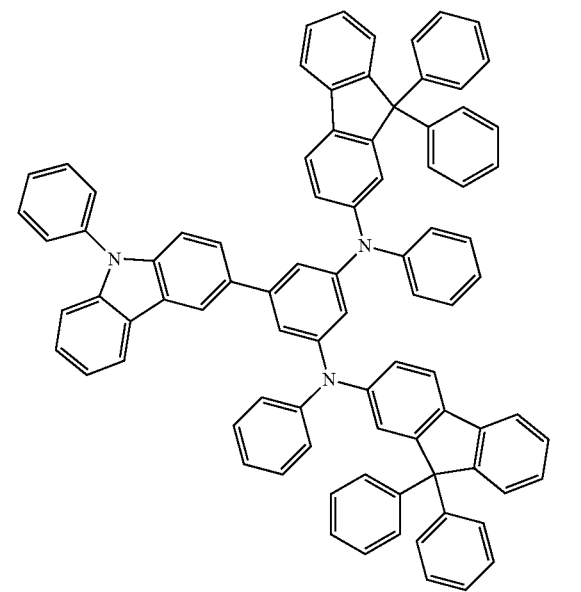

5-C25
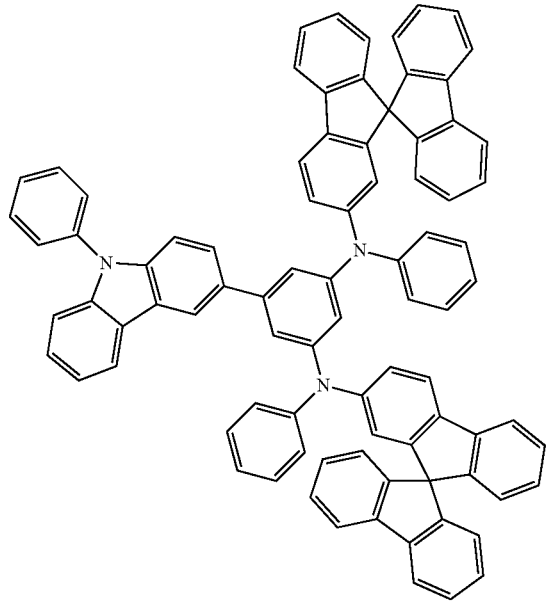
5-C26
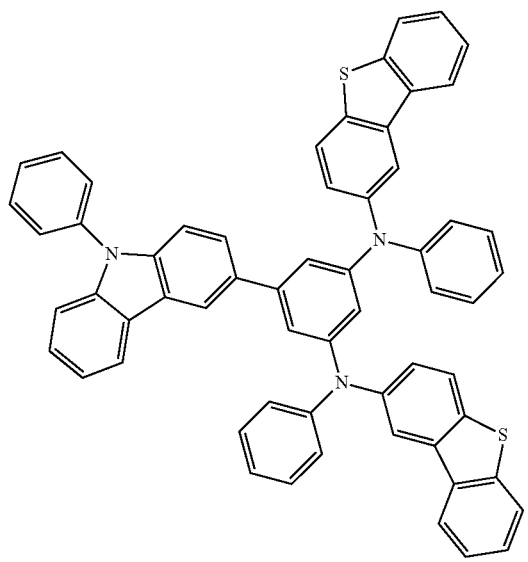
5-C27
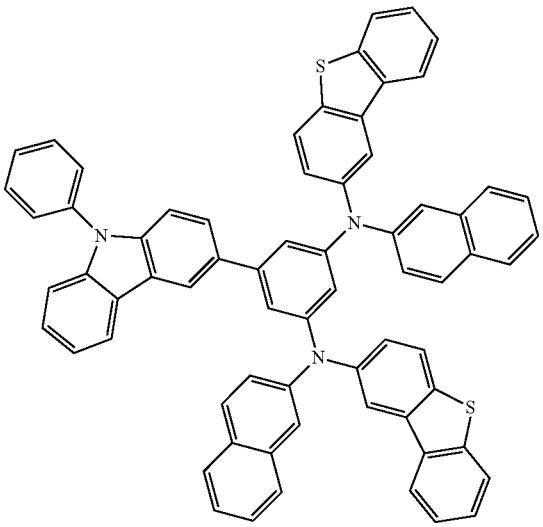
5-C28
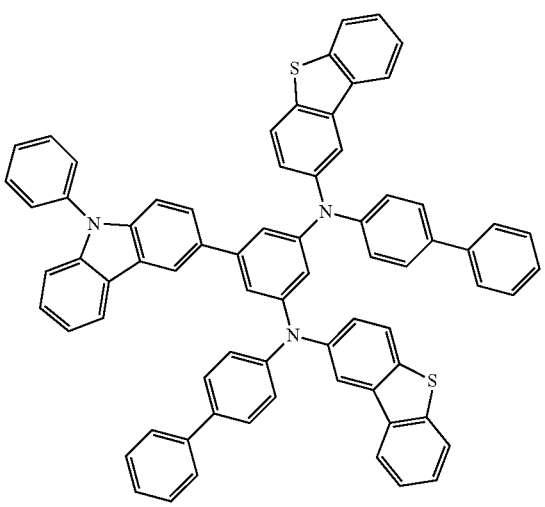
5-C29
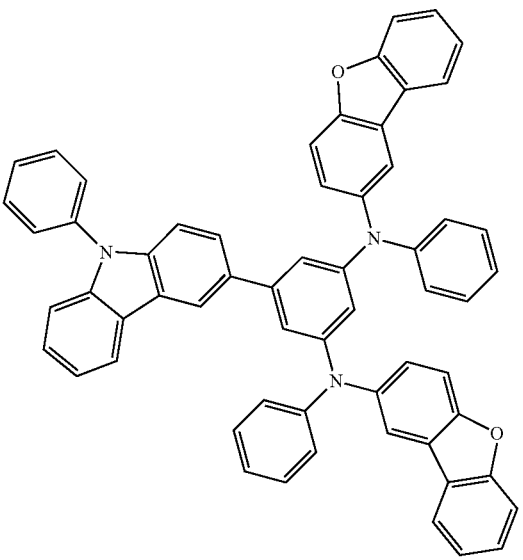

5-C30
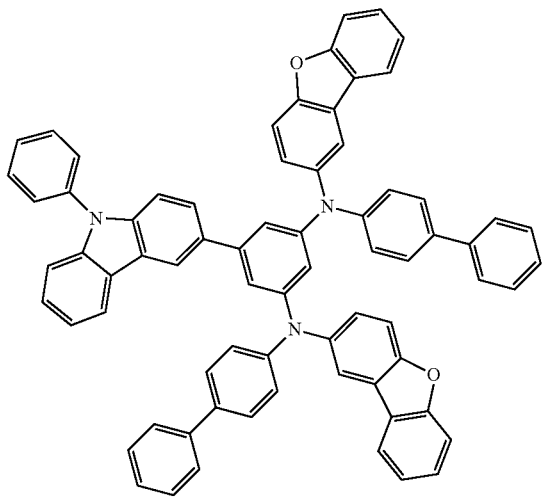
5-C31
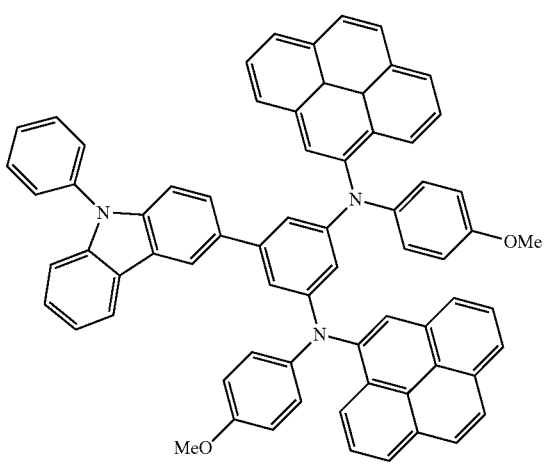
5-C32
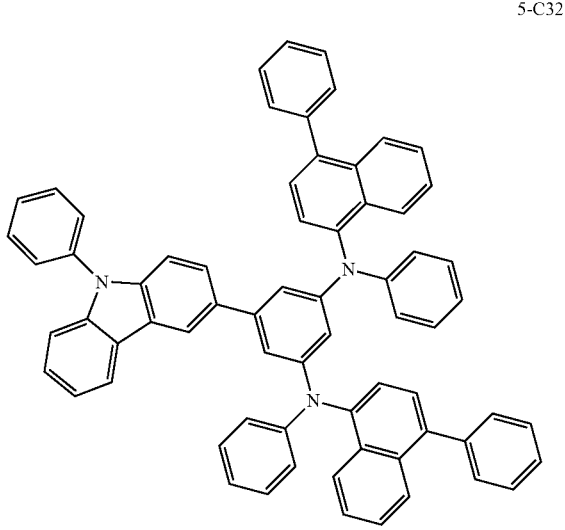
5-C33
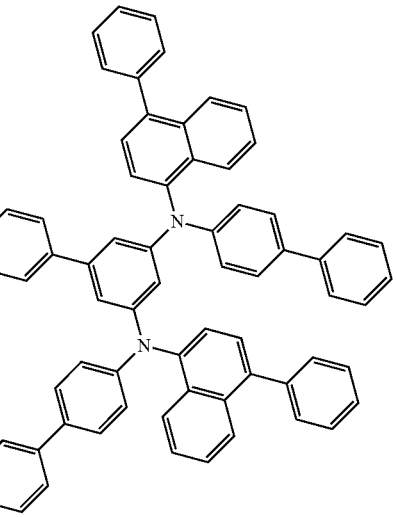
5-C34
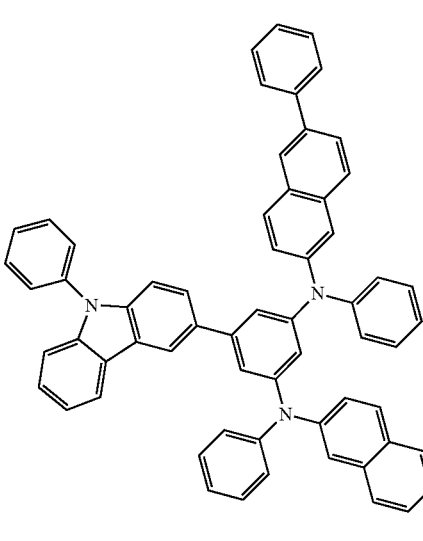
5-C35
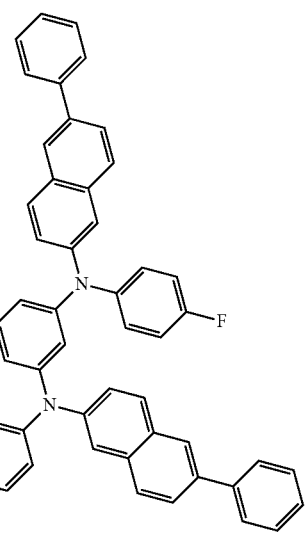

There are various organic electronic devices employing the compounds, as described with reference to Formulas 1 to 9, as organic material layers, wherein the compounds include a substituted or unsubstituted carbazole derivative in which two tertiary amines are substituted. The organic electronic devices in which the compounds including a substituted or unsubstituted carbazole derivative in which two tertiary amines are substituted, as described with reference to Formulas 1 to 9, can be employed, may include, for example, an organic light emitting diode (OLED), an organic solar cell, an organic photo conductor (OPC) drum, an organic transistor (organic TFT), and the like.

As one example of the organic electronic devices in which the compounds including a substituted or unsubstituted carbazole derivative in which two tertiary amines are substituted, as described with reference to Formulas 1 to 9, can be used, an organic light-emitting diode (OLED) will be described below, but the present invention is not limited thereto. The above described compounds may be applied to various organic electronic devices.

In another embodiment of the present invention, there is provided an organic electronic device (organic electro-luminescence element) including a first electrode, a second electrode, and an organic material layer interposed between these electrodes, in which at least one of organic material layers includes the compounds represented by Formulas 1 to 9.

Figure 2:
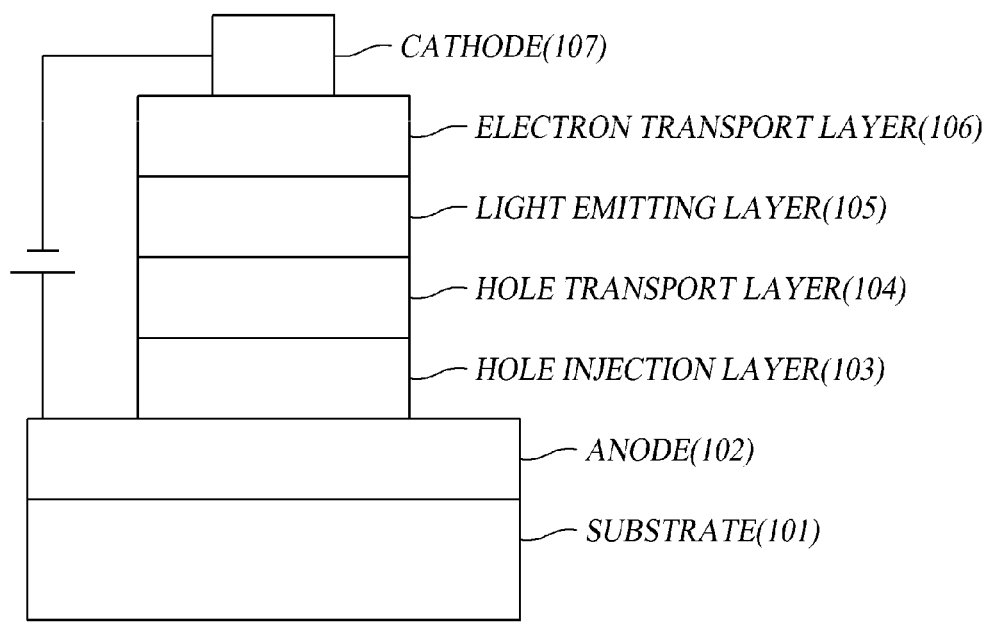
Figure 3:
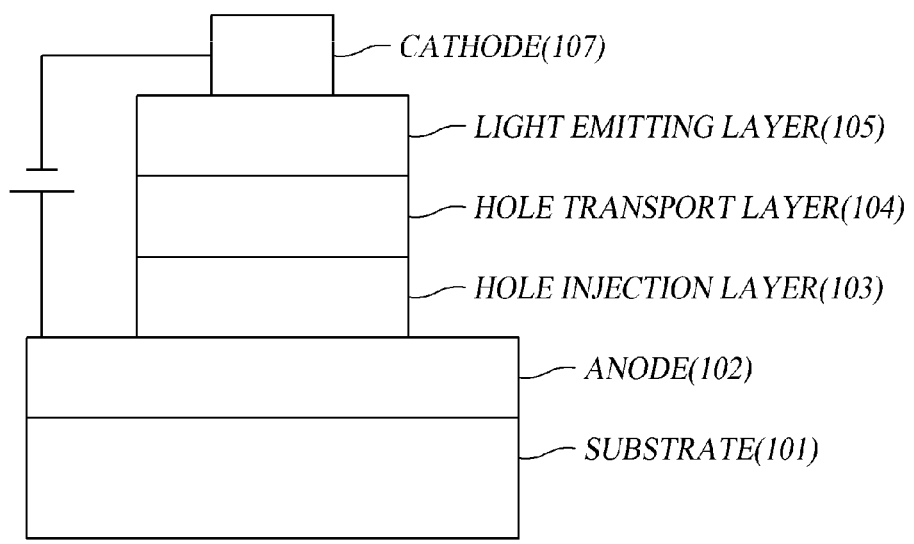
Figure 4:
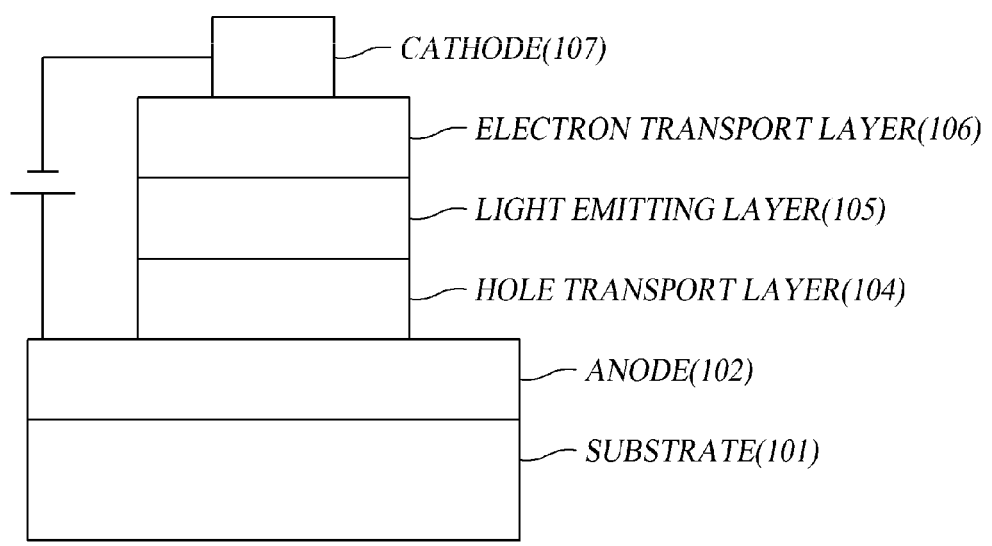
Figure 5:
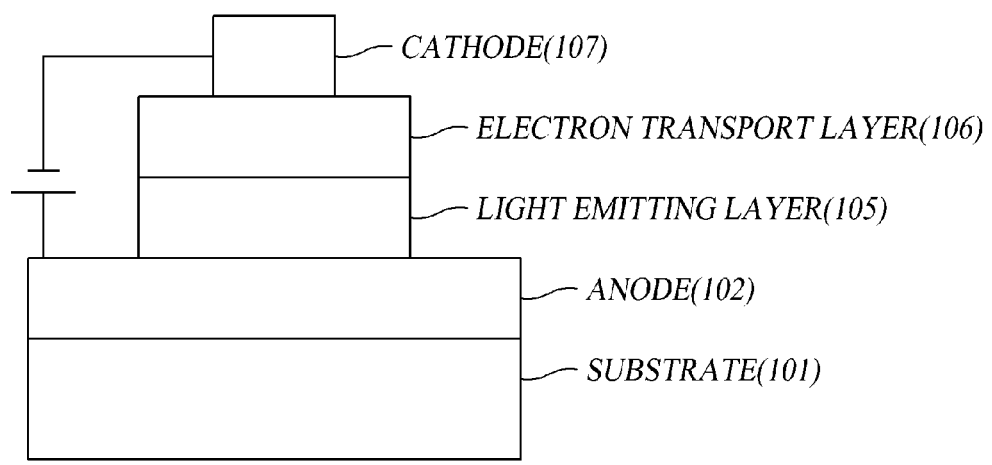
Figure 6:
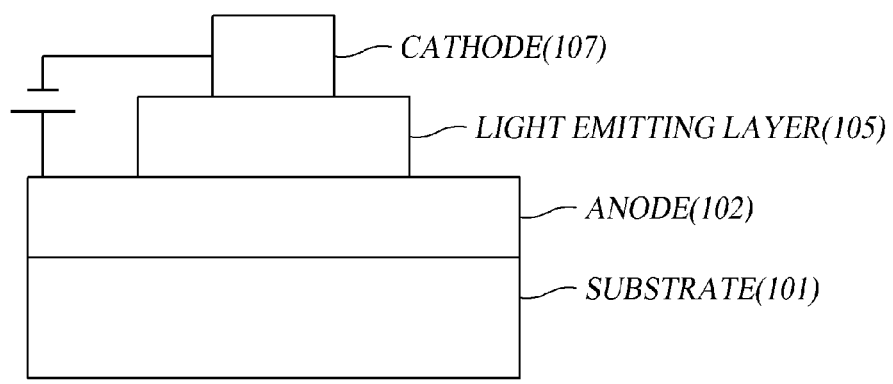

FIGS. 1 to 6 show examples of an organic electroluminescence element which can employ a compound according to the present invention.

The organic electro-luminescence element according to another embodiment of the present invention may be manufactured by means of a manufacturing method and materials conventionally known in the art in such a manner that it can have a conventionally known structure, except that at least one of organic material layers including a hole injection layer, a hole transport layer, an emitting layer, an electron transport layer, and an electron injection layer is formed in such a manner that it can include the compounds represented by Formulas 1 to 9.

The structures of the organic electro-luminescence element according to another embodiment of the present invention are shown in FIGS. 1 to 6, but the present invention is not limited to the structures. Herein, the reference numeral 101 indicates a substrate, 102 indicates an anode, 103 indicates a hole injection layer (HIL), 104 indicates a hole transport layer (HTL), 105 indicates an emitting layer (EML), 106 indicates an electron injection layer (EIL), 107 indicates an electron transport layer (ETL), and 108 indicates a cathode. Although not shown, such an organic electroluminescence element may further include a hole blocking layer (HBL) for blocking movement of holes, an electron blocking layer (EBL) for blocking movement of electrons, a light emission assisting layer for supporting or assisting light emission, and a protective layer. The protective layer may be formed in such a manner that it, as an uppermost layer, can protect an organic material layer or a cathode.

Herein, the compound including a substituted or unsubstituted carbazole derivative in which two tertiary amines are substituted, as described with reference to Formulas 1 to 9, may be included in at least one of organic material layers including a hole injection layer, a hole transport layer, an emitting layer, and an electron transport layer. Specifically, the compound including a substituted or unsubstituted carbazole derivative in which two tertiary amines are substituted, as described with reference to Formulas 1 to 9, may be substituted for at least one of a hole injection layer, a hole transport layer, an emitting layer, an electron transport layer, an electron injection layer, a hole blocking layer, an electron blocking layer, an light emission assisting layer, and a protective layer, or may be used in combination with these layers so as to form a multi-layered structure. Of course, the compound may be used for not only one layer of the organic material layers but also two or more layers.

Especially, the compound including a substituted or unsubstituted carbazole derivative in which two tertiary amines are substituted, as described with reference to Formulas 1 to 9, may be used as a material for hole injection, hole transport, electron injection, electron transport, light emission, and passivation (capping). Especially, it may be used alone as a light emitting material, a host or a dopant in host/dopant, and may be used as a hole injection layer or a hole transport layer.

For example, in manufacturing of the organic electro-luminescence element according to another embodiment of the present invention, a metal, a conductive metal oxide, or an alloy thereof may be deposited on a substrate by means of PVD (physical vapor deposition) such as sputtering or e-beam evaporation so as to form an anode, and then an organic material layer including a hole injection layer, a hole transport layer, an emitting layer, an electron transport layer, and an electron injection layer may be formed thereon, and a material capable of being used as a cathode may be deposited thereon.

Besides, on a substrate, a cathode material, an organic material layer, and an anode material may be sequentially deposited so as to provide an organic electronic device. The organic material layer may be formed in a multi-layered structure including a hole injection layer, a hole transport layer, an emitting layer, an electron transport layer, and an electron injection layer, but the present invention is not limited thereto. It may be formed in a single layer structure. Further, the organic material layer may be manufactured with a smaller number of layers by using various polymer materials by means of a solvent process (e.g., spin coating, dip coating, doctor blading, screen printing, inkjet printing, or thermal transfer) instead of deposition.

In the organic electro-luminescence element according to another embodiment of the present invention, the above described compound including a substituted or unsubstituted carbazole derivative in which two tertiary amines are substituted, may be used in a soluble process such as a spin coating process or an ink jet process.

The substrate is a support for the organic electroluminescence element, and may employ a silicon wafer, a quartz or glass plate, a metal plate, a plastic film or sheet.

On the substrate, an anode is positioned. Such an anode allows holes to be injected into a hole injection layer positioned thereon. As an anode material, a material having a high work function is preferably used so that injection of holes into an organic material layer can be smoothly carried out. Specific examples of an anode material used for the present invention may include: metals (such as vanadium, chromium, copper, zinc, gold) or alloys thereof; metal oxides such as zinc oxide, indium oxide, indium tin oxide (ITO), indium zinc oxide (IZO); a metal-oxide combination such as ZnO:Al or $SnO_2$:Sb; and conductive polymers such as poly(3-methylthiophene), poly[3,4-(ethylene-1,2-dioxy)thiophene] (PEDT), polypyrrole and polyaniline, but the present invention is not limited thereto.

On the anode, a hole injection layer is positioned. A material for such a hole injection layer is required to have a high efficiency for injecting holes from an anode, and to be able to efficiently transport the injected holes. For this, the material has to have a low ionization potential, a high transparency against visible ray, and a high stability for holes.

As a hole injection material, a material into which holes can be efficiently injected from an anode at a low voltage is used. HOMO (highest occupied molecular orbital) of the hole injection material preferably ranges from a work function of an anode material to HOMO of adjacent organic material layers. Specific examples of the hole injection material may include metal porphyrine-, oligothiophene-, and arylamine-based organic materials, hexanitrile hexaazatriphenylene- and quinacridone-based organic materials, perylene-based organic materials, and anthraquinone-, polyaniline-, and polythiophene-based conductive polymers, but the present invention is not limited thereto.

On the hole injection layer, a hole transport layer is positioned. Such a hole transport layer receives holes transferred from the hole injection layer and transfers them to an organic emitting layer positioned thereon. Further, the hole transport layer has a high hole mobility and a high hole stability and performs a role of blocking electrons. Besides these general requirements, it requires heat-resistance against a device when applied for an automobile display, and thus is preferably made of a material having a glass transition temperature (Tg) of 70° C. or more. The examples of a material satisfying these conditions may include NPD (or NPB), Spiro-arylamine-based compound, perylenearylamine-based compound, azacycloheptatriene compound, bis(diphenylvinylphenyl)anthracene, silicongermaniumoxide compound, silicon-based arylamine compound, and the like.

On the hole transport layer, an organic emitting layer is positioned. Such an organic emitting layer is made of a material having a high quantum efficiency, in which holes and electrons which are injected from an anode and a cathode, respectively, are recombined so as to emit light. As a light emitting material, a material allowing holes and electrons transferred from a hole transport layer and an electron transport layer, respectively, to be combined so as to emit light in a visible ray range is used. Preferably, a material having a high quantum efficiency against fluorescence or phosphorescence may be used.

As a material or a compound satisfying these conditions, for a green color, Alq3 may be used, and for a blue color, Balq(8-hydroxyquinoline beryllium salt), DPVBi (4,4'-bis(2, 2-diphenylethenyl)-1,1'-biphenyl) based material, Spiro material, spiro-DPVBi (Spiro-4,4'-bis(2,2-diphenylethenyl)-1,1'-biphenyl), LiPBO (2-(2-benzoxazoyl)-phenol lithium salt), bis(diphenylvinylphenylvinyl)benzene, aluminum-quinoline metal complex, imidazole, thiazol and oxazole-metal complex, or the like may be used. In order to improve the luminous efficiency of a blue color, perylene, and BczVBi (3,3'[(1,1'-biphenyl)-4,4'-diyldi-2,1-ethenediyl]bis(9-ethyl)-9H-carbazole; DSA (distrylamine)) may be doped in a small amount. For a red color, a green light emitting material may be doped with DCJTB ([2-(1,1-dimethylethyl)-6-[2-(2,3,6,7-tetrahydro-1,1,7,7-tetramethyl-1H,5H-benzo(ij)quinolizin-9-yl)ethenyl]-4H-pyran-4-ylidene]-propanedinitrile) in a small amount. When a process such as inkjet printing, roll coating, spin coating, is used to form an emitting layer, a polymer such as polyphenylenevinylene (PPV)-based polymer or poly fluorene may be used for an organic emitting layer.

On the organic emitting layer, an electron transport layer is positioned. Such an electron transport layer requires a material which has a high efficiency for electrons injected from a cathode positioned thereon, and can efficiently transport the injected electrons. For this, a material having a high electron affinity, a high electron mobility, and a high electron stability is required. Specific examples of an electron transport material satisfying these conditions may include Al complex of 8-hydroxyquinoline; complex including Alq$_3$; organic radical compound; and hydroxyflavone-metal complex, but the present invention is not limited thereto.

On the electron transport layer, an electron injection layer is layered. The electron injection layer may be manufactured by using a metal complex compound (such as Balq, Alq$_3$, Be(bq)$_2$, Zn(BTZ)$_2$, Zn(phq)$_2$, PBD, spiro-PBD, TPBI, and Tf-6P) or a low molecular material including an aromatic compound having an imidazole ring or a boron compound. Herein, the electron injection layer may be formed in a thickness range of 100 Å to 300 Å.

On the electron injection layer, a cathode is positioned. Such a cathode performs a role of injecting electrons into the electron injection layer. As a material for the cathode, the same material as that used for an anode may be used. In order to achieve efficient electron injection, a metal having a low work function is more preferably used. Especially, metals such as tin, magnesium, indium, calcium, sodium, lithium, aluminum, silver, or alloys thereof may be used. Further, a double-layered electrode (e.g., lithium fluoride and aluminum, lithium oxide and aluminum, and strontium oxide and aluminum) with a thickness of 100 μm or less may be used.

As described above, the compound including a substituted or unsubstituted carbazole derivative in which two tertiary amines are substituted, as described with reference to Formulas 1 to 9, may be used as a hole injection material, a hole transport material, a light emitting material, an electron transport material and an electron injection material, which are appropriate for fluorescent and phosphorescent elements of all colors (such as red, green, blue, white). Also, the compound may be used as a material of a host (or a dopant) of various colors.

The organic electro-luminescence element according to the present invention may be manufactured in a front luminescent type, a rear luminescent type, or a both-side luminescent type according to its materials.

Meanwhile, the present invention provides a terminal which includes a display device and a control part for driving the display device, the display device including the above described organic electronic device. The terminal means a wired/wireless communication terminal which is currently used or will be used in the future. The above described terminal according to the present invention may be a mobile communication terminal such as a cellular phone, and may include all kinds of terminals such as a PDA, an electronic dictionary, a PMP, a remote control, a navigation unit, a game player, various kinds of TVs, and various kinds of computers.

EXAMPLE

Hereinafter, the present invention will be described more specifically with reference to Preparation Examples and Test Examples. However, the following examples are only for illustrative purposes and are not intended to limit the scope of the invention.

Preparation Example

Hereinafter, Preparation Examples or Synthesis Examples of the compounds including a substituted or unsubstituted carbazole derivative in which two tertiary amines are substituted, represented by Formulas 1 to 9, will be described. However, since there are many compounds including a substituted or unsubstituted carbazole derivative in which two tertiary amines are substituted, represented by Formulas 1 to 9, only one compound or two compounds from among the compounds will be exemplified. A person skilled in the art of the invention should realize that other compounds including a substituted or unsubstituted carbazole derivative in which two tertiary amines are substituted can be prepared through Preparation Examples as described below although they are not exemplified.

Whole Synthesis Method

As a whole, as shown in Reaction Scheme 1a below, from a starting material 1, an intermediate 2-1 was synthesized, from the intermediate 2-1, an intermediate 2-2 was synthesized, and from the intermediate 2-2, an intermediate 2-3 was synthesized. Then, as shown in Reaction Schemes 1a and 1b, an intermediate 2-1 or an intermediate 2-3 was reacted with 3a-B(OH)$_2$, 4a-B(OH)$_2$, and 5a-B(OH)$_2$, respectively, so as to finally synthesize compounds represented by Formula 4 (in Reaction Schemes and 2, compounds represented by compound "3", hereinafter the same), compounds represented by Formula (In Reaction Schemes 1 and 2, compounds represented by compound "4", hereinafter the same), and compounds represented by Formula 8 (in Reaction Schemes 1 and 2, compounds represented by compound "5", hereinafter the same).

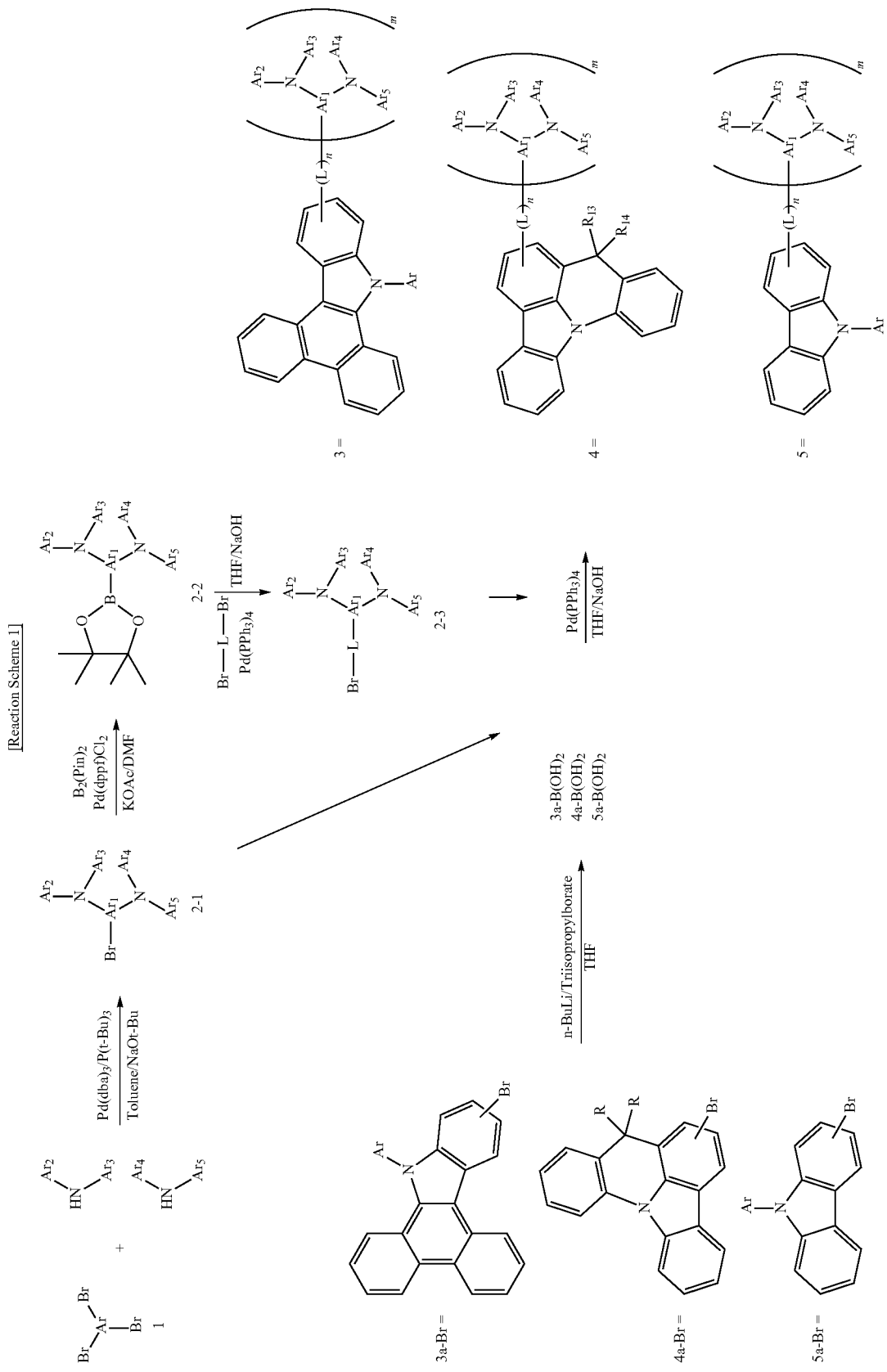

[Reaction Scheme 2]

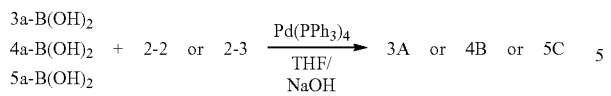

Specifically, a round bottom flask was charged with a compound of 3a-B(OH)₂, 4a-B(OH)₂ or 5a-B(OH)₂ (1 equivalent), an intermediate 2-2 or 2-3r (1.1 equivalents), Pd(PPh₃)₄ (0.03~0.05 equivalents), NaOH (3 equivalents), THF (3 mL/1 mmol), and water (1.5 mL/1 mmol).

The mixture was heated under reflux at 80° C.~90° C. After the reaction was completed, the resultant product was diluted with addition of distilled water at room temperature. Then, the resultant product was extracted with methylene chloride and water. The organic layer was dried with MgSO₄, and concentrated. Then, the produced compound was purified by silica gel column and recrystallized to give compounds represented by Formulas 4, 6, and 8.

Hereinafter, synthesis methods of the starting material, intermediates, and final compounds, as described above, will be described in detail.

Synthesis Method of a Starting Material

Synthesis of 3a-Br-1
(12-bromo-9-phenyl-9H-dibenzo[a,c]carbazole) as a Starting Material Intermediate 1: Synthesis of
9-(5-bromo-2-nitrophenyl)phenanthrene

[Reaction Scheme 2]

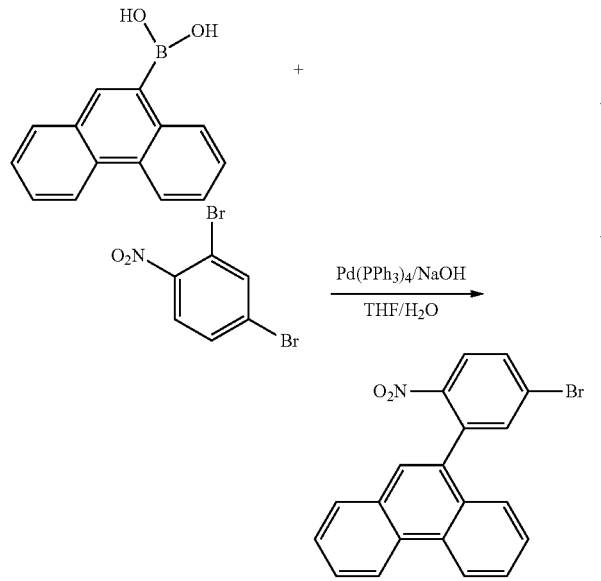

A 2 L round bottom flask was charged with phenanthracene-9-boronic acid (76.61 g, 345 mmol), THF (700 mL), and H₂O (350 mL), and the mixture was dissolved. To the resultant mixture, 2,4-dibromo-1-nitrobenzene (146 g, 518 mmol), NaOH (42 g, 1035 mmol), and Pd(PPh₃)₄ (20 g, 17.3 mmol) were sequentially added, followed by reaction at 80° C. for 24 hours. After the reaction was completed, the resultant product was extracted with methylene chloride, water, and brine, and the organic layer was dried with MgSO₄. The obtained organic layer was purified by silica gel column (methylene chloride:hexane=1:3) so as to give 80.4 g of a product (62%).

Intermediate 2: Synthesis of
12-bromo-9H-dibenzo[a,c]carbazole

[Reaction Scheme 3]

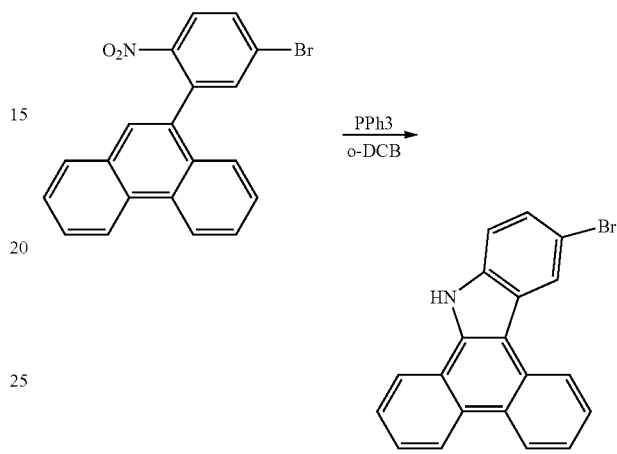

A 2 L round bottom flask was charged with intermediate 1 (80.4 g, 213 mmol), PPh₃ (139 g, 531 mmol), and o-dichlorobenzene (700 mL), and the mixture was dissolved. The resultant mixture was reacted at 190° C. for 24 hours.

After the reaction was completed, o-dichlorobenzene was removed, and the remaining filtrate was extracted with methylene chloride and water. The resultant product was purified by short phase column (methylene chloride:hexane=1:2) so as to give 44.3 g of a product (60%).

Starting Material 3a-Br-1: Synthesis of
12-bromo-9-phenyl-9H-dibenzo[a,c]carbazole

[Reaction Scheme 4]

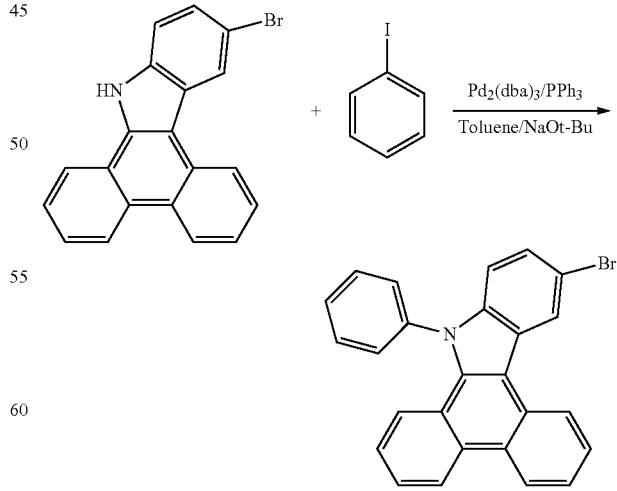

A 500 mL round bottom flask was charged with 3a-3 compound (5 g, 14.442 mmol), Iodobenzene (4.42 g, 21.663 mmol), Pd₂(dba)₃ (0.4 g, 0.433 mmol), PPh₃ (0.38 g, 1.444 mmol), NaOt-Bu (4.164 g, 43.33 mmol), and toluene (150 mL), and reacted at 100° C. for 8 hours.

After the reaction was completed, the resultant product was extracted with ether and water. The organic layer was dried with MgSO₄, and purified by short phase column (methylene chloride). Then, the solvent of the obtained organic matter was removed. The resultant product was recrystallized by methylene chloride and hexane to give 3.72 g of a product (61%).

Starting Material

Synthesis of 3a-Br-2(11-bromo-9-phenyl-9H-dibenzo[a,c]carbazole)

Intermediate 1: Synthesis of 9-(4-bromo-2-nitrophenyl)phenanthrene

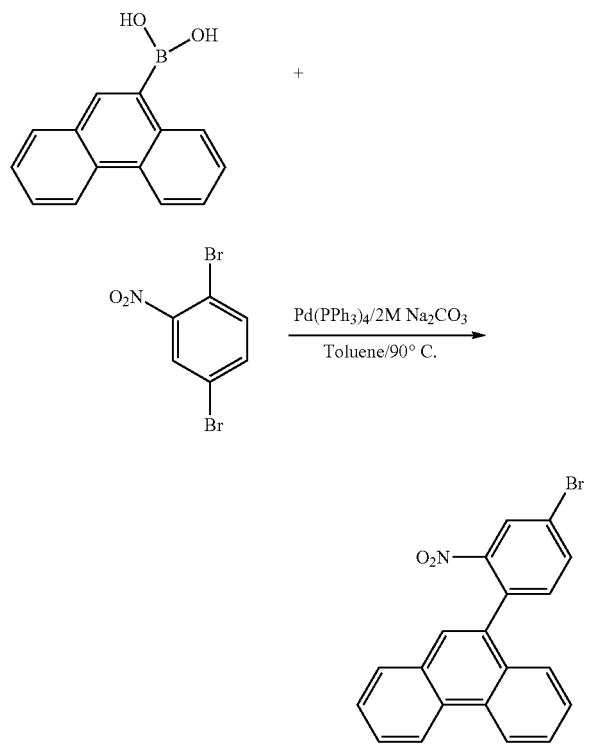

A 500 mL round bottom flask was charged with toluene (250 mL), phenanthracene-9-boronic acid (18.2 g, 82 mmol), 2,5-dibromonitrobenzene (23.1 g, 82.3 mmol), Pd(PPh₃)₄ (2.8 g, 2.5 mmol), and 2M Na₂CO₃ aqueous solution (124 mL).

Then, at 90° C., the mixture was heated under reflux for 6 hours. After the reaction was completed, the resultant product was diluted with addition of distilled water at room temperature. Then, the resultant product was extracted with methylene chloride and water. The organic layer was dried with MgSO₄, and concentrated. Then, the produced compound was purified by silica gel column (methylene chloride:hexane=1:2) to give 26.36 g of a product (85%).

Intermediate 2: Synthesis of 11-bromo-9H-dibenzo[a,c]carbazole

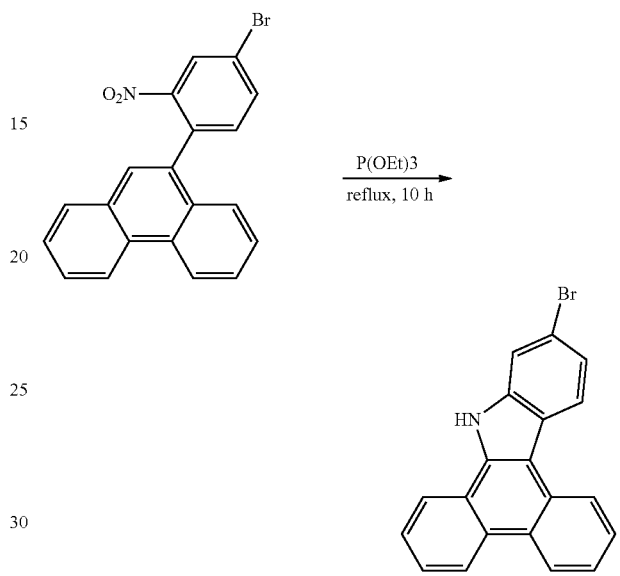

A 250 mL round bottom flask was charged with 9-(4-bromo-2-nitrophenyl)phenanthrene (26.36 g, 69.69 mmol), and triethyl phosphate (84.84 mL, 487.86 mmol), and the mixture was heated under reflux at 160° C. to 165° C. for 14 hours. After the reaction was completed, the remaining triethyl phosphate was removed by vacuum distillation. The resultant product was diluted with a mixed solvent of MeOH:H₂O=1:1, and the produced solid was filtered. The obtained solid was washed with a mixed solvent of MeOH:H₂O=1:1, and petroleum ether. The solid was dissolved in methylene chloride, dried with MgSO₄, and concentrated, and purified by silica gel column (petroleum ether:methylene chloride=2:1). Then, 14.96 g of a product (62%) was obtained.

3a-Br-2: Synthesis of 11-bromo-9-phenyl-9H-dibenzo[a,c]carbazole

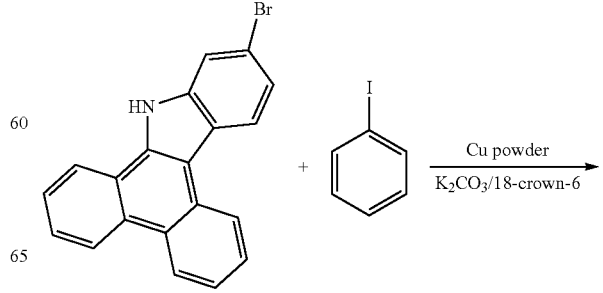

-continued

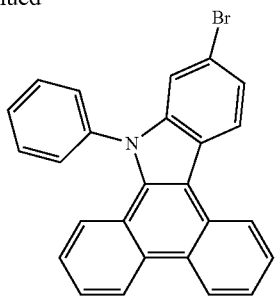

A 250 mL round bottom flask was charged with 11-bromo-9H-dibenzo[a,c]carbazole (7 g, 20.22 mmol), iodobenzene (8.25 g, 40.44 mmol), K₂CO₃ (8.384 g, 60.66 mmol), Cu powder (1.29 g, 20.22 mmol), 18-crown-6 (2.672 g, 10.11 mmol), and o-dichlorobenzene (130 mL), and the mixture was heated under reflux for 24 hours. After the reaction was completed, the resultant product was extracted with methylene chloride and water. The obtained organic layer was washed with 5% hydrochloric acid, and brine. The organic layer was dried with MgSO₄, and concentrated. The resultant compound was purified by silica gel column (ethyl acetate:hexane=1:1.5) to give 6.06 g of a product (71%).

Starting Material

Synthesis of 4a-Br(6-bromo-8,8-dimethyl-8H-indolo[3,2,1-de]acridine)

Intermediate 1: Synthesis of methyl 2-(9H-carbazol-9-yl)benzoate

[Reaction Scheme 8]

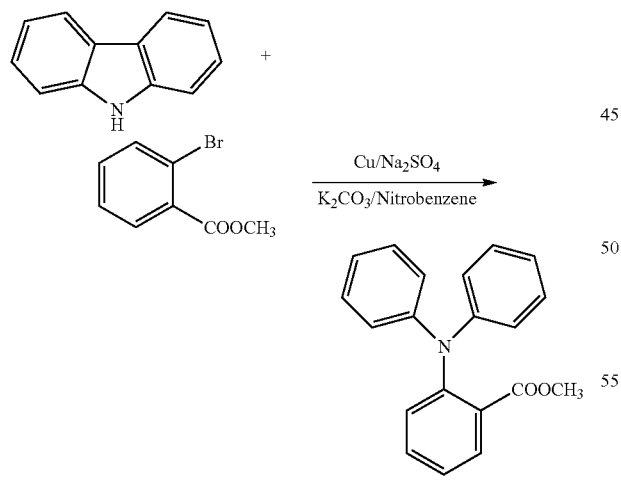

A 1 L round bottom flask was charged with carbazole (8.36 g, 50 mmol), methyl-2-bromobenzoate (15 g, 75 mmol), K₂CO₃ (7 g, 50 mmol), Na₂SO₄ (7.1 g, 50 mmol), Cu powder (0.3 g, 5 mmol), and nitrobenzene, and the mixture was reacted at 190° C. for 24 hours. After the reaction was completed, the resultant product was extracted with methylene chloride and water. The organic layer was dried with MgSO₄, and purified by silica gel column (ethyl acetate:hexane=1:5) to give 12 g of a product (79.6%).

Intermediate 2: Synthesis of 2-(2-(9H-carbazol-9-yl)phenyl)propan-2-ol

[Reaction Scheme 9]

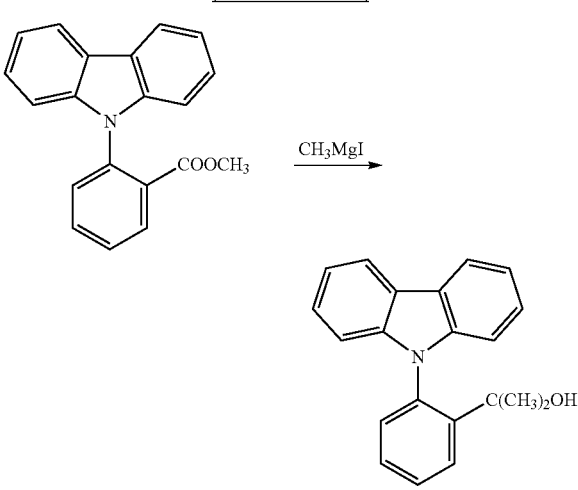

In a 500 mL round bottom flask, 4a-1 compound (9 g, 30 mmol) was dissolved in benzene (50 mL), and diluted with addition of ether (100 mL). Then, the reaction flask was set to 0° C., and CH₃MgI (10 mL, 100 mmol) was slowly dropped thereto, followed by stirring for 30 minutes. The reaction flask was set to 70° C., followed by reflux for 2 hours. After the reaction was completed, an ammonium chloride aqueous solution was added thereto, and ether was used for extraction.

The obtained organic layer was dried with MgSO₄, concentrated, and purified by silica gel column so as to give 4.7 g of a product (52%).

Intermediate 3: Synthesis of 8,8-dimethyl-8H-indolo[3,2,1-de]acridine

[Reaction Scheme 10]

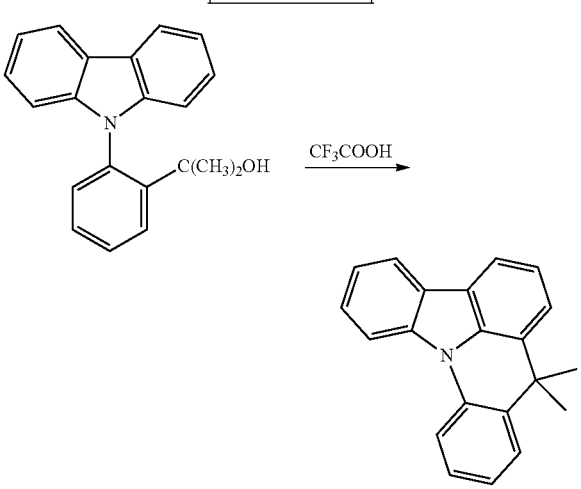

A 250 mL round bottom flask was charged with intermediate 2 (4.7 g, 15.6 mmol), and trifluoroacetic acid (78 mL), and heated under reflux at 80° C. for 2 hours. After the reaction was completed, the resultant product was extracted with methylene chloride and water, dried with MgSO$_4$, and concentrated. Then, the produced compound was purified by silica gel column (ethyl acetate:hexane=1:2.5) to give 2.6 g of a product (59%).

4a-Br: Synthesis of
6-bromo-8,8-dimethyl-8H-indolo[3,2,1-de]acridine

[Reaction Scheme 11]

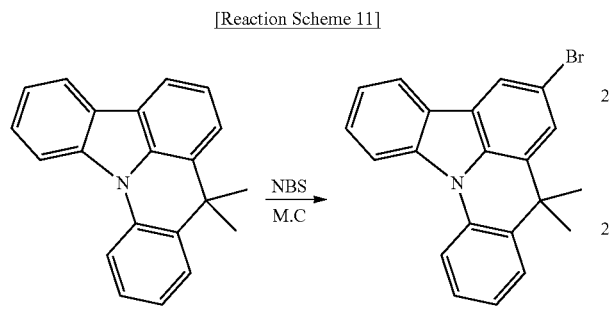

A 250 mL round bottom flask was charged with intermediate 3 (8.5 g, 30 mmol), NBS (5.8 g, 33 mmol), and methylene chloride (100 mL), and the mixture was reacted at room temperature for 5 hours. After the reaction was completed, the resultant product was extracted with methylene chloride and Na$_2$CO$_3$ aqueous solution, dried with MgSO$_4$, and concentrated. Then, the produced compound was purified by silica gel column (methylene chloride:hexane=1:1) to give 9.67 g of a product (89%).

Starting Material: Synthesis of
5a-Br-1(9-Phenylcarbazole)

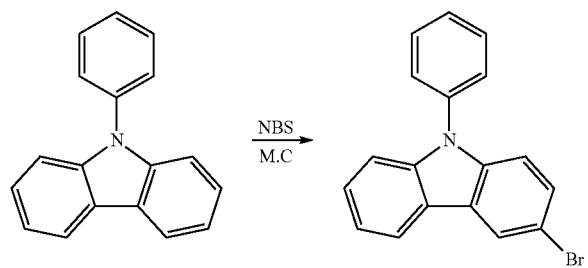

A 500 mL reaction flask was charged with 9-phenyl carbazole (20 g, 82.2 mmol), NBS (15.36 g, 86.31 mmol), and methylene chloride (200 mL), and the mixture was reacted at room temperature for 5 hours. After the reaction was completed, the resultant product was extracted with methylene chloride and Na$_2$CO$_3$ aqueous solution, dried with MgSO$_4$, and concentrated. Then, the produced compound was purified by short phase column (methylene chloride:hexane=1:1) and recrystallized by methylene chloride and hexane to give 23 g of a product (87%).

Starting Material: Synthesis of 5a-Br-2

Intermediate 1: Synthesis of
(4-Bromo-2-nitrobiphenyl)

[Reaction Scheme 12]

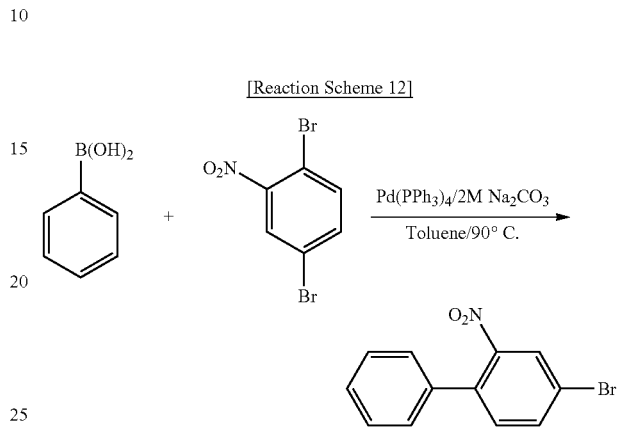

A 500 mL round bottom flask was charged with toluene (250 mL), phenyl boronic acid (10 g, 82 mmol), 2,5-dibromonitrobenzene (23.1 g, 82.3 mmol), Pd(PPh$_3$)$_4$ (2.8 g, 2.5 mmol), and 2M Na$_2$CO$_3$ aqueous solution (124 mL). Then, at 90° C., the mixture was heated under reflux for 6 hours. After the reaction was completed, the resultant product was diluted with addition of distilled water at room temperature. Then, the resultant product was extracted with methylene chloride and water. The organic layer was dried with MgSO$_4$, and concentrated. Then, the produced compound was purified by silica gel column (methylene chloride:hexane=1:1) to give 19.2 g of a product (84.2%).

Intermediate 1: Synthesis of (2-Bromocarbazole)

[Reaction Scheme 13]

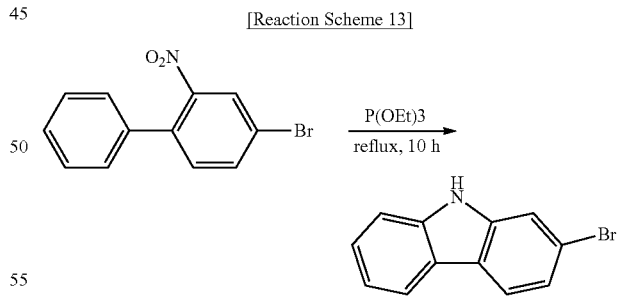

A 250 mL round bottom flask was charged with 4-Bromo-2-nitrobenzene (19.2 g, 69.04 mmol), and triethyl phosphate (84 mL, 483.28 mmol). Then, at 160° C. to 165° C., the mixture was heated under reflux for 14 hours. After the reaction was completed, the remaining triethyl phosphate was removed by vacuum distillation. The resultant product was diluted with a mixed solvent of MeOH:H$_2$O=1:1, and the produced solid was filtered. The obtained solid was washed with a mixed solvent of MeOH:H$_2$O=1:1 and petroleum ether.

The solid was dissolved in methylene chloride, dried with MgSO₄, and concentrated, and then purified by silica gel column. Then, 10.2 g of a product (60%) was obtained.

5a-Br-2: Synthesis of (2-bromo-9-phenyl carbazole)

[Reaction Scheme 14]

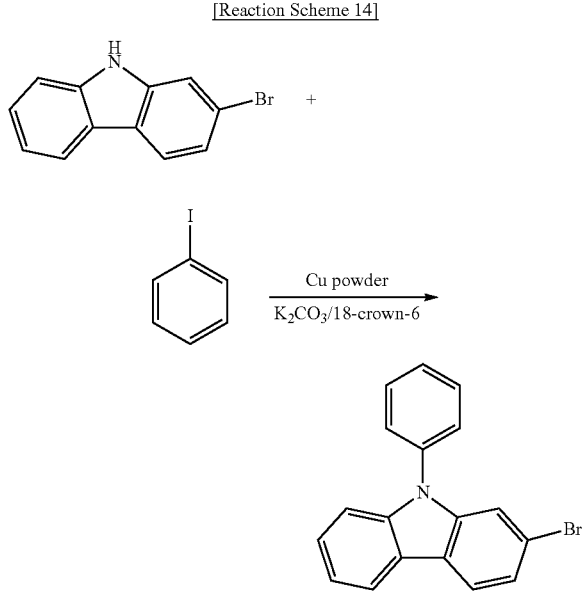

A 250 mL round bottom flask was charged with 2-Bromocarbazole (6 g, 24.38 mmol), iodobenzene (9.95 g, 48.76 mmol), K₂CO₃ (10.11 g, 73.14 mmol), Cu powder (1.55 g, 24.38 mmol), 18-crown-6 (3.22 g, 12.19 mmol), and o-dichlorobenzene (150 mL). The mixture was heated under reflux for 24 hours. After the reaction was completed, the resultant product was extracted with methylene chloride, and water, and the obtained organic layer was washed with 5% hydrochloric acid, and brine. The organic layer was dried with MgSO₄, and concentrated. The resultant compound was purified by silica gel column (ethylacetate:hexane=1:1) to give 5.5 g of a product (70%).

Synthesis of Intermediates

Synthesis of Intermediates 2-1, and 2-2

[Reaction Scheme 15]

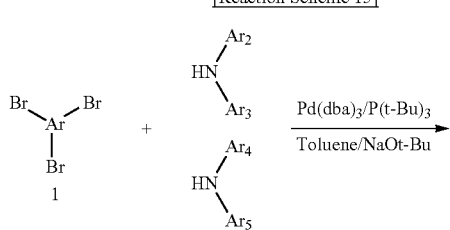

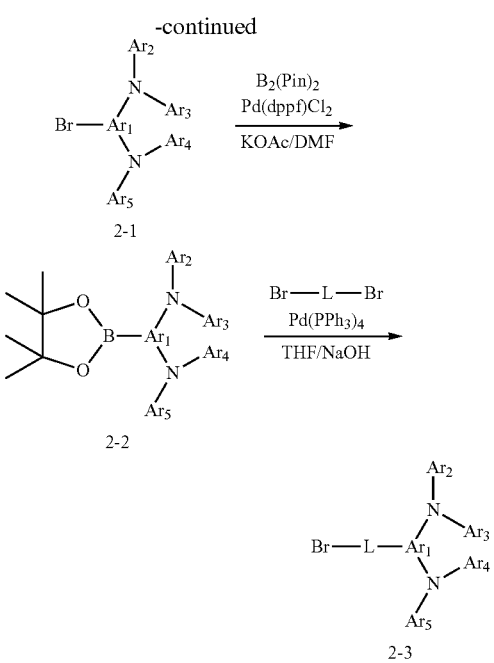

Synthesis Method of Intermediate 2-1

A round bottom flask was charged with a compound (1) (1 equivalent), an amine compound (2 equivalents), Pd₂(dba)₃ (0.06~0.1 mmol), PPh₃ (0.2 equivalents), NaOt-Bu (6 equivalents), and toluene (10.5 mL/1 mmol). The mixture was subjected to a reaction at 100° C. After the reaction was completed, the resultant product was extracted with ether and water. The organic layer was dried with MgSO₄, and concentrated. Then, the produced organic matter was purified by silica gel column and recrystallized to give a product.

Synthesis Method of Intermediate 2-2

A round bottom flask was charged with a compound (2-1) (1 equivalent), Bis(pinacolato)diboron (1 equivalents), Pd(dppf)Cl₂ (0.03 equivalents). KOAc (3 equivalents), and DMF (6.3 mL/1 mmol), and the mixture was heated under reflux at 130° C. After the reaction was completed, the resultant product was extracted with ether and water. The obtained organic layer was dried with MgSO₄, and concentrated. Then, the concentrated product was purified by silica gel column and recrystallized to give a product.

Synthesis Method of Intermediate 2-3

A round bottom flask was charged with a compound (2-2) (1 equivalent), Br-L-Br (1.1 equivalents), Pd(PPh₃)₄ (0.03~0.05 equivalents), NaOH (3 equivalents), THF (3 mL/1 mmol), and water (1.5 mL/1 mmol).

Then, at 80° C.~90° C., the mixture was heated under reflux. After the reaction was completed, the resultant product was diluted with addition of distilled water at room temperature. Then, the resultant product was extracted with methylene chloride and water. The organic layer was dried with MgSO₄, and concentrated. Then, the produced compound was purified by silica gel column and recrystallized to give a product.

Hereinafter, as shown in Reaction Scheme 1a and 1b, the process in which an intermediate 2-1 or an intermediate 2-3 is reacted with 3a-B(OH)$_2$, 4a-B(OH)$_2$, and 5a-B(OH)$_2$, so as to finally synthesize a compound "3", a compound "4", and compound "5" will be described.

Synthesis Method of Compounds "3" to "5"

(1) Synthesis of 5-bromo-$N^1,N^1,N^3,N^3$-tetraphenyl-benzene-1,3-diamine

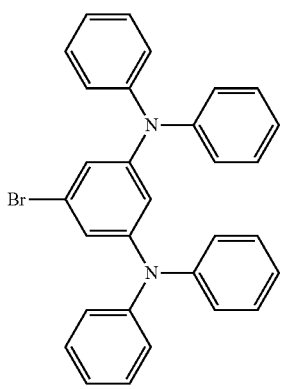 [SMILES: Brc1cc(N(c2ccccc2)c2ccccc2)cc(N(c2ccccc2)c2ccccc2)c1]

17.45 g of a product (yield: 71%) was obtained in the same manner as described in the synthesis method of intermediate 2-1 except that 1,3,5-tribromobenzene (15.74 g, 50 mmol), diphenylamine (16.92 g, 100 mmol), Pd$_2$(dba)$_3$ (2.75 g, 3 mmol), PPh$_3$ (2.62 g, 10 mmol), NaOt-Bu (28.83 g, 300 mmol), and toluene (525 mL) were used.

(2) Synthesis of 2-bromo-$N^1,N^1,N^4,N^4$-tetraphenyl-benzene-1,4-diamine

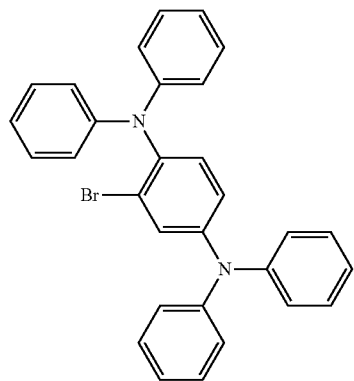 [SMILES: Brc1cc(N(c2ccccc2)c2ccccc2)ccc1N(c1ccccc1)c1ccccc1]

14.74 g of a product (yield: 60%) was obtained in the same manner as described in the synthesis method of intermediate 2-1 except that 1,2,5-tribromobenzene (15.74 g, 50 mmol), diphenylamine (16.92 g, 100 mmol), Pd$_2$(dba)$_3$ (2.75 g, 3 mmol), PPh$_3$ (2.62 g, 10 mmol), NaOt-Bu (28.83 g, 300 mmol), and toluene (525 mL) were used.

(3) Synthesis of 5-bromo-$N^1,N^3$-diphenyl-$N^1,N^3$-dip-tolylbenzene-1,3-diamine

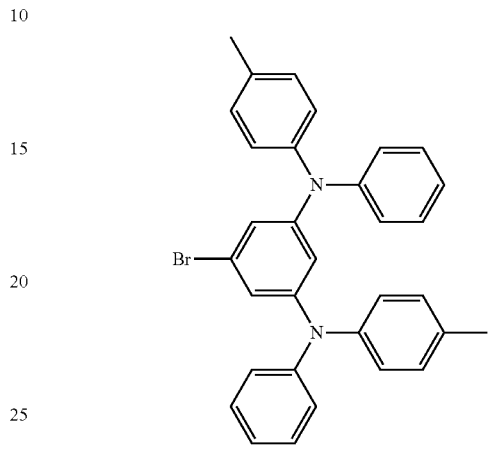

17.66 g of a product (yield: 68%) was obtained in the same manner as described in the synthesis method of intermediate 2-1 except that 1,3,5-tribromobenzene (15.74 g, 50 mmol), 4-methyl-N-phenylaniline (18.33 g, 100 mmol), Pd$_2$(dba)$_3$ (2.75 g, 3 mmol), PPh$_3$ (2.62 g, 10 mmol), NaOt-Bu (28.83 g, 300 mmol), and toluene (525 mL) were used.

(4) Synthesis of 5-bromo-$N^1, N^1, N^3, N^3$-tetra-p-tolylbenzene-1,3-diamine

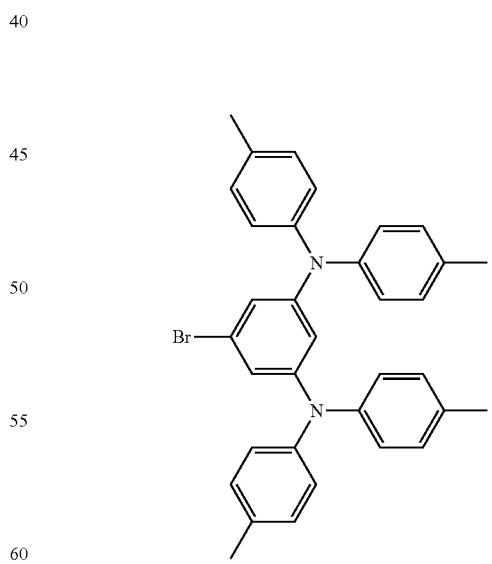

17.52 g of a product (yield: 64%) was obtained in the same manner as described in the synthesis method of intermediate 2-1 except that 1,3,5-tribromobenzene (15.74 g, 50 mmol), di-p-tolylamine (19.73 g, 100 mmol), Pd$_2$(dba)$_3$ (2.75 g, 3 mmol), PPh$_3$ (2.62 g, 10 mmol), NaOt-Bu (28.83 g, 300 mmol), and toluene (525 mL) were used.

(5) Synthesis of 5-bromo-N$^1$,N$^1$,N$^3$,N$_3$-tetra(naphthalen-2-yl)benzene-1,3-diamine

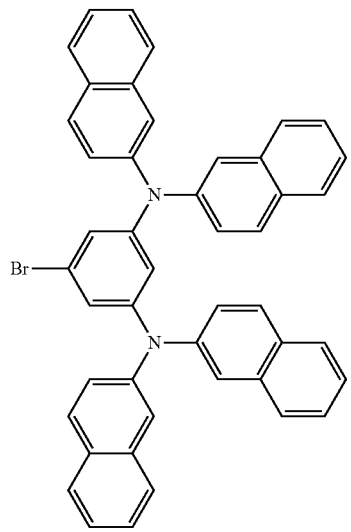 [SMILES: Brc1cc(N(c2ccc3ccccc3c2)c2ccc3ccccc3c2)cc(N(c2ccc3ccccc3c2)c2ccc3ccccc3c2)c1]

23.86 g of a product (yield: 69%) was obtained in the same manner as described in the synthesis method of intermediate 2-1 except that 1,3,5-tribromobenzene (15.74 g, 50 mmol), dinaphthalen-2-ylamine (26.934 g, 100 mmol), Pd$_2$(dba)$_3$ (2.75 g, 3 mmol), PPh$_3$ (2.62 g, 10 mmol), NaOt-Bu (28.83 g, 300 mmol), and toluene (525 mL) were used.

(6) Synthesis of 5-bromo-N$^1$,N$^1$,N$^3$,N$^3$-tetra(naphthalen-1-yl)benzene-1,3-diamine

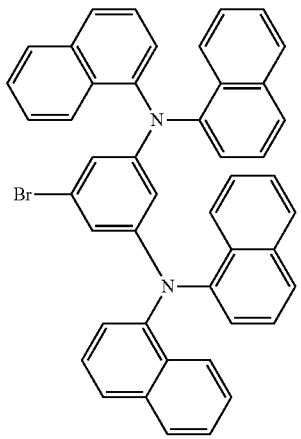 [SMILES: Brc1cc(N(c2cccc3ccccc23)c2cccc3ccccc23)cc(N(c2cccc3ccccc23)c2cccc3ccccc23)c1]

23.86 g of a product (yield: 69%) was obtained in the same manner as described in the synthesis method of intermediate 2-1 except that 1,3,5-tribromobenzene (15.74 g, 50 mmol), dinaphthalen-1-ylamine (26.934 g, 100 mmol), Pd$_2$(dba)$_3$ (2.75 g, 3 mmol), PPh$_3$ (2.62 g, 10 mmol), NaOt-Bu (28.83 g, 300 mmol), and toluene (525 mL) were used.

(7) Synthesis of 4'-bromo-N$^3$,N$^5$-diphenyl-N$^3$,N$^5$-di-p-tolylbiphenyl-3,5-diamine

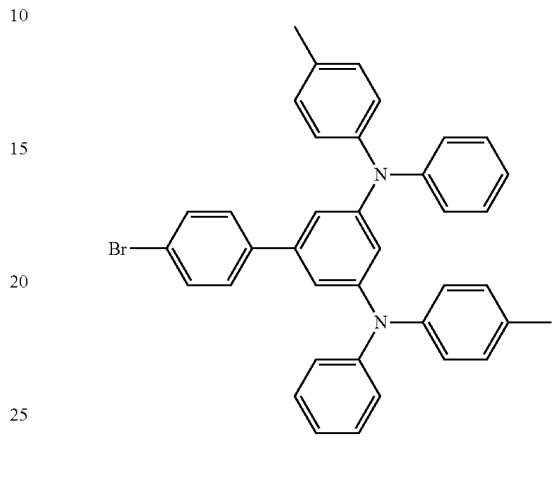

11.61 g of a product (yield: 65%) was obtained in the same manner as described in the synthesis method of intermediate 2-3 except that N$^1$,N$^3$-diphenyl-5-(4,4,5,5-tetramethyl-1,3,2-dioxaborolan-2-yl)-N$^1$,N$^3$-di-p-tolybenzene-1,3-diamine (17 g, 30 mmol), 1,4-Dibromobenzene (7.78 g, 33 mmol), Pd(PPh$_3$)$_4$ (1.04 g, 0.9 mmol), K$_2$CO$_3$ (12.44 g, 90 mmol), THF (90 mL), and water (45 mL) were used.

(8) Synthesis of 5-(4-bromonaphthalen-1-yl)-N$^1$,N$^3$-bis(3,5-dimethylphenyl)-N$^1$,N$^3$-diphenylbenzene-1,3-diamine

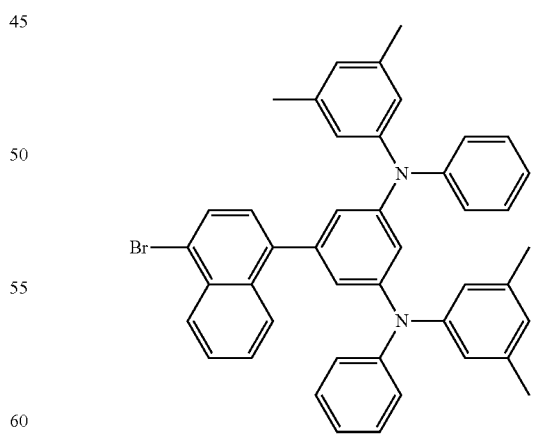

13.74 g of a product (yield: 68%) was obtained in the same manner as described in the synthesis method of intermediate 2-3 except that N$^1$,N$^3$-bis(3,5-dimethylphenyl)-N$^1$,N$^3$-diphenyl-5-(4,4,5,5-tetramethyl-1,3,2-dioxaborolan-2-yl)benzene-1,3-diamine (17.84 g, 30 mmol), 1,4-dibromonaphthalene (9.44 g, 33 mmol), Pd(PPh₃)₄ (1.04 g, 0.9 mmol), K₂CO₃ (12.44 g, 90 mmol), THF (90 mL), and water (45 mL) were used.

(9) Synthesis of 5-(6-bromonaphthalen-2-yl)-N¹,N³-bis(4-methoxyphenyl)-N¹,N³-diphenylbenzene-1,3-Diamine

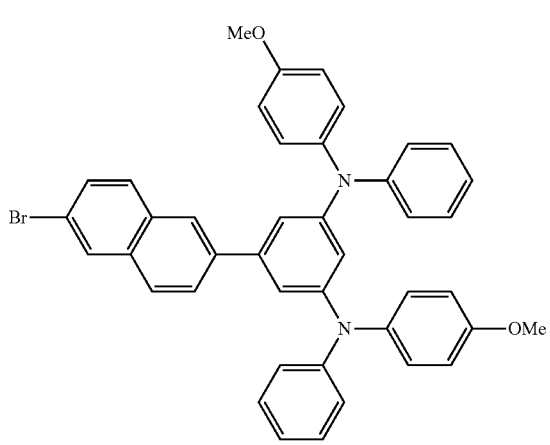 [SMILES: COc1ccc(N(c2ccccc2)c2cc(-c3ccc4cc(Br)ccc4c3)cc(N(c3ccccc3)c3ccc(OC)cc3)c2)cc1]

13.42 g of a product (yield: 66%) was obtained in the same manner as described in the synthesis method of intermediate 2-3 except that N¹,N³-bis(4-methoxyphenyl)-N¹,N³-diphenyl-5-(4,4,5,5-tetramethyl-1,3,2-dioxaborolan-2-yl)benzene-1,3-diamine (17.76 g, 30 mmol), 2,6-dibromonaphthalene (9.44 g, 33 mmol), Pd(PPh₃)₄ (1.04 g, 0.9 mmol), K₂CO₃ (12.44 g, 90 mmol), THF (90 mL), and water (45 mL) were used.

(10) Synthesis of 3-Bromo-N²N²,N⁵,N⁵-tetraphenylthiophene-2,5-diamine

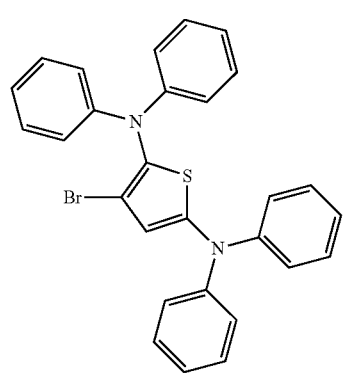 [SMILES: Brc1cc(N(c2ccccc2)c2ccccc2)sc1N(c1ccccc1)c1ccccc1]

17.16 g of a product (yield: 69%) was obtained in the same manner as described in the synthesis method of intermediate 2-1 except that 2,3,5-tribromothiophene (16.04 g, 50 mmol), diphenylamine (16.92 g, 100 mmol), Pd₂(dba)₃ (2.75 g, 3 mmol), PPh₃ (2.62 g, 10 mmol), NaOt-Bu (28.83 g, 300 mmol), and toluene (525 mL) were used.

(11) Synthesis of 3-Bromo-N²,N²,N⁵,N⁵-tetra(naphthalen-2-yl)thiophene-2,5-diamine

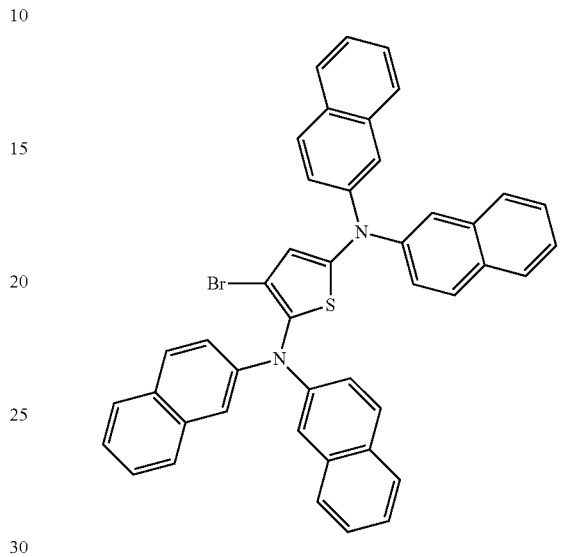

23.7 g of a product (yield: 68%) was obtained in the same manner as described in the synthesis method of 2-1 except that 2,3,5-tribromothiophene (16.04 g, 50 mmol), dinaphthalen-2-ylamine (26.94 g, 100 mmol), Pd₂(dba)₃ (2.75 g, 3 mmol), PPh₃ (2.62 g, 10 mmol), NaOt-Bu (28.83 g, 300 mmol), and toluene (525 mL) were used.

(12) Synthesis of 3-Bromo-N²,N⁵-bis(9,9-dimethyl-9H-fluoren-2-yl)-N²,N⁵-diphenylfuran-2,5-diamine

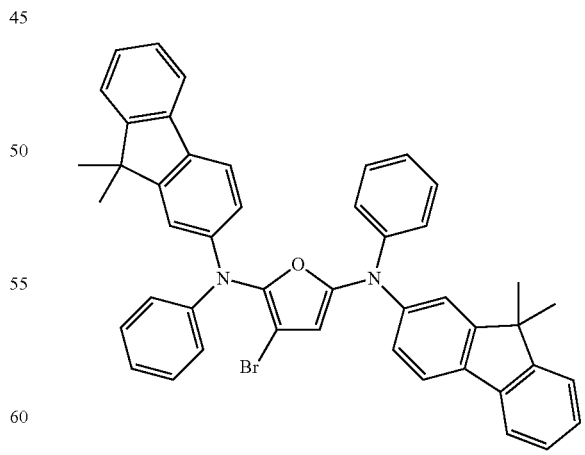

21.77 g of a product (yield: 61%) was obtained in the same manner as described in the synthesis method of 2-1 except that 2,3,5-tribromofuran (15.24 g, 50 mmol), 9,9-dimethyl-N-phenyl-9H-fluoren-2-amine (28.54 g, 100 mmol), Pd₂

(dba)₃ (2.75 g, 3 mmol), PPh₃ (2.62 g, 10 mmol), NaOt-Bu (28.83 g, 300 mmol), and toluene (525 mL) were used.

(13) Synthesis of N³,N⁴-di(naphthalen-2-yl)-N³,N⁴-diphenyl-1H-pyrrole-3,4-diamine

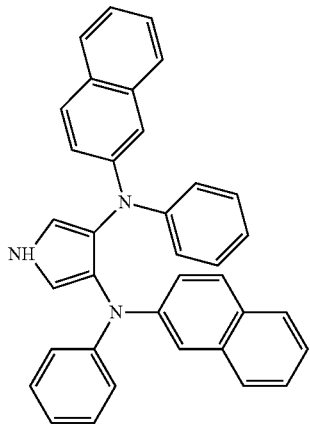 [SMILES: c1ccc(N(c2ccc3ccccc3c2)c2c[nH]cc2N(c2ccccc2)c2ccc3ccccc3c2)cc1]

15.05 g of a product (yield: 60%) was obtained in the same manner as described in the synthesis method of intermediate 2-1 except that 3,4-dibromo-1H-pyrrole (11.24 g, 50 mmol), N-phenylnaphthalen-2-amine (21.93 g, 100 mmol), Pd₂(dba)₃ (2.75 g, 3 mmol), PPh₃ (2.62 g, 10 mmol), NaOt-Bu (28.83 g, 300 mmol), and toluene (525 mL) were used.

(14) Synthesis of N¹,N³-di(biphenyl-4-yl)-5-bromo-N¹,N³-diphenylbenzene-1,3-diamine

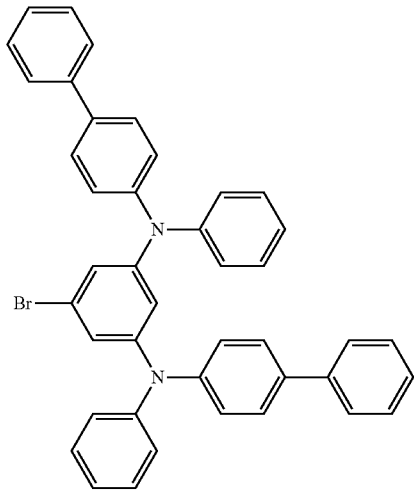 [SMILES: Brc1cc(N(c2ccccc2)c2ccc(-c3ccccc3)cc2)cc(N(c2ccccc2)c2ccc(-c3ccccc3)cc2)c1]

22.53 g of a product (yield: 70%) was obtained in the same manner as described in the synthesis method of 2-1 except that 1,3,5-tribromobenzene (15.74 g, 50 mmol), N-phenylbiphenyl-4-amine (24.53 g, 100 mmol), Pd₂(dba)₃ (2.75 g, 3 mmol), PPh₃ (2.62 g, 10 mmol), NaOt-Bu (28.83 g, 300 mmol), and toluene (525 mL) were used.

(15) Synthesis of 5-Bromo-N¹,N³-bis(4-fluorophenyl)-N¹,N³-diphenylbenzene-1,3-diamine

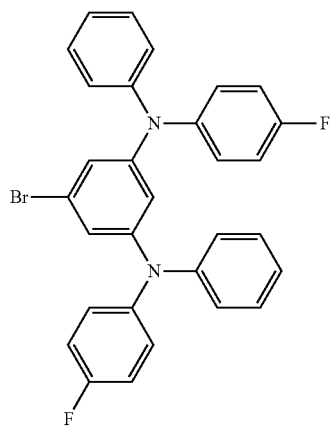 [SMILES: Fc1ccc(N(c2ccccc2)c2cc(Br)cc(N(c3ccccc3)c3ccc(F)cc3)c2)cc1]

17.67 g of a product (yield: 67%) was obtained in the same manner as described in the synthesis method of intermediate 2-1 except that 1,3,5-tribromobenzene (15.74 g, 50 mmol), 4-fluoro-N-phenylaniline (18.72 g, 100 mmol), Pd₂(dba)₃ (2.75 g, 3 mmol), PPh₃ (2.62 g, 10 mmol), NaOt-Bu (28.83 g, 300 mmol), and toluene (525 mL) were used.

(16) Synthesis of 5-Bromo-N¹,N³-bis(9,9-dimethyl-9H-fluoren-2-yl)-N¹,N³-diphenylbenzene-1,3-diamine

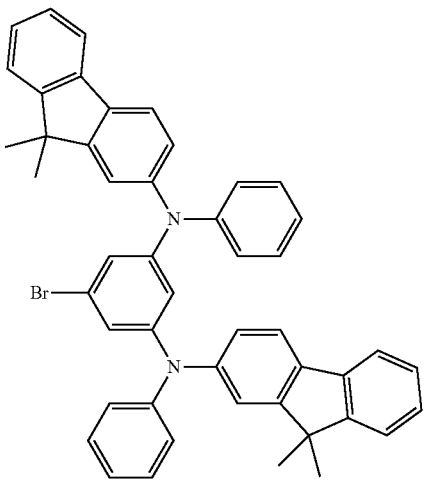 [SMILES: CC1(C)c2ccccc2-c2ccc(N(c3ccccc3)c3cc(Br)cc(N(c4ccccc4)c4ccc5c(c4)C(C)(C)c4ccccc4-5)c3)cc21]

24.25 g of a product (yield: 67%) was obtained in the same manner as described in the synthesis method of intermediate 2-1 except that 1,3,5-tribromobenzene (15.74 g, 50 mmol), 9,9-dimethyl-N-phenyl-9H-fluoren-2-amine (28.54 g, 100 mmol), Pd$_2$(dba)$_3$ (2.75 g, 3 mmol), PPh$_3$ (2.62 g, 10 mmol), NaOt-Bu (28.83 g, 300 mmol), and toluene (525 mL) were used.

(17) Synthesis of N$^1$, N$^3$-di(biphenyl-4-yl)-5-bromo-N$^1$, N$^3$-bis(9,9-dimethyl-9H-fluoren-2-yl)benzene-1,3-Diamine

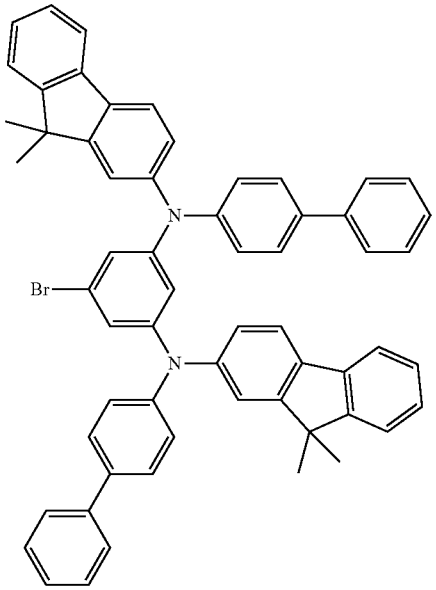 [SMILES: CC1(C)c2ccccc2-c2ccc(N(c3ccc(-c4ccccc4)cc3)c3cc(Br)cc(N(c4ccc(-c5ccccc5)cc4)c4ccc5c(c4)C(C)(C)c4ccccc4-5)c3)cc21]

28.47 g of a product (yield: 65%) was obtained in the same manner as described in the synthesis method of intermediate 2-1 except that 1,3,5-tribromobenzene (15.74 g, 50 mmol), N-(biphenyl-4-yl)-9,9-dimethyl-9H-fluoren-2-amine (36.15 g, 100 mmol), Pd$_2$(dba)$_3$ (2.75 g, 3 mmol), PPh$_3$ (2.62 g, 10 mmol), NaOt-Bu (28.83 g, 300 mmol), and toluene (525 mL) were used.

(18) 3-(4-bromophenyl)-N-5-(9,9-dimethyl-9H-fluoren-2-yl)-N$^2$-(9,9-dimethyl-9H-fluoren-3-yl)-N$^2$,N$^5$-diphenylthiophene-2,5-diamine

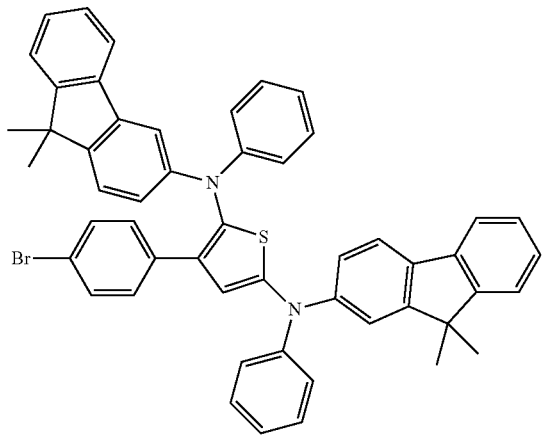 [SMILES: CC1(C)c2ccccc2-c2cc(N(c3ccccc3)c3sc(N(c4ccccc4)c4ccc5c(c4)C(C)(C)c4ccccc4-5)cc3-c3ccc(Br)cc3)ccc21]

14.99 g of a product (yield: 62%) was obtained in the same manner as described in the synthesis method of intermediate 2-3 except that N$^5$-(9,9-dimethyl-9H-fluoren-2-yl)-N$^2$-(9,9-dimethyl-9H-fluoren-3-yl)-N$^2$,N$^5$-diphenyl-3-(4,4,5,5-tetramethyl-1,3,2-dioxaborolan-2-yl)thiophene-2,5-diamine (23.30 g, 30 mmol), 1,4-dibromobenzene (7.78 g, 33 mmol), Pd(PPh$_3$)$_4$ (1.04 g, 0.9 mmol), K$_2$CO$_3$ (12.44 g, 90 mmol), THF (90 ml), and water (45 mL) were used.

(19) Synthesis of 5-bromo-N$^1$,N$^3$-di(naphthalen-2-yl)-N$^1$, N$^3$-diphenylbenzene-1,3-diamine

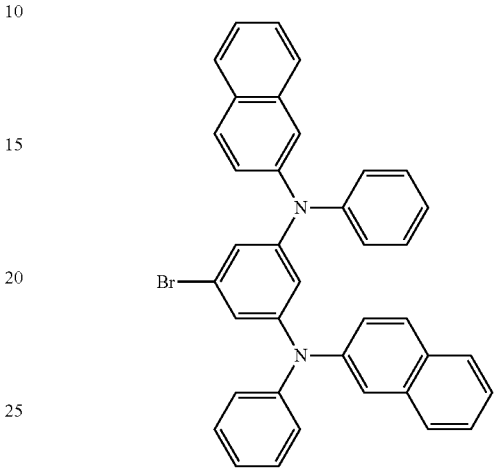

20.11 g of a product (yield: 68%) was obtained in the same manner as described in the synthesis method of intermediate 2-1 except that 1,3,5-tribromobenzene (15.74 g, 50 mmol), N-phenylnaphthalen-2-amine (21.93 g, 100 mmol), Pd$_2$(dba)$_3$ (2.75 g, 3 mmol), PPh$_3$ (2.62 g, 10 mmol), NaOt-Bu (28.83 g, 300 mmol), and toluene (525 mL) were used.

(20) Synthesis of N$^1$, N$^3$-di(biphenyl-4-yl)-5-bromo-N$^1$, N$^3$-di(naphthalen-2-yl)benzene-1,3-diamine

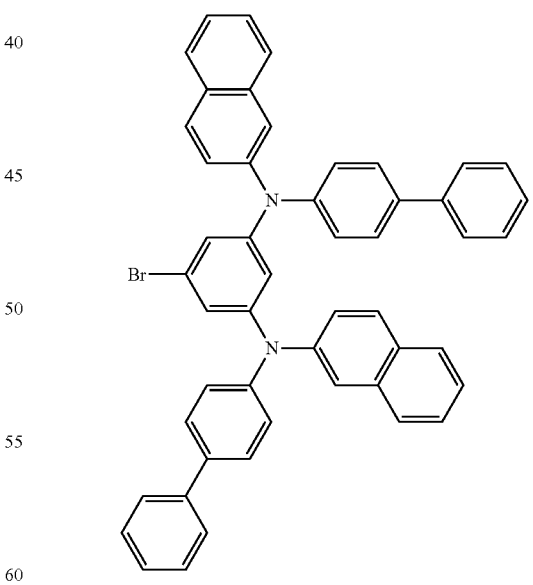

23.80 g of a product (yield: 64%) was obtained in the same manner as described in the synthesis method of intermediate 2-1 except that 1,3,5-tribromobenzene (15.74 g, 50 mmol), N-(biphenyl-4-yl)naphthalen-2-amine (29.54 g, 100 mmol), Pd$_2$(dba)$_3$ (2.75 g, 3 mmol), PPh$_3$ (2.62 g, 10 mmol), NaOt-Bu (28.83 g, 300 mmol), and toluene (525 mL) were used.

131

(21) Synthesis of 5-Bromo-N$^1$,N$^3$-bis(9,9-diphenyl-9H-fluoren-2-yl)-N$^1$,N$^3$-diphenylbenzene-1,3-diamine

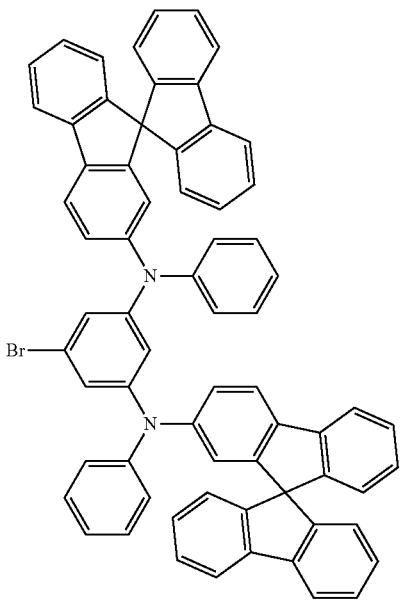 [SMILES: Brc1cc(N(c2ccccc2)c2ccc3c(c2)C2(c4ccccc4-c4ccccc42)c2ccccc2-3)cc(N(c2ccccc2)c2ccc3c(c2)C2(c4ccccc4-c4ccccc42)c2ccccc2-3)c1]

31.10 g of a product (yield: 64%) was obtained in the same manner as described in the synthesis method of intermediate 2-1 except that 1,3,5-tribromobenzene (15.74 g, 50 mmol), N-9,9-triphenyl-9H-fluoren-2-amine (40.95 g, 100 mmol), Pd$_2$(dba)$_3$ (2.75 g, 3 mmol), PPh$_3$ (2.62 g, 10 mmol), NaOt-Bu (28.83 g, 300 mmol), and toluene (525 mL) were used.

(22) Synthesis of N$^1$, N$^3$-di(9,9'-spirobi[fluorene]-2-yl)-5-bromo-N$^1$,N$^3$-diphenylbenzene-1,3-diamine

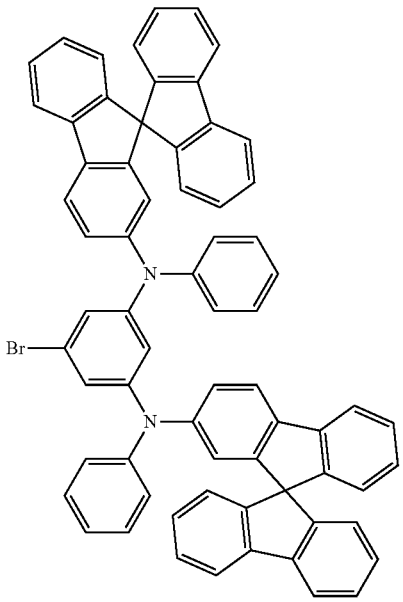 [SMILES: Brc1cc(N(c2ccccc2)c2ccc3c(c2)C2(c4ccccc4-c4ccccc42)c2ccccc2-3)cc(N(c2ccccc2)c2ccc3c(c2)C2(c4ccccc4-c4ccccc42)c2ccccc2-3)c1]

31.46 g of a product (yield: 65%) was obtained in the same manner as described in the synthesis method of intermediate 2-1 except that 1,3,5-tribromobenzene (15.74 g, 50 mmol), N-phenyl-9,9'-spirobi[fluoren]-2-amine (40.75 g, 100

132 mmol), Pd$_2$(dba)$_3$ (2.75 g, 3 mmol), PPh$_3$ (2.62 g, 10 mmol), NaOt-Bu (28.83 g, 300 mmol), and toluene (525 mL) were used.

(23) Synthesis of 5-Bromo-N$^1$,N$^3$-bis(dibenzo[b,d]thiophen-2-yl)-N$^1$,N$^3$-diphenylbenzene-1,3-diamine

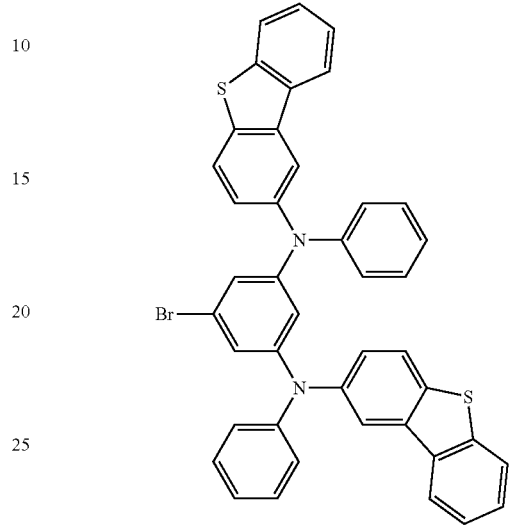

23.57 g of a product (yield: 67%) was obtained in the same manner as described in the synthesis method of intermediate 2-1 except that 1,3,5-tribromobenzene (15.74 g, 50 mmol), N-phenyldibenzo[b,d]thiophen-2-amine (27.54 g, 100 mmol), Pd$_2$(dba)$_3$ (2.75 g, 3 mmol), PPh$_3$ (2.62 g, 10 mmol), NaOt-Bu (28.83 g, 300 mmol), and toluene (525 mL) were used

(24) Synthesis of 5-Bromo-N$^1$,N$^3$-bis(dibenzo[b,d]thiophen-2-yl)-N$^1$,N$^3$-di(naphthalen-2-yl)benzene-1,3-diamine

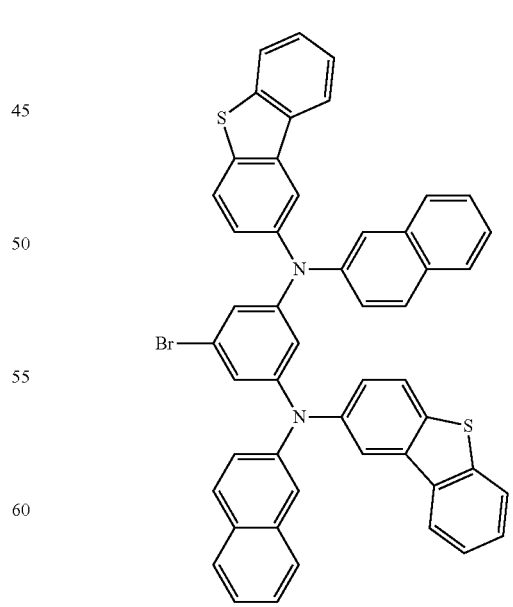

23.57 g of a product (yield: 67%) was obtained in the same manner as described in the synthesis method of intermediate 2-1 except that 1,3,5-tribromobenzene (15.74 g, 50 mmol), N-(naphthalen-2-yl)dibenzo[b,d]thiophen-2-amine (32.54 g, 100 mmol), Pd$_2$(dba)$_3$ (2.75 g, 3 mmol), PPh$_3$ (2.62 g, 10 mmol), NaOt-Bu (28.83 g, 300 mmol), and toluene (525 mL) were used.

(25) Synthesis of N$^1$,N$^3$-di(biphenyl-4-yl)-5-bromo-N$^1$,N$^3$-bis(dibenzo[b,d]thiophen-2-yl)benzene-1,3-diamine

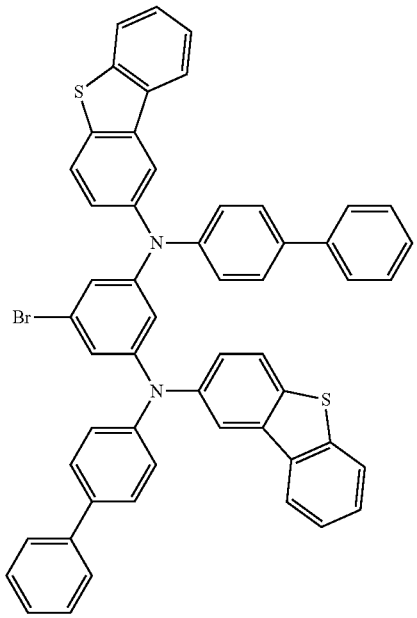

27.82 g of a product (yield: 65%) was obtained in the same manner as described in the synthesis method of intermediate 2-1 except that 1,3,5-tribromobenzene (15.74 g, 50 mmol), N-(biphenyl-4-yl)dibenzo[b,d]thiophen-2-amine (35.15 g, 100 mmol), Pd$_2$(dba)$_3$ (2.75 g, 3 mmol), PPh$_3$ (2.62 g, 10 mmol), NaOt-Bu (28.83 g, 300 mmol), and toluene (525 mL) were used.

(26) Synthesis of 5-Bromo-N$^1$,N$^3$-bis(dibenzo[b,d]furan-2-yl)-N$^1$,N$^3$-diphenylbenzene-1,3-diamine

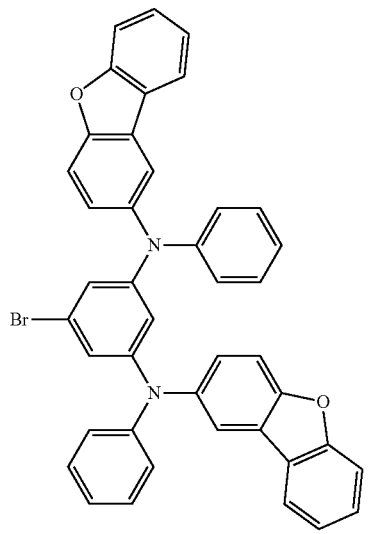 [SMILES: Brc1cc(N(c2ccccc2)c2ccc3oc4ccccc4c3c2)cc(N(c2ccccc2)c2ccc3oc4ccccc4c3c2)c1]

22.83 g of a product (yield: 68%) was obtained in the same manner as described in the synthesis method of intermediate 2-1 except that 1,3,5-tribromobenzene (15.74 g, 50 mmol), N-phenyldibenzo[b,d]furan-2-amine (25.93 g, 100 mmol), Pd$_2$(dba)$_3$ (2.75 g, 3 mmol), PPh$_3$ (2.62 g, 10 mmol), NaOt-Bu (28.83 g, 300 mmol), and toluene (525 mL) were used.

(27) Synthesis of N$^1$,N$^3$-di(biphenyl-4-yl)-5-bromo-N$^1$,N$^3$-bis(dibenzo[b,d]furan-2-yl)benzene-1,3-diamine

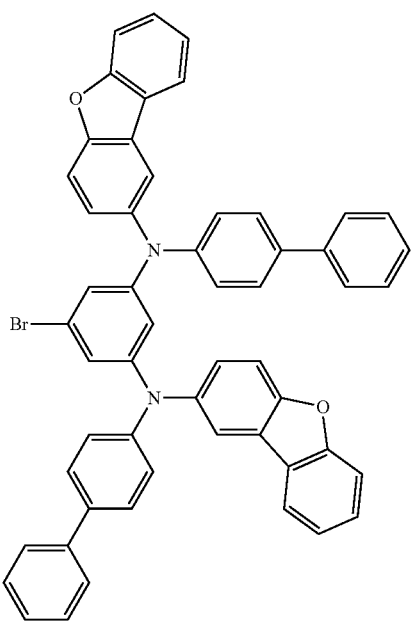 [SMILES: Brc1cc(N(c2ccc(-c3ccccc3)cc2)c2ccc3oc4ccccc4c3c2)cc(N(c2ccc(-c3ccccc3)cc2)c2ccc3oc4ccccc4c3c2)c1]

27.18 g of a product (yield: 66%) was obtained in the same manner as described in the synthesis method of intermediate 2-1 except that 1,3,5-tribromobenzene (15.74 g, 50 mmol), N-(biphenyl-4-yl)dibenzo[b,d]furan-2-amine (33.54 g, 100 mmol), Pd$_2$(dba)$_3$ (2.75 g, 3 mmol), PPh$_3$ (2.62 g, 10 mmol), NaOt-Bu (28.83 g, 300 mmol), and toluene (525 mL) were used.

(28) Synthesis of 5-Bromo-N$^1$-(3a1,3a2-dihydropyren-4-yl)-N$^1$,N$^3$-bis(4-methoxyphenyl)-N$^3$-(pyren-4-yl)benzene-1,3-diamine

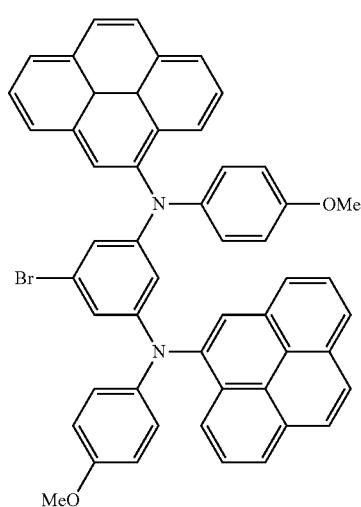 [SMILES: COc1ccc(N(C2=C3C=CC=C4C=CC5=CC=CC(=C2)C5C43)c2cc(Br)cc(N(c3ccc(OC)cc3)c3cc4cccc5ccc6cccc3c6c54)c2)cc1]

27.26 g of a product (yield: 68%) was obtained in the same manner as described in the synthesis method of intermediate 2-1 except that 1,3,5-tribromobenzene (15.74 g, 50 mmol), N-(4-methoxyphenyl)-3a$^1$,3a$^2$-dihydropyren-4-amine (32.54 g, 100 mmol), Pd$_2$(dba)$_3$ (2.75 g, 3 mmol), PPh$_3$ (2.62 g, 10 mmol), NaOt-Bu (28.83 g, 300 mmol), and toluene (525 mL) were used.

(29) Synthesis of 5-Bromo-N$^1$,N$^3$-diphenyl-N$^1$,N$^3$-bis(4-phenylnaphthalen-1-yl)benzene-1,3-diamine

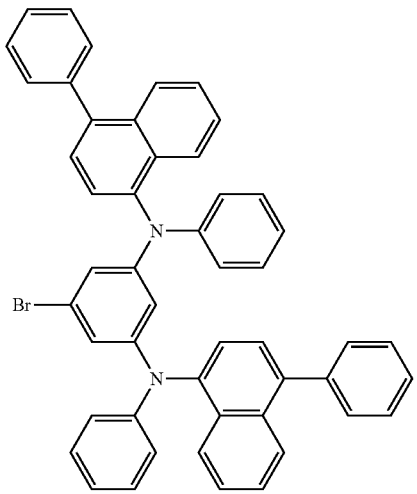 [SMILES: Brc1cc(N(c2ccccc2)c2ccc(-c3ccccc3)c3ccccc23)cc(N(c2ccccc2)c2ccc(-c3ccccc3)c3ccccc23)c1]

26.03 g of a product (yield: 70%) was obtained in the same manner as described in the synthesis method of intermediate 2-1 except that 1,3,5-tribromobenzene (15.74 g, 50 mmol), N-4-diphenylnaphthalen-1-amine (29.54 g, 100 mmol), Pd$_2$(dba)$_3$ (2.75 g, 3 mmol), PPh$_3$ (2.62 g, 10 mmol), NaOt-Bu (28.83 g, 300 mmol), and toluene (525 mL) were used.

(30) Synthesis of N$^1$,N$^3$-di(biphenyl-4-yl)-5-bromo-N$^1$,N$^3$-bis(4-phenylnaphthalen-1-yl)benzene-1,3-diamine

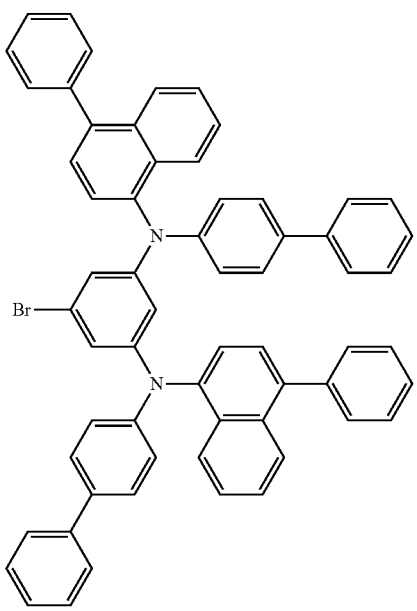 [SMILES: Brc1cc(N(c2ccc(-c3ccccc3)cc2)c2ccc(-c3ccccc3)c3ccccc23)cc(N(c2ccc(-c3ccccc3)cc2)c2ccc(-c3ccccc3)c3ccccc23)c1]

30.46 g of a product (yield: 68%) was obtained in the same manner as described in the synthesis method of intermediate 2-1 except that 1,3,5-tribromobenzene (15.74 g, 50 mmol), N-(biphenyl-4-yl)-4-phenylnaphthalen-1-amine (37.15 g, 100 mmol), Pd$_2$(dba)$_3$ (2.75 g, 3 mmol), PPh$_3$ (2.62 g, 10 mmol), NaOt-Bu (28.83 g, 300 mmol), and toluene (525 mL) were used.

(31) Synthesis of 5-Bromo-N$^1$,N$^3$-diphenyl-N$^1$,N$^3$-bis(6-phenylnaphthalen-2-yl)benzene-1,3-diamine

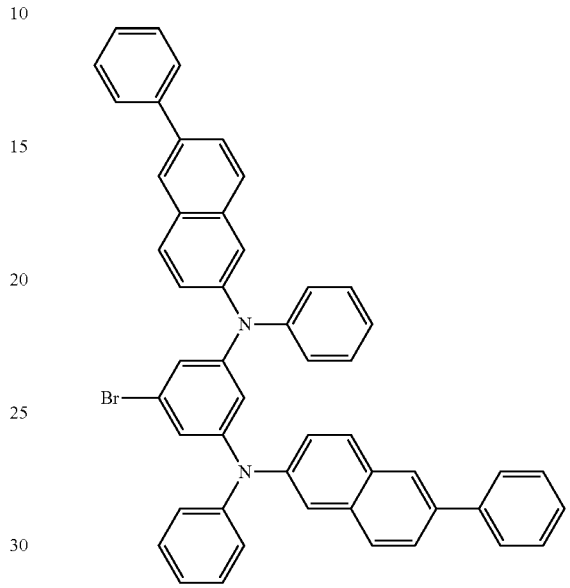

25.29 g of a product (yield: 68%) was obtained in the same manner as described in the synthesis method of intermediate 2-1 except that 1,3,5-tribromobenzene (15.74 g, 50 mmol), N-6-diphenylnaphthalen-2-amine (29.54 g, 100 mmol), Pd$_2$(dba)$_3$ (2.75 g, 3 mmol), PPh$_3$ (2.62 g, 10 mmol), NaOt-Bu (28.83 g, 300 mmol), and toluene (525 mL) were used.

(32) Synthesis of 5-Bromo-N$^1$,N$^3$-bis(4-fluorophenyl)-N$^1$,N$^3$-bis(6-phenylnaphthalen-2-yl)benzene-1,3-diamine

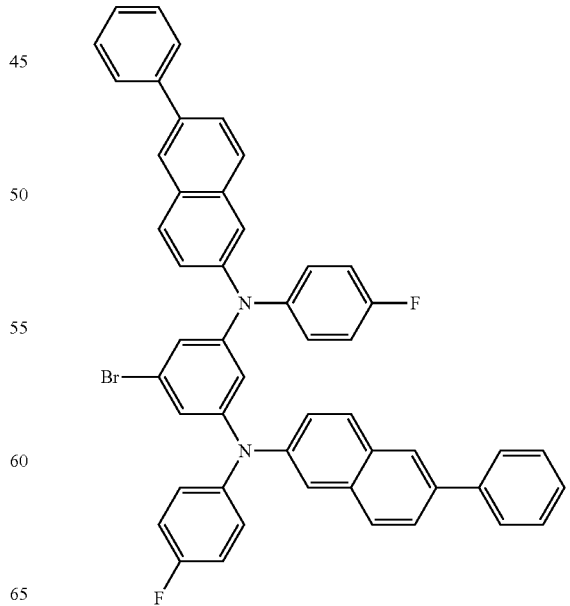

24.56 g of a product (yield: 63%) was obtained in the same manner as described in the synthesis method of intermediate 2-1 except that 1,3,5-tribromobenzene (15.74 g, 50 mmol), N-(4-fluorophenyl)-6-phenylnaphthalen-2-amine (31.34 g, 100 mmol), Pd$_2$(dba)$_3$ (2.75 g, 3 mmol), PPh$_3$ (2.62 g, 10 mmol), NaOt-Bu (28.83 g, 300 mmol), and toluene (525 mL) were used.

Furthermore, the molecular weight and m/z of compounds "3" to "5" are noted in Table 2 below. In general, on final compounds, through nuclear magnetic resonance (NMR), mass spectrometry (Mass), etc. the structure can be analyzed. However, since the above described final compound may have many aromatic structures, in preference to nuclear magnetic resonance (NMR), mass spectrometry (Mass) was mainly used for structure analysis.

Herein, FD-MS indicates a mass spectrometer. When mass spectrometry was carried out by the mass spectrometer, several peaks from broken final compounds occur. Herein, m/z indicates a peak. In other words, m/z indicates a mass spectrometry main peak of the above described final compounds. Through this, it can be confirm that there exist compounds.

TABLE 2

| compound | FD-MS | compound | FD-MS |
| --- | --- | --- | --- |
| 3-A1 | m/z = 753.31($C_{56}H_{39}N_3$ = 753.93) | 3-A2 | m/z = 753.31($C_{56}H_{39}N_3$ = 753.93) |
| 3-A3 | m/z = 753.31($C_{56}H_{39}N_3$ = 753.93) | 3-A4 | m/z = 781.35($C_{58}H_{43}N_3$ = 781.98) |
| 3-A5 | m/z = 809.38($C_{60}H_{47}N_3$ = 810.04) | 3-A6 | m/z = 953.38($C_{72}H_{47}N_3$ = 954.16) |
| 3-A7 | m/z = 953.38($C_{72}H_{47}N_3$ = 954.16) | 3-A8 | m/z = 857.38($C_{64}H_{47}N_3$ = 858.08) |
| 3-A9 | m/z = 935.42($C_{70}H_{53}N_3$ = 936.19) | 3-A10 | m/z = 939.38($C_{68}H_{49}N_3O_2$ = 940.14) |
| 3-A11 | m/z = 759.27($C_{54}H_{37}N_3S$ = 759.96) | 3-A12 | m/z = 959.33($C_{70}H_{45}N_3S$ = 960.19) |
| 3-A13 | m/z = 975.42($C_{72}H_{53}N_3O$ = 976.21) | 3-A14 | m/z = 842.34($C_{62}H_{42}N_4$ = 843.02) |
| 3-A15 | m/z = 905.38($C_{68}H_{47}N_3$ = 906.12) | 3-A16 | m/z = 1057.44($C_{80}H_{55}N_3$ = 1058.31) |
| 3-A17 | m/z = 829.35($C_{62}H_{43}N_3$ = 830.02) | 3-A18 | m/z = 865.33($C_{62}H_{41}F_2N_3$ = 866.01) |
| 3-A19 | m/z = 985.44($C_{74}H_{55}N_3$ = 986.25) | 3-A20 | m/z = 1137.50($C_{86}H_{63}N_3$ = 1138.44) |
| 3-A21 | m/z = 1067.43($C_{78}H_{57}N_3S$ = 1068.37) | 3-A22 | m/z = 929.38($C_{70}H_{47}N_3$ = 930.14) |
| 3-A23 | m/z = 1005.41($C_{76}H_{51}N_3$ = 1006.24) | 3-A24 | m/z = 1233.50($C_{94}H_{63}N_3$ = 1234.53) |
| 3-A25 | m/z = 1229.47($C_{94}H_{59}N_3$ = 1230.49) | 3-A26 | m/z = 965.29($C_{68}H_{43}N_3S_2$ = 966.22) |
| 3-A27 | m/z = 1065.32($C_{76}H_{47}N_3S_2$ = 1066.34) | 3-A28 | m/z = 1117.35($C_{80}H_{51}N_3S_2$ = 1118.41) |
| 3-A29 | m/z = 933.34($C_{68}H_{43}N_3O_2$ = 934.09) | 3-A30 | m/z = 1085.40($C_{80}H_{51}N_3O_2$ = 1086.28) |
| 3-A31 | m/z = 1063.41($C_{78}H_{53}N_3O_2$ = 1064.27) | 3-A32 | m/z = 1005.41($C_{76}H_{51}N_3$ = 1006.24) |
| 3-A33 | m/z = 1157.47($C_{88}H_{59}N_3$ = 1158.43) | 3-A34 | m/z = 1005.41($C_{76}H_{51}N_3$ = 1006.24) |
| 3-A35 | m/z = 1041.39($C_{76}H_{49}F_2N_3$ = 1042.22) | 4-B1 | m/z = 693.31($C_{51}H_{39}N_3$ = 693.88) |
| 4-B2 | m/z = 693.31($C_{51}H_{39}N_3$ = 693.88) | 4-B3 | m/z = 763.39($C_{56}H_{49}N_3$ = 764.01) |
| 4-B4 | m/z = 749.38($C_{55}H_{47}N_3$ = 749.98) | 4-B5 | m/z = 969.41($C_{73}H_{51}N_3$ = 970.21) |
| 4-B6 | m/z = 893.38($C_{67}H_{47}N_3$ = 894.11) | 4-B7 | m/z = 769.35($C_{57}H_{43}N_3$ = 769.97) |
| 4-B8 | m/z = 875.42($C_{65}H_{53}N_3$ = 876.14) | 4-B9 | m/z = 879.38($C_{63}H_{49}N_3O_2$ = 880.08) |
| 4-B10 | m/z = 699.27($C_{49}H_{37}N_3S$ = 699.90) | 4-B11 | m/z = 899.33($C_{65}H_{45}N_3S$ = 900.14) |
| 4-B12 | m/z = 915.42($C_{67}H_{53}N_3O$ = 916.16) | 4-B13 | m/z = 782.34($C_{57}H_{42}N_4$ = 782.97) |
| 4-B14 | m/z = 845.38($C_{63}H_{47}N_3$ = 846.07) | 4-B15 | m/z = 997.44($C_{75}H_{55}N_3$ = 998.26) |
| 4-B16 | m/z = 805.33($C_{57}H_{41}F_2N_3$ = 805.95) | 4-B17 | m/z = 925.44($C_{69}H_{55}N_3$ = 926.20) |
| 4-B18 | m/z = 1077.50($C_{81}H_{63}N_3$ = 1078.39) | 4-B19 | m/z = 1007.43($C_{73}H_{57}N_3S$ = 1008.32) |
| 4-B20 | m/z = 1001.47($C_{75}H_{59}N_3$ = 1002.29) | 4-B21 | m/z = 1173.50($C_{89}H_{63}N_3$ = 1174.47) |
| 4-B22 | m/z = 1169.47($C_{89}H_{59}N_3$ = 1170.44) | 4-B23 | m/z = 905.29($C_{63}H_{43}N_3S_2$ = 906.17) |
| 4-B24 | m/z = 1005.32($C_{71}H_{47}N_3S_2$ = 1006.28) | 4-B25 | m/z = 1057.35($C_{75}H_{51}N_3S_2$ = 1058.36) |
| 4-B26 | m/z = 873.34($C_{63}H_{43}N_3O_2$ = 874.03) | 4-B27 | m/z = 1025.40($C_{75}H_{51}N_3O_2$ = 1026.23) |
| 4-B28 | m/z = 1003.41($C_{73}H_{53}N_3O_2$ = 1004.22) | 4-B29 | m/z = 945.41($C_{71}H_{51}N_3$ = 946.18) |
| 4-B30 | m/z = 1097.47($C_{83}H_{59}N_3$ = 1098.38) | 4-B31 | m/z = 945.41($C_{71}H_{51}N_3$ = 946.18) |
| 4-B32 | m/z = 981.39($C_{71}H_{49}F_2N_3$ = 982.17) | 5-C1 | m/z = 653.28($C_{48}H_{35}N_3$ = 653.81) |
| 5-C2 | m/z = 653.28($C_{48}H_{35}N_3$ = 653.81) | 5-C3 | m/z = 653.28($C_{48}H_{35}N_3$ = 653.81) |
| 5-C4 | m/z = 681.31($C_{50}H_{39}N_3$ = 681.86) | 5-C5 | m/z = 709.35($C_{52}H_{43}N_3$ = 709.92) |
| 5-C6 | m/z = 853.35($C_{64}H_{43}N_3$ = 854.05) | 5-C7 | m/z = 853.35($C_{64}H_{43}N_3$ = 854.05) |
| 5-C8 | m/z = 757.35($C_{56}H_{43}N_3$ = 757.96) | 5-C9 | m/z = 835.39($C_{62}H_{49}N_3$ = 836.07) |
| 5-C10 | m/z = 839.35($C_{60}H_{45}N_3O_2$ = 840.02) | 5-C11 | m/z = 659.24($C_{46}H_{33}N_3S$ = 659.84) |
| 5-C12 | m/z = 859.30($C_{62}H_{41}N_3S$ = 860.07) | 5-C13 | m/z = 875.39($C_{64}H_{49}N_3O$ = 876.09) |
| 5-C14 | m/z = 742.31($C_{54}H_{38}N_4$ = 742.91) | 5-C15 | m/z = 805.35($C_{60}H_{43}N_3$ = 806.00) |
| 5-C16 | m/z = 957.41($C_{72}H_{51}N_3$ = 958.20) | 5-C17 | m/z = 729.31($C_{54}H_{39}N_3$ = 729.91) |
| 5-C18 | m/z = 765.30($C_{54}H_{37}F_2N_3$ = 765.89) | 5-C19 | m/z = 885.41($C_{66}H_{51}N_3$ = 886.13) |
| 5-C20 | m/z = 1037.47($C_{78}H_{59}N_3$ = 1038.32) | 5-C21 | m/z = 967.40($C_{70}H_{53}N_3S$ = 968.25) |
| 5-C22 | m/z = 829.35($C_{62}H_{43}N_3$ = 830.02) | 5-C23 | m/z = 905.38($C_{68}H_{47}N_3$ = 906.12) |
| 5-C24 | m/z = 1133.47($C_{86}H_{59}N_3$ = 1134.41) | 5-C25 | m/z = 1129.44($C_{86}H_{55}N_3$ = 1130.38) |
| 5-C26 | m/z = 865.26($C_{60}H_{39}N_3S_2$ = 866.10) | 5-C27 | m/z = 965.29($C_{68}H_{43}N_3S_2$ = 966.22) |
| 5-C28 | m/z = 1017.32($C_{72}H_{47}N_3S_2$ = 1018.29) | 5-C29 | m/z = 833.30($C_{60}H_{39}N_3O_2$ = 833.97) |
| 5-C30 | m/z = 985.37($C_{72}H_{47}N_3O_2$ = 986.16) | 5-C31 | m/z = 963.38($C_{70}H_{49}N_3O_2$ = 964.16) |
| 5-C32 | m/z = 905.38($C_{68}H_{47}N_3$ = 906.12) | 5-C33 | m/z = 1057.44($C_{80}H_{55}N_3$ = 1058.31) |
| 5-C34 | m/z = 905.38($C_{68}H_{47}N_3$ = 906.12) | 5-C35 | m/z = 941.36($C_{68}H_{45}F_2N_3$ = 942.10) |

Hereinafter, compounds were synthesized in the synthesis method as described above. Then, the case where the compounds were applied to an organic material layer for an organic electronic device, e.g., organic electro-luminescence element, was compared to other generally used compounds.

Comparative Example 1

Synthesis Method of Intermediate

In the case of dibenzocarbazole (intermediate 1), the compounds in Examples below were synthesized by the synthesis method described in Korean Patent Application Nos. KR10-2009-0091482 and KR10-2009-0101343. Accordingly, Korean Patent Application Nos. KR10-2009-0091482 and KR10-2009-0101343 are included in this specification.

However, since there are many compounds in which two tertiary amines are substituted, included in Formula 4, only one compound or two compounds from among the compounds in which two tertiary amines are substituted will be exemplified.

A person skilled in the art of the invention should realize that the inventive compounds in which two tertiary amines are substituted can be prepared through Preparation Examples as described below although they are not exemplified.

Synthesis Method of Compound

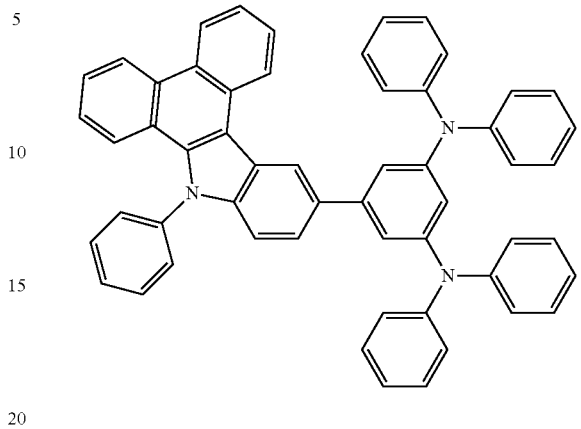

Example 1-1

9-Phenyl-9H-dibenzo[a,c]carbazol-12-ylboronicacid, 4'-bromo-$N^3$,$N^3$,$N^5$,$N^5$-tetraphenylbiphenyl-3,5-diamine, Pd(PPh$_3$)$_4$, and K$_2$CO$_3$ were dissolved in THF 500 ml, and water 250 ml, and heated under reflux for 24 hours. The obtained solid was washed with water and methanol, and purified by silica gel column chromatography to give a white solid, a compound (yield: 65%).

[Reaction Scheme 16]

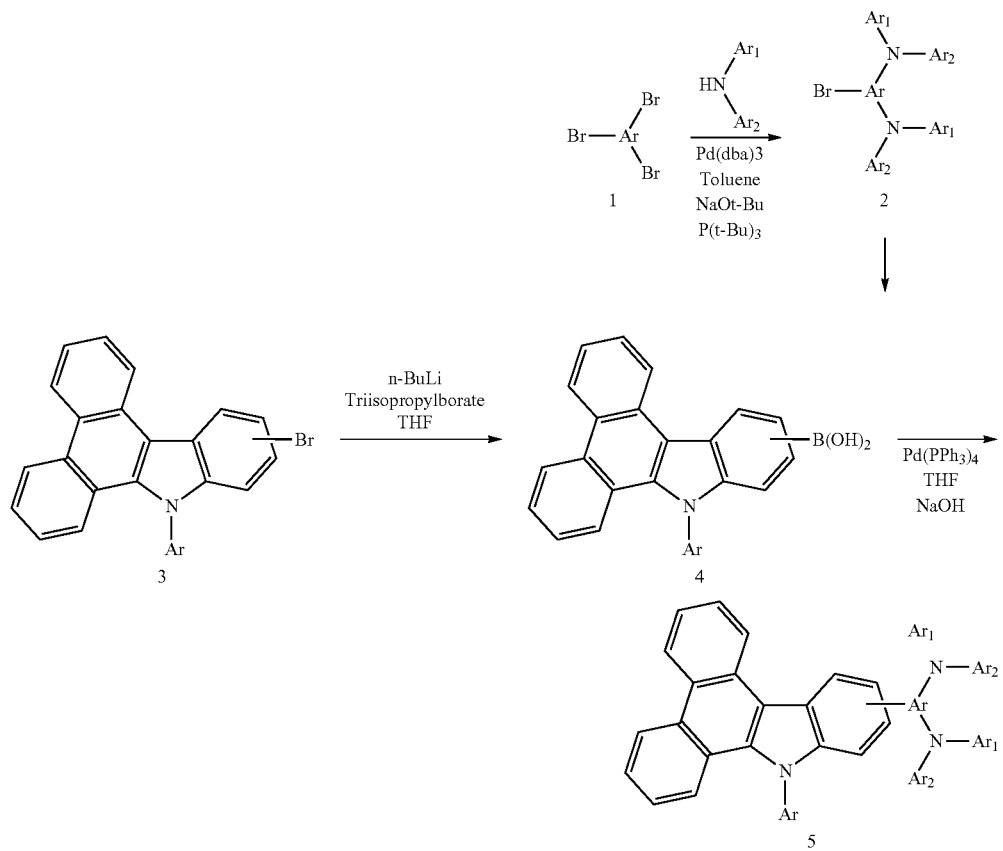

Synthesis Method of Compound

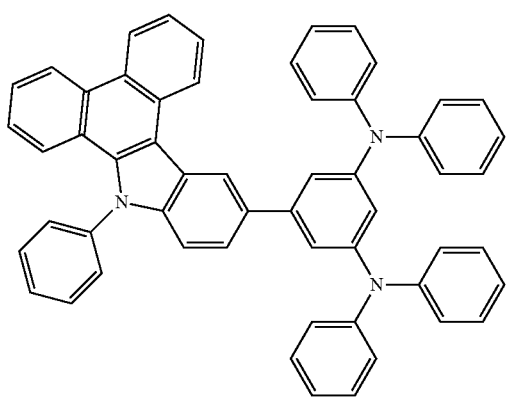 [SMILES: c1ccc(N(c2ccccc2)c2cc(-c3ccc4c(c3)c3c5ccccc5c5ccccc5c3n4-c3ccccc3)cc(N(c3ccccc3)c3ccccc3)c2)cc1]

Example 1-4

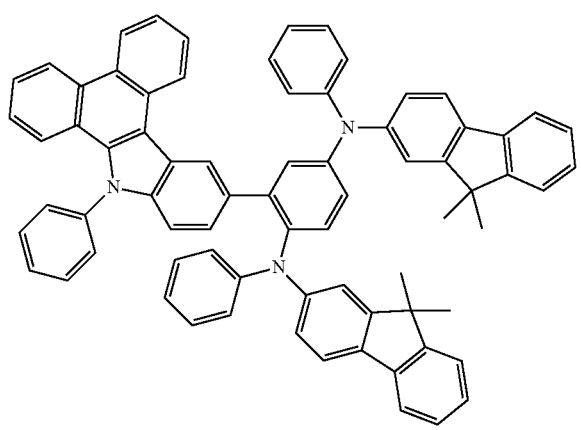 [SMILES: CC1(C)c2ccccc2-c2ccc(N(c3ccccc3)c3ccc(N(c4ccccc4)c4ccc5c(c4)C(C)(C)c4ccccc4-5)c(-c4ccc5c(c4)c4c6ccccc6c6ccccc6c4n5-c4ccccc4)c3)cc21]

The compound was synthesized (synthesis yield: 57%) in the same manner as described in the synthesis method of the compound

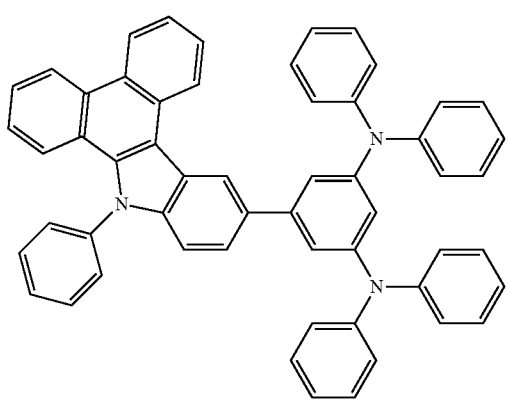 [SMILES: c1ccc(N(c2ccccc2)c2cc(-c3ccc4c(c3)c3c5ccccc5c5ccccc5c3n4-c3ccccc3)cc(N(c3ccccc3)c3ccccc3)c2)cc1]

except that instead of 4'-bromo-$N^3,N^3,N^5,N^5$-tetraphenylbiphenyl-3,5-diamine, 4'-bromo-$N^3,N^5$-bis(9,9-dimethyl-9H-fluoren-2-yl)-$N^3,N^5$-diphenylbiphenyl-3,5-diamine was used.

Furthermore,

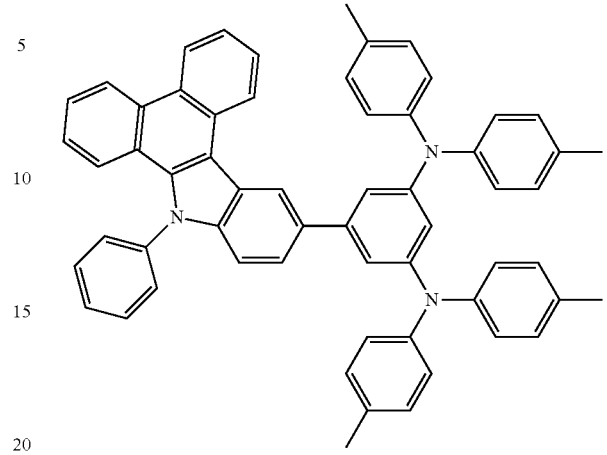

(Example 1-2) and

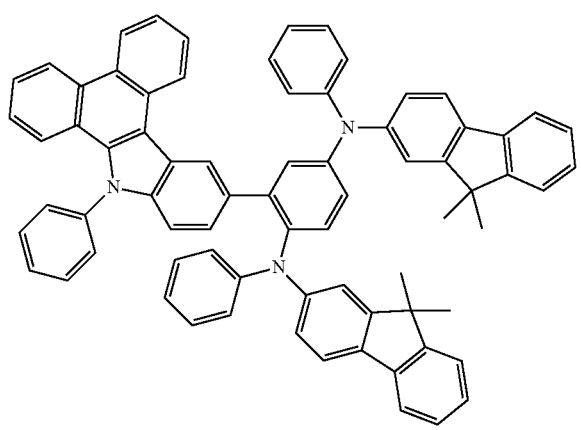 [SMILES: CC1(C)c2ccccc2-c2ccc(N(c3ccccc3)c3ccc(N(c4ccccc4)c4ccc5c(c4)C(C)(C)c4ccccc4-5)c(-c4ccc5c(c4)c4c6ccccc6c6ccccc6c4n5-c4ccccc4)c3)cc21]

(Example 1-3) were synthesized in the same manner as described in the synthesis methods of the above compounds.

Fabrication Test of Organic Electro-Luminescence Device

Then, an organic electro-luminescence element was manufactured through a conventional method by using the synthesized compounds as a light emitting host material of an emitting layer or as a hole transport layer. First, on an ITO layer (anode) formed on a glass substrate, a copper phthalocyanine (hereinafter, referred to as CuPc) film as a hole injection layer was vacuum-deposited with a thickness of 10 nm.

Then, for measurement as a green host, on this film, any one of the compounds according to Examples 1-1 to 1-4 was vacuum-deposited as a hole transport layer with a thickness of 30 nm. After the hole transport layer was formed, for the measurement on the hole transport layer, on the hole transport layer, an emitting layer doped with 7% BD-052X (Idemitus) with a thickness of 45 nm, (herein, BD-052X was a blue fluorescent dopant, and an emitting host material was 9,10-di(naphthalene-2-anthracene (AND)) was applied.

For measurement as a phosphorescent host material, a phosphorescent material was deposited to film-form an emitting layer. At the same time, as a phosphorescent Ir metal complex dopant, tris(2-phenylpyridine)iridium (hereinafter, referred to as Ir(ppy)₃) was added. Herein, in the emitting layer, the concentration of Ir(ppy)₃ was 10 wt %. As a hole blocking layer, (1,1-bisphenyl)-4-olato)bis(2-methyl-8-quinolinolato)aluminum (hereinafter, referred to as BAlq) was vacuum-deposited with a thickness of 10 nm, and then as an electron injection layer, tris(8-quinolinol)aluminum (hereinafter, referred to as Alq₃) was film-formed with a thickness of 40 nm. Then, LiF (alkali-metal halide) was deposited with a thickness of 0.2 nm, and Al was deposited with a thickness of 150 nm. The Al/LiF was used as a cathode while the organic electro-luminescence device was fabricated.

Comparison Test Example 1

In order to compare to the case where the inventive compounds were used as hole transport layers, instead of the inventive compound, the compound represented by Formula 10 below (hereinafter, referred to as NPD) was used as a hole transport material so as to fabricate an organic electro-luminescence device with the same structure as that of Test Example.

[Formula 10]

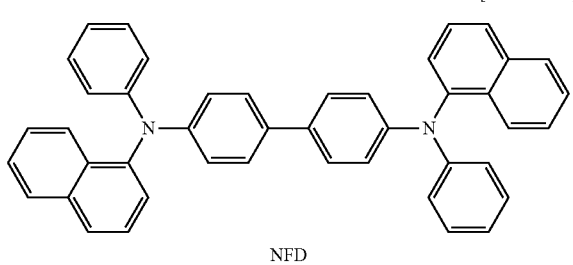

NFD

TABLE 3

| hole transport material | Voltage (V) | current density (mA/cm²) | luminous efficiency (cd/A) | chromaticity coordinates (x, y) |
|---|---|---|---|---|
| Example 1-1 | 6.5 | 12.98 | 8.5 | (0.15, 0.13) |
| Example 1-2 | 6.6 | 12.88 | 8.5 | (0.15, 0.13) |
| Example 1-3 | 6.6 | 13.01 | 8.4 | (0.15, 0.13) |
| Example 1-4 | 5.7 | 12.84 | 8.5 | (0.15, 0.14) |
| Comparative Example 1 (NPD) | 7.2 | 13.35 | 7.5 | (0.15, 0.15) |

From the results noted in Table 3, it can be seen that in an organic electro-luminescence device using the inventive material for the organic electro-luminescence device, it is possible to obtain long-life blue light with a high efficiency, and an improved color purity. Thus, the inventive material as a hole transport material for an organic electro-luminescence device can lower a driving voltage, and significantly improve the luminous efficiency and life span.

It is natural that even though the inventive compounds are employed in other organic material layers of an organic electro-luminescence element, e.g., an emitting layer, an emission assisting layer, an electron injection layer, an electron transport layer and a hole injection layer as well as a hole transport layer, it is possible to achieve the same effects.

Comparative Example 2

Hereinafter, Preparation Examples or Synthesis Examples of the compounds including the indoloacridine derivative, included in Formula 6, will be described. However, since there are many compounds including the indoloacridine derivative, included in Formula 6, one compound or two compounds from among the compounds included in Formula 6 will be exemplified. A person skilled in the art of the invention should realize that the inventive compounds including the indoloacridine derivative in which two tertiary amines are substituted can be prepared through Preparation Examples as described below although they are not exemplified.

Synthesis of Intermediate

[Reaction Sceme 17]

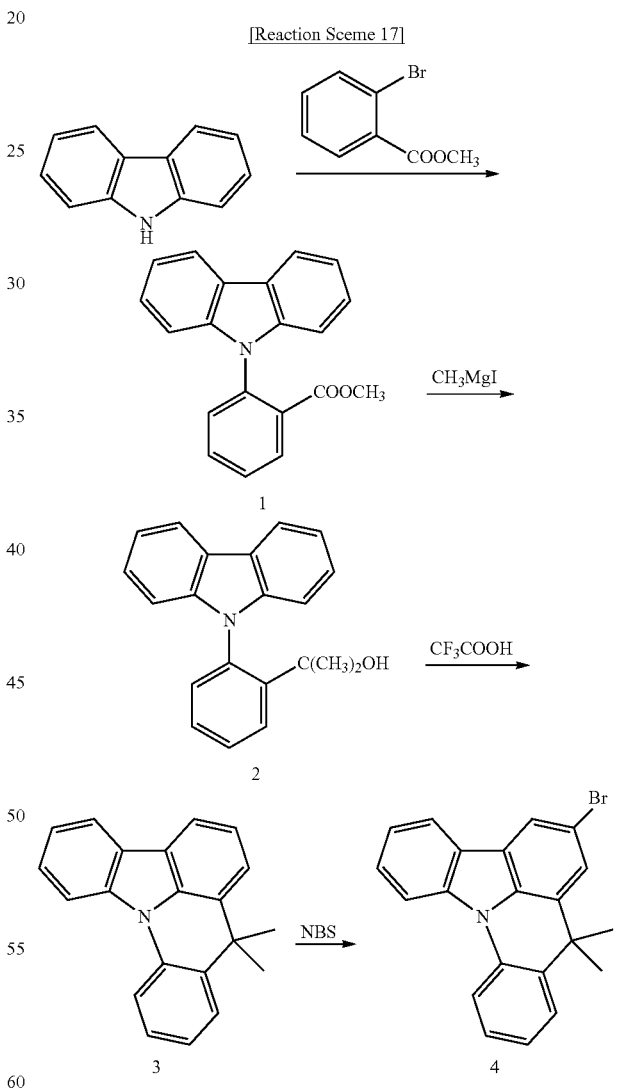

Step 1) Synthesis Method of Intermediate 1

Carbazole, methyl 2-bromobenzoate, K₂CO₃, Na₂SO₄, and Cu were added with Nitrobenzene, and heated under reflux at 190° C. for 24 hours. After the reaction was completed, the resultant product was extracted with MC and water, dried with MgSO$_4$, and concentrated. The produced compound was purified by column chromatography so as to give a required compound, the intermediate 1 (yield: 63%).

Step 2) Synthesis Method of Intermediate 2

The intermediate 1 was dissolved in benzene, and diluted in ether, and CH$_3$MgI was slowly dropped thereto at 0° C. The mixture was left for 30 minutes while stirred. Then, the resultant mixture was heated under reflux for 2 hours at 70° C. After the reaction was completed, the resultant product was extracted with MC and ice water, dried with MgSO$_4$, and concentrated. The produced compound was purified by column chromatography so as to give a required compound, the intermediate 2 (yield: 52%).

Step 3) Synthesis Method of Intermediate 3

The intermediate 2 was added to CF$_3$COOH, and then heated under reflux at 80° C. for about 2 hours. After the reaction was completed, the resultant product was extracted with MC and water, dried with MgSO$_4$, and concentrated. Then, the produced compound was purified by column chromatography so as to give a required compound, the intermediate 3 (yield: 59%).

Step 4) Synthesis Method of Intermediate 4

The intermediate 3 was added to MC, and NBS was added thereto, followed by a reaction with CF$_3$COOH for 5 hours at room temperature. After the reaction was completed, the resultant product was extracted with MC and water having sodium bicarbonate dissolved therein, dried with MgSO$_4$, and concentrated. Then, the produced compound was purified by column chromatography so as to give a required compound, the intermediate 4 (yield: 89%).

Step 5) Synthesis Method of Intermediate 6

Dibiphenyl-4-ylamine, 1,3,5-Tribromobenzene, Pd$_2$(dba)$_3$, Triphenylphosphine, and Sodium tert-butoxide were dissolved in toluene solvent, followed by stirring under reflux at 130° C. for 24 hours. After the reaction was completed, the resultant product was extracted with MC and water, dried with MgSO$_4$, and concentrated. Then, the produced compound was purified by column chromatography so as to give a required compound, the intermediate 6 (yield: 36%).

Step 6) Synthesis Method of Intermediate 8

The intermediate 7 was dissolved in THF, and at −78° C., n-BuLi was slowly dropped thereto, followed by stirring for about 1 hour. Then, Triisopropylborate was slowly dropped thereto at −78° C., followed by stirring. The resultant product was acidified with 1N HCl, extracted with water and EA, and dried with MgSO$_4$. Then, through recrystallization with hexane, the intermediate 8 was obtained (yield: 54%).

Step 7) Synthesis Method of Compound

A-1

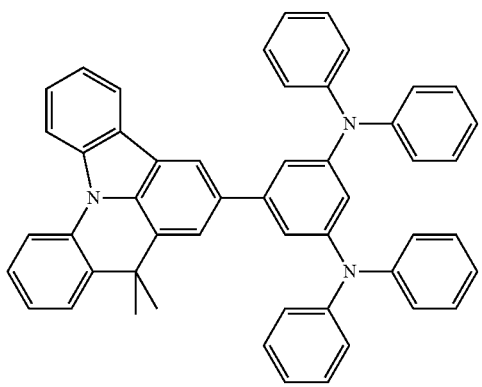

[Reaction Scheme 18]

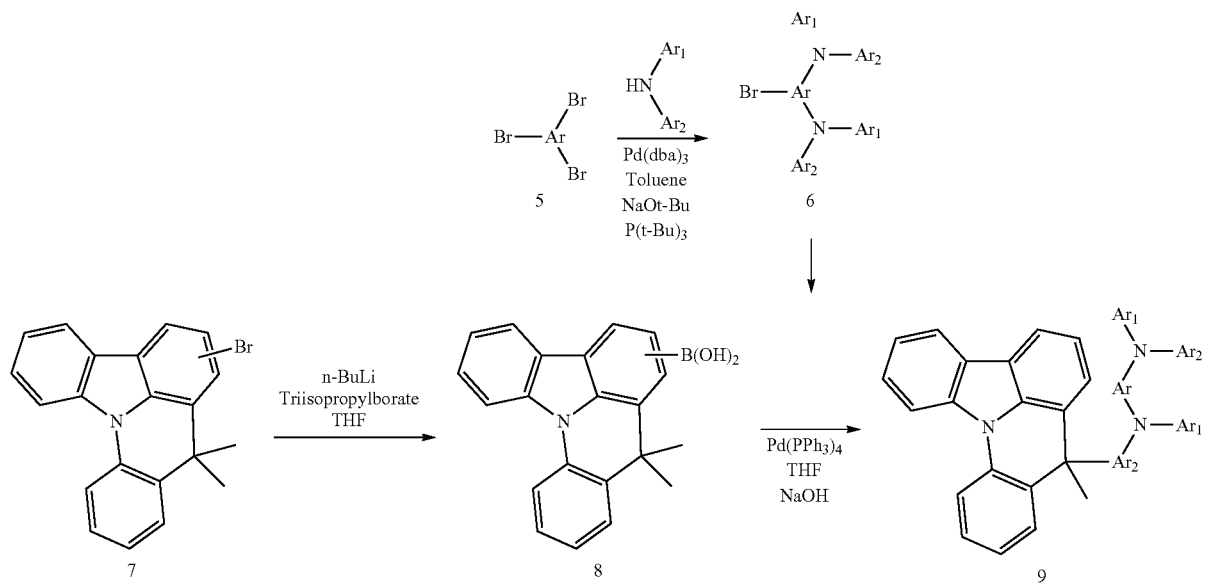

Example 2-1

The intermediate 7, $N^1,N^1,N^3,N^3$-tetra(biphenyl-4-yl)-5-bromobenzene-1,3-diamine, Pd(PPh$_3$)$_4$ and NaOH were dissolved in THF 500 ml, and water 250 ml, and the resultant solution was heated under reflux for 24 hours. The obtained solid was washed with water and methanol, and purified by silica gel column chromatography to give a white solid, a compound 4-B1 (yield: 73%).

Step 8) Synthesis Method of Compound

B-7

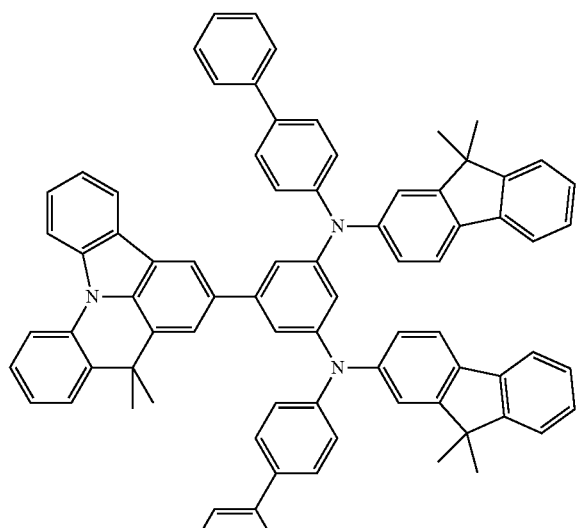

Example 2-2

The compound was obtained in the same manner as described in the synthesis method of the compound in Example 1 (synthesis yield: 70%) except that instead of $N^1,N^1,N^3,N^3$-tetra(biphenyl-4-yl)-5-bromobenzene-1,3-diamine, $N^1,N^3$-di(biphenyl-4-yl)-5-bromo-$N^1,N^3$-bis(9,9-dimethyl-9H-fluoren-2-yl)benzene-1,3-diamine was used.

Further, compound

A-7

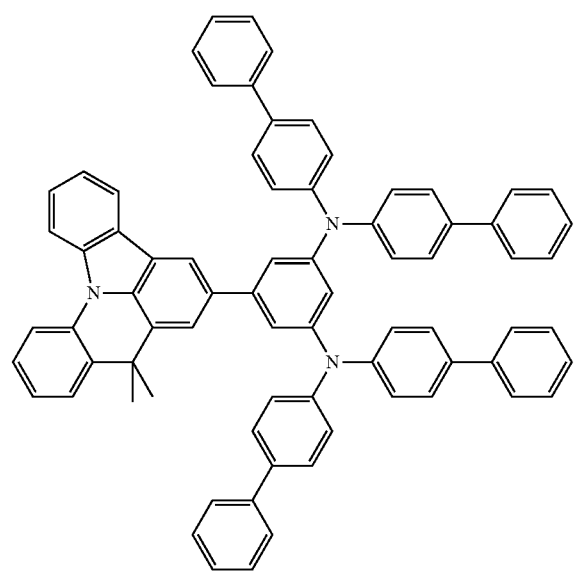

(Example 2-3) and

B-1

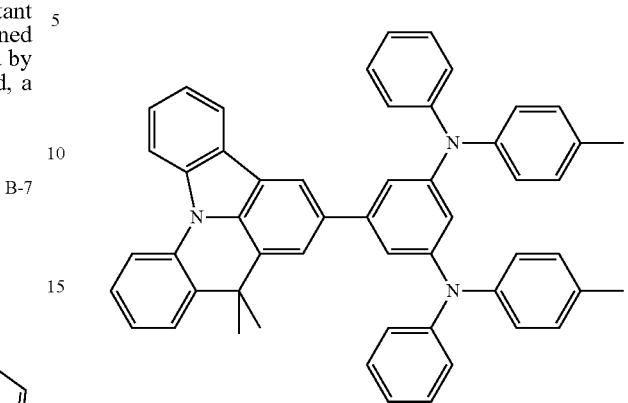

(Example 2-4) were synthesized in the same or similar manner as described in the synthesis method of compounds in Example 2-1 and Example 2-2 except that the starting material or the intermediate was varied.

Fabrication Test of Organic Electro-Luminescence Device

An organic electro-luminescence device was manufactured according to a conventional method by using each of compounds obtained by synthesis as a light emitting host material for an emitting layer as a hole transport layer.

First, on an ITO layer (anode) formed on a glass substrate, a 4,4',4"-tris(N-(2-naphtyl)-N-phenylamino)-triphenylamine (hereinafter, referred to as 2T-NATA) film as a hole injection layer was vacuum-deposited with a thickness of 10 nm.

Then, on this film, one of compounds of Examples 2-1 to 2-4 as a hole transport compound was vacuum-deposited with a thickness of 30 nm so as to form a hole transport layer. After the hole transport layer was formed, for the measurement on the developed material as the hole transport layer, on the hole transport layer, an emitting layer doped with 7% BD-052X (Idemitus), with a thickness of 45 nm, (herein, BD-052X was a blue fluorescent dopant, and an emitting host material was 9,10-di(naphthalene-2-anthracene (AND)) was applied.

As a hole blocking layer, (1,1-bisphenyl)-4-olato)bis(2-methyl-8-quinolinolato)aluminum (hereinafter, referred to as BAlq) was vacuum-deposited with a thickness of 10 nm, and then as an electron injection layer, tris(8-quinolinol)aluminum (hereinafter, referred to as Alq$_3$) was film-formed with a thickness of 40 nm. Then, LiF (alkali-metal halide) was deposited with a thickness of 0.2 nm, and Al was deposited with a thickness of 150 nm. The Al/LiF was used as a cathode while the organic electro-luminescence device was fabricated.

Comparison Test Example 2

In order to compare to the case where the inventive compounds were used as hole transport layers, instead of the inventive compound, the compound represented by Formula 10 was used as a hole transport material so as to fabricate an organic electro-luminescence device with the same structure as that of Test Example.

TABLE 4

| hole transport material | Voltage (V) | current density (mA/cm$^2$) | luminous efficiency (cd/A) | chromaticity coordinates (x, y) |
|---|---|---|---|---|
| Example 2-1 | 4.9 | 12.07 | 8.9 | (0.15, 0.14) |
| Example 2-2 | 5.1 | 12.12 | 8.7 | (0.15, 0.13) |
| Example 2-3 | 4.8 | 12.09 | 9.0 | (0.15, 0.14) |
| Example 2-4 | 5.0 | 12.30 | 8.4 | (0.15, 0.15) |
| Comparative Example 1 (NPD) | 6.0 | 13.35 | 7.5 | (0.15, 0.15) |

From the results noted in Table 4, it can be seen that in an organic electro-luminescence device using the inventive material for the organic electro-luminescence device, it is possible to obtain long-life blue light with a high efficiency, and an improved color purity. Thus, the inventive material as a hole transport material for an organic electro-luminescence device can lower a driving voltage, and significantly improve the luminous efficiency and life span.

It is natural that even though the inventive compounds are employed in other organic material layers of an organic electro-luminescence element, e.g., an emitting layer, an emission assisting layer, an electron injection layer, an electron transport layer and a hole injection layer as well as a hole transport layer, it is possible to achieve the same effects.

Comparative Example 3

Hereinafter, Preparation Examples or Synthesis Examples of the compounds including the carbazole derivative in which two tertiary amines are substituted, included in Formula 8, will be described. However since there are many compounds including the carbazole derivative in which two tertiary amines are substituted, included in Formula 1, only one compound or two compounds from among the compounds included in Formula 8 will be exemplified. A person skilled in the art of the invention should realize that the inventive compounds including the carbazole derivative in which two tertiary amines are substituted can be prepared through Preparation Examples as described below although they are not exemplified.

Synthesis Method of Intermediate

Hereinafter, Preparation Examples or Synthesis Examples of the compounds including the carbazole derivative included in Formula 8 will be described.

However since there are many compounds in which two tertiary amines are substituted, included in Formula 8, only one compound or two compounds from among the compounds will be exemplified.

A person skilled in the art of the invention should realize that the inventive compounds in which two tertiary amines are substituted can be prepared through Preparation Examples as described below although they are not exemplified.

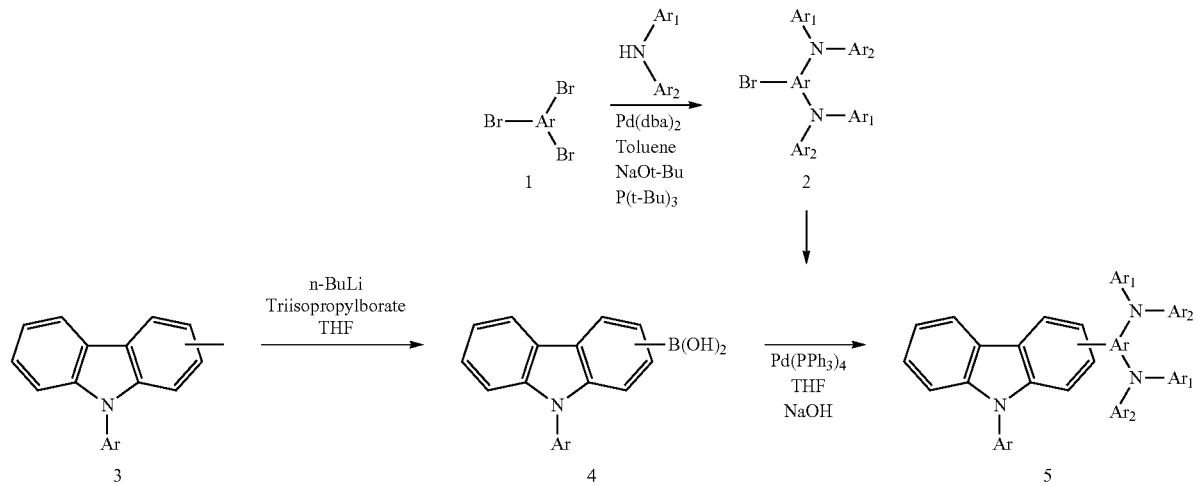

[Reaction Scheme 19]

Synthesis Method of Compound

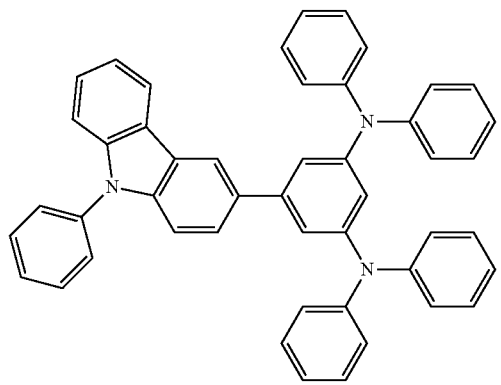 [SMILES: c1ccc(N(c2ccccc2)c2cc(-c3ccc4c(c3)c3ccccc3n4-c3ccccc3)cc(N(c3ccccc3)c3ccccc3)c2)cc1]

Example 3-1

9-phenyl-9H-carbazol-3-ylboronic acid, 4'-bromo-N$^3$,N$^3$, N$^5$,N$^5$-tetraphenylbiphenyl-3,5-diamine, Pd(PPh$_3$)$_4$ and K$_2$CO$_3$ were dissolved in THF 500 ml, and water 250 ml, and the resultant solution was heated under reflux for 24 hours. The obtained solid was washed with water and methanol, and purified by silica gel column chromatography to give a white solid, a compound

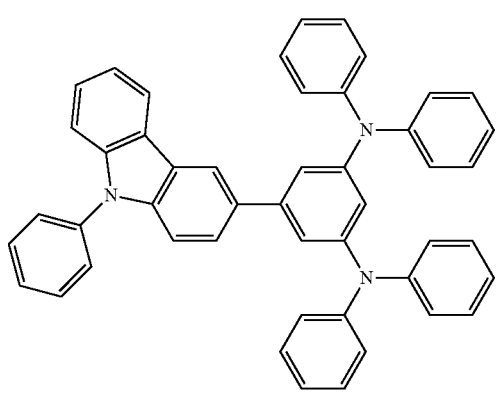 [SMILES: c1ccc(N(c2ccccc2)c2cc(-c3ccc4c(c3)c3ccccc3n4-c3ccccc3)cc(N(c3ccccc3)c3ccccc3)c2)cc1]

(yield: 71%).

Synthesis Method of Compound

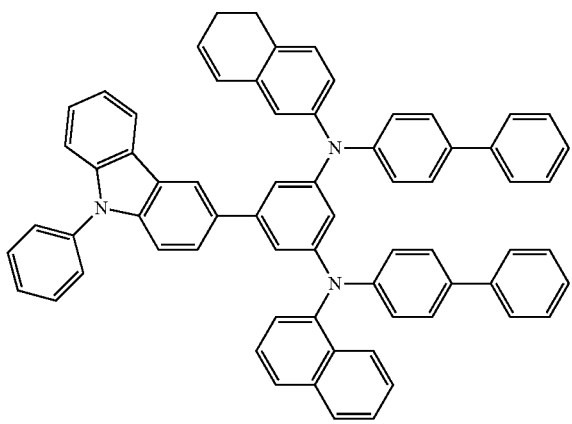 [SMILES: C1=Cc2cc(N(c3ccc(-c4ccccc4)cc3)c3cc(-c4ccc5c(c4)c4ccccc4n5-c4ccccc4)cc(N(c4ccc(-c5ccccc5)cc4)c4cccc5ccccc45)c3)ccc2CC1]

Example 3-4)

The compound was obtained in the same manner as described in the synthesis method of the compound in Example 3-1 except that instead of 4'-bromo-N³,N³,N⁵,N⁵-tetraphenylbiphenyl-3,5-diamine, N³,N⁵-di(biphenyl-4-yl)-4'-bromo-N³,N⁵-di(naphthalen-2-yl)biphenyl-3,5-diamine was used.

The compound

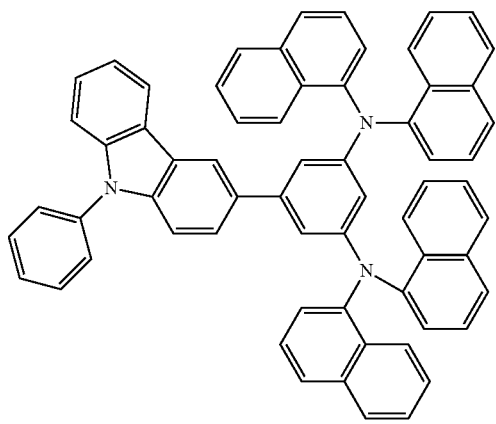 [SMILES: c1ccc(-n2c3ccccc3c3cc(-c4cc(N(c5cccc6ccccc56)c5cccc6ccccc56)cc(N(c5cccc6ccccc56)c5cccc6ccccc56)c4)ccc32)cc1]

in Example 3-2 and the compound

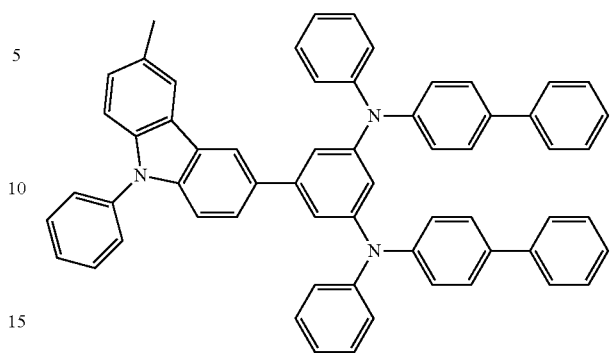

in Example 3-3 are obtained in the same manner as described in the compounds in Examples 3-1 and Examples 3-4, except that the starting material or the intermediate was replaced by a proper one.

Fabrication Test of Organic Electro-Luminescence Device

An organic electro-luminescence device was manufactured according to a conventional method by using each of compounds obtained by synthesis as a light emitting host material for an emitting layer as a hole transport layer. First, on an ITO layer (anode) formed on a glass substrate, a 4,4',4"tris(N(2naphtyl)Nphenylamino)triphenylamine (hereinafter, referred to as 2TNATA) film as a hole injection layer was vacuum-deposited with a thickness of 10 nm.

Then, on this film, one of compounds of Example 3-1 to 3-4 as a hole transport compound was vacuum-deposited with a thickness of 30 nm so as to form a hole transport layer. After the hole transport layer was formed, for the measurement on the developed material as the hole transport layer, on the hole transport layer, an emitting layer doped with 7% BD052X (Idemitus), with a thickness of 45 nm, (herein, BD052X was a blue fluorescent dopant, and an emitting host material was 9,10di(naphthalene2anthracene (AND)) was applied.

As a hole blocking layer, (1,1-bisphenyl)-4-olato)bis(2-methyl-8-quinolinolato)aluminum (hereinafter, referred to as BAlq) was vacuum-deposited with a thickness of 10 nm, and then as an electron injection layer, tris(8-quinolinol)aluminum (hereinafter, referred to as $Alq_3$) was film-formed with a thickness of 40 nm. Then, LiF (alkali-metal halide) was deposited with a thickness of 0.2 nm, and Al was deposited with a thickness of 150 nm. The Al/LiF was used as a cathode while the organic electro-luminescence device was fabricated.

Comparison Test Example 3

In order to compare to the case where the inventive compounds were used as hole transport layers, instead of the inventive compound, the compound represented by Formula 10 was used as a hole transport material so as to fabricate an organic electro-luminescence device with the same structure as that of Test Example.

TABLE 5

| hole transport material | voltage (V) | current density (mA/cm²) | luminous efficiency (cd/A) | chromaticity coordinates (x, y) |
|---|---|---|---|---|
| Example 1 | 6.2 | 12.21 | 9.7 | (0.15, 0.14) |
| Example 2 | 6.1 | 12.75 | 9.5 | (0.15, 0.14) |
| Example 3 | 6.4 | 12.69 | 9.0 | (0.15, 0.12) |
| Example 4 | 5.8 | 12.77 | 8.9 | (0.15, 0.14) |

TABLE 5-continued

| hole transport material | voltage (V) | current density (mA/cm²) | luminous efficiency (cd/A) | chromaticity coordinates (x, y) |
|---|---|---|---|---|
| Comparative Example 1 (NPB) | 7.2 | 13.35 | 7.5 | (0.15, 0.15) |

From the results noted in Table 5, it can be seen that in an organic electro-luminescence device using the inventive material for the organic electro-luminescence device, it is possible to obtain long-life blue light with a high efficiency, and an improved color purity. Thus, the inventive material as a hole transport material for an organic electro-luminescence device can lower a driving voltage, and significantly improve the luminous efficiency and life span.

It is natural that even though the inventive compounds are employed in other organic material layers of an organic electro-luminescence element, e.g., an emitting layer, an emission assisting layer, an electron injection layer, an electron transport layer and a hole injection layer as well as a hole transport layer, it is possible to achieve the same effects.

Although a preferred embodiment of the present invention has been described for illustrative purposes, those skilled in the art will appreciate that various modifications, additions and substitutions are possible, without departing from the scope and spirit of the invention as disclosed in the accompanying claims. Therefore, the embodiments disclosed in the present invention are intended to illustrate the scope of the technical idea of the present invention, and the scope of the present invention is not limited by the embodiment. The scope of the present invention shall be construed on the basis of the accompanying claims in such a manner that all of the technical ideas included within the scope equivalent to the claims belong to the present invention.

CROSS-REFERENCE TO RELATED APPLICATION

This application claims priority from and the benefit under 35 U.S.C. §119(a) of Korean Patent Application No. 10-2009-0106439, filed on Nov. 5, 2009, Korean Patent Application No. 10-2010-0011499, filed on Feb. 8, 2010, Korean Patent Application No. 10-2010-0031311, filed on Apr. 6, 2010, and Korean Patent Application No. 10-2010-0095400, filed on Sep. 30, 2010, which is hereby incorporated by reference for all purposes as if fully set forth herein. Further, this application claims the benefit of priority in other countries than U.S., which are hereby incorporated by reference herein.

The invention claimed is:

1. A compound represented by Formula below,

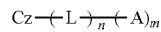
<Formula 1> wherein in Formula 1 above, (1) Cz represents a substituted or unsubstituted carbazole derivative represented by Formula 2 below,

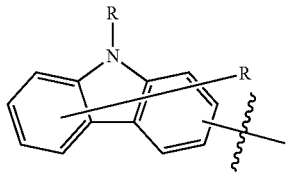
<Formula 2> wherein in Formula 2, each R is the same or different, and is independently selected from the group consisting of a hydrogen atom, deuterium, tritium, a substituted or unsubstituted aryl group having 5~60 nuclear carbon atoms, a substituted or unsubstituted hetero aryl group having 5~60 nuclear carbon atoms, a substituted or unsubstituted $C_1$~$C_{60}$ alkyl group, a substituted or unsubstituted $C_1$~$C_{60}$ alkoxy group, a substituted or unsubstituted aryloxy group having 5~60 nuclear carbon atoms, a substituted or unsubstituted arylthio group having 5~60 nuclear carbon atoms, a substituted or unsubstituted alkoxycarbonyl group having 5~60 nuclear carbon atoms, an amino group substituted by a substituted or unsubstituted alkyl or aryl group having 5~60 nuclear carbon atoms, a halogen atom, a cyano group, a nitro group, a hydroxyl group and a carboxyl group, and R optionally forms an aliphatic or hetero ring together with an adjacent R group, or N of carbazole optionally forms a ring together with an adjacent R group, (2) L is selected from the group including a substituted or unsubstituted arylene group having 5~40 nuclear carbon atoms, a substituted or unsubstituted hetero arylene group having 5~60 nuclear atoms, and a divalent or trivalent, substituted or unsubstituted aliphatic hydrocarbon group, and (3) A represents a diamine derivative represented by Formula 3 below,

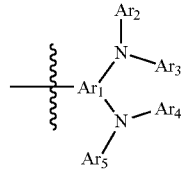
<Formula 3> wherein in Formula 3, $Ar_1$ is selected from the group including a substituted or unsubstituted pheny group, a biphenyl group, a 1-naphthyl group, a 2-naphthyl group, a thiophene group, a pyrrole group, a furan group, and a pyridyl group, and $Ar_2$ through $Ar_5$ are the same or different, and each is independently a substituted or unsubstituted aryl group having 6~60 nuclear atoms, or a substituted or unsubstituted heteroaryl group having 5~60 nuclear atoms, and 4) n represents an integer of 0 to 3 and m represents an integer of 1 to 4.

2. The compound as claimed in claim 1, wherein in Formula 3, $Ar_2$ through $Ar_5$ are selected from the group consisting of functional groups noted in Table 1 below,

TABLE 1

| | Ar₂, Ar₄ | Ar₃, Ar₅ |
|---|---|---|
| 1 | phenyl | phenyl |
| 2 | phenyl | 4-methylphenyl |
| 3 | phenyl | 3-methylphenyl |
| 4 | phenyl | 3,5-dimethylphenyl |
| 5 | phenyl | 4-methoxyphenyl |
| 6 | phenyl | 4-fluorophenyl |
| 7 | phenyl | 4-biphenyl |
| 8 | phenyl | 4'-phenyl-4-biphenyl |
| 9 | phenyl | 3'-phenyl-4-biphenyl |
| 9 | phenyl | 1-naphthyl |
| 10 | phenyl | 2-naphthyl |

TABLE 1-continued
| | Ar₂, Ar₄ | Ar₃, Ar₅ |
|---|---|---|
| 11 | 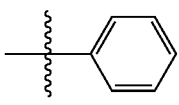 [SMILES: *c1ccccc1] | 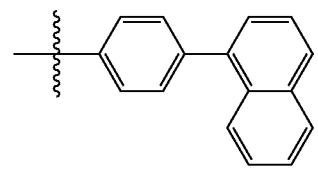 [SMILES: *c1ccc(-c2cccc3ccccc23)cc1] |
| 12 | 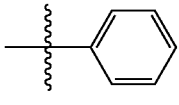 | 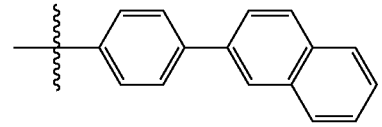 |
| 13 | 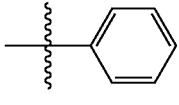 [SMILES: *c1ccccc1] | 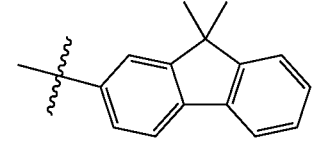 [SMILES: *c1ccc2c(c1)C(C)(C)c1ccccc1-2] |
| 14 | 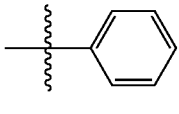 | 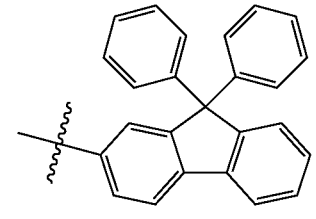 [SMILES: *c1ccc2c(c1)C(c1ccccc1)(c1ccccc1)c1ccccc1-2] |
| 15 | 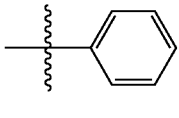 | 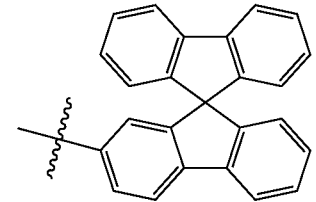 [SMILES: *c1ccc2c(c1)C1(c3ccccc3-c3ccccc31)c1ccccc1-2] |
| 16 | 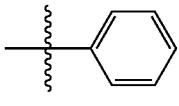 [SMILES: *c1ccccc1] | 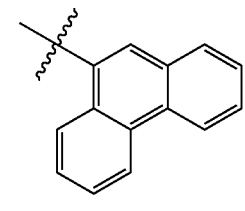 [SMILES: *c1cc2ccccc2c2ccccc12] |
| 17 | 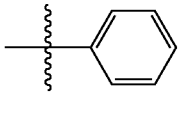 | 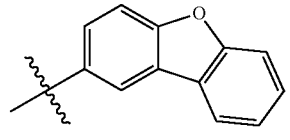 |
| 18 | 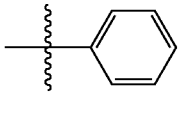 | 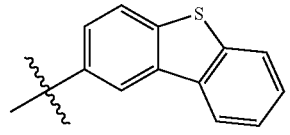 |
| 19 | 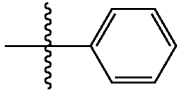 | 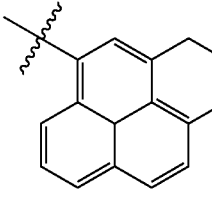 |

TABLE 1-continued
| | Ar$_2$, Ar$_4$ | Ar$_3$, Ar$_5$ |
|---|---|---|
| 20 | 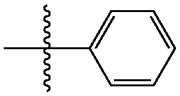 | 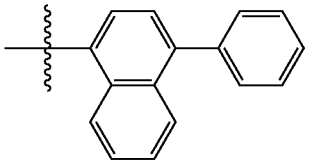 [SMILES: *c1ccc(-c2ccccc2)c2ccccc12] |
| 21 | 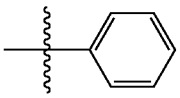 | 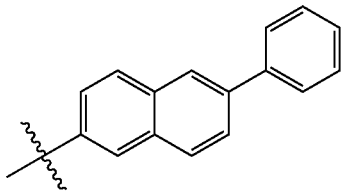 [SMILES: *c1ccc2cc(-c3ccccc3)ccc2c1] |
| 22 | 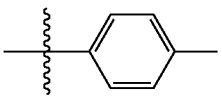 [SMILES: *c1ccc(C)cc1] | 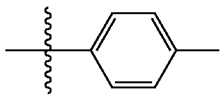 |
| 23 | 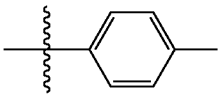 | 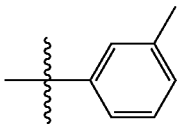 |
| 24 | 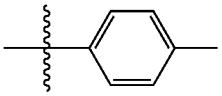 | 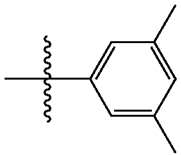 |
| 25 | 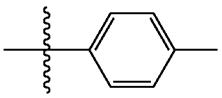 | 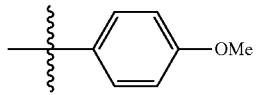 [SMILES: *c1ccc(OC)cc1] |
| 26 | 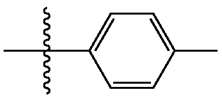 | 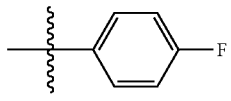 [SMILES: *c1ccc(F)cc1] |
| 27 | 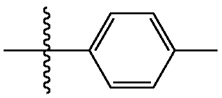 [SMILES: *c1ccc(C)cc1] | 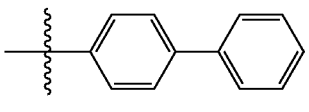 |
| 28 | 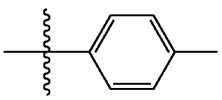 [SMILES: *c1ccc(C)cc1] | 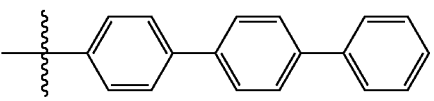 |
| 29 | 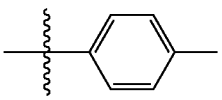 | 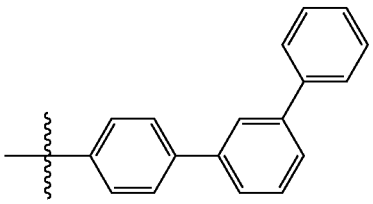 [SMILES: *c1ccc(-c2cccc(-c3ccccc3)c2)cc1] |

TABLE 1-continued
| | Ar₂, Ar₄ | Ar₃, Ar₅ |
|---|---|---|
| 30 | 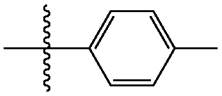 | 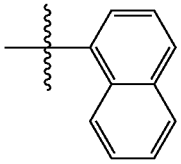 [SMILES: *c1cccc2ccccc12] |
| 31 | 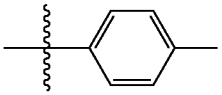 | 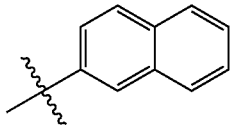 [SMILES: *c1ccc2ccccc2c1] |
| 32 | 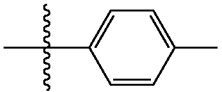 | 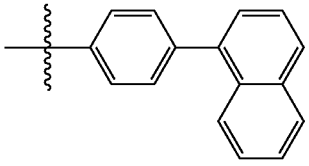 [SMILES: *c1ccc(-c2cccc3ccccc23)cc1] |
| 33 | 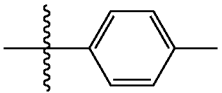 | 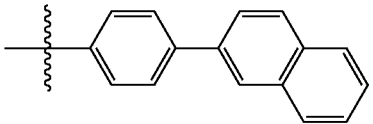 [SMILES: *c1ccc(-c2ccc3ccccc3c2)cc1] |
| 34 | 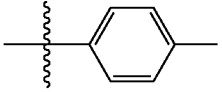 | 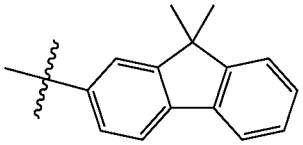 [SMILES: *c1ccc2c(c1)C(C)(C)c1ccccc1-2] |
| 35 | 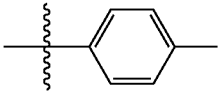 [SMILES: *c1ccc(C)cc1] | 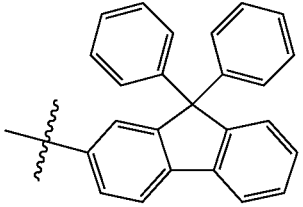 [SMILES: *c1ccc2c(c1)C(c1ccccc1)(c1ccccc1)c1ccccc1-2] |
| 36 | 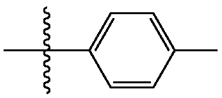 | 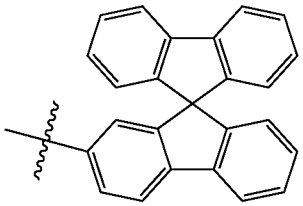 [SMILES: *c1ccc2c(c1)C1(c3ccccc3-c3ccccc31)c1ccccc1-2] |
| 37 | 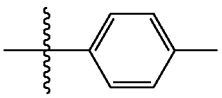 | 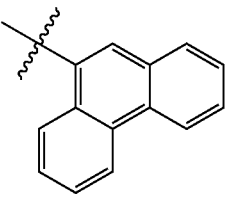 [SMILES: *c1cc2ccccc2c2ccccc12] |
| 38 | 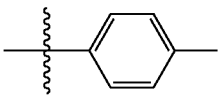 | 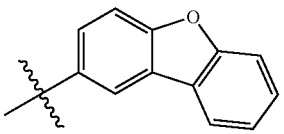 |

TABLE 1-continued
| | Ar₂, Ar₄ | Ar₃, Ar₅ |
|---|---|---|
| 39 | 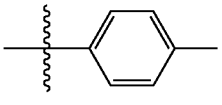 | 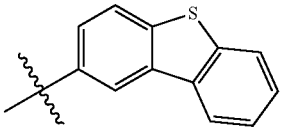 |
| 40 | 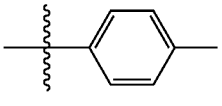 [SMILES: *c1ccc(C)cc1] | 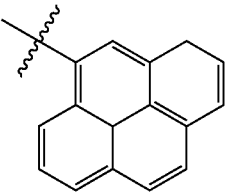 [SMILES: *C1=C2C=CC=C3C=CC4=C(C(=C1)CC=C4)C32] |
| 41 | 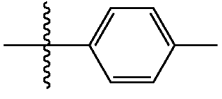 | 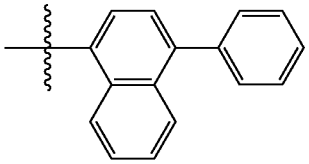 [SMILES: *c1ccc(-c2ccccc2)c2ccccc12] |
| 42 | 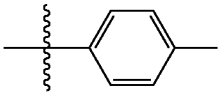 [SMILES: *c1ccc(C)cc1] | 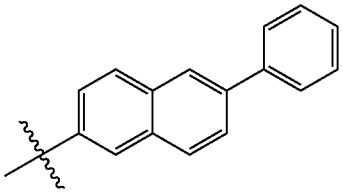 [SMILES: *c1ccc2cc(-c3ccccc3)ccc2c1] |
| 43 | 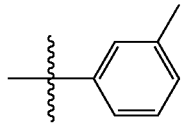 [SMILES: *c1cccc(C)c1] | 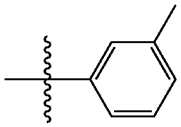 |
| 44 | 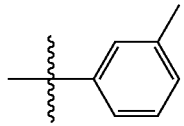 | 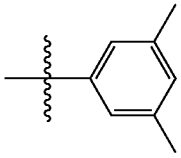 |
| 45 | 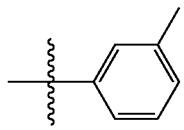 [SMILES: *c1cccc(C)c1] | 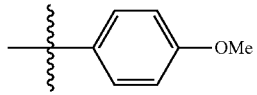 [SMILES: *c1ccc(OC)cc1] |
| 46 | 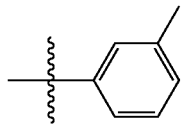 | 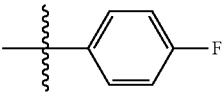 |
| 47 | 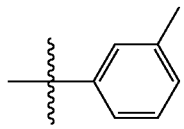 | 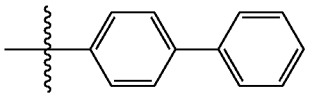 |
| 48 | 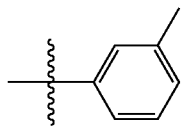 | 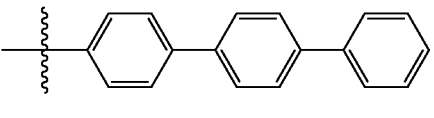 [SMILES: *c1ccc(-c2ccc(-c3ccccc3)cc2)cc1] |

TABLE 1-continued
| | Ar₂, Ar₄ | Ar₃, Ar₅ |
|---|---|---|
| 49 | 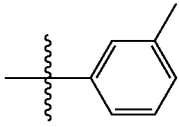 [SMILES: *c1cccc(C)c1] | 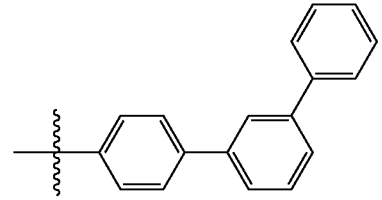 |
| 50 | 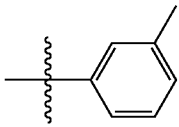 | 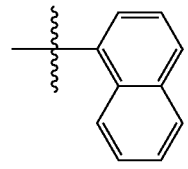 [SMILES: *c1cccc2ccccc12] |
| 51 | 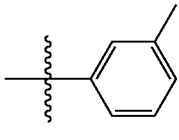 [SMILES: *c1cccc(C)c1] | 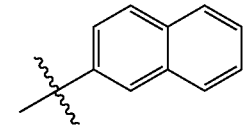 [SMILES: *c1ccc2ccccc2c1] |
| 52 | 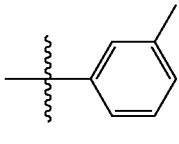 [SMILES: *c1cccc(C)c1] | 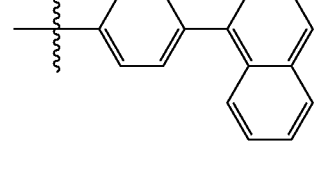 |
| 53 | 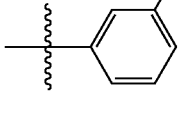 | 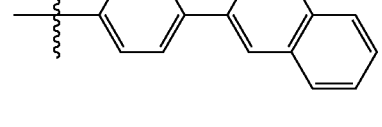 |
| 54 | 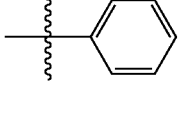 | 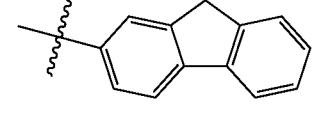 |
| 55 | 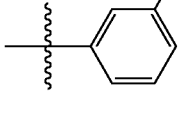 | 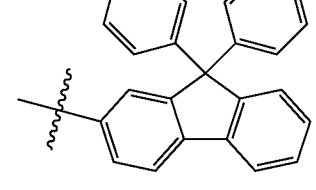 |
| 56 | 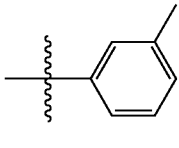 [SMILES: *c1cccc(C)c1] | 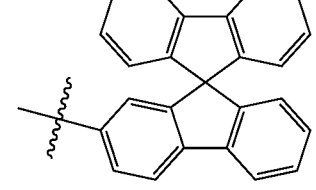 |

TABLE 1-continued

| | Ar₂, Ar₄ | Ar₃, Ar₅ |
|---|---|---|
| 57 | 3-phenylene | phenanthren-9-yl |
| 58 | 3-phenylene | dibenzofuran-2-yl |
| 59 | 3-phenylene | dibenzothiophen-2-yl |
| 60 | 3-phenylene | pyren-1-yl |
| 61 | 3-phenylene | 4-phenylnaphthalen-1-yl |
| 62 | 3-phenylene | 6-phenylnaphthalen-2-yl |
| 63 | 3,5-phenylene | 3,5-dimethylphenyl |
| 64 | 3,5-phenylene | 4-methoxyphenyl |
| 65 | 3,5-phenylene | 4-fluorophenyl |

TABLE 1-continued
| | Ar₂, Ar₄ | Ar₃, Ar₅ |
|---|---|---|
| 66 | 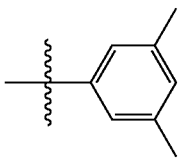 [SMILES: *c1cc(C)cc(C)c1] | 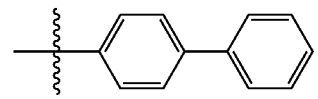 |
| 67 | 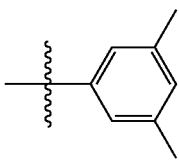 [SMILES: *c1cc(C)cc(C)c1] | 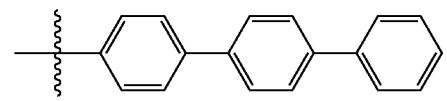 |
| 68 | 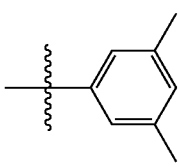 [SMILES: *c1cc(C)cc(C)c1] | 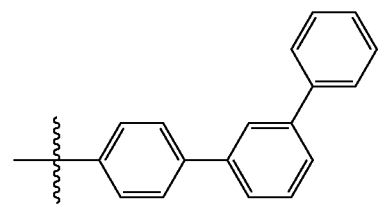 |
| 69 | 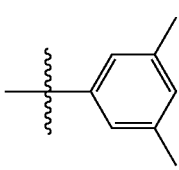 [SMILES: *c1cc(C)cc(C)c1] | 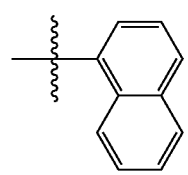 |
| 70 | 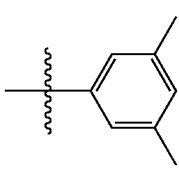 [SMILES: *c1cc(C)cc(C)c1] | 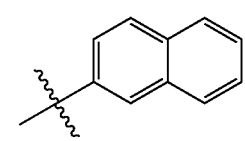 [SMILES: *c1ccc2ccccc2c1] |
| 71 | 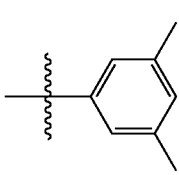 [SMILES: *c1cc(C)cc(C)c1] | 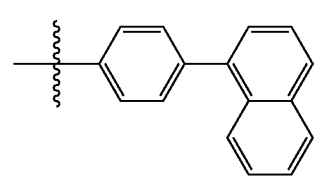 [SMILES: *c1ccc(-c2cccc3ccccc23)cc1] |
| 72 | 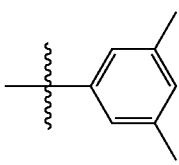 [SMILES: *c1cc(C)cc(C)c1] | 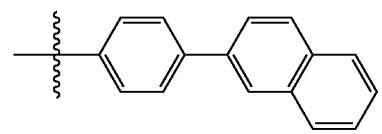 |
| 73 | 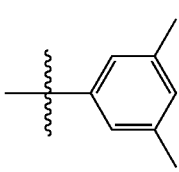 [SMILES: *c1cc(C)cc(C)c1] | 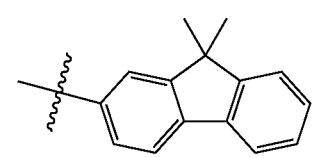 [SMILES: *c1ccc2c(c1)C(C)(C)c1ccccc1-2] |

TABLE 1-continued

| | Ar$_2$, Ar$_4$ | Ar$_3$, Ar$_5$ |
|---|---|---|
| 74 | 3,5-dimethylphenyl | 9,9-diphenylfluoren-2-yl |
| 75 | 3,5-dimethylphenyl | 9,9'-spirobifluoren-2-yl |
| 76 | 3,5-dimethylphenyl | phenanthren-9-yl |
| 77 | 3,5-dimethylphenyl | dibenzofuran-2-yl |
| 78 | 3,5-dimethylphenyl | dibenzothiophen-2-yl |
| 79 | 3,5-dimethylphenyl | pyren-1-yl |
| 80 | 3,5-dimethylphenyl | 4-phenylnaphthalen-1-yl |
| 81 | 3,5-dimethylphenyl | 6-phenylnaphthalen-2-yl |

TABLE 1-continued

| | Ar$_2$, Ar$_4$ | Ar$_3$, Ar$_5$ |
|---|---|---|
| 82 | 4-MeO-C$_6$H$_4$– | 4-MeO-C$_6$H$_4$– |
| 83 | 4-MeO-C$_6$H$_4$– | 4-F-C$_6$H$_4$– |
| 84 | 4-MeO-C$_6$H$_4$– | 4-biphenyl |
| 85 | 4-MeO-C$_6$H$_4$– | 4-(4-phenylphenyl)phenyl |
| 86 | 4-MeO-C$_6$H$_4$– | 4-(3-phenylphenyl)phenyl |
| 87 | 4-MeO-C$_6$H$_4$– | 1-naphthyl |
| 88 | 4-MeO-C$_6$H$_4$– | 2-naphthyl |
| 89 | 4-MeO-C$_6$H$_4$– | 4-(1-naphthyl)phenyl |
| 90 | 4-MeO-C$_6$H$_4$– | 4-(2-naphthyl)phenyl |
| 91 | 4-MeO-C$_6$H$_4$– | 9,9-dimethylfluoren-2-yl |

TABLE 1-continued
| | Ar₂, Ar₄ | Ar₃, Ar₅ |
|---|---|---|
| 92 | 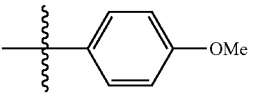 | 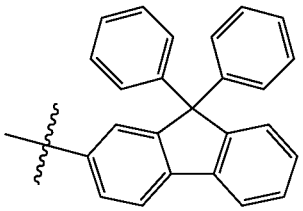 [SMILES: *c1ccc2c(c1)C(c1ccccc1)(c1ccccc1)c1ccccc1-2] |
| 93 | 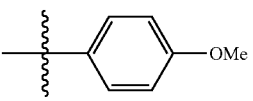 | 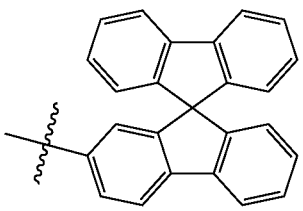 [SMILES: *c1ccc2c(c1)C1(c3ccccc3-c3ccccc31)c1ccccc1-2] |
| 94 | 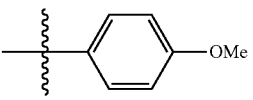 | 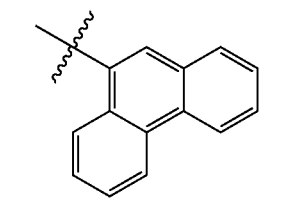 [SMILES: *c1cc2ccccc2c2ccccc12] |
| 95 | 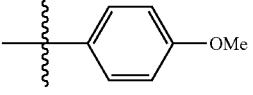 | 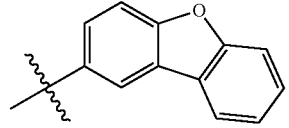 [SMILES: *c1ccc2oc3ccccc3c2c1] |
| 96 | 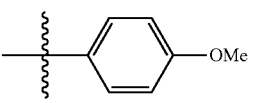 [SMILES: *c1ccc(OC)cc1] | 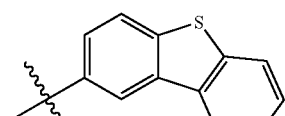 |
| 97 | 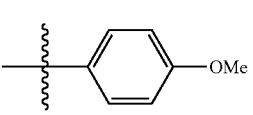 [SMILES: *c1ccc(OC)cc1] | 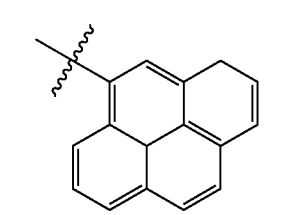 [SMILES: *C1=C2C=CC=C3C=CC4=C(C(=C1)CC=C4)C32] |
| 98 | 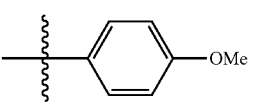 [SMILES: *c1ccc(OC)cc1] | 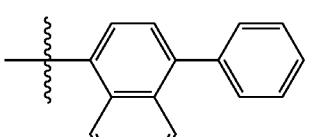 |
| 99 | 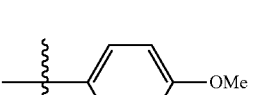 | 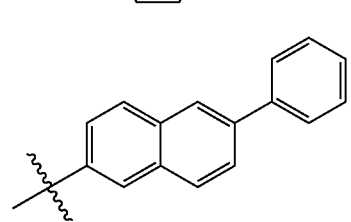 |

TABLE 1-continued
| | Ar₂, Ar₄ | Ar₃, Ar₅ |
|---|---|---|
| 100 | 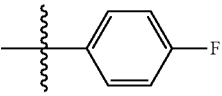 [SMILES: *c1ccc(F)cc1] | 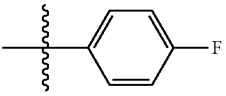 |
| 101 | 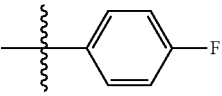 [SMILES: *c1ccc(F)cc1] | 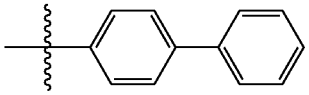 |
| 102 | 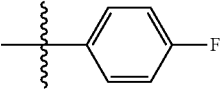 [SMILES: *c1ccc(F)cc1] | 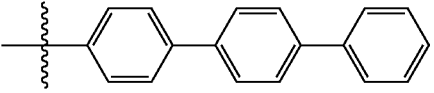 |
| 103 | 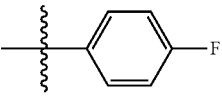 [SMILES: *c1ccc(F)cc1] | 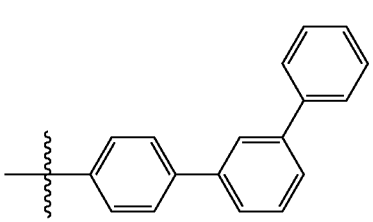 [SMILES: *c1ccc(-c2cccc(-c3ccccc3)c2)cc1] |
| 104 | 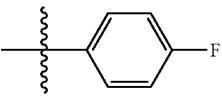 [SMILES: *c1ccc(F)cc1] | 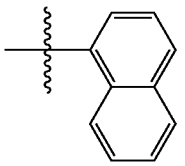 |
| 105 | 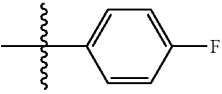 | 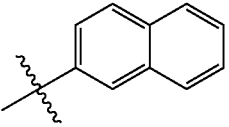 [SMILES: *c1ccc2ccccc2c1] |
| 106 | 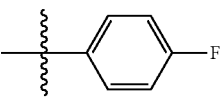 [SMILES: *c1ccc(F)cc1] | 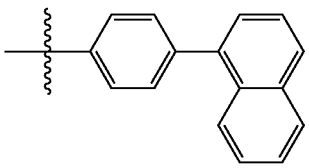 [SMILES: *c1ccc(-c2cccc3ccccc23)cc1] |
| 107 | 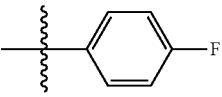 [SMILES: *c1ccc(F)cc1] | 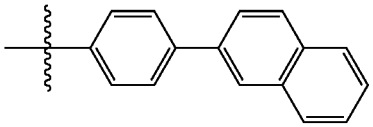 [SMILES: *c1ccc(-c2ccc3ccccc3c2)cc1] |
| 108 | 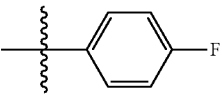 | 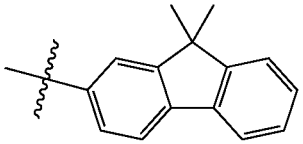 [SMILES: *c1ccc2c(c1)C(C)(C)c1ccccc1-2] |
| 109 | 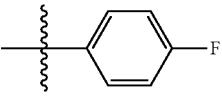 | 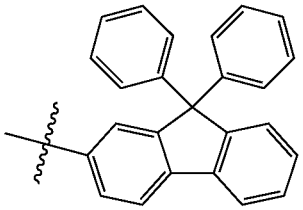 [SMILES: *c1ccc2c(c1)C(c1ccccc1)(c1ccccc1)c1ccccc1-2] |

TABLE 1-continued
| | Ar₂, Ar₄ | Ar₃, Ar₅ |
|---|---|---|
| 110 | 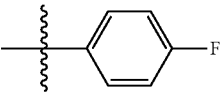 | 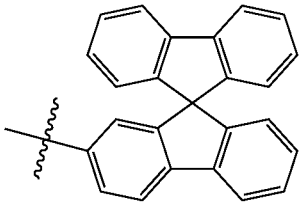 [SMILES: *c1ccc2c(c1)C1(c3ccccc3-c3ccccc31)c1ccccc1-2] |
| 111 | 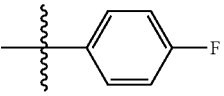 | 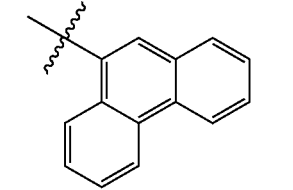 [SMILES: *c1cc2ccccc2c2ccccc12] |
| 112 | 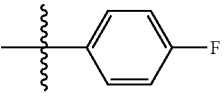 [SMILES: *c1ccc(F)cc1] | 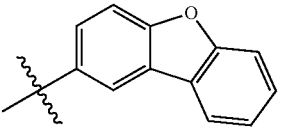 |
| 113 | 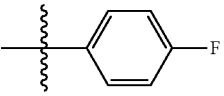 | 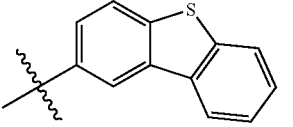 [SMILES: *c1ccc2sc3ccccc3c2c1] |
| 114 | 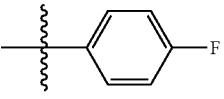 [SMILES: *c1ccc(F)cc1] | 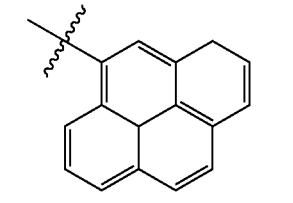 [SMILES: *C1=C2C=CC=C3C=CC4=C(C(=C1)CC=C4)C32] |
| 115 | 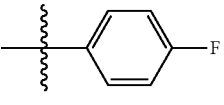 | 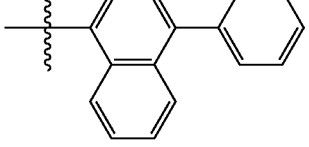 |
| 116 | 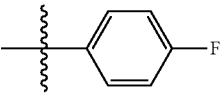 [SMILES: *c1ccc(F)cc1] | 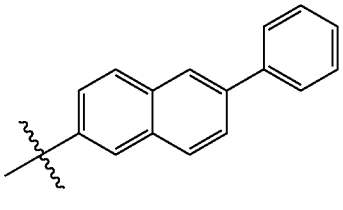 [SMILES: *c1ccc2cc(-c3ccccc3)ccc2c1] |
| 117 | 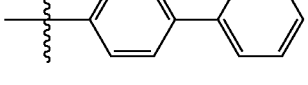 | 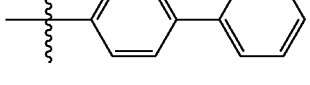 |
| 118 | 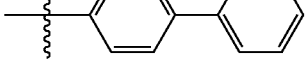 | 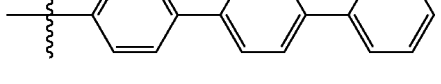 |

TABLE 1-continued

| | Ar₂, Ar₄ | Ar₃, Ar₅ |
|---|---|---|
| 119 | 4-biphenyl | 4-(3-phenylphenyl)phenyl |
| 120 | 4-biphenyl | 1-naphthyl |
| 121 | 4-biphenyl | 2-naphthyl |
| 122 | 4-biphenyl | 4-(1-naphthyl)phenyl |
| 123 | 4-biphenyl | 4-(2-naphthyl)phenyl |
| 124 | 4-biphenyl | 9,9-dimethylfluoren-2-yl |
| 125 | 4-biphenyl | 9,9-diphenylfluoren-2-yl |
| 126 | 4-biphenyl | 9,9'-spirobifluoren-2-yl |

TABLE 1-continued

| | Ar₂, Ar₄ | Ar₃, Ar₅ |
|---|---|---|
| 127 | biphenyl | phenanthren-9-yl |
| 128 | biphenyl | dibenzofuran-2-yl |
| 129 | biphenyl | dibenzothiophen-2-yl |
| 130 | biphenyl | pyren-1-yl |
| 131 | biphenyl | 4-phenylnaphthalen-1-yl |
| 132 | biphenyl | 6-phenylnaphthalen-2-yl |
| 133 | p-terphenyl | p-terphenyl |
| 134 | p-terphenyl | 3'-phenylbiphenyl |
| 135 | p-terphenyl | naphthalen-1-yl |

TABLE 1-continued

| | Ar₂, Ar₄ | Ar₃, Ar₅ |
|---|---|---|
| 136 | | |
| 137 | | |
| 138 | | |
| 139 | | |
| 140 | | |
| 141 | | |
| 142 | | |
| 143 | | |
| 144 | | |

TABLE 1-continued

| | Ar₂, Ar₄ | Ar₃, Ar₅ |
|---|---|---|
| 145 | p-terphenyl | pyrenyl |
| 146 | p-terphenyl | 4-phenylnaphthalen-1-yl |
| 147 | p-terphenyl | 6-phenylnaphthalen-2-yl |
| 148 | 3'-phenyl-biphenyl-4-yl | 3'-phenyl-biphenyl-4-yl |
| 149 | 3'-phenyl-biphenyl-4-yl | naphthalen-1-yl |
| 150 | 3'-phenyl-biphenyl-4-yl | naphthalen-2-yl |
| 151 | 3'-phenyl-biphenyl-4-yl | 4-(naphthalen-1-yl)phenyl |

TABLE 1-continued
| Ar₂, Ar₄ | Ar₃, Ar₅ |
|---|---|
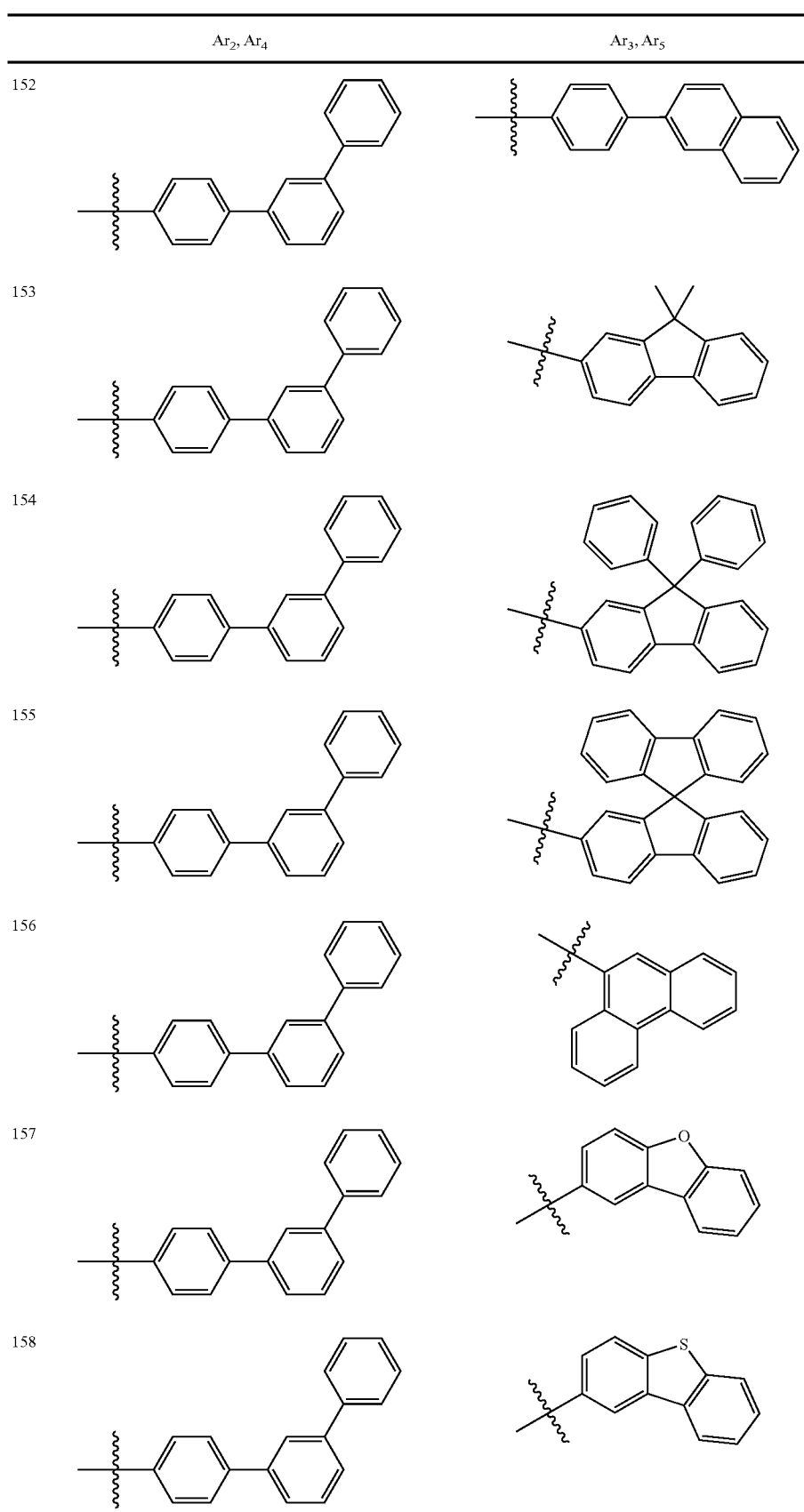

TABLE 1-continued
| | Ar₂, Ar₄ | Ar₃, Ar₅ |
|---|---|---|
| 159 | 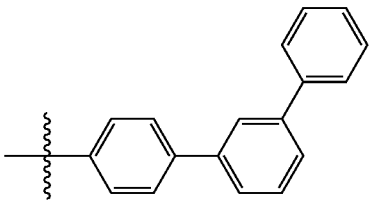 [SMILES: *c1ccc(-c2cccc(-c3ccccc3)c2)cc1] | 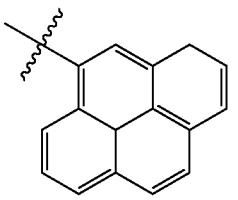 [SMILES: *C1=C2C=CC=C3C=CC4=C(C(=C1)CC=C4)C32] |
| 160 | 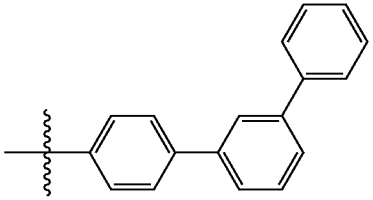 | 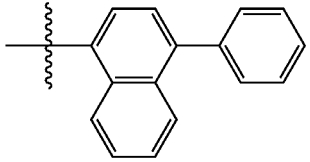 [SMILES: *c1ccc(-c2ccccc2)c2ccccc12] |
| 161 | 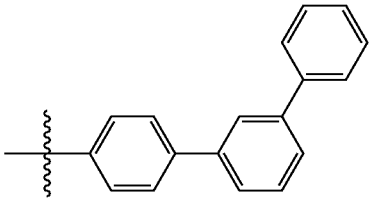 [SMILES: *c1ccc(-c2cccc(-c3ccccc3)c2)cc1] | 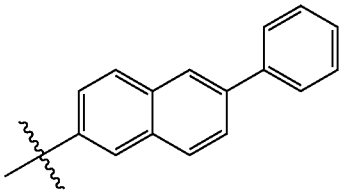 [SMILES: *c1ccc2cc(-c3ccccc3)ccc2c1] |
| 162 | 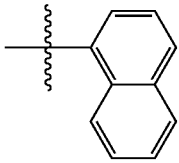 [SMILES: *c1cccc2ccccc12] | 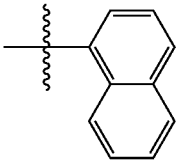 [SMILES: *c1cccc2ccccc12] |
| 163 | 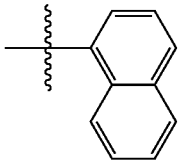 [SMILES: *c1cccc2ccccc12] | 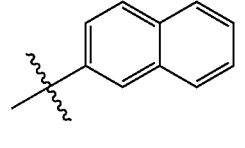 [SMILES: *c1ccc2ccccc2c1] |
| 164 | 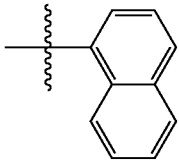 [SMILES: *c1cccc2ccccc12] | 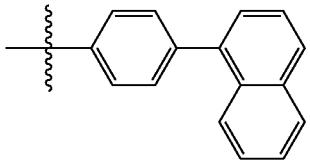 [SMILES: *c1ccc(-c2cccc3ccccc23)cc1] |
| 165 | 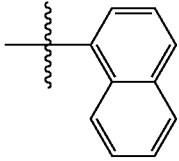 [SMILES: *c1cccc2ccccc12] | 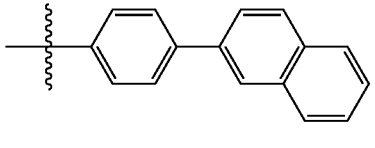 [SMILES: *c1ccc(-c2ccc3ccccc3c2)cc1] |
| 166 | 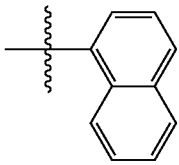 [SMILES: *c1cccc2ccccc12] | 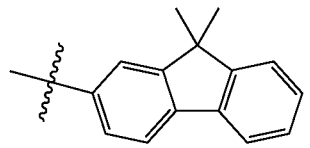 [SMILES: *c1ccc2c(c1)C(C)(C)c1ccccc1-2] |

TABLE 1-continued

| | Ar₂, Ar₄ | Ar₃, Ar₅ |
|---|---|---|
| 167 | 1-naphthyl | 9,9-diphenylfluoren-2-yl |
| 168 | 1-naphthyl | 9,9'-spirobifluoren-2-yl |
| 170 | 1-naphthyl | phenanthren-9-yl |
| 171 | 1-naphthyl | dibenzofuran-2-yl |
| 172 | 1-naphthyl | dibenzothiophen-2-yl |
| 173 | 1-naphthyl | pyren-1-yl |
| 174 | 1-naphthyl | 4-phenylnaphthalen-1-yl |
| 175 | 1-naphthyl | 6-phenylnaphthalen-2-yl |

TABLE 1-continued
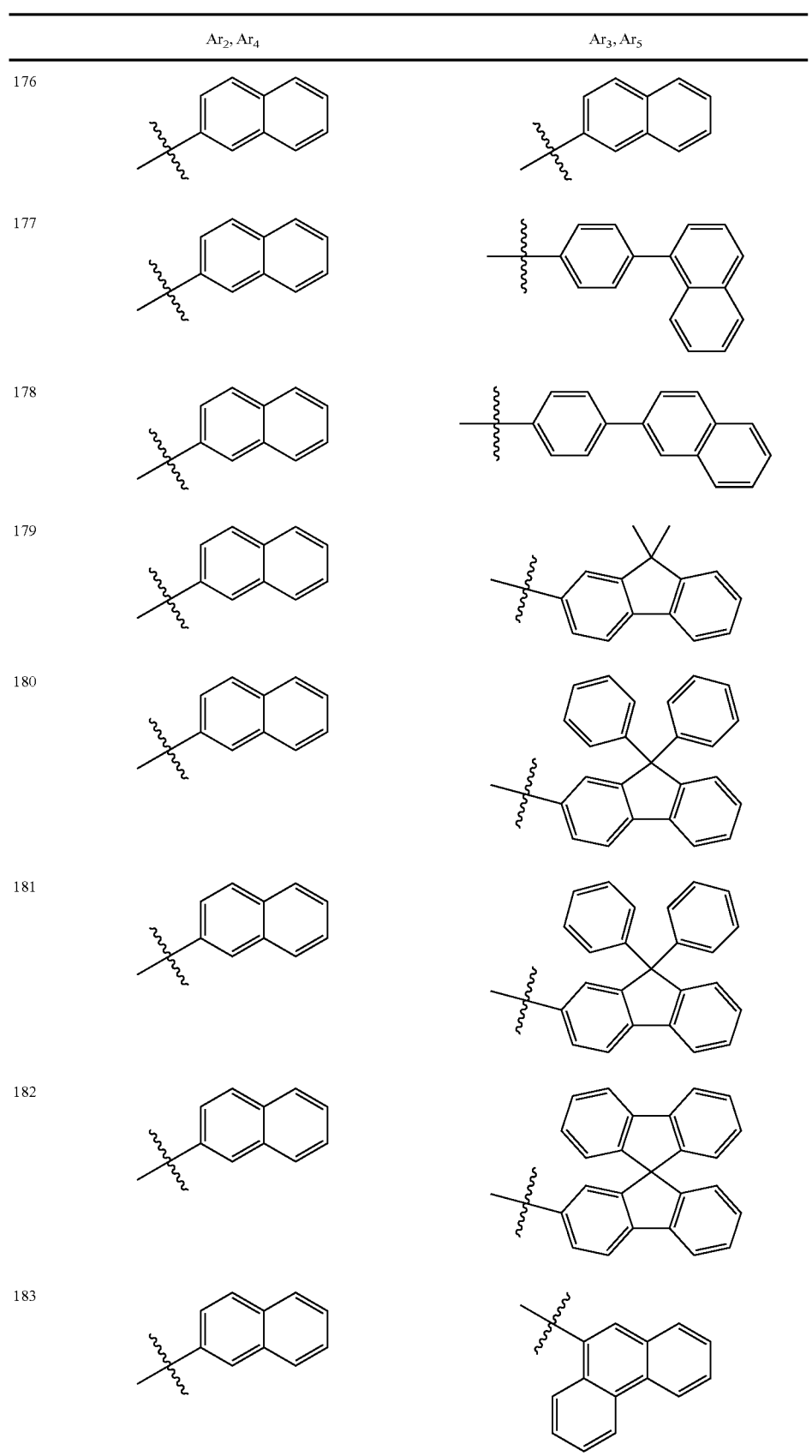

US 9,102,616 B2
TABLE 1-continued
| | Ar₂, Ar₄ | Ar₃, Ar₅ |
|---|---|---|
| 184 | 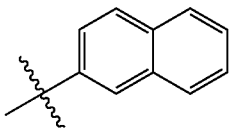 [SMILES: *c1ccc2ccccc2c1] | 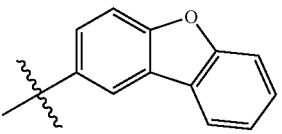 |
| 185 | 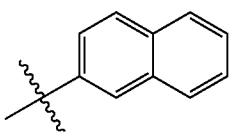 [SMILES: *c1ccc2ccccc2c1] | 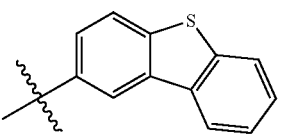 |
| 186 | 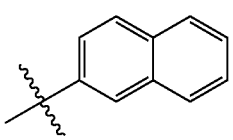 [SMILES: *c1ccc2ccccc2c1] | 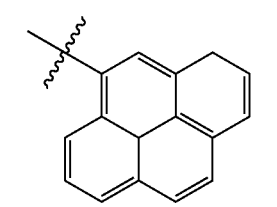 [SMILES: *C1=C2C=CC=C3C=CC4=C(C(=C1)CC=C4)C32] |
| 187 | 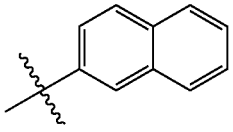 [SMILES: *c1ccc2ccccc2c1] | 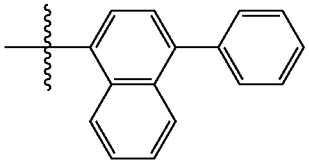 |
| 188 | 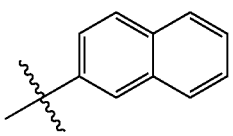 [SMILES: *c1ccc2ccccc2c1] | 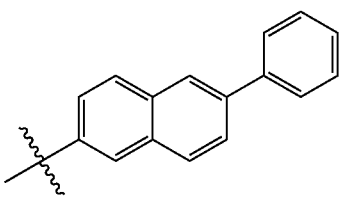 [SMILES: *c1ccc2cc(-c3ccccc3)ccc2c1] |
| 189 | 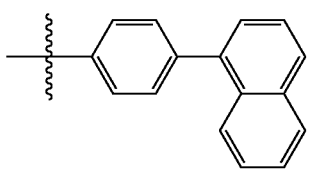 [SMILES: *c1ccc(-c2cccc3ccccc23)cc1] | 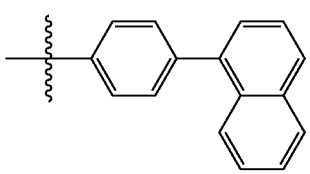 [SMILES: *c1ccc(-c2cccc3ccccc23)cc1] |
| 190 | 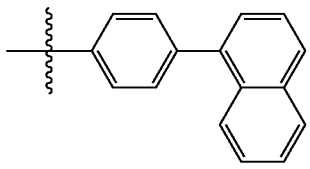 [SMILES: *c1ccc(-c2cccc3ccccc23)cc1] | 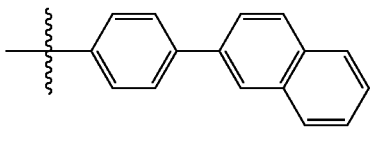 [SMILES: *c1ccc(-c2ccc3ccccc3c2)cc1] |
| 191 | 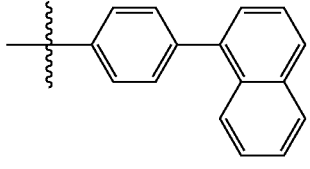 [SMILES: *c1ccc(-c2cccc3ccccc23)cc1] | 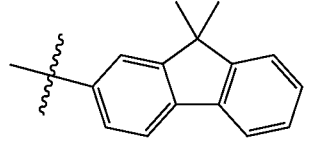 [SMILES: *c1ccc2c(c1)C(C)(C)c1ccccc1-2] |

TABLE 1-continued
| Ar₂, Ar₄ | Ar₃, Ar₅ |
|---|---|
| 192 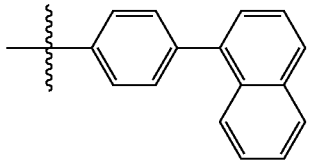 [SMILES: *c1ccc(-c2cccc3ccccc23)cc1] | 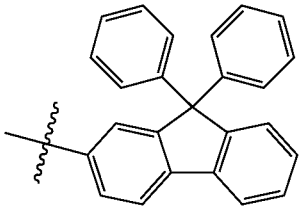 [SMILES: *c1ccc2c(c1)C(c1ccccc1)(c1ccccc1)c1ccccc1-2] |
| 193 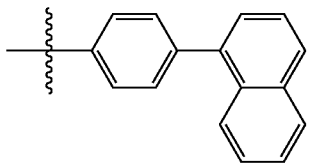 [SMILES: *c1ccc(-c2cccc3ccccc23)cc1] | 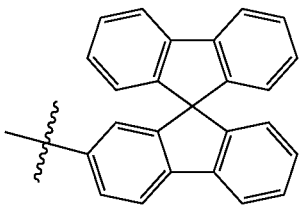 [SMILES: *c1ccc2c(c1)C1(c3ccccc3-c3ccccc31)c1ccccc1-2] |
| 194 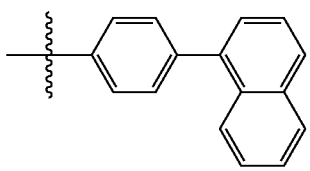 [SMILES: *c1ccc(-c2cccc3ccccc23)cc1] | 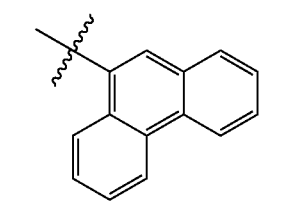 [SMILES: *c1cc2ccccc2c2ccccc12] |
| 195 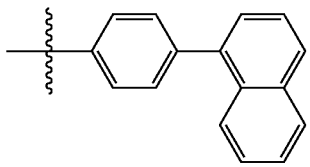 [SMILES: *c1ccc(-c2cccc3ccccc23)cc1] | 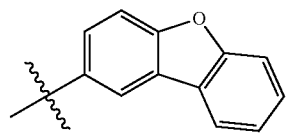 |
| 196 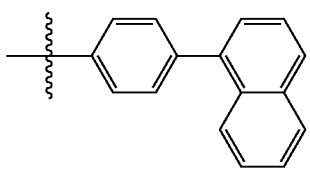 [SMILES: *c1ccc(-c2cccc3ccccc23)cc1] | 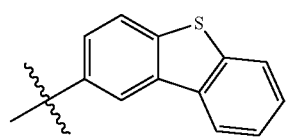 |
| 197 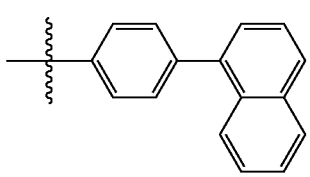 [SMILES: *c1ccc(-c2cccc3ccccc23)cc1] | 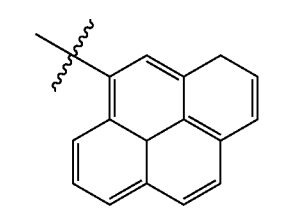 [SMILES: *C1=C2C=CC=C3C=CC4=C(C(=C1)CC=C4)C32] |
| 198 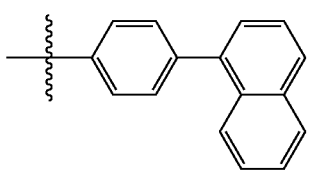 [SMILES: *c1ccc(-c2cccc3ccccc23)cc1] | 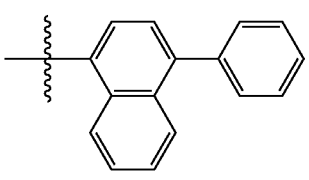 [SMILES: *c1ccc(-c2ccccc2)c2ccccc12] |
| 199 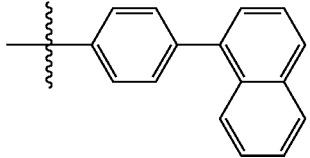 [SMILES: *c1ccc(-c2cccc3ccccc23)cc1] | 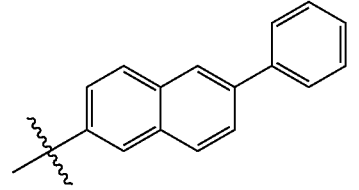 [SMILES: *c1ccc2cc(-c3ccccc3)ccc2c1] |

TABLE 1-continued
| | Ar₂, Ar₄ | Ar₃, Ar₅ |
|---|---|---|
| 200 | 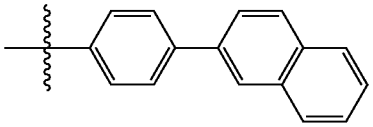 | 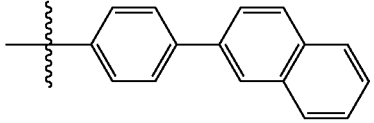 [SMILES: *c1ccc(-c2ccc3ccccc3c2)cc1] |
| 201 | 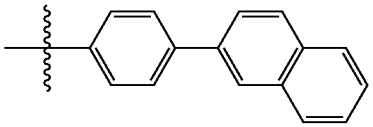 [SMILES: *c1ccc(-c2ccc3ccccc3c2)cc1] | 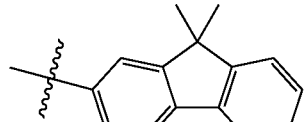 |
| 202 | 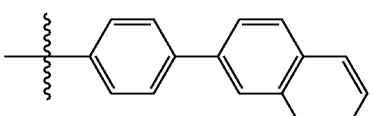 | 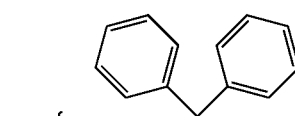 |
| 203 | 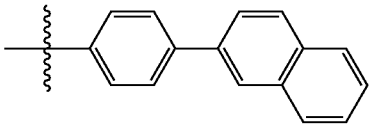 [SMILES: *c1ccc(-c2ccc3ccccc3c2)cc1] | 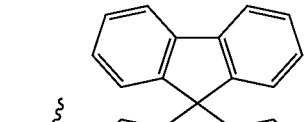 |
| 204 | 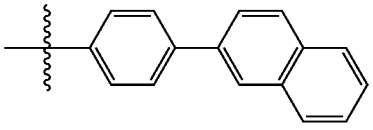 | 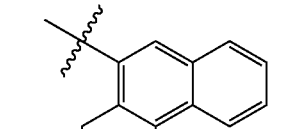 |
| 205 | 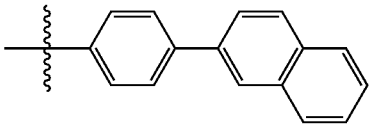 [SMILES: *c1ccc(-c2ccc3ccccc3c2)cc1] | 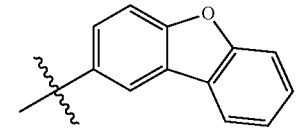 |
| 206 | 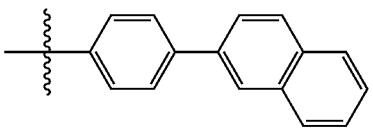 [SMILES: *c1ccc(-c2ccc3ccccc3c2)cc1] | 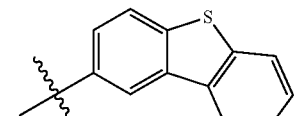 |
| 207 | 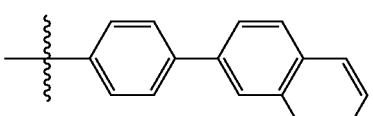 | 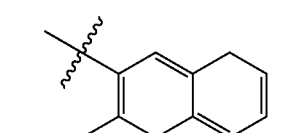 |
| 208 | 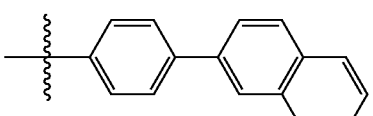 | 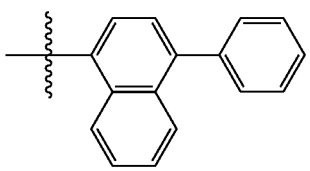 [SMILES: *c1ccc(-c2ccccc2)c2ccccc12] |

US 9,102,616 B2
203                                                                                                                                          204
TABLE 1-continued
| Ar₂, Ar₄ | Ar₃, Ar₅ |
|---|---|
| 209 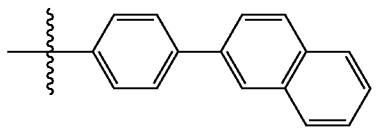 | 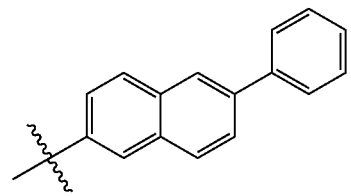 [SMILES: *c1ccc2cc(-c3ccccc3)ccc2c1] |
| 210 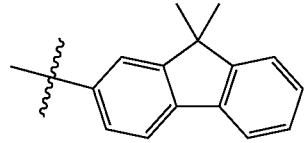 [SMILES: *c1ccc2c(c1)C(C)(C)c1ccccc1-2] | 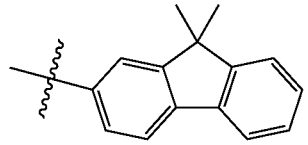 [SMILES: *c1ccc2c(c1)C(C)(C)c1ccccc1-2] |
| 211 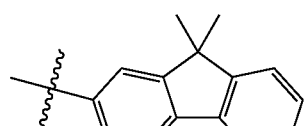 | 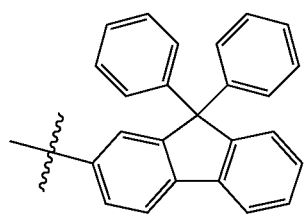 [SMILES: *c1ccc2c(c1)C(c1ccccc1)(c1ccccc1)c1ccccc1-2] |
| 212 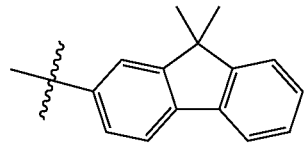 [SMILES: *c1ccc2c(c1)C(C)(C)c1ccccc1-2] | 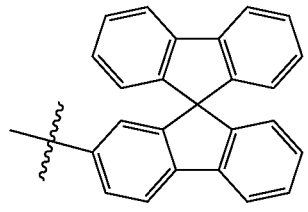 [SMILES: *c1ccc2c(c1)C1(c3ccccc3-c3ccccc31)c1ccccc1-2] |
| 213 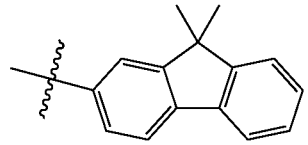 [SMILES: *c1ccc2c(c1)C(C)(C)c1ccccc1-2] | 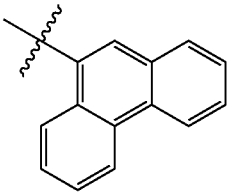 [SMILES: *c1cc2ccccc2c2ccccc12] |
| 214 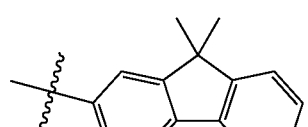 | 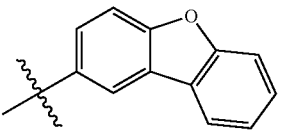 |
| 215 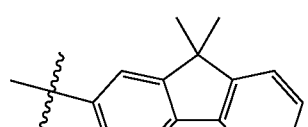 | 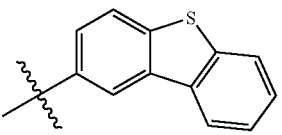 |
| 216 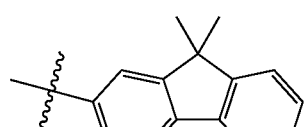 | 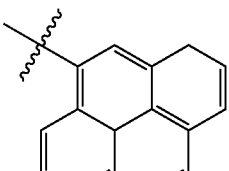 |

TABLE 1-continued

| | Ar₂, Ar₄ | Ar₃, Ar₅ |
|---|---|---|
| 217 | | |
| 218 | | |
| 219 | | |
| 220 | | |
| 221 | | |
| 223 | | |
| 224 | | |

TABLE 1-continued

| | Ar₂, Ar₄ | Ar₃, Ar₅ |
|---|---|---|
| 225 | | |
| 226 | | |
| 227 | | |
| 228 | | |
| 229 | | |
| 230 | | |
| 231 | | |

TABLE 1-continued

| | Ar₂, Ar₄ | Ar₃, Ar₅ |
|---|---|---|
| 232 | (9,9'-spirobifluorenyl) | (1-phenylnaphthalen-4-yl) |
| 233 | (9,9'-spirobifluorenyl) | (6-phenylnaphthalen-2-yl) |
| 234 | (phenanthrenyl) | (phenanthrenyl) |
| 235 | (phenanthrenyl) | (dibenzofuranyl) |

| | Ar₂, Ar₄ | Ar₃, Ar₅ |
|---|---|---|
| 236 | (phenanthrenyl) | (dibenzothiophenyl) |
| 237 | (phenanthrenyl) | (pyrenyl) |
| 238 | (phenanthrenyl) | (4-phenylnaphthalen-1-yl) |

-continued
| Ar₂, Ar₄ | Ar₃, Ar₅ |
|---|---|
| 239 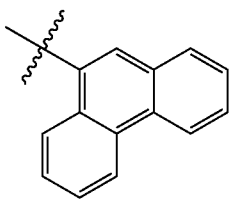 [SMILES: *c1cc2ccccc2c2ccccc12] | 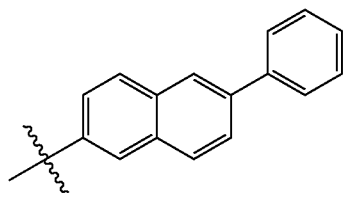 [SMILES: *c1ccc2cc(-c3ccccc3)ccc2c1] |
| 240 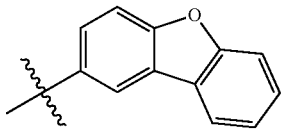 | 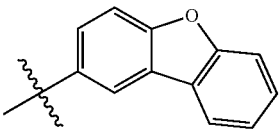 |
| 241 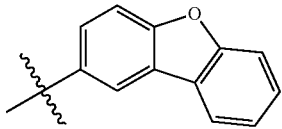 | 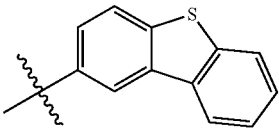 [SMILES: *c1ccc2sc3ccccc3c2c1] |
| 242 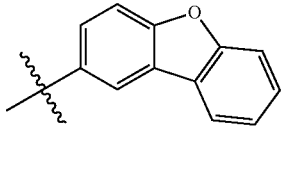 | 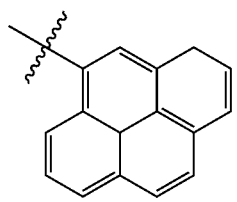 [SMILES: *C1=C2C=CC=C3C=CC4=C(C(=C1)CC=C4)C32] |
| 243 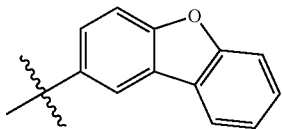 | 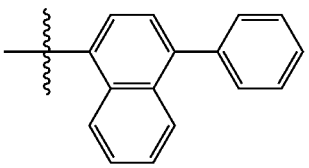 [SMILES: *c1ccc(-c2ccccc2)c2ccccc12] |
| 244 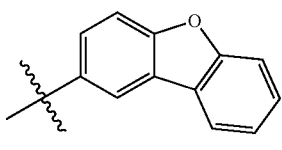 | 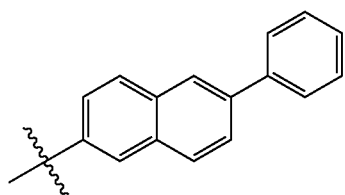 [SMILES: *c1ccc2cc(-c3ccccc3)ccc2c1] |
| 245 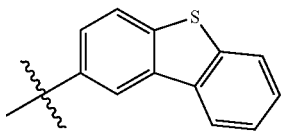 | 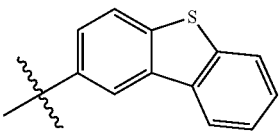 |
| 246 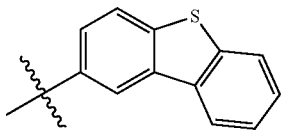 | 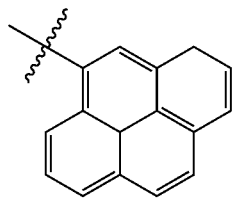 [SMILES: *C1=C2C=CC=C3C=CC4=C(C(=C1)CC=C4)C32] |

-continued
| | Ar₂, Ar₄ | Ar₃, Ar₅ |
|---|---|---|
| 247 | | |
| 248 | | |
| 249 | | |
| 250 | | |
| 251 | | |
| 252 | | |
| 253 | | |
| 254 | | |
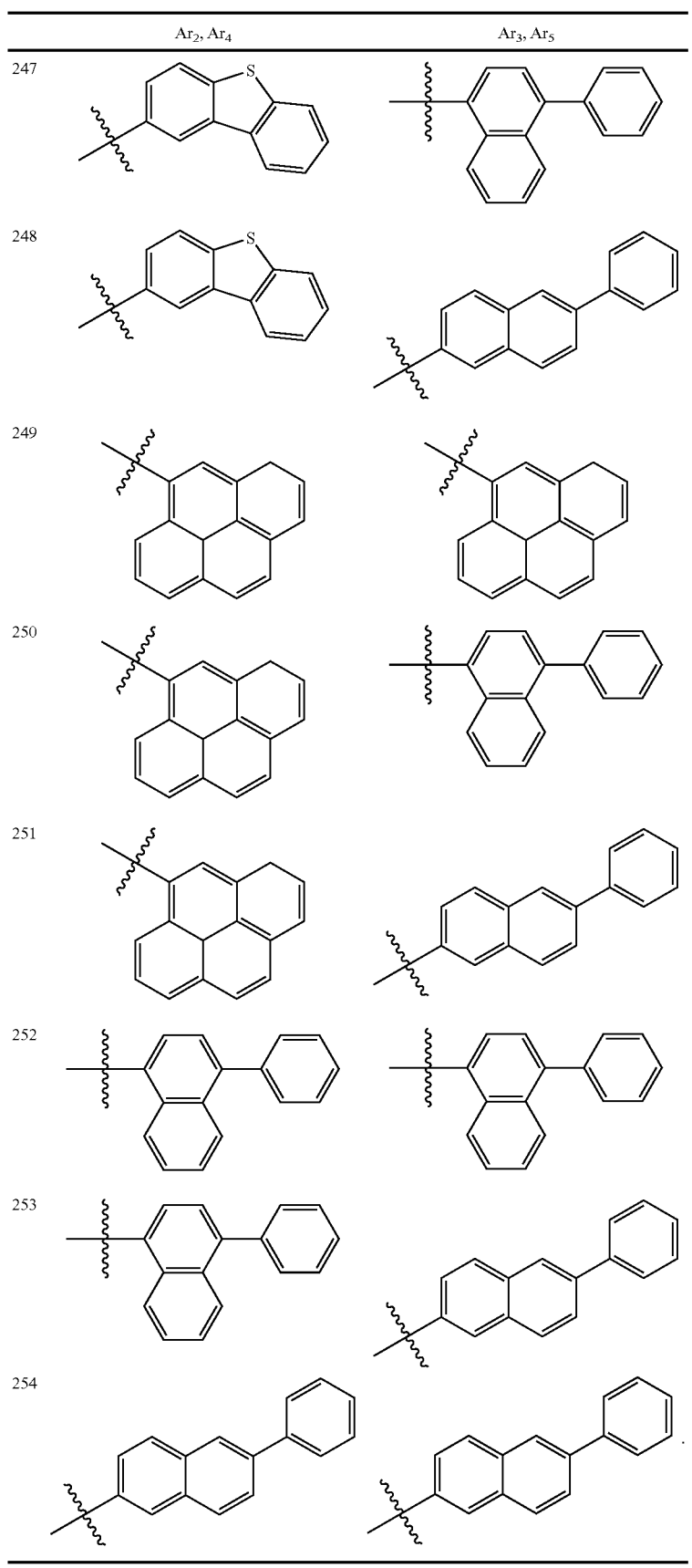

3. The compound as claimed in claim 1, wherein the compound represented by Formula 1 above comprises an aromatic compound represented by Formula 4 below, <Formula 4>

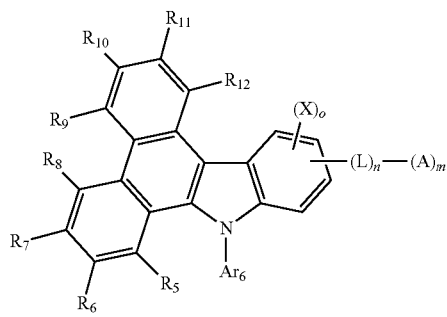

wherein in Formula 4 above,
(1) $R_5$ through $R_{12}$, and X are the same or different, and each is independently selected from the group consisting of a hydrogen atom, a substituted or unsubstituted aryl group having 5~60 nuclear carbon atoms, a substituted or unsubstituted hetero aryl group having 5~60 nuclear carbon atoms, a substituted or unsubstituted $C_1$~$C_{60}$ alkyl group, a substituted or unsubstituted $C_1$~$C_{60}$ alkoxy group, a substituted or unsubstituted aryloxy group having 5~60 nuclear carbon atoms, a substituted or unsubstituted arylthio group having 5~60 nuclear carbon atoms, a substituted or unsubstituted alkoxycarbonyl group having 5~60 nuclear carbon atoms, an amino group substituted by a substituted or unsubstituted aryl group having 5~60 nuclear carbon atoms, a halogen atom, a cyano group, a nitro group, a hydroxyl group and a carboxyl group,
(2) $Ar_6$ is a substituted or unsubstituted aryl group having 6~60 nuclear atoms, a substituted or unsubstituted heteroaryl group having 5~60 nuclear atoms, or a substituted or unsubstituted $C_1$~$C_{60}$ alkyl group, and
(3) o represents an integer of 1 to 3.

4. The compound as claimed in claim 3, wherein the compound represented by Formula 4 above is any one of compounds represented by Formula 5 below, <Formula 5>

3-A1

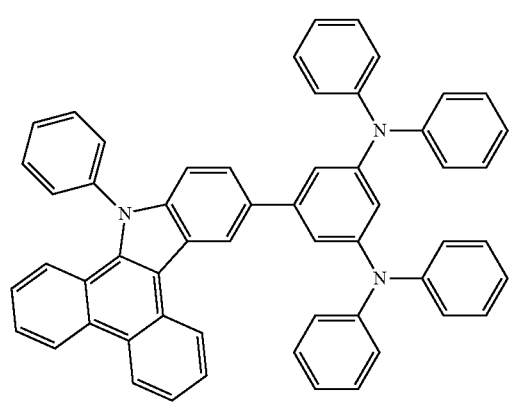

3-A2

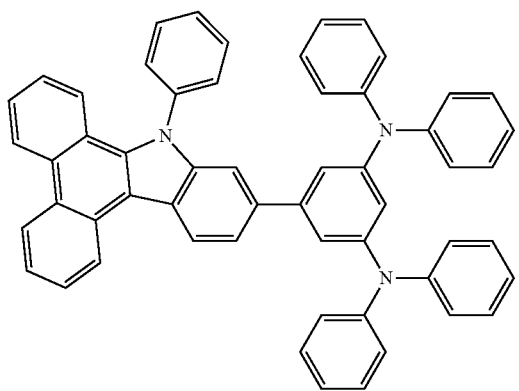

3-A3

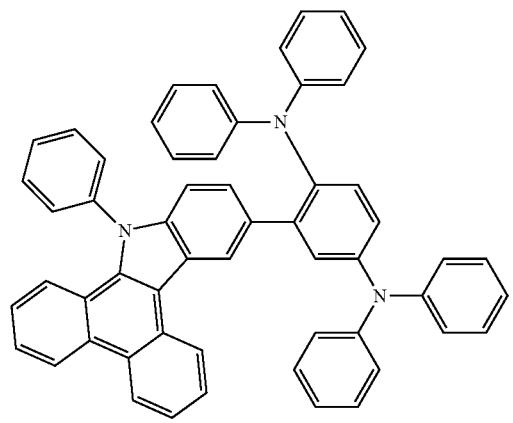

3-A4

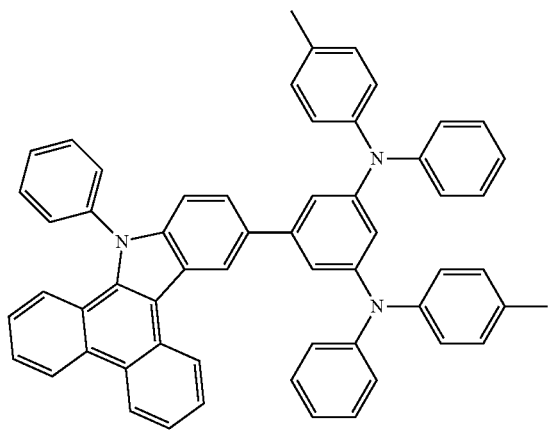

-continued
3-A5
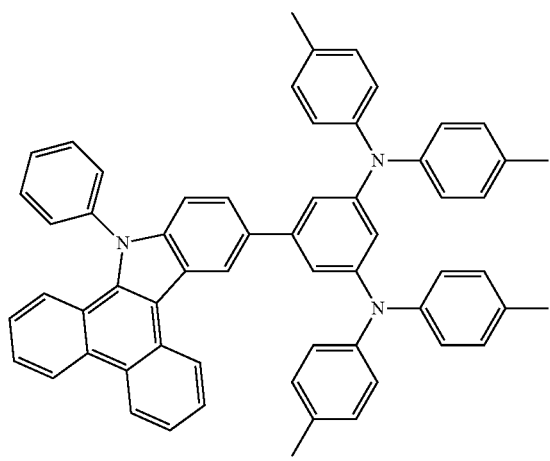
3-A6
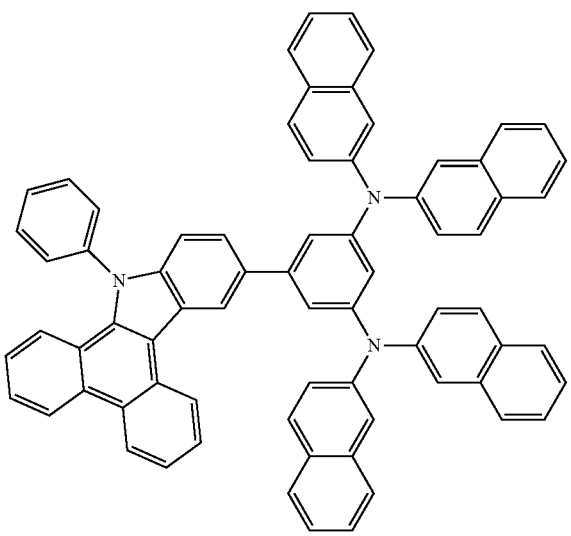
3-A7
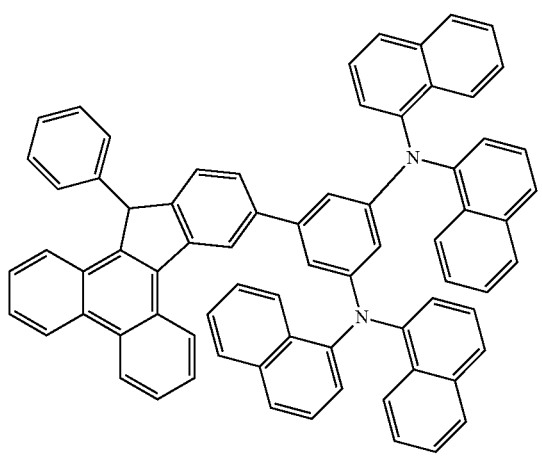
3-A8
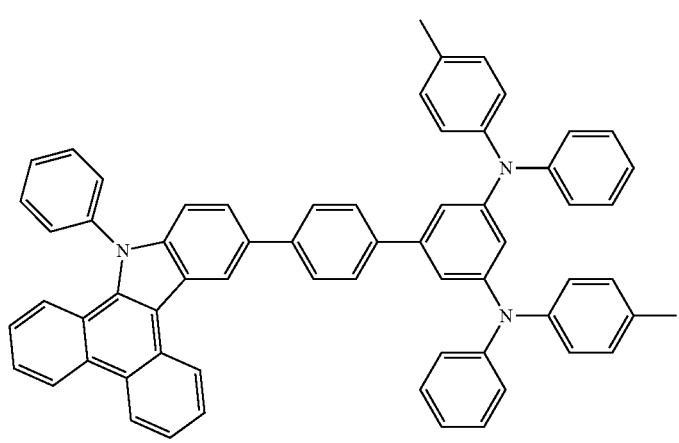

-continued
3-A9
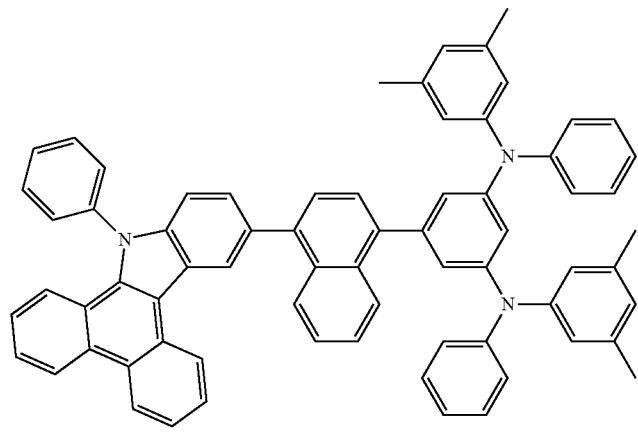
3-A10
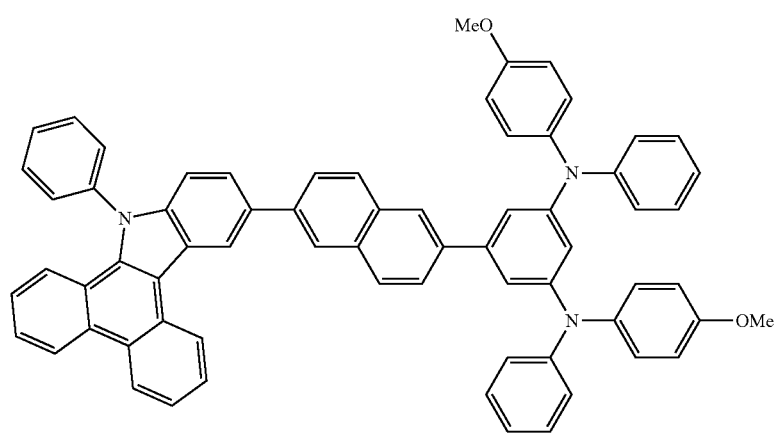
3-A11
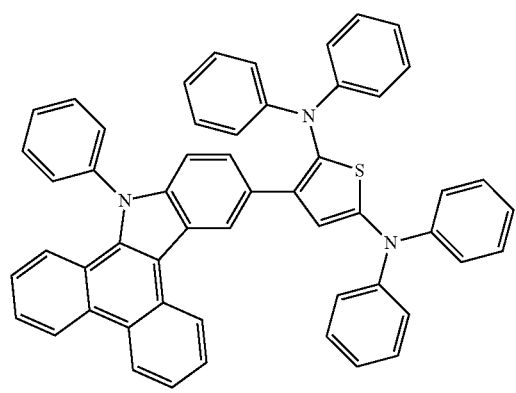
3-A12
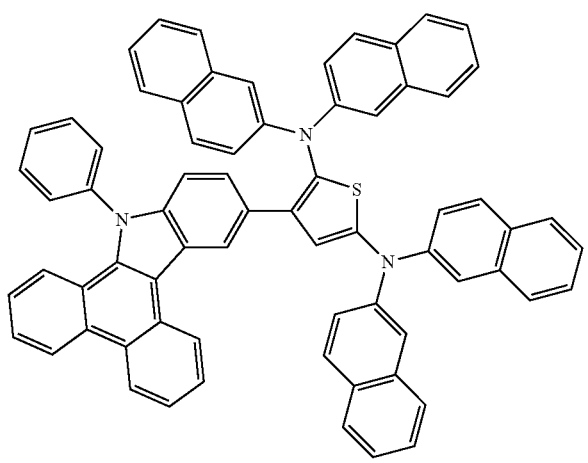

3-A13
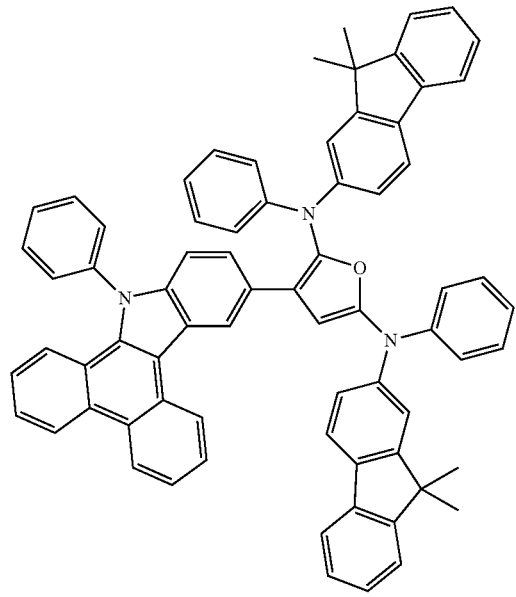
3-A14
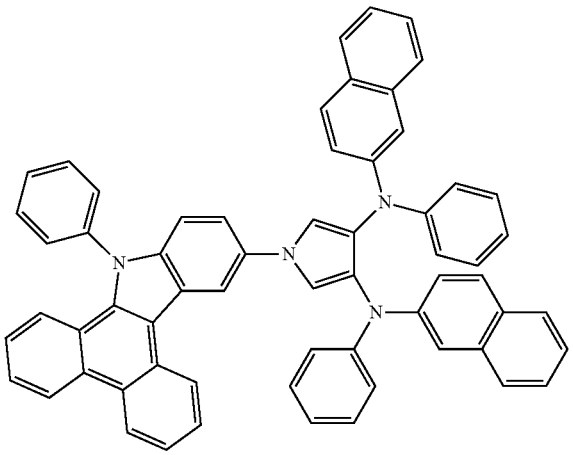
3-A15
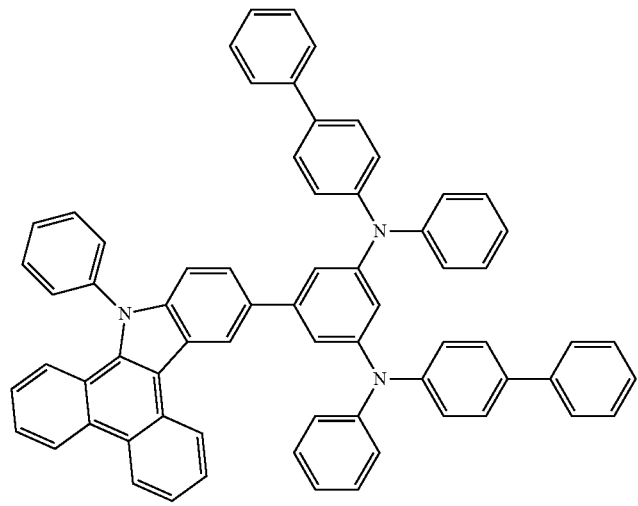

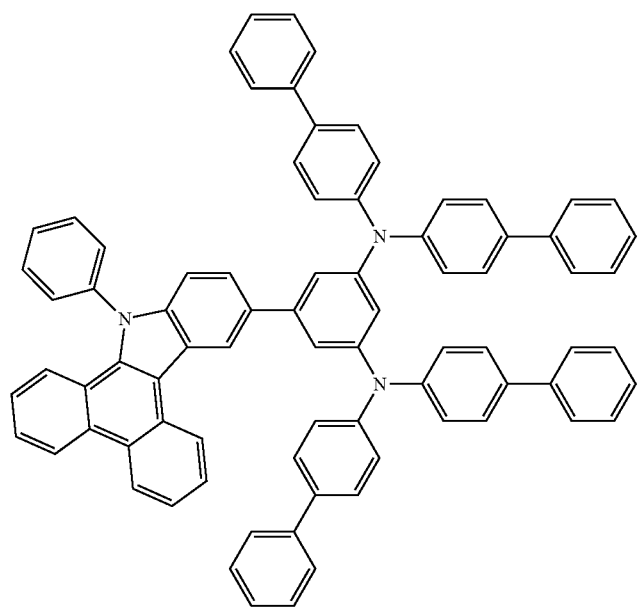
3-A16
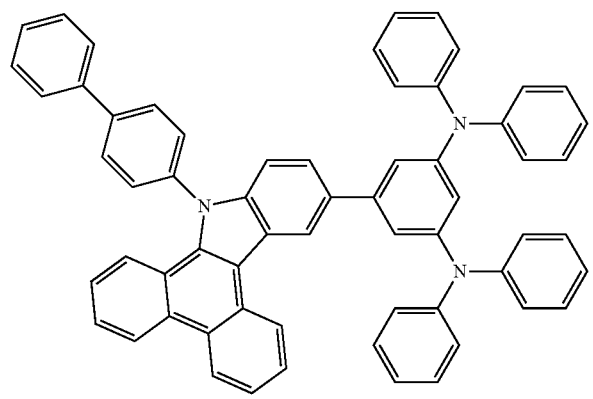
3-A17
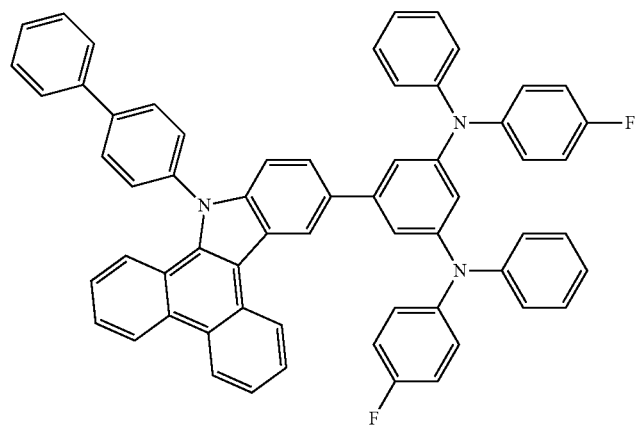
3-A18

-continued
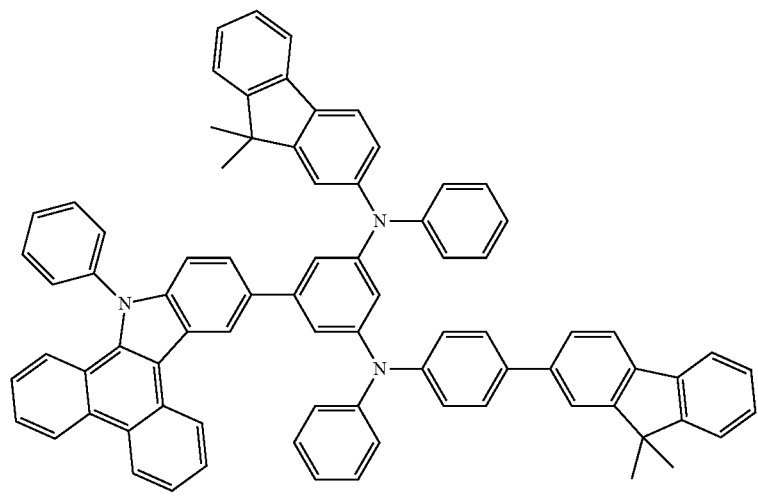
3-A19
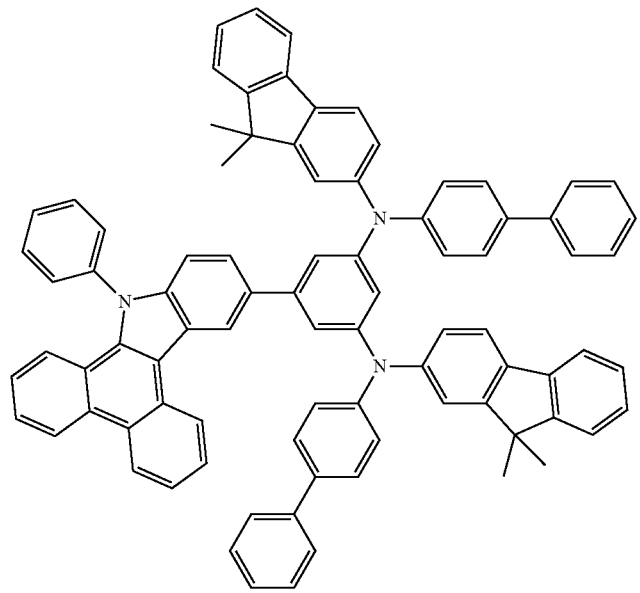
3-A20
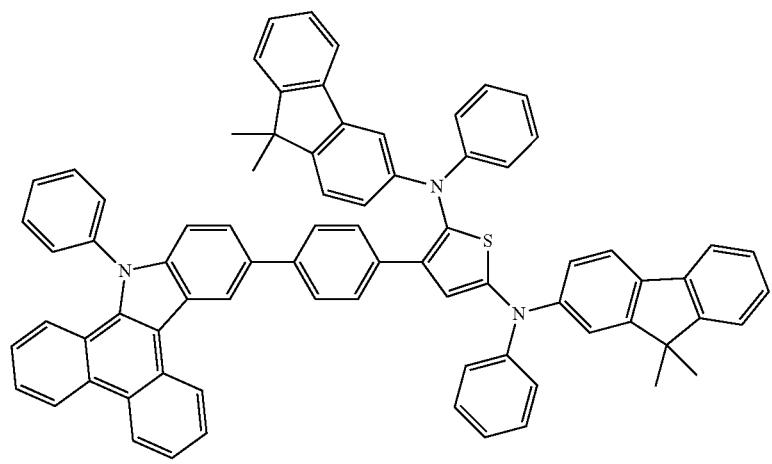
3-A21

-continued
3-A22
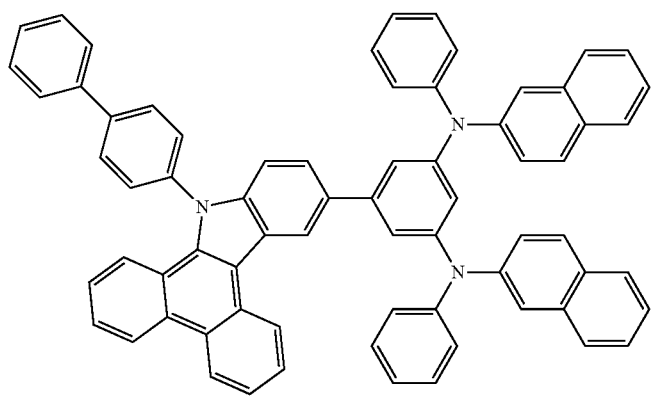
3-A23
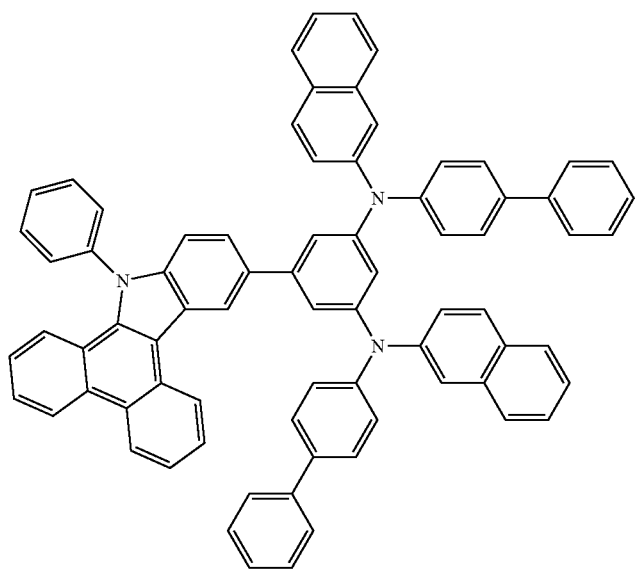
3-A24
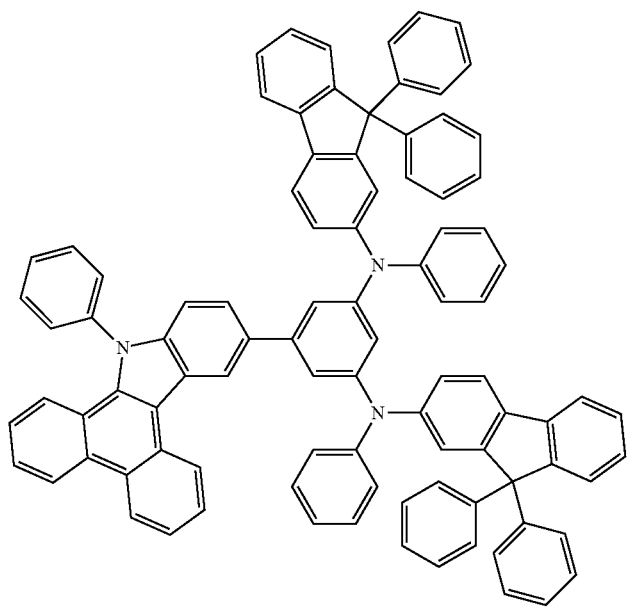

-continued
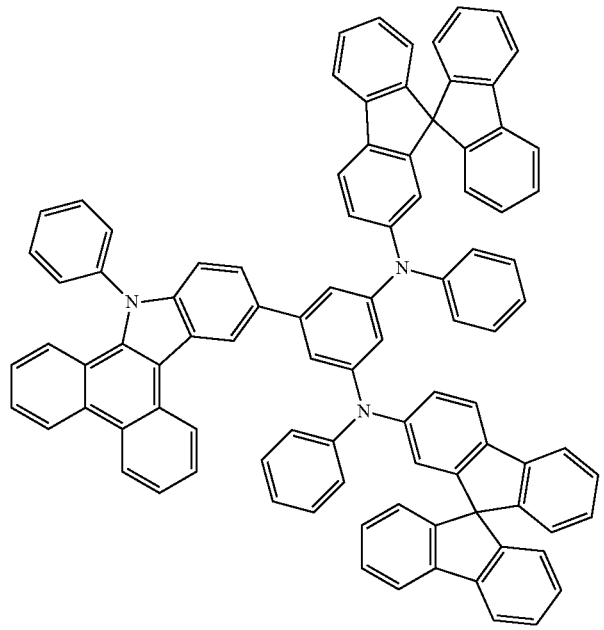
3-A25
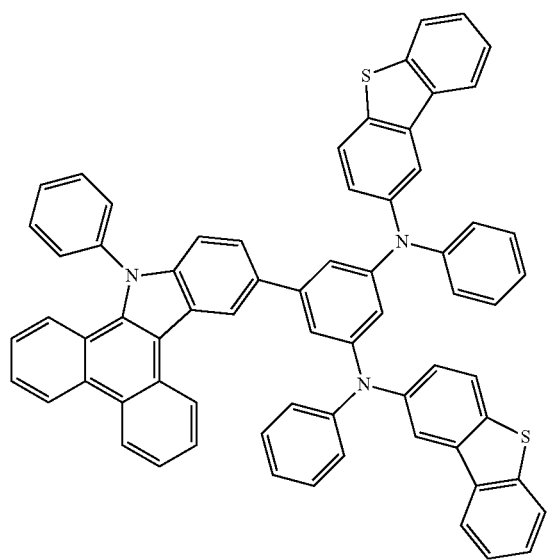
3-A26

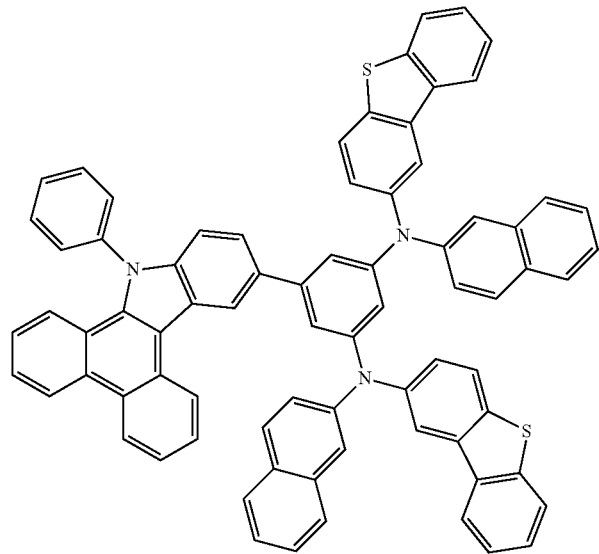
3-A27
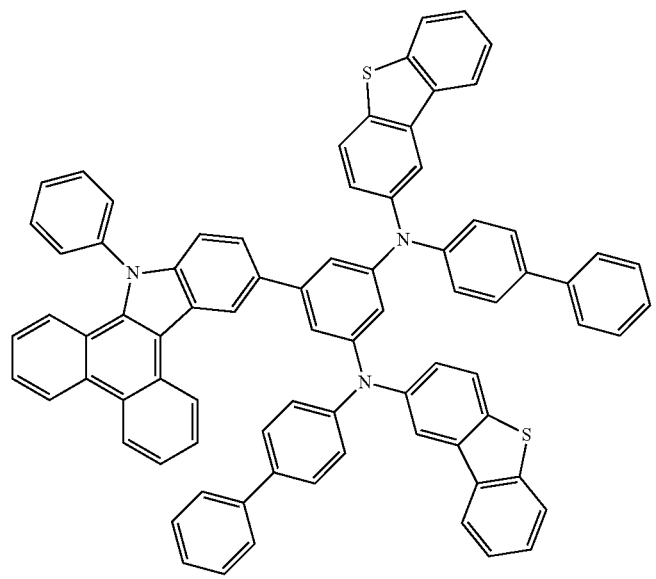
3-A28

3-A29
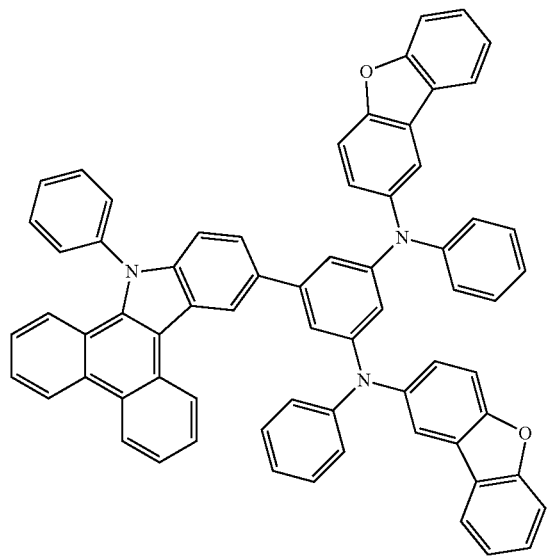
3-A30
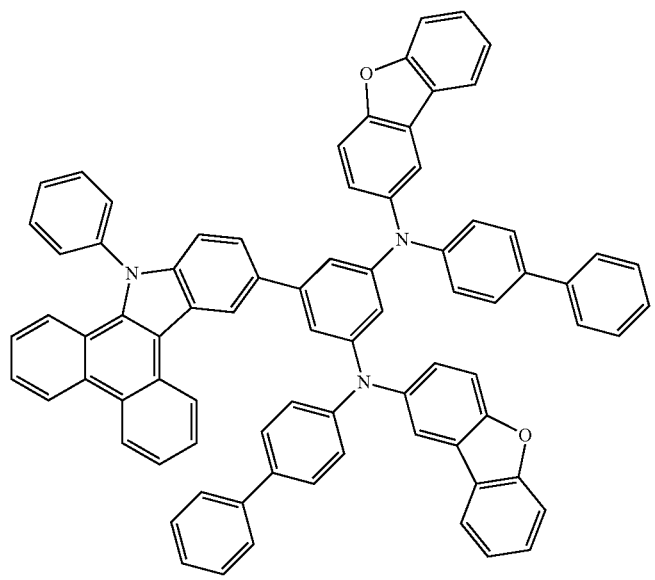
3-A31
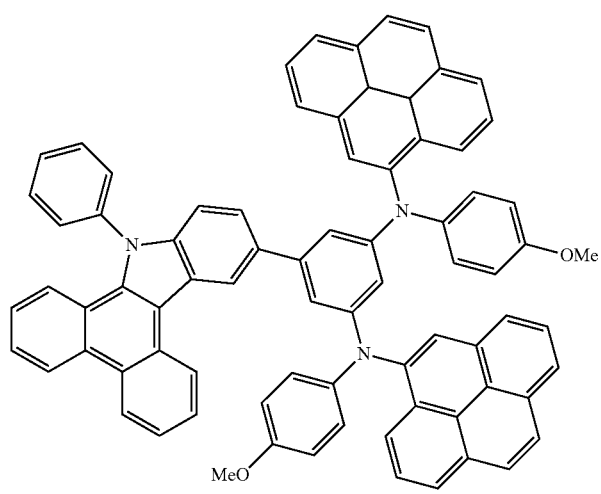

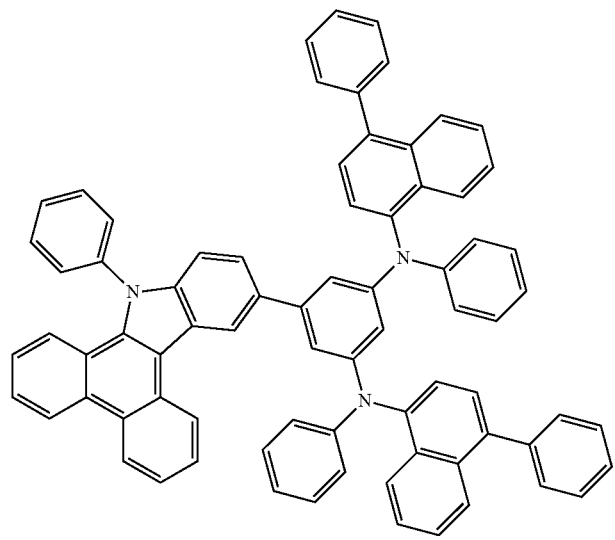
3-A32
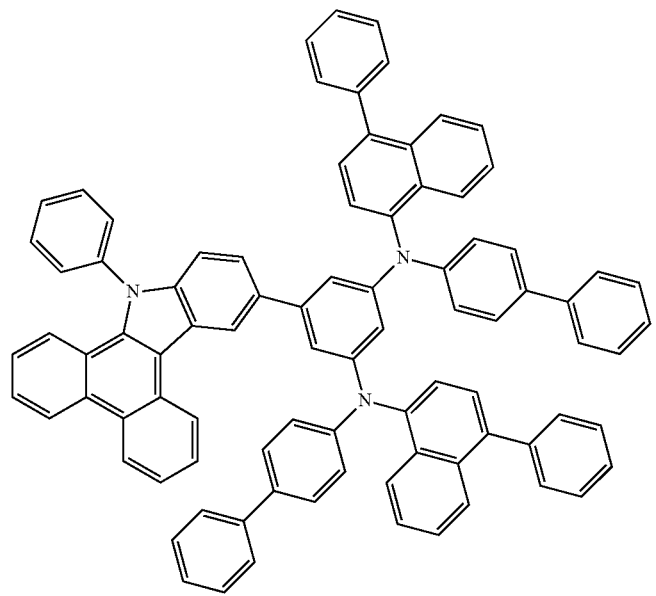
3-A33

-continued
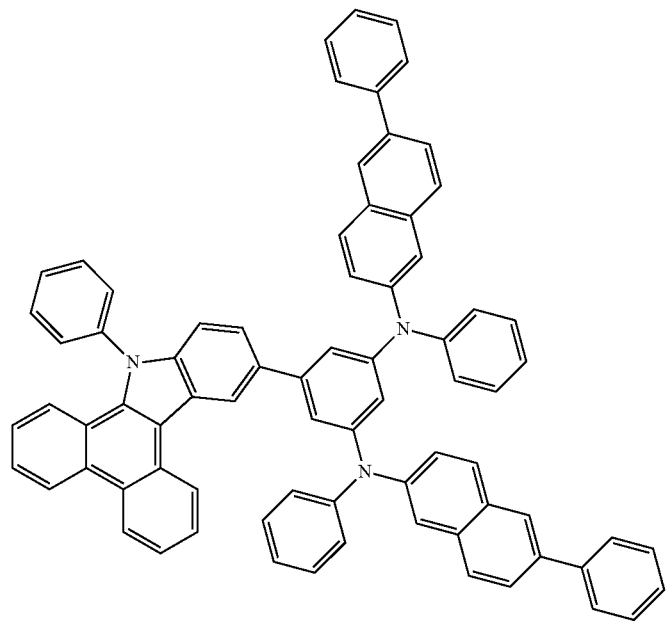
3-A34
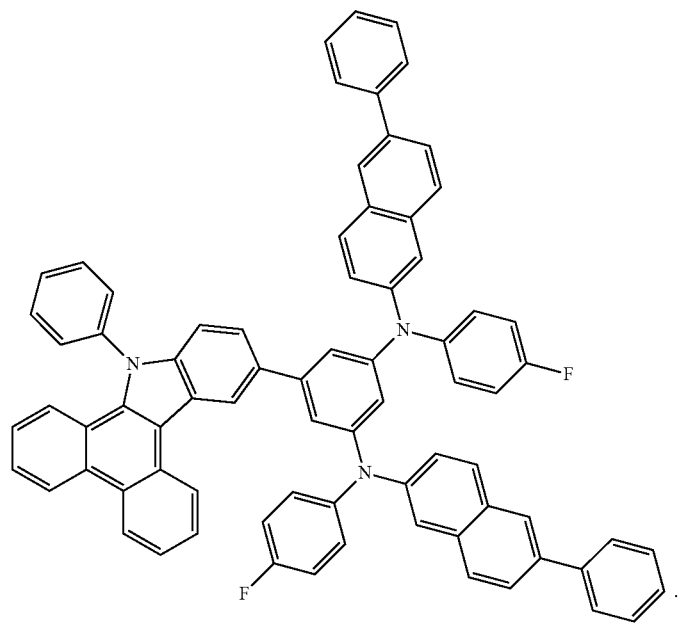
3-A35

5. The compound as claimed in claim 1, wherein the compound represented by Formula 1 above comprises an indoloacridine derivative comprising two or more diamine groups, represented by Formula 6 below, <Formula 6>

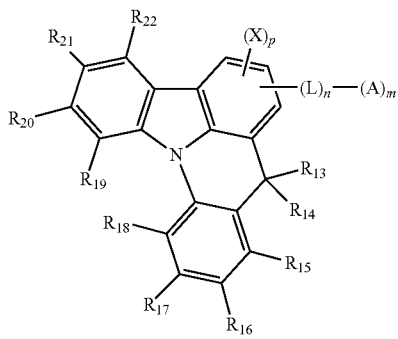

wherein in Formula 6 above, (1) $R_{13}$ through $R_{22}$, and X are the same or different, and each is independently selected from the group consisting of a hydrogen atom, a substituted or unsubstituted aryl group having 5~60 nuclear carbon atoms, a substituted or unsubstituted heteroaryl group having 5~60 nuclear carbon atoms, a substituted or unsubstituted $C_1$~$C_{60}$ alkyl group, a substituted or unsubstituted $C_1$~$C_{60}$ alkoxy group, a substituted or unsubstituted aryloxy group having 5~60 nuclear carbon atoms, a substituted or unsubstituted arylthio group having 5~60 nuclear carbon atoms, a substituted or unsubstituted alkoxycarbonyl group having 5~60 nuclear carbon atoms, an amino group substituted by a substituted or unsubstituted aryl group having 5~60 nuclear carbon atoms, a halogen atom, a cyano group, a nitro group, a hydroxyl group and a carboxyl group, and (2) p represents an integer of 1 to 2.

6. The compound as claimed in claim 5, wherein the compound represented by Formula 6 above is any one of compounds represented by Formula 7 below, <Formula 7>

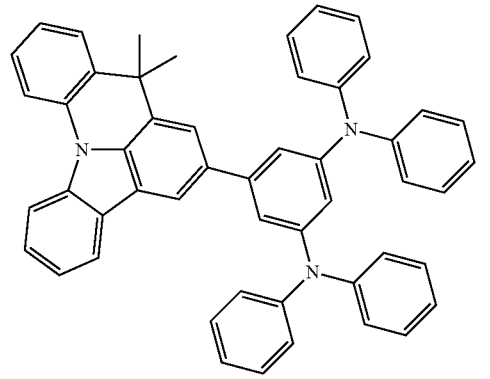

4-B1

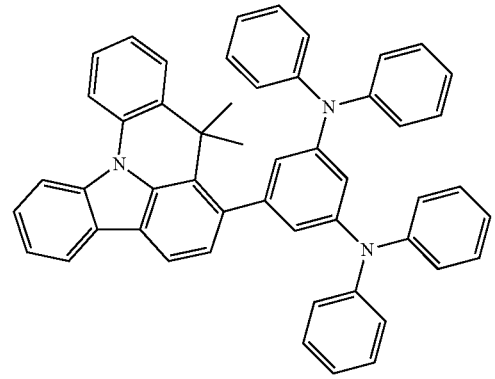

4-B2

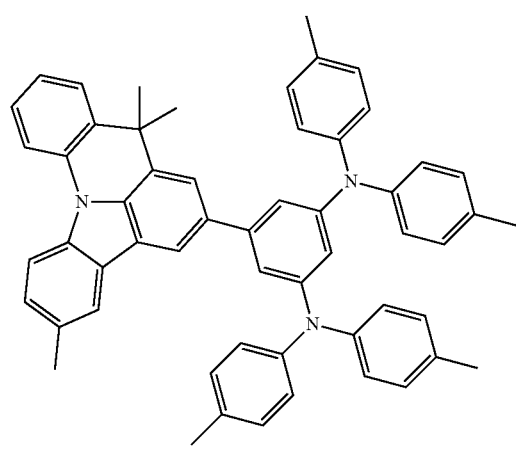

4-B3

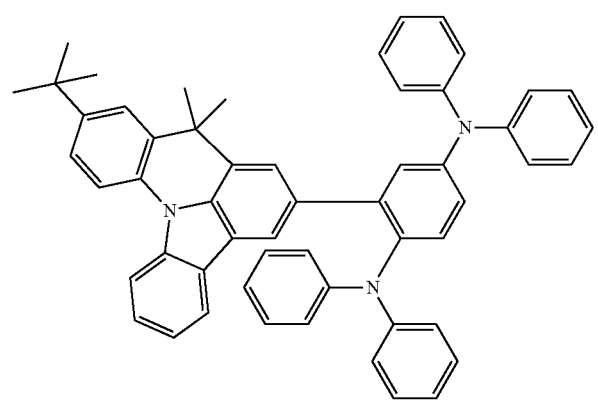

4-B4

4-B5
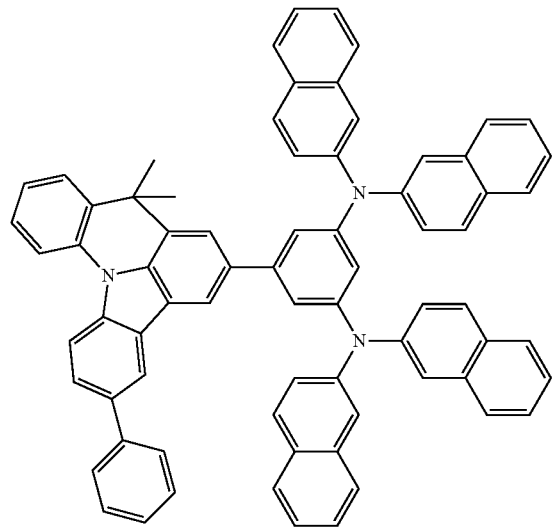
4-B6
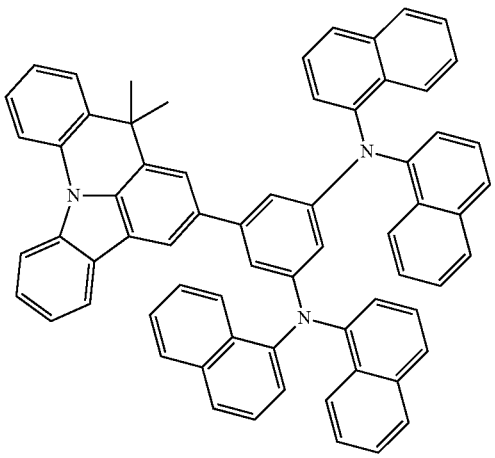
4-B7
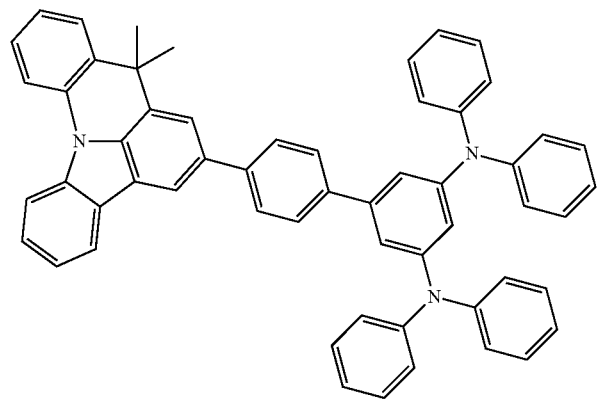
4-B8
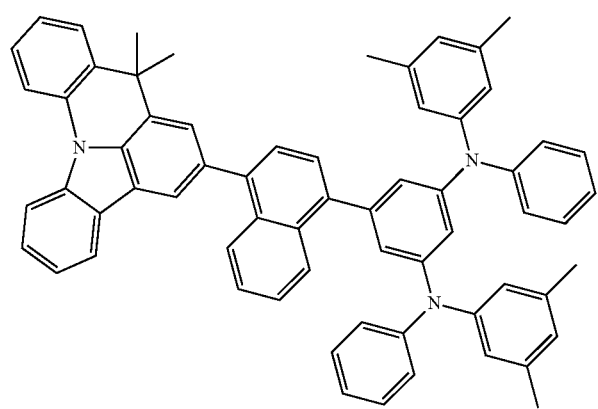

4-B9
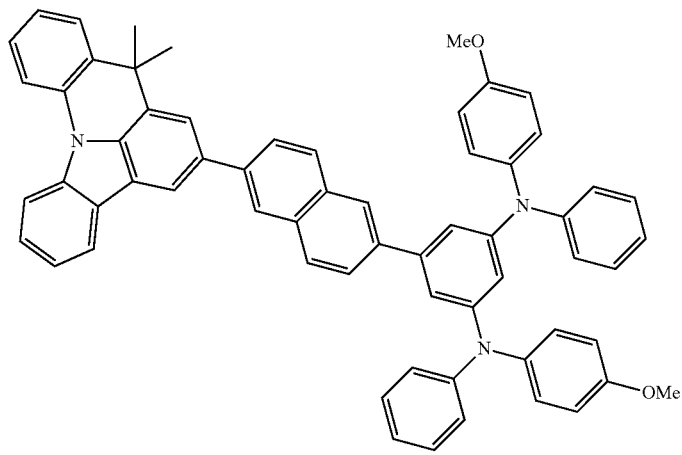
4-B10
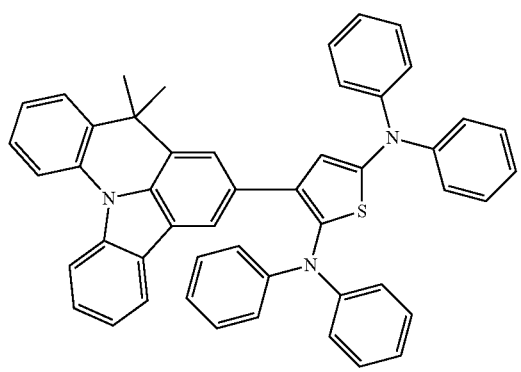
4-B11
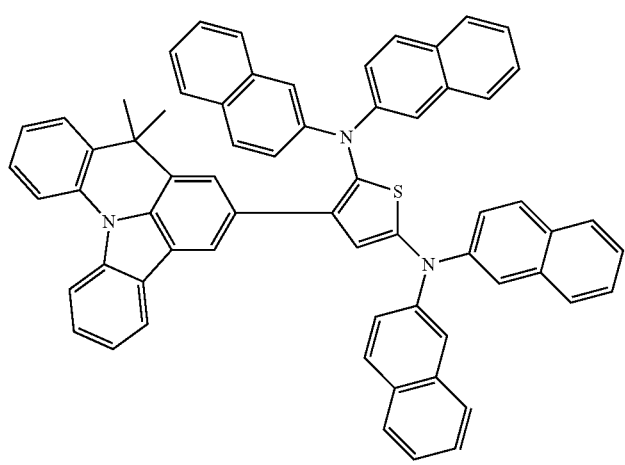

-continued
4-B12
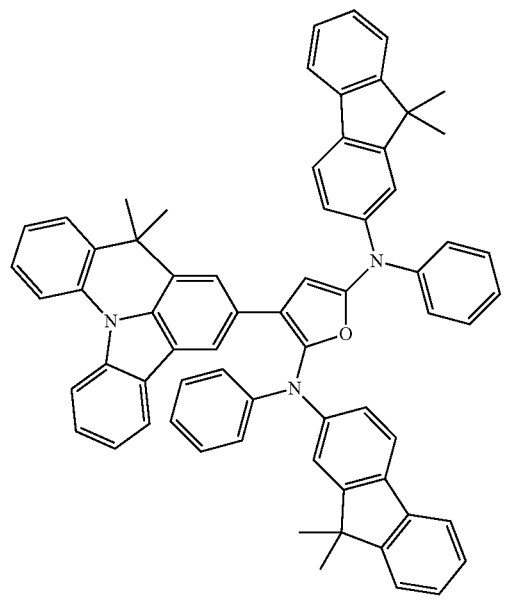
4-B13
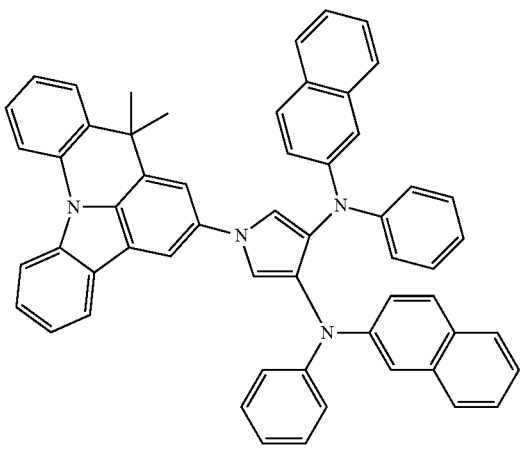
4-B14
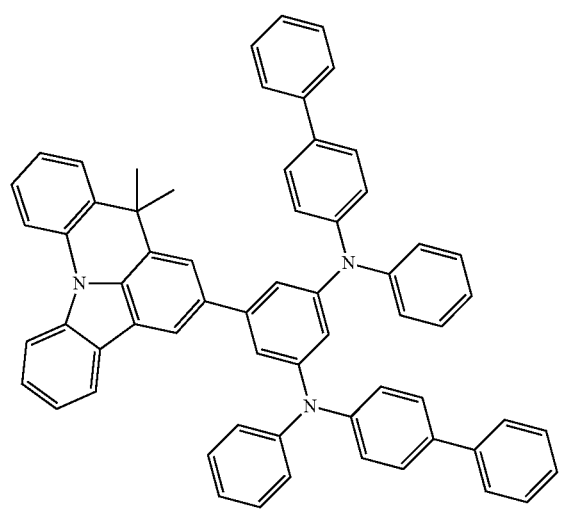
4-B15
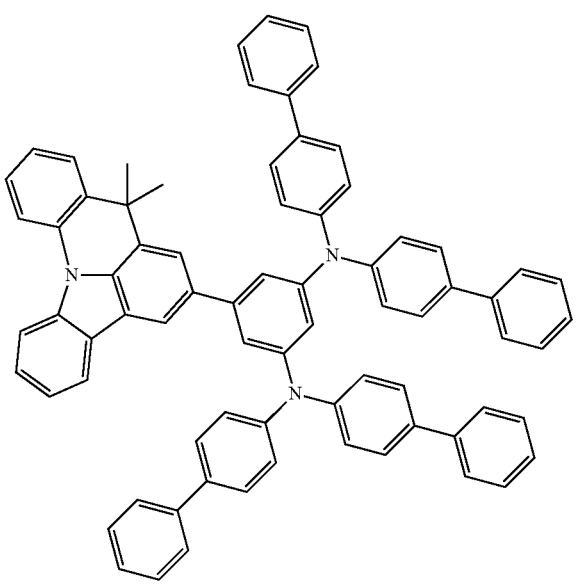

-continued
4-B16
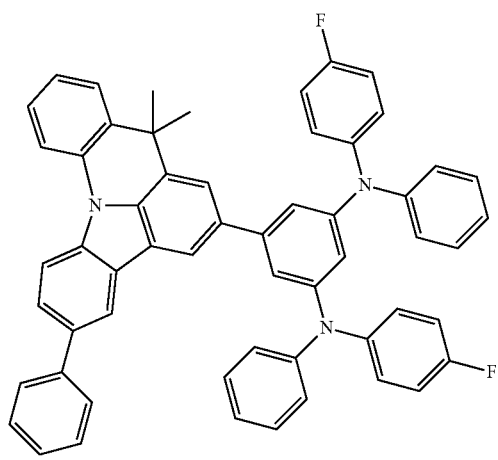
4-B17
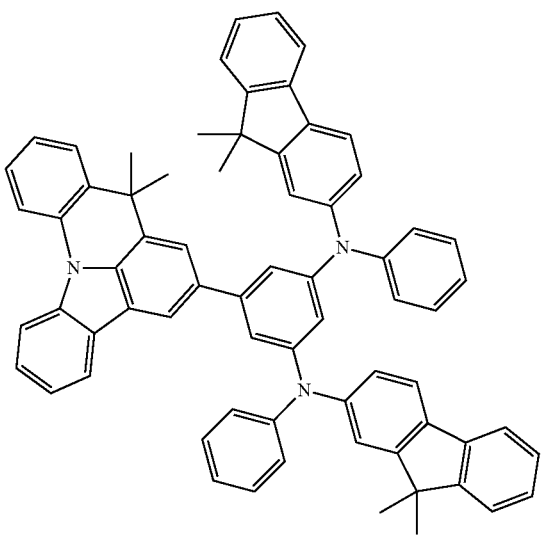
4-B18
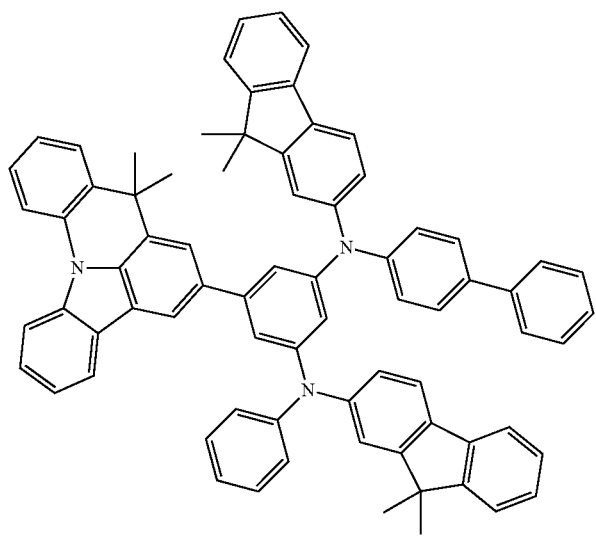
4-B19
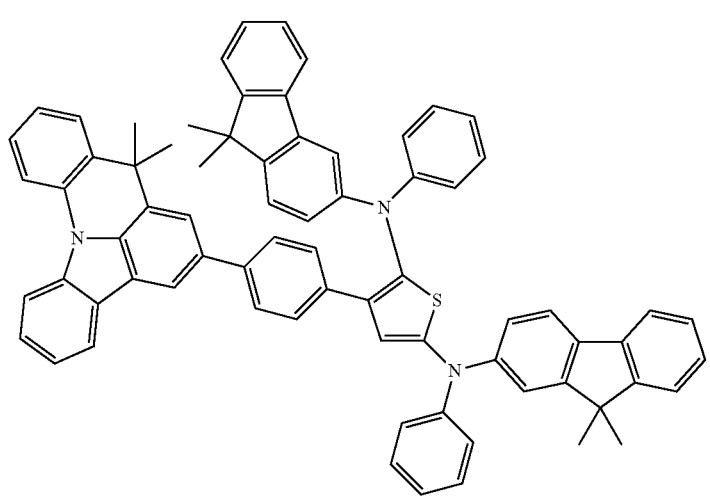

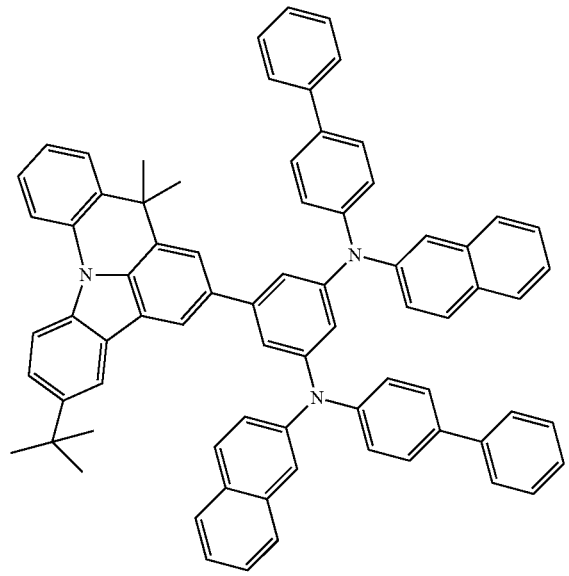
4-B20
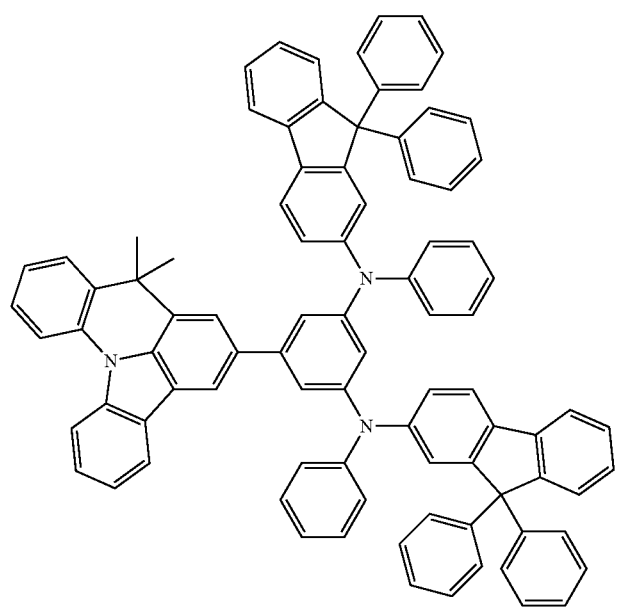
4-B21

-continued
4-B22
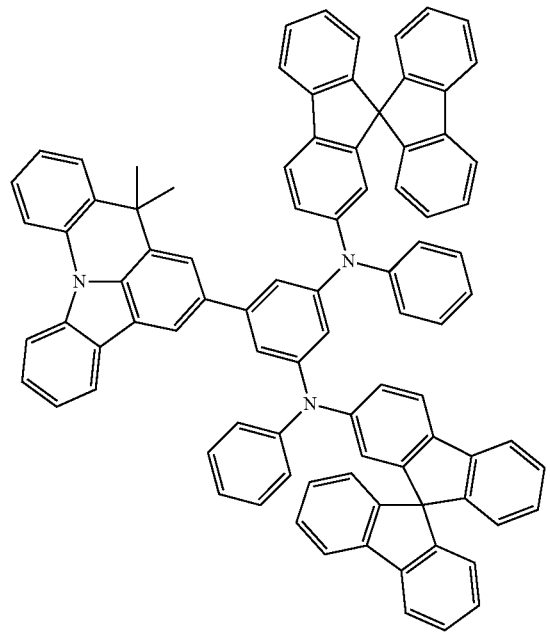
4-B23
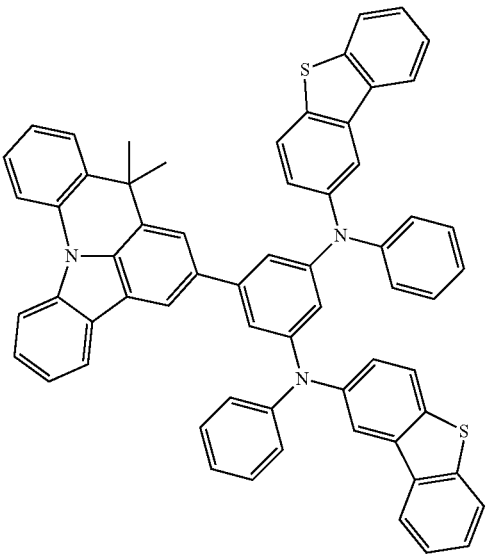
4-B24
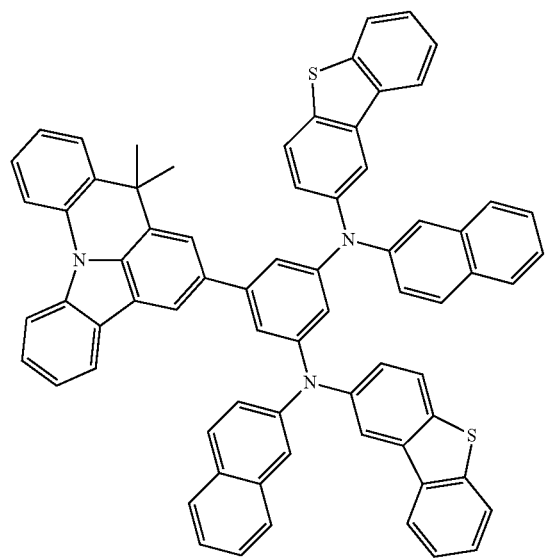
4-B25
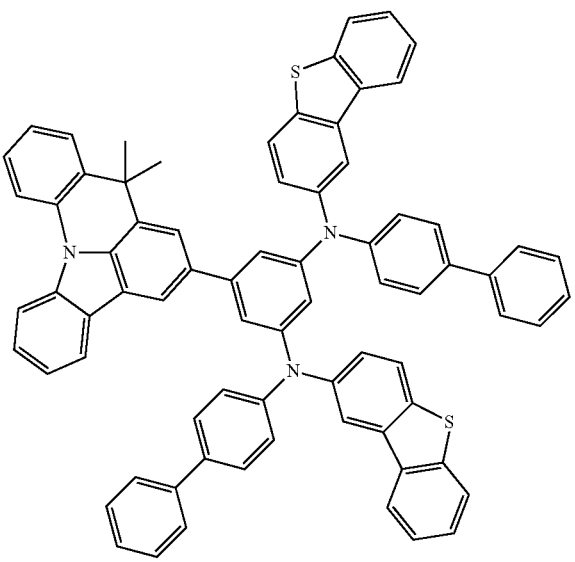

4-B26
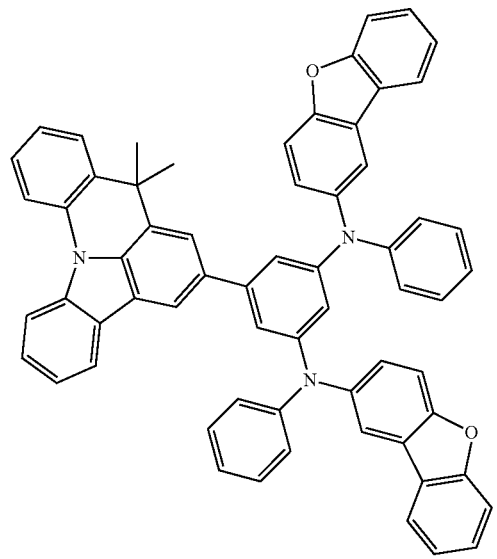
4-B27
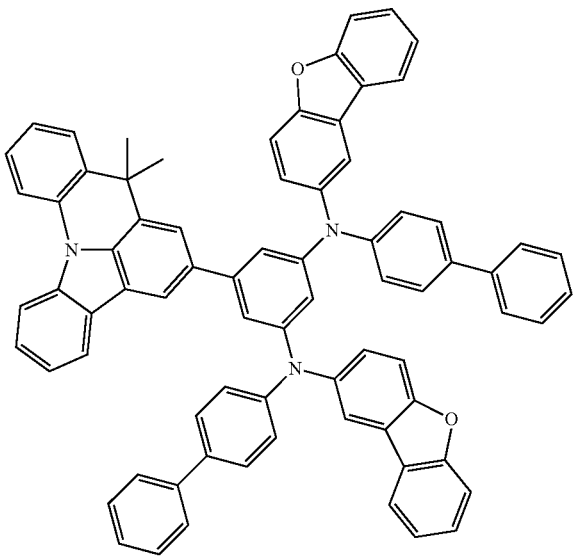
4-B28
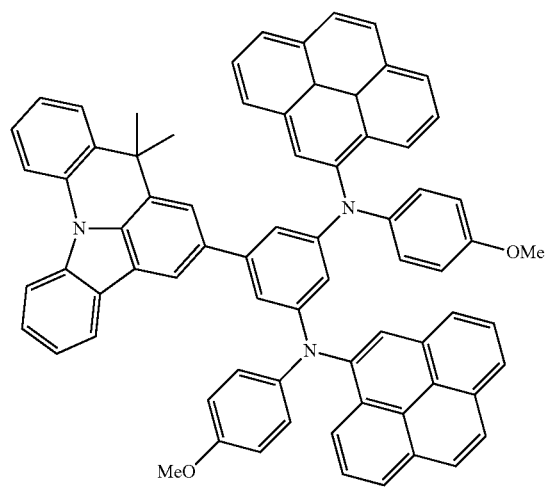
4-B29
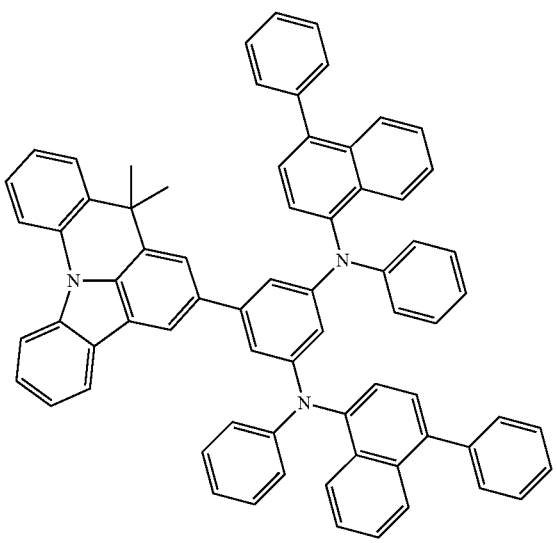

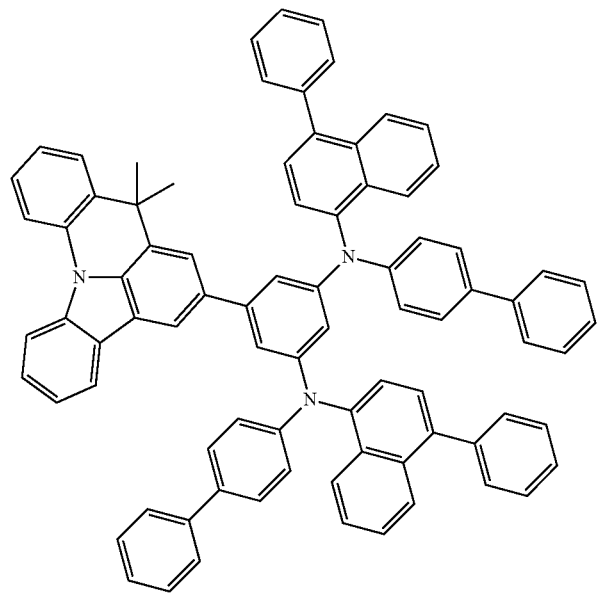
4-B30
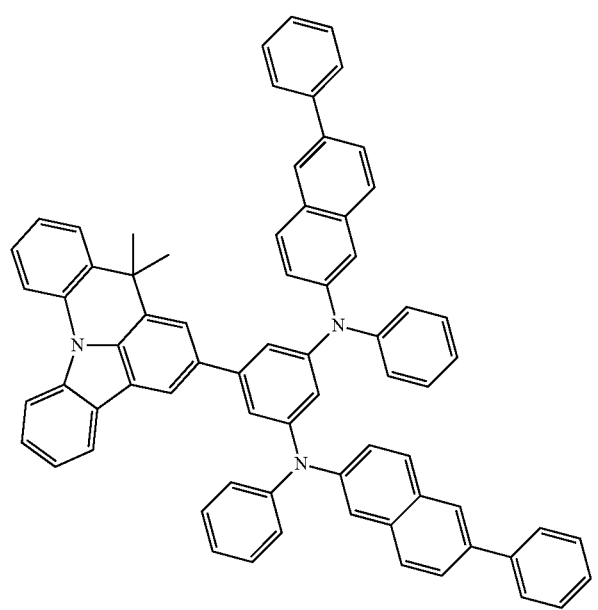
4-B31

-continued

4-B32

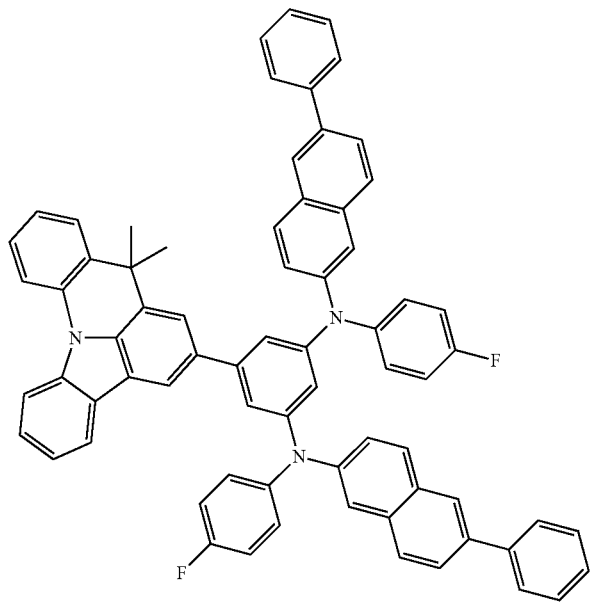

7. The compound as claimed in claim 1, wherein the compound represented by Formula 1 above comprises a compound represented by Formula 8 below, <Formula 8>

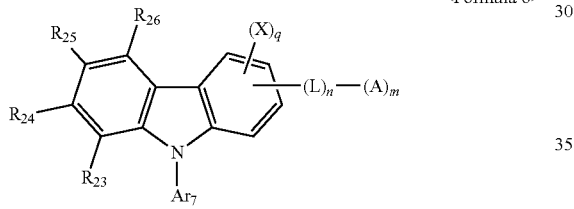

wherein in Formula 8 above,
(1) $R_{23}$ through $R_{25}$, and X are the same or different, and each is independently selected from the group consisting of a hydrogen atom, a substituted or unsubstituted aryl group having 5~60 nuclear carbon atoms, a substituted or unsubstituted heteroaryl group having 5~60 nuclear carbon atoms, a substituted or unsubstituted $C_1$~$C_{60}$ alkyl group, a substituted or unsubstituted $C_1$~$C_{60}$ alkoxy group, a substituted or unsubstituted aryloxy group having 5~60 nuclear carbon atoms, a substituted or unsubstituted arylthio group having 5~60 nuclear carbon atoms, a substituted or unsubstituted alkoxycarbonyl group having 5~60 nuclear carbon atoms, an amino group substituted by a substituted or unsubstituted aryl group having 5~60 nuclear carbon atoms, a halogen atom, a cyano group, a nitro group, a hydroxyl group and a carboxyl group; and (2) $Ar_7$ is the same or different, and is independently selected from the group consisting of a hydrogen atom, deuterium, tritium, a substituted or unsubstituted aryl group having 5~60 nuclear carbon atoms, a substituted or unsubstituted hetero aryl group having 5~60 nuclear carbon atoms, a substituted or unsubstituted $C_1$~$C_{60}$ alkyl group, a substituted or unsubstituted $C_1$~$C_{60}$ alkoxy group, a substituted or unsubstituted aryloxy group having 5~60 nuclear carbon atoms, a substituted or unsubstituted arylthio group having 5~60 nuclear carbon atoms, a substituted or unsubstituted alkoxycarbonyl group having 5~60 nuclear carbon atoms, an amino group substituted by a substituted or unsubstituted alkyl or aryl group having 5~60 nuclear carbon atoms, a halogen atom, a cyano group, a nitro group, a hydroxyl group and a carboxyl group; and (3) q represents an integer of 1 to 3.

8. The compound as claimed in claim 7, wherein the compound represented by Formula 8 above is any one of compounds represented by Formula 9 below, <Formula 9>

5-C1

5-C2

-continued
5-C3
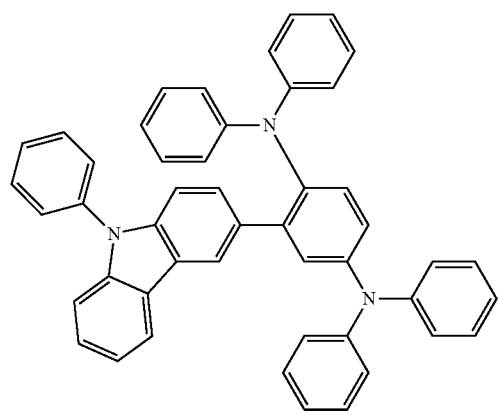
5-C4
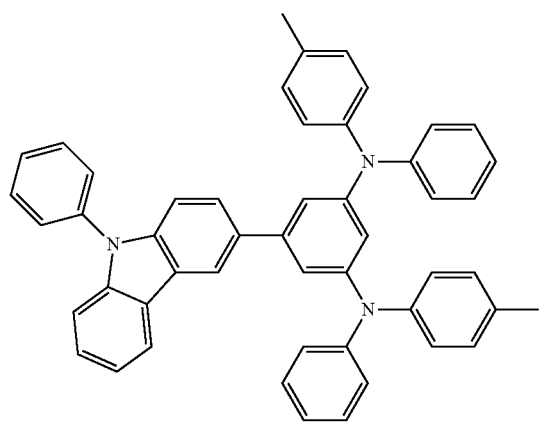
5-C5
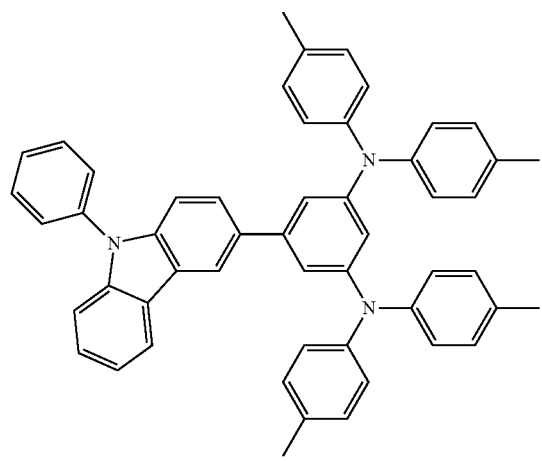
5-C6
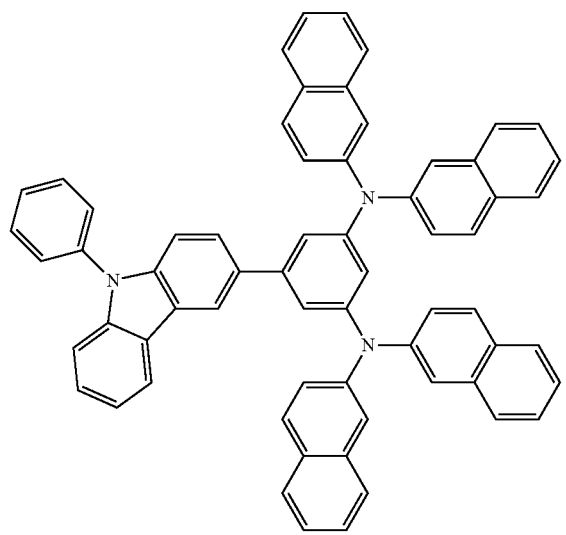
5-C7
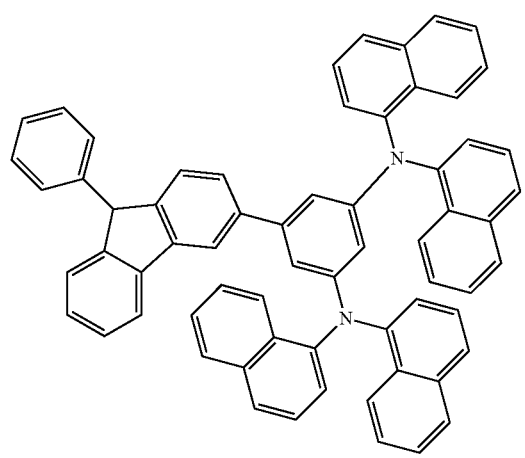

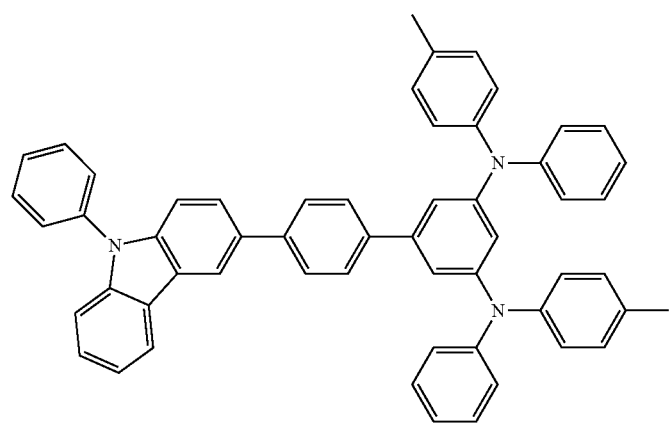
5-C8
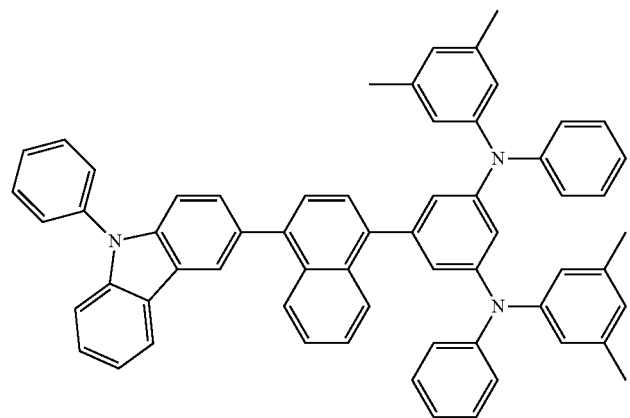
5-C9
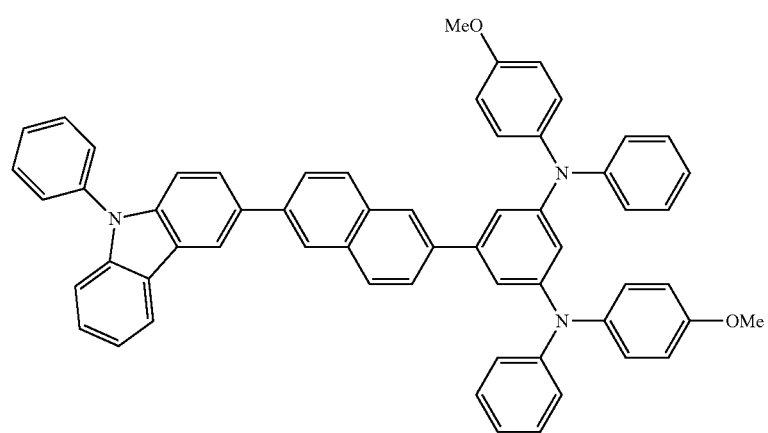
5-C10

-continued
5-C11
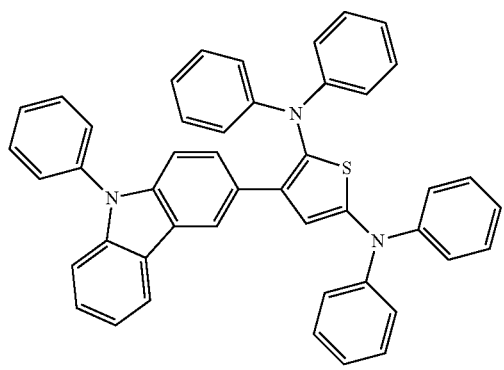
5-C12
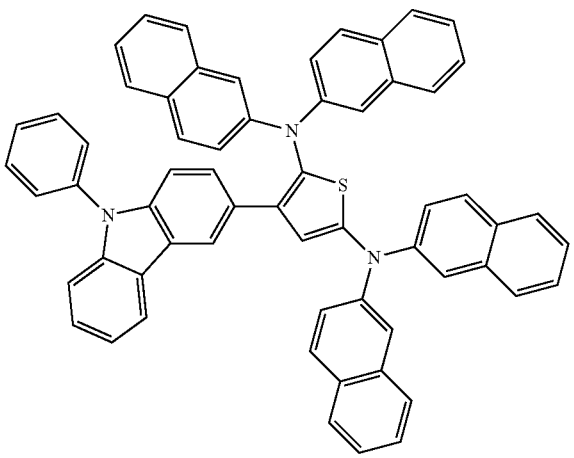
5-C13
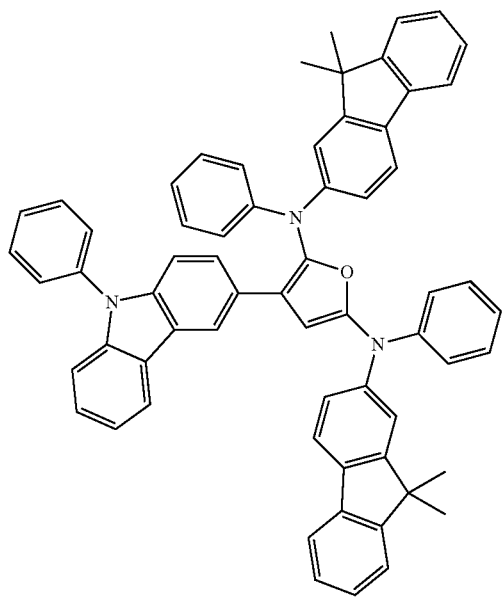
5-C14
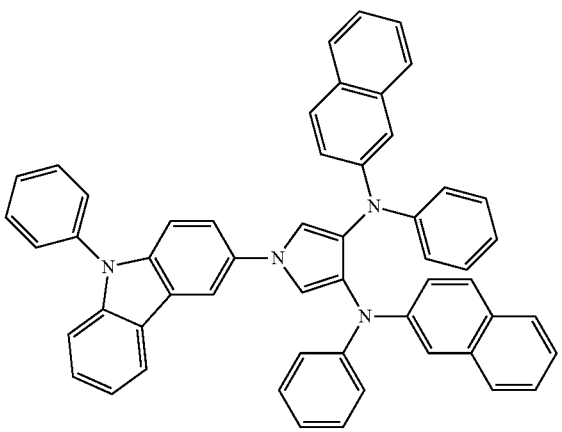
5-C15
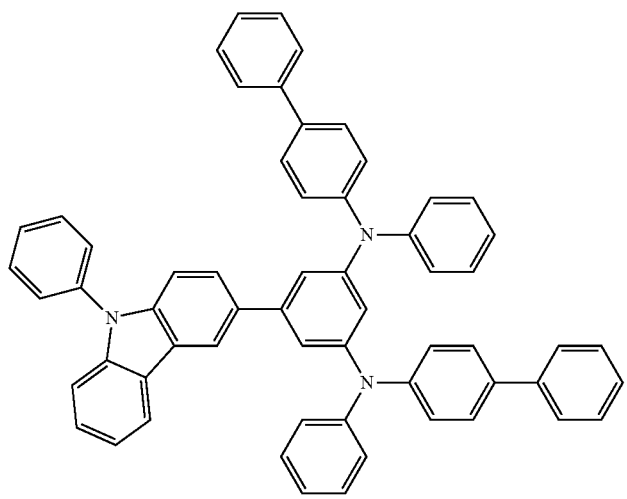

-continued
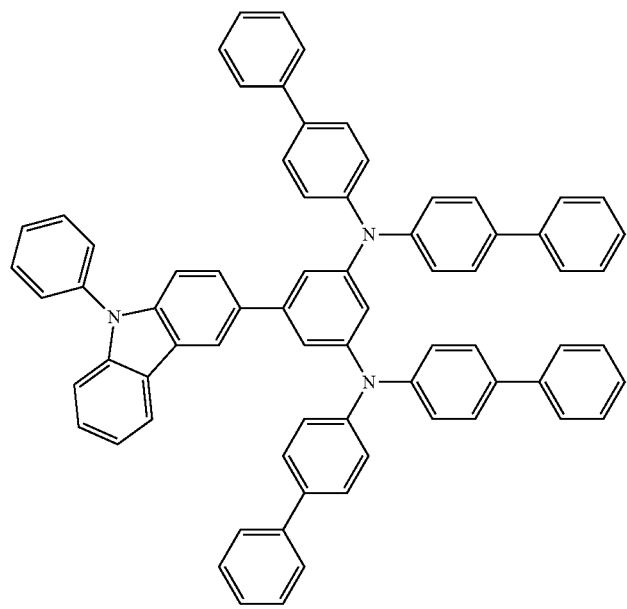
5-C16
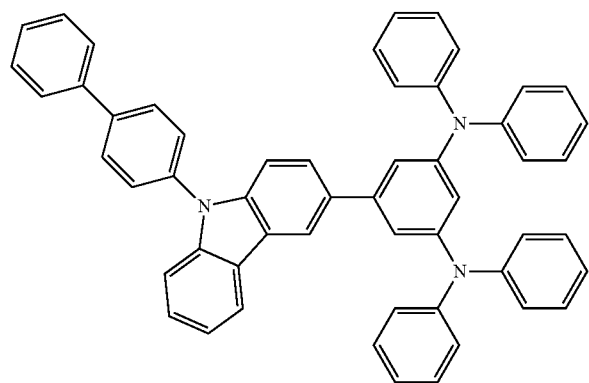
5-C17
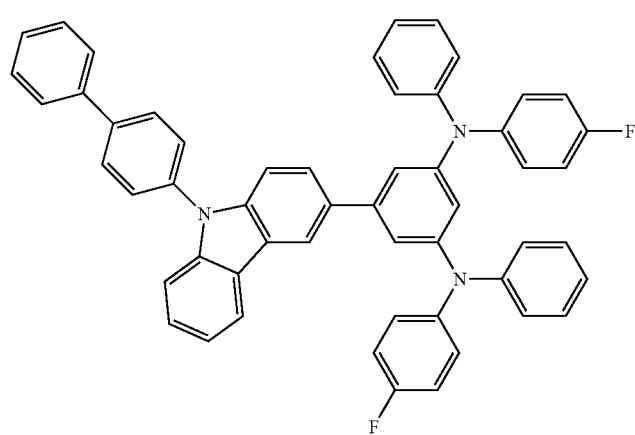
5-C18

-continued
5-C19
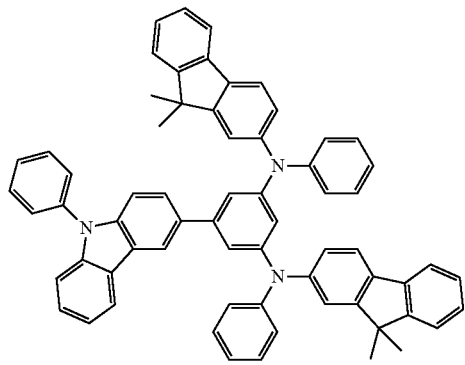
5-C20
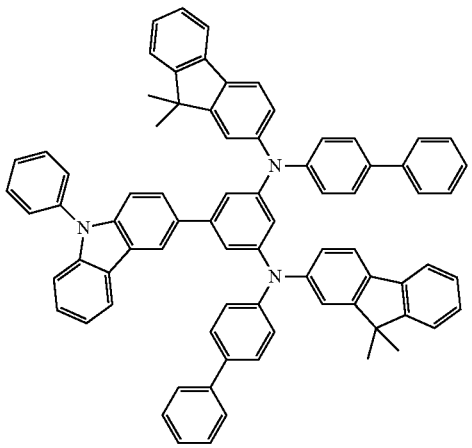
5-C21
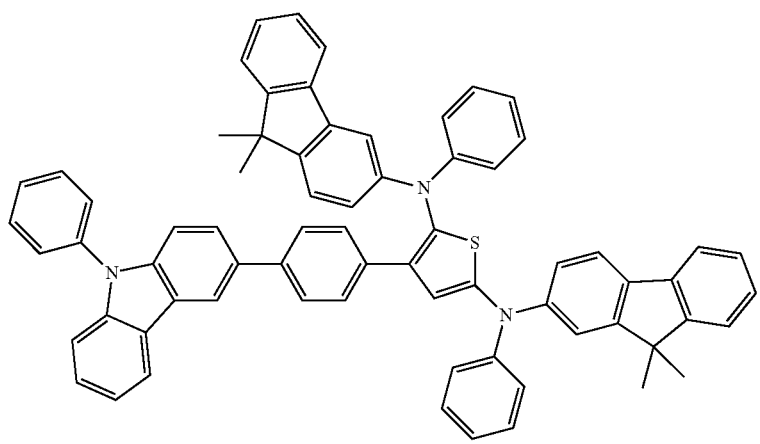
5-C22
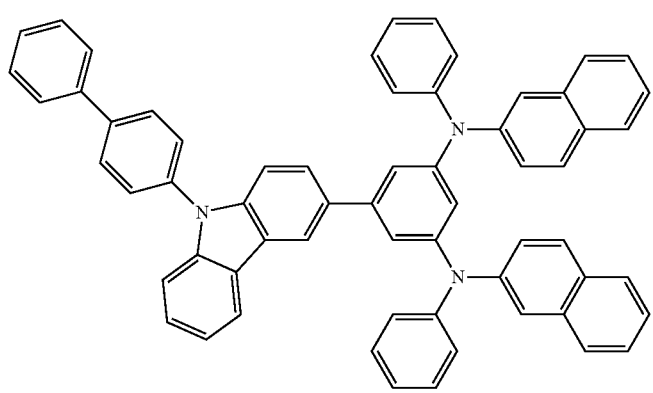

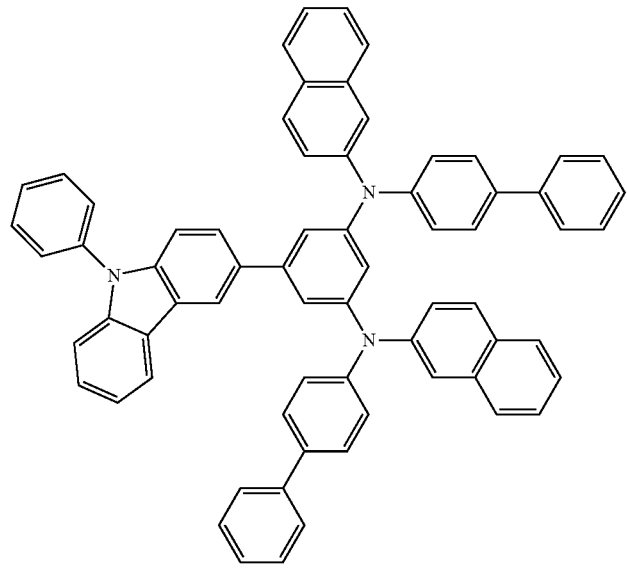
5-C23
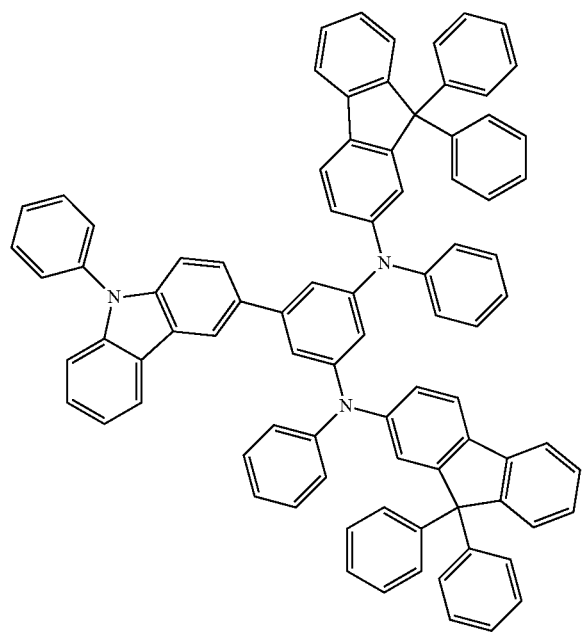
5-C24

-continued
5-C25
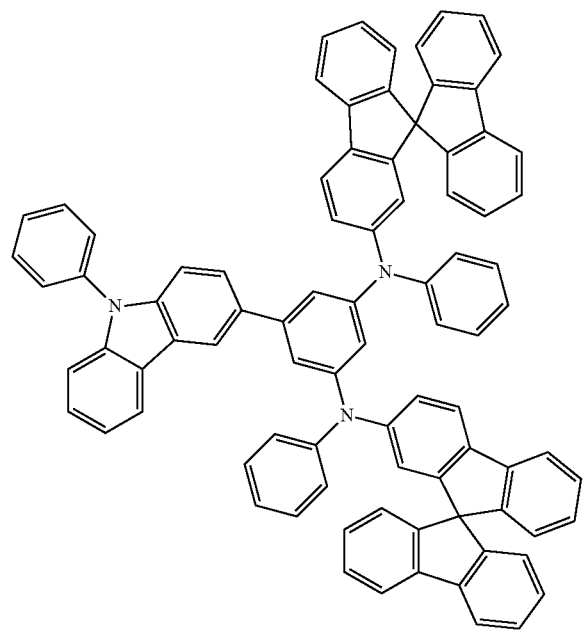
5-C26
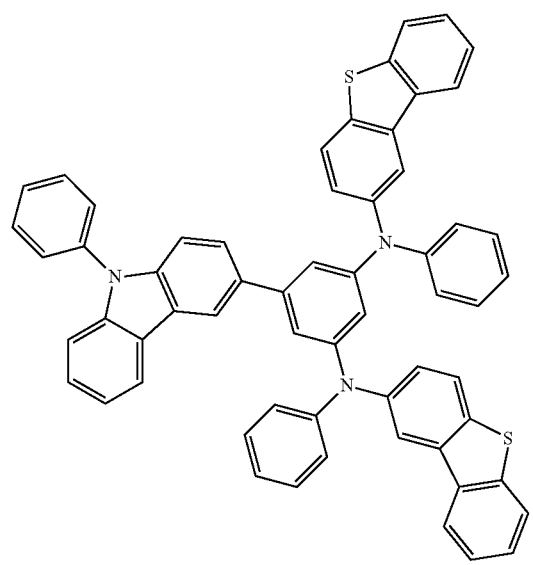

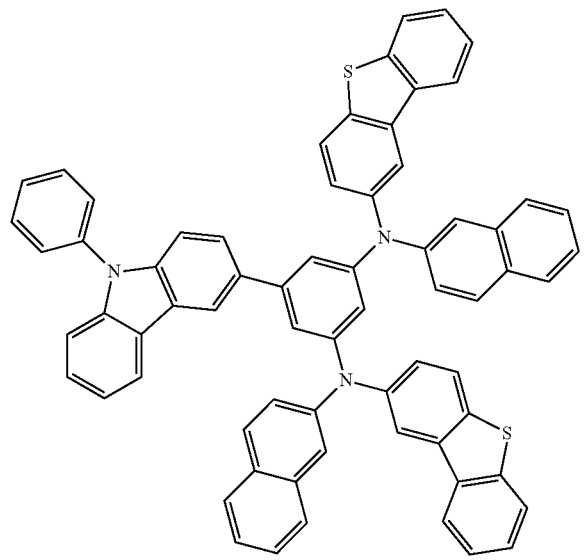
5-C27
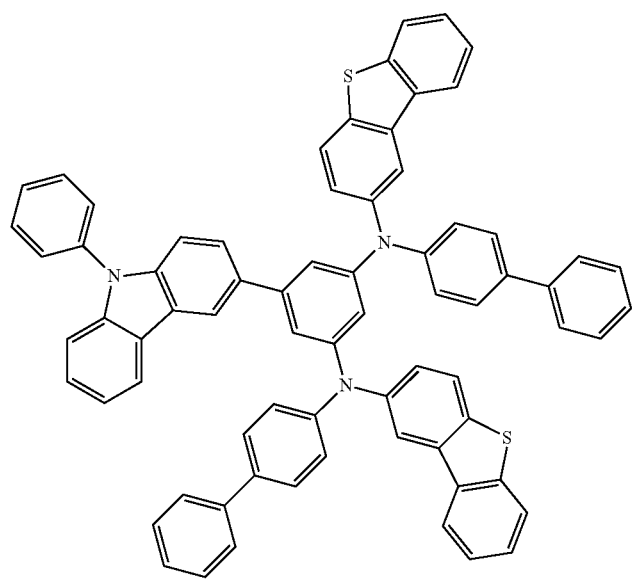
5-C28

5-C29
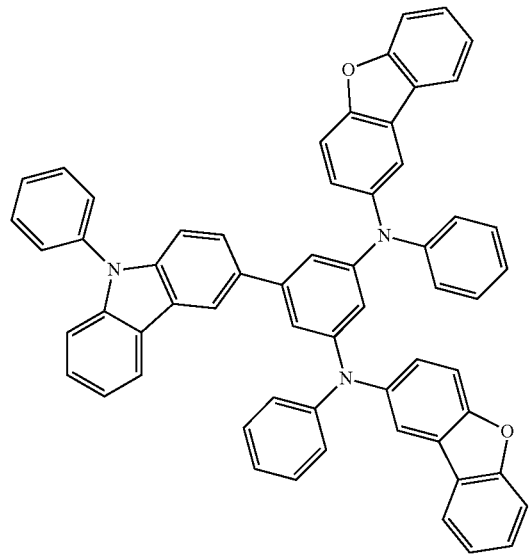
5-C30
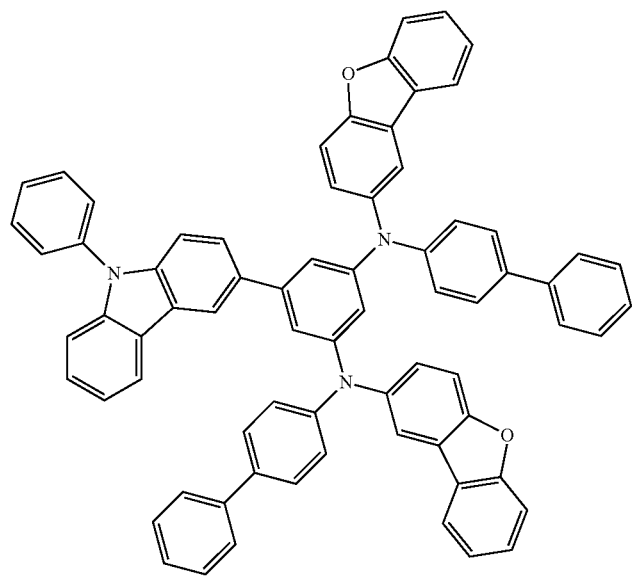
5-C31
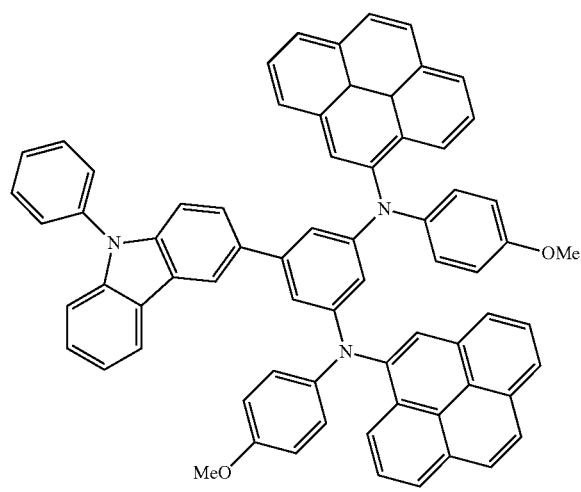

-continued
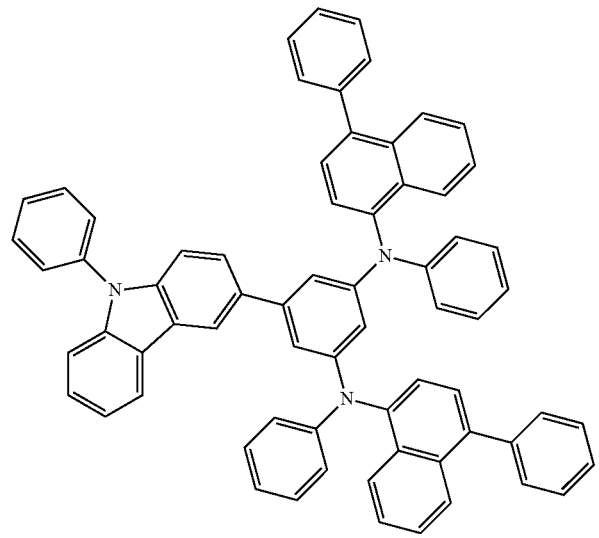
5-C32
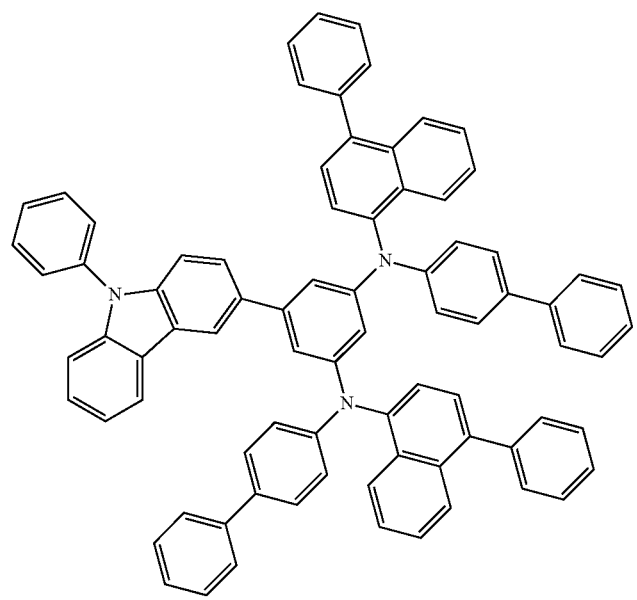
5-C33

-continued

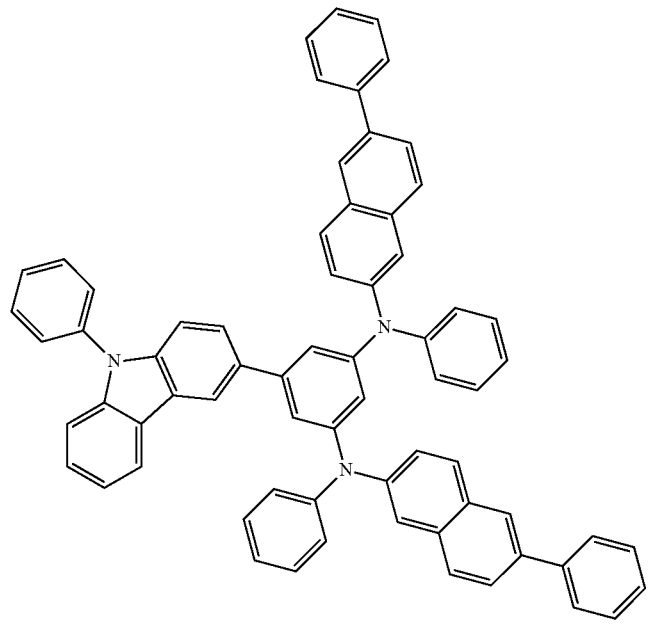

5-C34

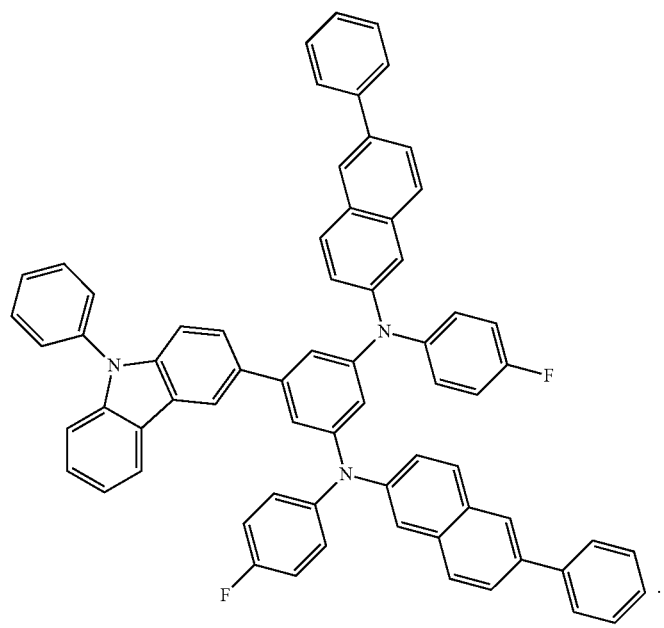

5-C35

9. An organic electronic device comprising one or more organic material layers comprising the compound as claimed in claim 1.

10. The organic electronic device as claimed in claim 9, wherein the organic material layers are formed by a soluble process.

11. The organic electronic device as claimed in claim 9, wherein the organic electronic device comprises a first electrode, said one or more organic material layers, and a second electrode.

12. The organic electronic device as claimed in claim 11, wherein the organic material layers comprise at least one of a hole injection layer, a hole transport layer, an emitting layer, an electron transport layer, an electron injection layer, and an emitting layer.

13. The organic electronic device as claimed in claim 11, wherein the organic material layers comprise a hole injection layer, and the hole injection layer comprises the compound.

14. A terminal comprising a display device and a control part for driving the display device, the display device comprising the organic electronic device as claimed in claim 11.

15. The terminal as claimed in claim 14, wherein the organic electronic device is any one of an organic light emitting diode (OLED), an organic solar cell, an organic photo conductor (OPC) drum, and an organic transistor (organic TFT).

* * * * *